United States Patent
Qiu et al.

(10) Patent No.: US 10,407,445 B2
(45) Date of Patent: Sep. 10, 2019

(54) HEPATITIS C VIRUS INHIBITORS

(71) Applicants: ENANTA PHARMACEUTICALS, INC., Watertown, MA (US); NOVARTIS AG, Basel (CH)

(72) Inventors: Yao-Ling Qiu, Andover, MA (US); Hui Cao, Belmont, MA (US); Xiaowen Peng, Sudbury, MA (US); Xuri Gao, Newton, MA (US); Yat Sun Or, Watertown, MA (US); Zachary Kevin Sweeney, Redwood City, CA (US)

(73) Assignees: Enanta Pharmaceuticals, Inc., Watertown, MA (US); Novartis AG, Basel (CH)

( * ) Notice: Subject to any disclaimer, the term of this patent is extended or adjusted under 35 U.S.C. 154(b) by 0 days.

(21) Appl. No.: 15/007,567

(22) Filed: Jan. 27, 2016

(65) Prior Publication Data

US 2016/0222034 A1     Aug. 4, 2016

Related U.S. Application Data

(63) Continuation of application No. PCT/US2014/048563, filed on Jul. 29, 2014.

(60) Provisional application No. 61/859,582, filed on Jul. 29, 2013.

(51) Int. Cl.

| | |
|---|---|
| C07D 491/107 | (2006.01) |
| C07D 519/00 | (2006.01) |
| A61K 31/4178 | (2006.01) |
| A61K 45/06 | (2006.01) |
| A61K 31/13 | (2006.01) |
| A61K 31/4184 | (2006.01) |
| A61K 31/4188 | (2006.01) |
| A61K 31/427 | (2006.01) |
| A61K 31/7056 | (2006.01) |
| A61K 38/19 | (2006.01) |
| A61K 38/21 | (2006.01) |
| C07D 405/14 | (2006.01) |
| C07D 403/14 | (2006.01) |

(52) U.S. Cl.
CPC ............ *C07D 519/00* (2013.01); *A61K 31/13* (2013.01); *A61K 31/4178* (2013.01); *A61K 31/4184* (2013.01); *A61K 31/4188* (2013.01); *A61K 31/427* (2013.01); *A61K 31/7056* (2013.01); *A61K 38/19* (2013.01); *A61K 38/212* (2013.01); *A61K 38/215* (2013.01); *A61K 38/217* (2013.01); *A61K 45/06* (2013.01); *C07D 403/14* (2013.01); *C07D 405/14* (2013.01); *C07D 491/107* (2013.01)

(58) Field of Classification Search
CPC .......................... C07D 491/107; C07D 519/00
See application file for complete search history.

(56) References Cited

U.S. PATENT DOCUMENTS

| | | | |
|---|---|---|---|
| 8,101,643 B2 | 1/2012 | Qiu et al. | |
| 8,673,954 B2 | 3/2014 | Qiu et al. | |
| 8,778,938 B2* | 7/2014 | Qiu ................... | A61K 31/4178 514/210.18 |
| 2009/0104149 A1 | 4/2009 | Lin et al. | |
| 2010/0081658 A1 | 4/2010 | Chin et al. | |
| 2010/0158860 A1 | 6/2010 | Steiner et al. | |
| 2010/0226879 A1 | 9/2010 | Abbot et al. | |
| 2010/0226882 A1 | 9/2010 | Or et al. | |
| 2010/0260715 A1 | 10/2010 | Or et al. | |
| 2010/0316607 A1 | 12/2010 | Or et al. | |
| 2011/0070189 A1 | 3/2011 | Li et al. | |
| 2011/0217261 A1 | 9/2011 | Or et al. | |
| 2014/0193363 A1 | 7/2014 | Qiu et al. | |
| 2014/0341851 A1 | 11/2014 | Qiu et al. | |

FOREIGN PATENT DOCUMENTS

WO    WO-2011/153396 A1  * 12/2011

* cited by examiner

*Primary Examiner* — Laura L Stockton
(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts, esters, or prodrugs thereof:

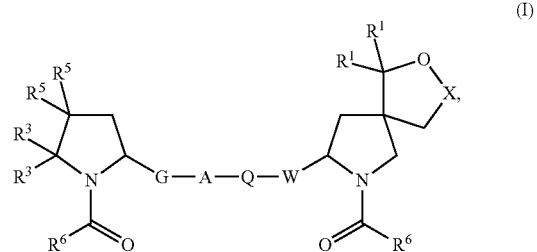

which inhibit RNA-containing virus, particularly the hepatitis C virus (HCV). Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

24 Claims, 1 Drawing Sheet

Specification includes a Sequence Listing.

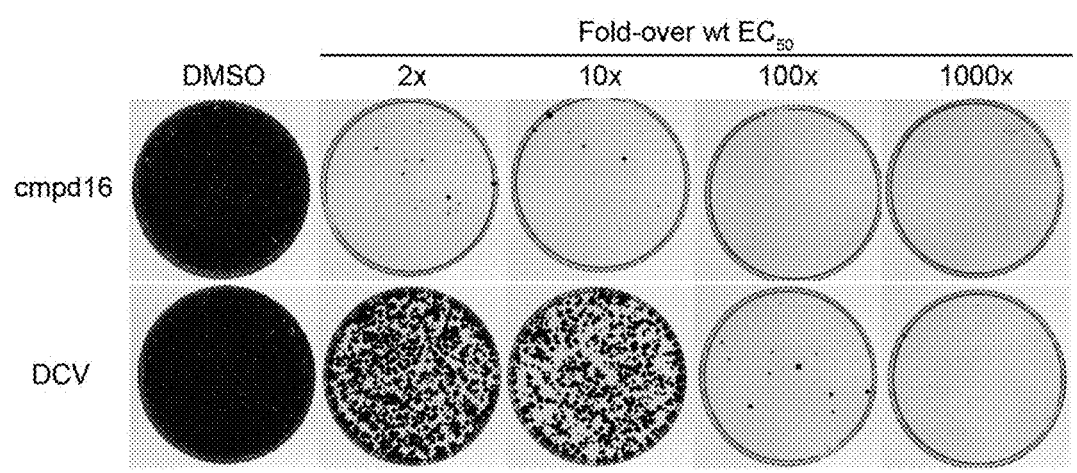

SEQUENCE LISTING

```
<160> NUMBER OF SEQ ID NOS: 44

<210> SEQ ID NO 1
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NotI KO forward primer

<400> SEQUENCE: 1
ctcaaactca ctccaatagc tgccgctggc cggctggac                               39

<210> SEQ ID NO 2
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NotI KO reverse primer

<400> SEQUENCE: 2
gtccagcggg ccagcggcag ctattggagt gagtttgag                               39

<210> SEQ ID NO 3
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AscI hRluc-Neo forward primer

<400> SEQUENCE: 3
gggcgcgcca tggcttccaa ggtgtacg                                           28

<210> SEQ ID NO 4
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NotI hRluc reverse primer

<400> SEQUENCE: 4
cgcggccgct cagaagaact cgtcaag                                            27

<210> SEQ ID NO 5
<211> LENGTH: 45
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NsiI forward primer

<400> SEQUENCE: 5
aagtacatcg ccacatgcat gcaagctgac cttgaggtca tgacc           45

<210> SEQ ID NO 6
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AfeI reverse primer

<400> SEQUENCE: 6
agcgctgcat gggatggggc agtcctcag                              29

<210> SEQ ID NO 7
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AfeI forward primer

<400> SEQUENCE: 7
cccatcccat gcagcgctct aataactccc tgtagccccg aag              43

<210> SEQ ID NO 8
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SnaBI reverse primer

<400> SEQUENCE: 8
catgggccct cctacgtaaa gtctctcagt cagcgagtgt atgg             44

<210> SEQ ID NO 9
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: J6NS5A forward primer

<400> SEQUENCE: 9
cccatcccat gcagcggctc gtggctccgc gatgtgtgg                   39

<210> SEQ ID NO 10
<211> LENGTH: 39
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<223> OTHER INFORMATION: S52NS5A forward primer

<400> SEQUENCE: 10
cccatcccat gcagcggcga ttggctgcgt gacatctgg                                 39

<210> SEQ ID NO 11
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: JFH-5B reverse primer

<400> SEQUENCE: 11
gggagttatt agagccccgg tccaggagta tgacatgga                                 39

<210> SEQ ID NO 12
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-M28T forward primer

<400> SEQUENCE: 12
gctgaaagcc aagctcacgc cacaactgcc tgg                                       33

<210> SEQ ID NO 13
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-M28T reverse primer

<400> SEQUENCE: 13
ccaggcagtt gtggcgtgag cttggctttc agc                                       33

<210> SEQ ID NO 14
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-Q30R forward primer

<400> SEQUENCE: 14
gccaagctca tgccacgcct gcctgggatt cc                                        32

<210> SEQ ID NO 15
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-Q30R reverse primer

<400> SEQUENCE: 15
```

```
ggaatcccag gcaggcgtgg catgagcttg gc                                    32
```

<210> SEQ ID NO 16
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-L31V forward primer

<400> SEQUENCE: 16

```
gctcatgcca caagtgcctg ggattccctt tg                                    32
```

<210> SEQ ID NO 17
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-L31V reverse primer

<400> SEQUENCE: 17

```
caaagggaat cccaggcact tgtggcatga gc                                    32
```

<210> SEQ ID NO 18
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-Y93C forward primer

<400> SEQUENCE: 18

```
cgttccccat taacgcctgc accacgggcc cctg                                  34
```

<210> SEQ ID NO 19
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-Y93C reverse primer

<400> SEQUENCE: 19

```
caggggcccg tggtgcaggc gttaatgggg aacg                                  34
```

<210> SEQ ID NO 20
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-Y93H forward primer

<400> SEQUENCE: 20

```
cgttccccat taacgcccac accacgggcc cctg                                  34
```

```
<210> SEQ ID NO 21
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-Y93H reverse primer

<400> SEQUENCE: 21 cagggggcccg tggtgtgggc gttaatgggg aacg                                  34

<210> SEQ ID NO 22
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GT2a-2a-J6 forward primer

<400> SEQUENCE: 22
cccatcccat gcagcggctc gtggctccgc gatgtgtgg                              39

<210> SEQ ID NO 23
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GT2a-2a-J6 reverse primer
<220> FEATURE:
<221> NAME/KEY: misc_feature
<223> OTHER INFORMATION: GT2a-2b-MD2b reverse primer
<220> FEATURE:
<221> NAME/KEY: misc_feature
<223> OTHER INFORMATION: GT2a-3a-S52 reverse primer
<220> FEATURE:
<221> NAME/KEY: misc_feature
<223> OTHER INFORMATION: GT2a-5a-SA13 reverse primer
<220> FEATURE:
<221> NAME/KEY: misc_feature
<223> OTHER INFORMATION: GT2a-7a-QC69 reverse primer

<400> SEQUENCE: 23
gggagttatt agagccccgg tccaggagta tgacatgga                              39

<210> SEQ ID NO 24
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GT2a-2b-MD2b forward primer

<400> SEQUENCE: 24
cccatcccat gcagcgggtc ttggctccgg gacgtttgg                              39

<210> SEQ ID NO 25
<211> LENGTH: 30
<212> TYPE: DNA
<213> ORGANISM: Artificial Sequence
<220> FEATURE:
<223> OTHER INFORMATION: Synthetic
<220> FEATURE:
```

<221> NAME/KEY: misc_feature
<223> OTHER INFORMATION: GT2a-2b-J8 forward primer

<400> SEQUENCE: 25
cccatcccat gcagcgggtc ttggctccag                30

<210> SEQ ID NO 26
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GT2a-2b-J8 reverse primer

<400> SEQUENCE: 26
gggagttatt agagccccgg tccaggagta tgacatggag cagcagataa cag                53

<210> SEQ ID NO 27
<211> LENGTH: 39
<212> TYPE: DNA
<213> ORGANISM: Artificial Sequence
<220> FEATURE:
<223> OTHER INFORMATION: Synthetic

<400> SEQUENCE: 27
cccatcccat gcagcggcga ttggctgcgt gacatctgg                39

<210> SEQ ID NO 28
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GT2a-5a-SA13 forward primer

<400> SEQUENCE: 28
cccatcccat gcagcggcac atggctaagg gccatttgg                39

<210> SEQ ID NO 29
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GT2a-6a-EUKH2 forward primer

<400> SEQUENCE: 29
cccatcccat gcagcacctc atggttacgc gacgtgtgg                39

<210> SEQ ID NO 30
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GT2a-6a-EUKH2 reverse primer

<400> SEQUENCE: 30
caccctccag atagcgaact tatagttcgg cgcaggagg                39

<210> SEQ ID NO 31
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GT2a-6a-HK6a forward primer

<400> SEQUENCE: 31
cccatcccat gcagcacctc atggttgcgc gacgtgtgg          39

<210> SEQ ID NO 32
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GT2a-6a-HK6a reverse primer

<400> SEQUENCE: 32
caccctccag atagcgaact tatagttcgg cgcaggagg          39

<210> SEQ ID NO 33
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GT2a-7a-QC69 forward primer

<400> SEQUENCE: 33
cccatcccat gcagcgggag ctggctccgg gaggtgtgg          39

<210> SEQ ID NO 34
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-M28T forward primer

<400> SEQUENCE: 34
gctgaaagcc aagctcacgc cacaactgcc tgg                33

<210> SEQ ID NO 35
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-M28T reverse primer

<400> SEQUENCE: 35
ccaggcagtt gtggcgtgag cttggctttc agc                33

<210> SEQ ID NO 36
<211> LENGTH: 32
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-Q30R forward primer

<400> SEQUENCE: 36
gccaagctca tgccacgcct gcctgggatt cc                            32

<210> SEQ ID NO 37
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-Q30R reverse primer

<400> SEQUENCE: 37
ggaatcccag gcaggcgtgg catgagcttg gc                            32

<210> SEQ ID NO 38
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-L31V forward primer

<400> SEQUENCE: 38
gctcatgcca caagtgcctg ggattcccett tg                           32

<210> SEQ ID NO 39
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-L31V reverse primer

<400> SEQUENCE: 39
caaagggaat cccaggcact tgtggcatga gc                            32

<210> SEQ ID NO 40
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-Y93C forward primer

<400> SEQUENCE: 40
cgttccccat taacgcctgc accacgggcc cctg                          34

<210> SEQ ID NO 41
<211> LENGTH: 34
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<223> OTHER INFORMATION: 1a-Y93C reverse primer

<400> SEQUENCE: 41 cagggggcccg tggtgcaggc gttaatgggg aacg                              34

<210> SEQ ID NO 42
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-Y93H forward primer

<400> SEQUENCE: 42
cgttccccat taacgcccac accacgggcc cctg                               34

<210> SEQ ID NO 43
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1a-Y93H reverse primer

<400> SEQUENCE: 43
caggggcccg tggtgtgggc gttaatgggg aacg                               34

<210> SEQ ID NO 44
<211> LENGTH: 24
<212> TYPE: DNA
<213> ORGANISM: Artificial Sequence
<220> FEATURE:
<223> OTHER INFORMATION: Synthetic

<400> SEQUENCE: 44
tccatgtcat actcctggac cggg                                          24
```

HEPATITIS C VIRUS INHIBITORS

RELATED APPLICATION

This application is a continuation of International Application No. PCT/US2014/048563, which designated the United States and was filed on Jul. 29, 2014, published in English, which claims the benefit of U.S. Provisional Application No. 61/859,582, filed on Jul. 29, 2013. The entire teachings of the above applications are incorporated herein by reference.

TECHNICAL FIELD

The present invention relates to novel antiviral agents. More specifically, the present invention relates to compounds which can inhibit the function of the NS5A protein encoded by Hepatitis C virus (HCV), compositions comprising such compounds, methods for inhibiting HCV viral replication, methods for treating or preventing HCV infection, and processes for making the compounds.

BACKGROUND OF THE INVENTION

Infection with HCV is a major cause of human liver disease throughout the world. In the U.S., an estimated 4.5 million Americans are chronically infected with HCV. Although only 30% of acute infections are symptomatic, greater than 85% of infected individuals develop chronic, persistent infection. Treatment costs for HCV infection have been estimated to be $5.46 billion for the US in 1997. Worldwide, over 200 million people are estimated to be chronically infected. HCV infection is responsible for 40-60% of all chronic liver disease and 30% of all liver transplants. Chronic HCV infection accounts for 30% of all cirrhosis, end-stage liver disease, and liver cancer in the U.S.

Due to the high degree of variability in the viral surface antigens, existence of multiple viral genotypes, and demonstrated specificity of immunity, the development of a successful vaccine in the near future is unlikely. Alpha-interferon (alone or in combination with ribavirin) has been widely used since its approval for treatment of chronic HCV infection. However, adverse side effects are commonly associated with this treatment: flu-like symptoms, leukopenia, thrombocytopenia, depression, as well as anemia induced by ribavirin (Lindsay, K. L. (1997) Hepatology 26 (suppl 1): 71S-77S). This therapy remains less effective against infections caused by HCV genotype 1 (which constitutes ~75% of all HCV infections in the developed markets) compared to infections caused by the other 5 major HCV genotypes. Unfortunately, only ~50-80% of the patients respond to this treatment (measured by a reduction in serum HCV RNA levels and normalization of liver enzymes) and, of responders, 50-70% relapse within 6 months of cessation of treatment. With the introduction of pegylated interferon (Peg-IFN), both initial and sustained response rates have improved substantially. However, the side effects associated with combination therapy and the impaired response in patients with genotype 1 present opportunities for improvement in the management of this disease.

First identified by molecular cloning in 1989 (Choo, Q-L et al (1989) Science 244:359-362), HCV is now widely accepted as the most common causative agent of post-transfusion non-A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 1-4) and pestiviruses (e.g. bovine viral diarrhea virus, border disease virus, and classic swine fever virus) (Choo, Q-L et al (1989) Science 244:359-362; Miller, R. H. and R. H. Purcell (1990) Proc. Natl. Acad. Sci. USA 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al 'An RNA pseudoknot is an essential structural element of the internal ribosome entry site located within the hepatitis C virus 5' noncoding region RNA—A Publication of the RNA Society. 1(5): 526-537, 1995 July). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology 2nd Edition, p 931-960; Raven Press, N.Y.). There are three structural proteins, C, E1 and E2. The P7 protein is of unknown function and is comprised of a highly variable sequence. There are several nonstructural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease. NS5A is a membrane-anchored phosphoprotein that is observed in basally phosphorylated (56 kDa) and hyper-phosphorylated (58 kDa) forms. While its function has not fully been elucidated, NS5A is believed to be important in viral replication. The NS5B protein (591 amino acids, 65 kDa) of HCV (Behrens, S. E. et at (1996) EMBO J. 151 2-22) encodes an RNA-dependent RNA polymerase (RdRp) activity and contains canonical motifs present in other RNA viral polymerases. The NS5B protein is fairly well conserved both intra-typically (~95-98% amino acid (aa) identity across 1b isolates) and inter-typically (~85% aa identity between genotype 1a and 1b isolates). The essentiality of the HCV NS5B RdRp activity for the generation of infectious progeny virions has been formally proven in chimpanzees (A. A. Kolykhalov et al. (2000) Journal of Virology, 74(4): 2046-2051). Thus, inhibition of NS5B RdRp activity (inhibition of RNA replication) is predicted to be useful to treat HCV infection.

Compounds useful for treating HCV-infected patients are desired which selectively inhibit HCV viral replication. In particular, compounds which are effective to inhibit the function of the NS5A protein are desired. The HCV NS5A protein is described, for example, in the following references: S. L. Tan, et al., *Virology,* 284:1-12 (2001); K.-J. Park, et al., *J. Biol. Chem.,* 30711-30718 (2003); T. L. Tellinghuisen, et al., *Nature,* 435, 374 (2005); R. A. Love, et al., *J. Virol,* 83, 4395 (2009); N. Appel, et al., *J. Biol. Chem.,* 281, 9833 (2006); L. Huang, *J. Biol. Chem.,* 280, 36417 (2005); C. Rice, et al., WO2006093867; R. Hamatake, et al., *Ann. Rep. Med. Chem.* 47, 331 (2012); D. G. Cordek, et al., *Drugs* of the Future, 36, 691 (2011); U. Schmitz, et al., Recent Patents on Anti-Infective Drug Discovery, 3, 77 (2008).

Daclatasvir (BMS-790052) is the most advanced NS5A inhibitor in clinic development. It has demonstrated significant viral suppression in various phase 2 studies on treatment-naïve patients, especially with genotype 1b (GT 1b) infections. Clinical response of Daclatasvir for patients with GT 1a (GT 1a) infectious is often less profound. For example, in an exploratory study (A. Lok, et al., 61$^{st}$ AASLD, The Liver Meeting, Boston, Mass., Oct. 29-Nov. 2, 2010, LB-8) when eleven GT 1 patients of prior null responders were dosed with Daclatasvir and an NS3 protease inhibitor Asunaprevir, only four patients achieved the primary endpoint of SVR12 (sustained virological response 12 weeks after treatment). The primary reason for treatment failure was viral breakthrough which occurred in six patients infected with GT 1a HCV. In contrast, the two GT 1b-infected patients in this group both had SVR12. A recently published study has also confirmed that the impressive efficacy can be achieved against GT 1b (K. Chayama, et al., Hepatology, 55, 742 (2012)). This is consistent with the relative in vitro potency of Daclatasvir against GT 1b-NS5A-resistant variants and GT-1a NS5A-resistant variants. It has been demonstrated NS5A inhibitor-associated mutations arise predominantly at residue positions 28, 30, 31, and 93 in domain I of the NS5A protein (M. Gao, et al., Nature, 465, 96 (2010); R. A. Fridell, et al., Antimicrob. Agents Chemother. 54, 3641 (2010); R. E. Nettles, et al., Hepatolgy, 54, 1956 (2011)). The most prominent mutation affects Tyr93. Importantly, mutations at this site confer cross-resistance to several NS5A inhibitors and, in the case of daclatasvir, reduce drug sensitivity by ~20-fold for genotype 1b subgenomic replicons and ~1,800-fold for genotype 1a subgenomic replicons.

In another study (M. Sulkowski, et al., 47th EASL Congress, Barcelona, Spain, Apr. 18-22, 2012, P-1422) when GT 1, 2 or 3 treatment nave patients were dosed with Daclatasvir and a nucleotide NS5B inhibitor GS-7977. The treatment response rate was noticeably lower in GT 2 and 3 than GT1 cohorts. In a 3-day monotherapy proof-of-concept study when another NS5A inhibitor IDX719 was administered to GT 1-4 treatment naïve patients, HCV viral RNA reduction was found to be significantly lower in GT 2 cohorts than GT 1, 3 and 4 cohorts (www.idenix.com/hcv/IDX719_HCVClinPharmMtg_FINAL%206%2027%2012.pdf). These clinical findings are consistent with the in vitro data indicating that these drugs are less potent against certain HCV genotypes such as the GT 2a-J6 strain. For example, it has been reported that Daclatasvir was much less potent against GT 2a-J6 ($EC_{50}$=7200 pM) than GT1a ($EC_{50}$=8 pM) (M. Gao, et al., 46$^{th}$ EASL Congress, Berlin, Germany, Mar. 30-April 2011, P-787). The HCV GT 2a-J6 strain has a point substitution at L31M, which is clinically relevant to an estimated 80% of the GT 2a-infected patient population based on a sequence alignment analysis from an EU HCV sequence database euH-CVdb (the European hepatitis C virus database, see also C. Combet, et al., Nucleic Acids Res. 2007, 35: D363-D366).

Based on the foregoing, there exists a significant need to identify compounds with the ability to inhibit HCV, especially compounds which are effective against GT 1a resistant variants and have activity against a broad range of HCV genotypes.

SUMMARY OF THE INVENTION

The present invention relates in part to the unexpected discovery that certain compounds with various scaffolds containing pyrrolidine groups substituted with spiro-oxacycloalkyl groups, such as spirotetrahydrofuranyl (THF) substituted pyrrolidine groups or spiro-tetrahydropyranyl (THP) substituted pyrrolidine groups can have potent activity against GT 1a variants resistant to many NS5A inhibitors and activity against several HCV genotypes, including the GT 2a-J6 virus. Surprisingly, the antiviral potency and pharmacokinetic properties of these compounds are highly dependent on the stereochemistry and identity of the spiro-substituted proline.

In one embodiment, the compound has a spiro-tetrahydrofuranyl (THF) substituted pyrrolidine and has increased activity against certain HCV GT 1a resistant variants, such as M28T, Q30R, L31V, Y93C, and Y93H, as compared to the corresponding reference compound.

In another embodiment, the compound has a spiro-tetrahydropyranyl (THP) substituted pyrrolidine and has increased activity against certain HCV GT 1a resistant variants, such as M28T, Q30R, L31V, Y93C, and Y93H, as compared to the corresponding reference compound.

It was unexpectedly discovered in the present invention that compounds containing certain spiro-THF or spiro-THP substituted pyrrolidine with certain stereochemistry at the spiro carbon center, e.g., compounds with an (S)-stereochemistry at the spiro carbon center, can have better activity against certain HCV GT 1a resistant variants (such as M28T, Q30R, L31V, Y93C), as compared to the corresponding compounds with an (R)-stereochemistry at the spiro carbon center.

It was still unexpectedly discovered in the present invention that compounds containing certain spiro-THP substituted pyrrolidine with certain stereochemistry at the spiro carbon center, e.g., compounds with an (S)-stereochemistry at the spiro carbon center, can have better activity against certain HCV genotypes, such as GT 2a-J6 and GT 3a, as compared to the corresponding compounds with an (R)-stereochemistry at the spiro carbon center. The present invention relates to novel antiviral compounds represented herein below, pharmaceutical compositions comprising such compounds, and methods for the treatment or prophylaxis of viral (particularly HCV) infection in a subject in need of such therapy with said compounds. Compounds of the present invention interfere with the life cycle of the hepatitis C virus and are useful as antiviral agents.

In one embodiment, the present invention provides a compound of Formula (I):

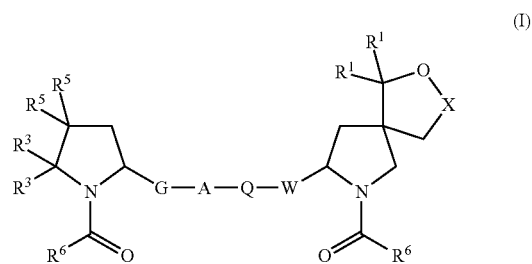

or a pharmaceutically acceptable salt thereof, wherein:

A and Q are each independently selected from the group consisting of optionally substituted phenyl;

Alternatively, A and Q are taken together to form an optionally substituted, tricyclic aryl or optionally substituted, tricyclic heteroaryl;

G and W are each independently an optionally substituted imidazolyl; wherein the said imidazolyl groups are C2-attached to the pyrrolidine rings;

Alternatively, G and A, or Q and W can be taken together to form an optionally substituted tricyclic as

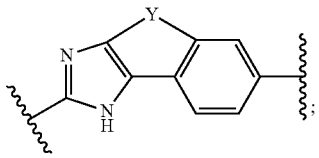

wherein Y is —CH=CH—, —CH$_2$O—, —CH$_2$CH$_2$—, —CH$_2$CH$_2$CH$_2$—, —OCH$_2$CH$_2$—, or —CH$_2$OCH$_2$—;

Yet alternatively, A and Q, or A, Q and W can be taken together to form an optionally substituted pentacyclic as

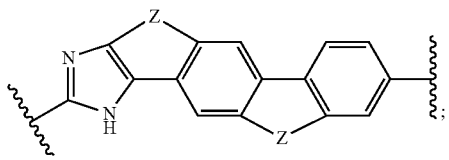

wherein Z at each occurrence is independently selected from the group consisting of —CH=CH—, —CH$_2$O—, and —CH$_2$CH$_2$—;

X is selected from a group consisting, —C(R$^{11}$)$_2$— and —C(R$^{11}$)$_2$C(R$^{11}$)$_2$—; preferably, X is —C(R$^{11}$)$_2$—; more preferably, X is —(CH$_2$)$_2$—;

R$^1$, R$^3$, and R$^{11}$ at each occurrence are each independently hydrogen, or optionally substituted C$_1$-C$_4$ alkyl;

R$^5$ at each occurrence is independently hydrogen, halogen, optionally substituted O(C$_1$-C$_4$ alkyl), optionally substituted C$_3$-C$_8$ cycloalkyl, or optionally substituted C$_1$-C$_4$ alkyl;

Alternatively, two geminal R$^5$ groups can be taken together with the carbon or silicon atom to which they are attached to form a spiro, optionally substituted C$_3$-C$_8$ cycloalkyl or optionally substituted heterocyclic ring; preferably two geminal R$^5$ groups can be taken together with the carbon atom to which they are attached to form a spiro, optionally substituted cyclopropyl, tetrahydrofuranyl or tetrahydropyranyl;

Yet alternatively, vicinal R$^3$ and R$^5$ can be taken together with the carbon atoms to which they are attached to form a fused and optionally substituted C$_3$-C$_8$ cycloalkyl or fused and optionally substituted heterocyclic; preferably, R$^5$ and R$^3$ are taken together with the carbon atoms to which they are attached to form a fused and optionally substituted cyclopentyl or cyclohexyl; and R$^6$ at each occurrence is independently C$_1$-C$_8$ alkyl substituted with one or more groups selected from amino, protected amino, N(C$_1$-C$_4$ alkyl)$_2$, hydroxy, O(C$_1$-C$_4$ alkyl), phenyl or tetrahydropyranyl. Preferably, each R$^6$ is independently C$_1$-C$_8$ alkyl substituted with one group selected from amino, protected amino, and N(C$_1$-C$_4$ alkyl)$_2$, or one group selected from amino, protected amino, and N(C$_1$-C$_4$ alkyl)$_2$ and one group selected from hydroxy, O(C$_1$-C$_4$ alkyl), phenyl and tetrahydropyranyl. In certain embodiments the two R$^6$ groups are the same. In other embodiments, the two R$^6$ groups are different.

In preferred embodiments, the stereochemistry of the spiro carbon atom is (S)-. The spiro carbon atom is designated below with an arrow.

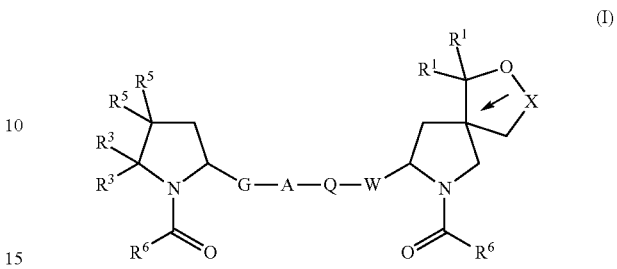

Each preferred group stated above can be taken in combination with one, any or all other preferred groups.

In preferred embodiments, the HCV genotype 1a resistant mutant variant is selected from M28T, Q30R, L31V, Y93C, and Y93H.

In another embodiment, the invention provides compounds of Formula I or a pharmaceutically acceptable salt thereof.

In another aspect, the present invention provides a pharmaceutical composition comprising a therapeutically effective amount of a compound or combination of compounds of the present invention, or a pharmaceutically acceptable salt thereof, in combination with a pharmaceutically acceptable carrier or excipient.

In yet another aspect, the present invention provides a method of inhibiting the replication of a RNA-containing virus comprising contacting said virus with a therapeutically effective amount of a compound or a combination of compounds of the present invention, or a pharmaceutically acceptable salt thereof. Particularly, this invention is directed to methods of inhibiting the replication of HCV.

In still another aspect, the present invention provides a method of treating or preventing infection caused by an RNA-containing virus comprising administering to a patient in need of such treatment a therapeutically effective amount of a compound or combination of compounds of the present invention, or a pharmaceutically acceptable salt thereof. Particularly, this invention is directed to methods of treating or preventing infection caused by HCV.

Yet another aspect of the present invention provides the use of a compound or combination of compounds of the present invention, or a therapeutically acceptable salt thereof, as defined hereinafter, in the preparation of a medicament for the treatment or prevention of infection caused by RNA-containing virus, specifically HCV.

BRIEF DESCRIPTION OF THE DRAWING

The FIGURE shows the effect of treating HCV genotype 1b replicon cells with either Compound 16 or daclatasvir (DCV): crystal violet staining was used to visualize surviving replicon cells after 3 weeks at concentrations 2×, 10×, 100×, or 1000× the EC$_{50}$ for the inhibitor (compound 16 or daclatasvir).

DETAILED DESCRIPTION OF THE INVENTION

The present invention relates to compounds of Formula (I) as illustrated above, or a pharmaceutically acceptable salt thereof.

The compounds of the invention have utility in inhibiting the replication of RNA-containing virus, including, for example, HCV. Other compounds useful for inhibiting the replication of RNA-containing viruses and/or for the treatment or prophylaxis of HCV infection have been described in copending U.S. application Ser. No. 12/702,673 filed Feb. 9, 2010 entitled "Linked Dibenzimidiazole Derivatives"; U.S. application Ser. No. 12/702,692 filed Feb. 9, 2010 entitled "Linked Dibenzimidiazole Derivatives"; U.S. application Ser. No. 12/702,802 filed Feb. 9, 2010 entitled "Linked Dibenzimidiazole Derivatives"; U.S. application Ser. No. 12/707,190 filed Feb. 17, 2010 entitled "Linked Diimidazole Antivirals"; U.S. application Ser. No. 12/707,200 filed Feb. 17, 2010 entitled "Linked Diimidazole Derivatives"; U.S. application Ser. No. 12/707,210 filed Feb. 17, 2010 entitled "Hepatitis C Virus Inhibitors"; U.S. application Ser. No. 12/714,583 filed Mar. 1, 2010 entitled "Novel Benzimidazole Derivatives"; and U.S. application Ser. No. 12/714,576 filed Mar. 1, 2010 entitled "Hepatitis C Virus Inhibitors"; U.S. application Ser. No. 12/816,148 filed Jun. 15, 2010 entitled "Hepatitis C Virus Inhibitors"; U.S. application Ser. No. 12/816,171 filed Jun. 15, 2010 entitled "Hepatitis C Virus Inhibitors"; U.S. application Ser. No. 12/879,025 filed Sep. 10, 2010 entitled "Hepatitis C Virus Inhibitors"; U.S. application Ser. No. 12/879,026 filed Sep. 10, 2010 entitled "Hepatitis C Virus Inhibitors"; U.S. application Ser. No. 12/879,027 filed Sep. 10, 2010 entitled "Hepatitis C Virus Inhibitors"; U.S. application Ser. No. 12/879,028 filed Sep. 10, 2010 entitled "Hepatitis C Virus Inhibitors"; U.S. application Ser. No. 12/879,029 filed Sep. 10, 2010 entitled "Hepatitis C Virus Inhibitors"; U.S. application Ser. No. 12/879,031 filed Sep. 10, 2010 entitled "Hepatitis C Virus Inhibitors"; U.S. application Ser. No. 12/967,486 filed Dec. 14, 2010 entitled "Hepatitis C Virus Inhibitors"; U.S. Provisional Application Ser. No. 61/322,438 filed Apr. 9, 2010 entitled "Hepatitis C Virus Inhibitors"; U.S. Provisional Application Ser. No. 61/351,327 filed Jun. 4, 2010 entitled "Hepatitis C Virus Inhibitors"; U.S. Provisional Application Ser. No. 61/372,999 filed Aug. 12, 2010 entitled "Hepatitis C Virus Inhibitors"; U.S. Provisional Application Ser. No. 61/415,447 filed Nov. 19, 2010 entitled "Hepatitis C Virus Inhibitors"; and the contents of each of which are expressly incorporated by reference herein.

As discussed above, a general strategy for the development of antiviral agents is to inactivate virally encoded proteins, including NS5A, that are essential for the replication of the virus. The relevant patent disclosures describing the synthesis of HCV NS5A inhibitors are: US 2009/0202478; US 2009/0202483; US 2010/0233120; US 2010/0260708; WO 2004/014852; WO 2006/079833; WO 2006/133326; WO 2007/031791; WO 2007/070556; WO 2007/070600; WO 2007/082554; WO 2008/021927; WO 2008/021928; WO 2008/021936; WO 2008/048589; WO 2008/064218; WO 2008/070447; WO 2008/144380; WO 2008/154601; WO 2009/020825; WO 2009/020828; WO 2009/034390; WO 2009/102318; WO 2009/102325; WO 2009/102694; WO 2010/017401; WO 2010/039793; WO 2010/065668; WO 2010/065674; WO 2010/065681; WO 2010/091413; WO 2010/096777; WO 2010/096462; WO 2010/096302; WO2010/099527; WO 2010/111483; WO 2010/111534; WO 2010/117635; WO 2010/111673; WO 2010/117704; WO 2010/132538; WO 2010/132601; WO 2010/138488; WO 2010/138368; WO 2010/138790; WO 2010/138791; and WO 2010/148006, the contents of each of which are expressly incorporated by reference herein.

In one embodiment, the present invention relates to compounds of Formula (I), and pharmaceutically acceptable salts thereof.

In yet another embodiment, the compound of Formula (I) is represented by Formula (II):

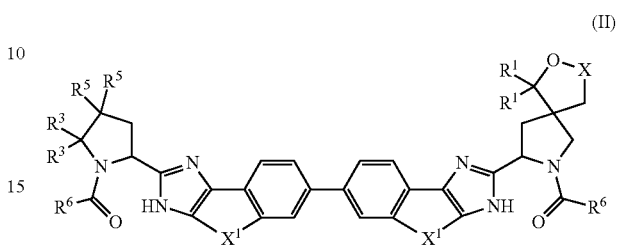

(II)

or pharmaceutically acceptable salts thereof, wherein $X^1$ at each occurrence is independently selected from the group consisting of absent, —CH═CH—, —CH$_2$O—, —CH$_2$CH$_2$—, —CH$_2$CH$_2$CH$_2$—, —OCH$_2$CH$_2$—, and —CH$_2$OCH$_2$—; and $R^1$, $R^3$, $R^5$, $R^6$ and X are as previously defined. In certain embodiments, at least one $X^1$ is not absent.

It is to be understood that when $X^1$ is absent, it is replaced by hydrogen atoms attached to each carbon atom connected to one of these variables in any of the formulas set forth herein.

In still another embodiment, the compound of Formula (I) is represented by Formula (III):

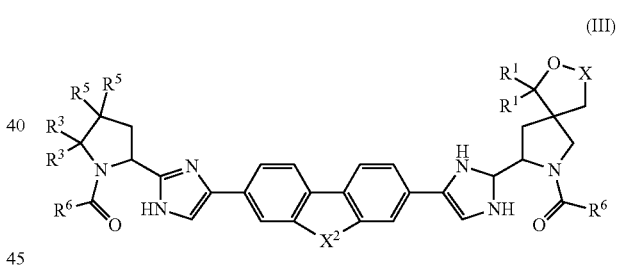

(III)

or pharmaceutically acceptable salts thereof, wherein $X^2$ at each occurrence is independently selected from the group consisting of —CH$_2$—, O, —CH═CH—, —CH$_2$O—, —CH$_2$CH$_2$—, —CH$_2$CH$_2$CH$_2$—, —OCH$_2$CH$_2$—, and —CH$_2$OCH$_2$—; and $R^3$, $R^5$, $R^6$, and X are as previously defined.

In still another embodiment, the compound of Formula (I) is represented by Formula (IVa) or (IVb):

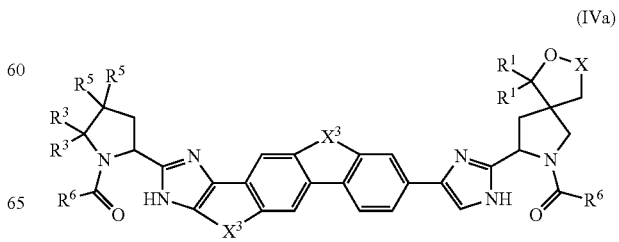

(IVa)

-continued (IVb)

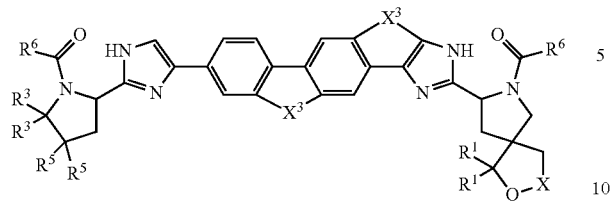

or pharmaceutically acceptable salts thereof, wherein $X^3$ at each occurrence is each independently selected from the group consisting of —CH=CH—, —CH$_2$O—, and —CH$_2$CH$_2$—; and $R^1$, $R^3$, $R^5$, $R^6$, and X are as previously defined.

In still another embodiment, the compound of Formula (I) is represented by one of Formulae (Va) to (Vc):

(Va)

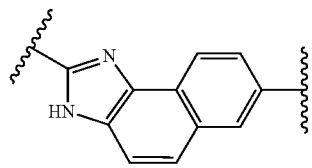

(Vb)

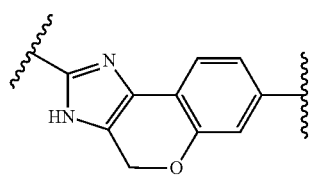

(Vc)

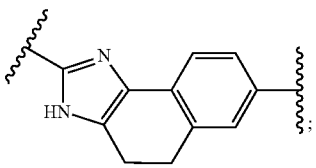

or a pharmaceutically acceptable salt thereof, wherein $R^1$, $R^3$, $R^5$, $R^6$, $X^3$, and X are as previously defined.

In still another embodiment, the present invention relates to compounds of Formula (I), and pharmaceutically acceptable salts thereof, wherein A and Q are taken together to form an optionally substituted biphenyl.

In certain embodiments of the compounds of Formula (I), -G-A-Q-W- is not

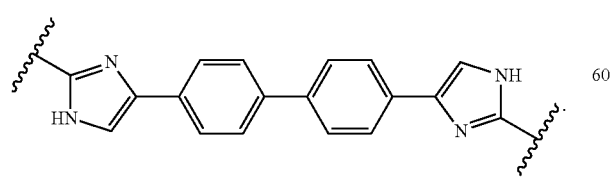

In still another embodiment, the present invention relates to compounds of Formula (I), and pharmaceutically acceptable salts thereof, wherein G and A, or Q and W are taken together to form an optionally substituted tricyclic selected from the following groups:

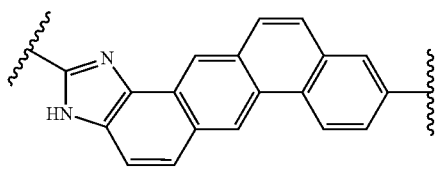

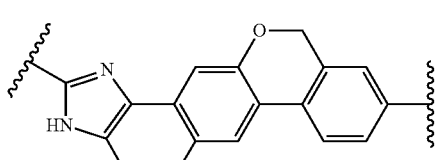

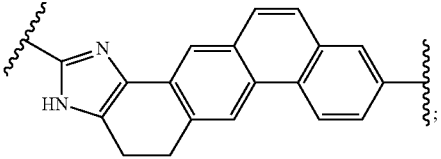

wherein each of the above shown cyclic groups is optionally substituted.

In still another embodiment, the present invention relates to compounds of Formula (I), and pharmaceutically acceptable salts thereof, wherein A, and Q, or A, Q, and W are taken together to form an optionally substituted pentacyclic selected from the following groups:

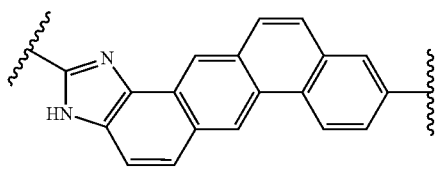

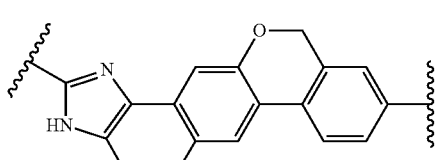

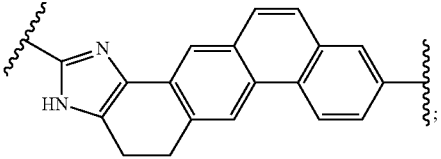

wherein each of the above shown cyclic groups is optionally substituted.

In still another embodiment, the compound of Formula (I) is represented by one of Formulae (VIa) to (VId):

(VIa)
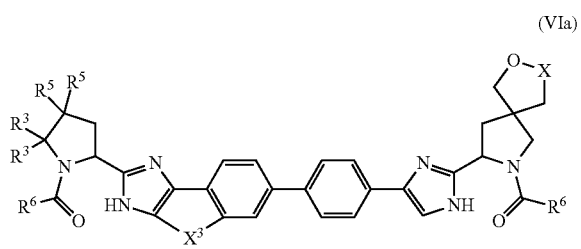

(VIb)
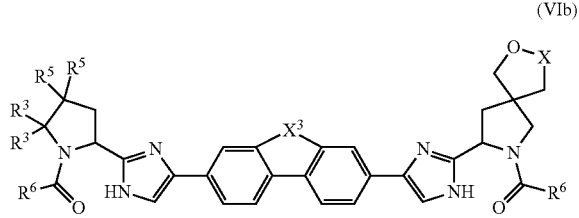

(VIc)
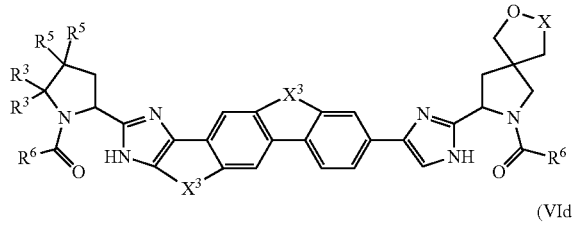

(VId)
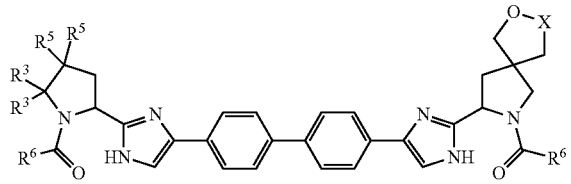

or a pharmaceutically acceptable salt thereof, wherein $R^1$, $R^3$, $R^5$, $R^6$, $X^3$, and X are as previously defined.

In an additional embodiment, the present invention relates to compounds of Formula (I), and pharmaceutically acceptable salts thereof, wherein $R^5$ at each occurrence is independently selected from the group consisting of hydrogen, halogen, $O(C_1-C_4$ alkyl), and optionally substituted $C_1-C_4$ alkyl.

In still another embodiment, the present invention relates to compounds of Formula (I), or a pharmaceutically acceptable salt thereof; wherein each $R^6C(O)$— is independently selected from the following:

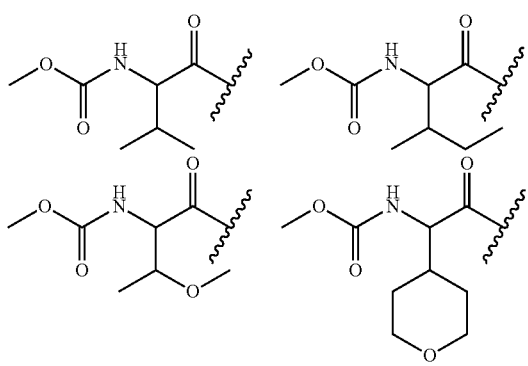

In one embodiment, both $R^6$ are the same.

In still another embodiment, the compound of Formula (I) is represented by one of Formulae (VIIa) to (VIId):

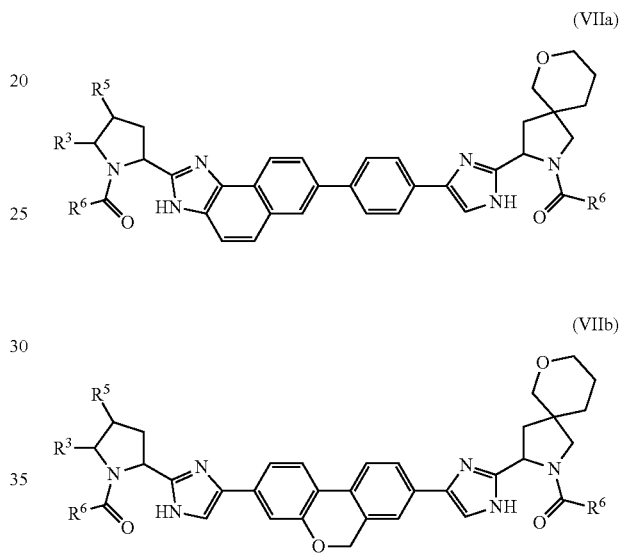

or a pharmaceutically acceptable salt thereof, wherein $R^3$ and $R^5$ are taken together with the carbon atoms to which they are attached to form a fused and optionally substituted $C_3$-$C_8$ cycloalkyl, or fused and optionally substituted heterocyclic; wherein $R^6$ is as previously defined.

In still another embodiment, the compound of Formula (I) is represented by one of Formulae (VIIIa) to (VIIId):

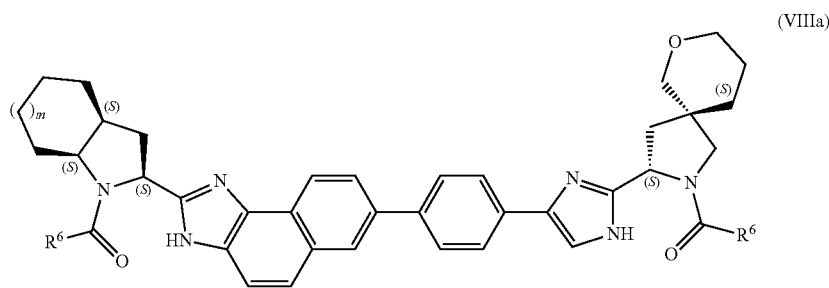
(VIIIa)
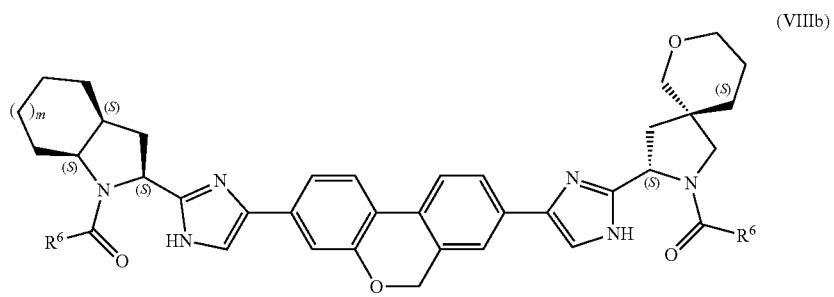
(VIIIb)
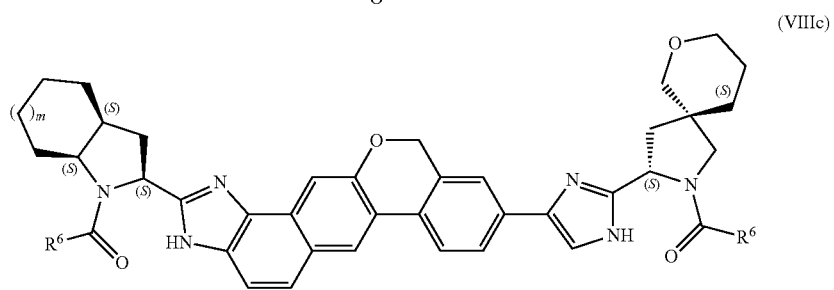
(VIIIc)
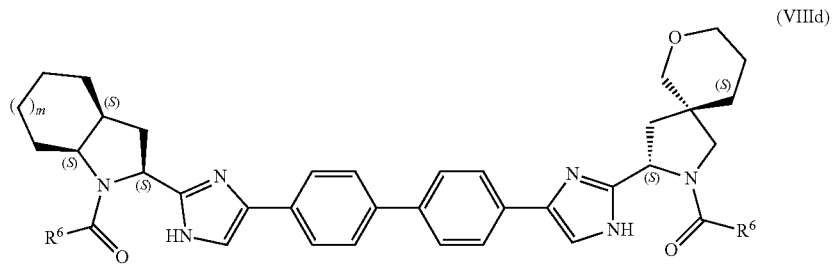
(VIIId)
or a pharmaceutically acceptable salt thereof, wherein m=0 or 1; each R⁶CO— is independently selected from the group below.
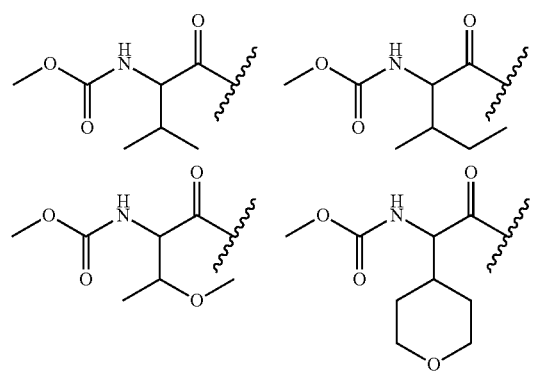
-continued
In one embodiment, both $R^6$ are the same.
In still another embodiment, the present invention provides a method of preparing:

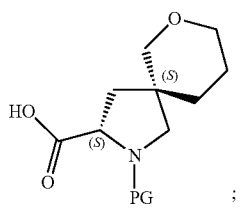

wherein PG is Boc or Cbz.

In still another embodiment, the compound of Formula (I) is represented by Formula (VIIIa), or pharmaceutically acceptable salts thereof, wherein m is 0 and each $R^6CO—$ is independently selected from the group below.

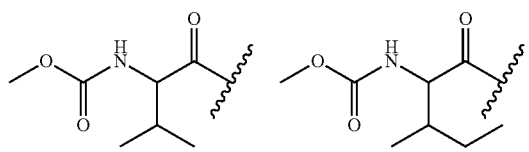

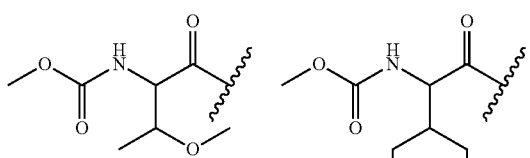

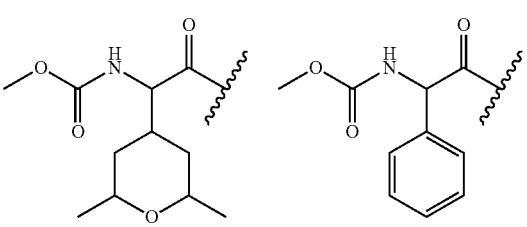

In one embodiment, both $R^6$ are the same.

In still another embodiment, the compound of Formula (I) is represented by Formula (VIIIa), or pharmaceutically acceptable salts thereof, wherein m is 1 and each $R^6CO—$ is selected from the group below.

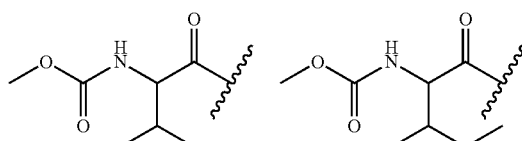

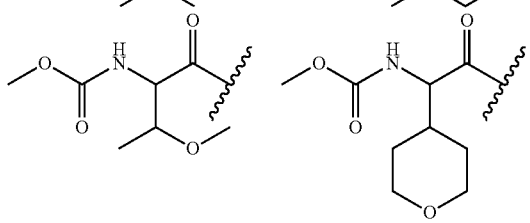

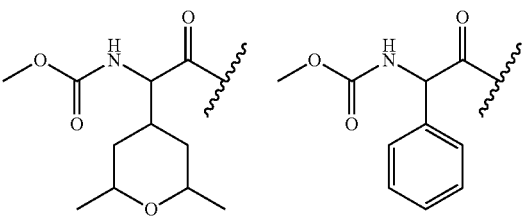

In one embodiment, both $R^6$ are the same.

In still another embodiment, the present invention relates to compounds of Formula (I), or a pharmaceutically acceptable salt thereof; wherein

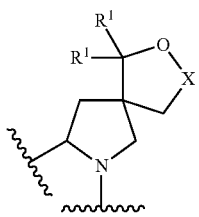

is independently illustrated by the following groups:

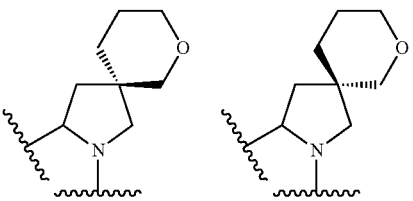

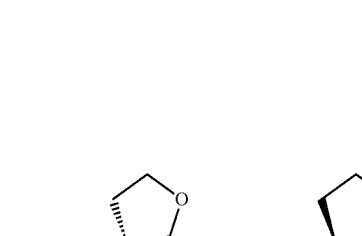

In still another embodiment, the present invention relates to compounds of Formula (I), or a pharmaceutically acceptable salt thereof; wherein

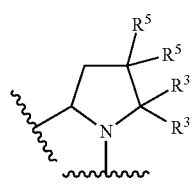

is one of the following groups:
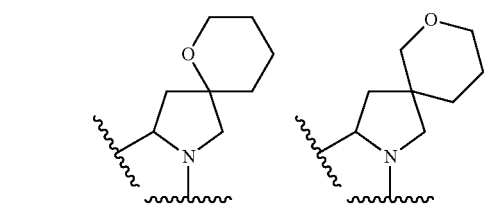
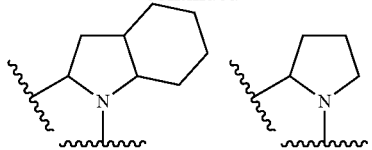
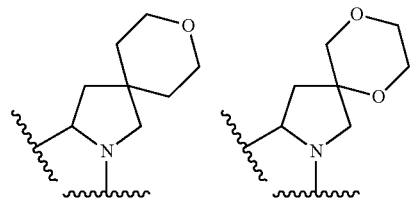
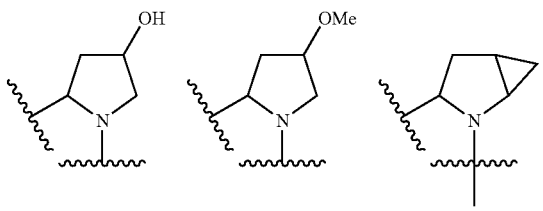
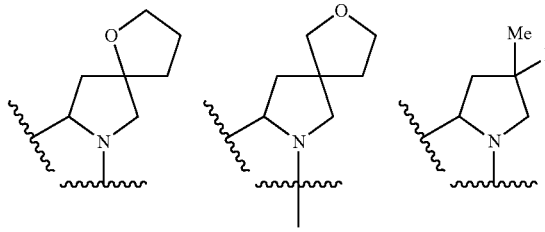
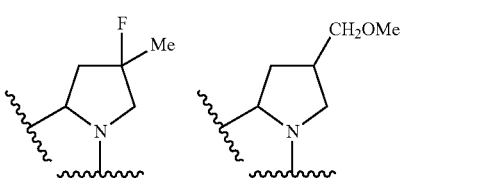
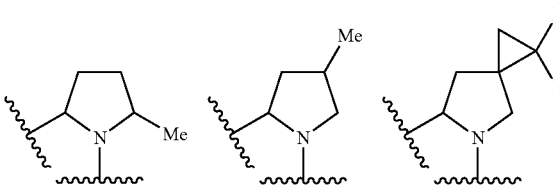
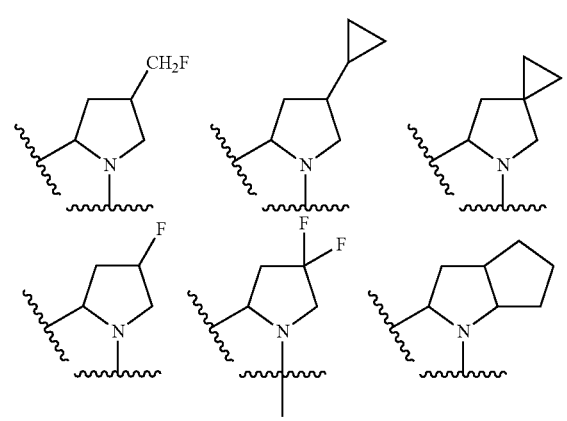
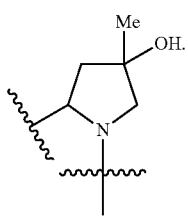
Representative compounds of the present invention include those set forth in the table below and pharmaceutically acceptable salts thereof:
| Compound | Structure |
| --- | --- |
| 5 | 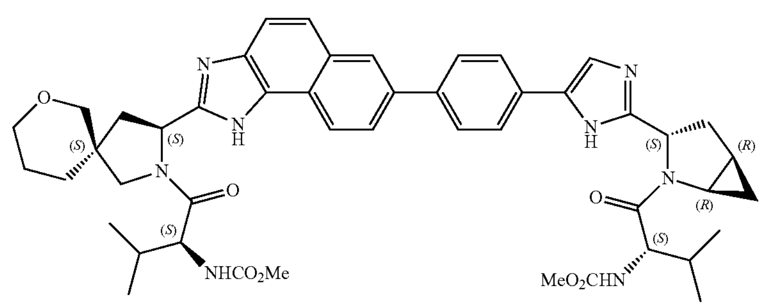 |

-continued

| Compound | Structure |
|---|---|
| 6 | 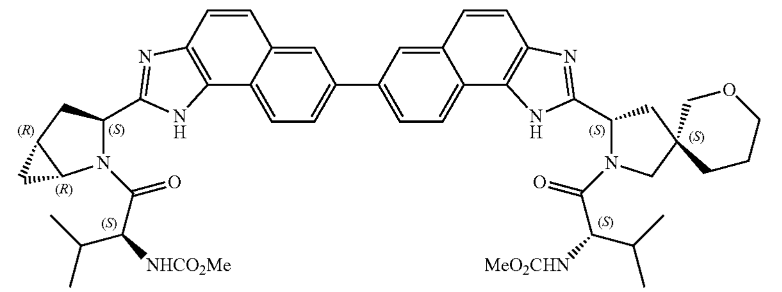 |
| 7 | 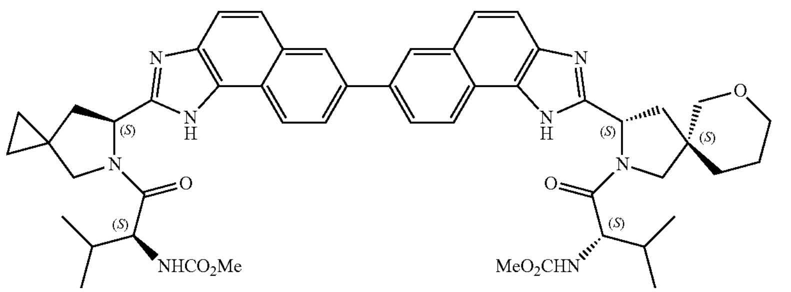 |
| 8 | 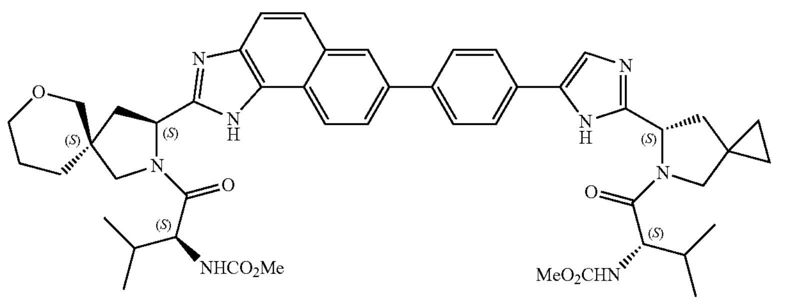 |
| 9 | 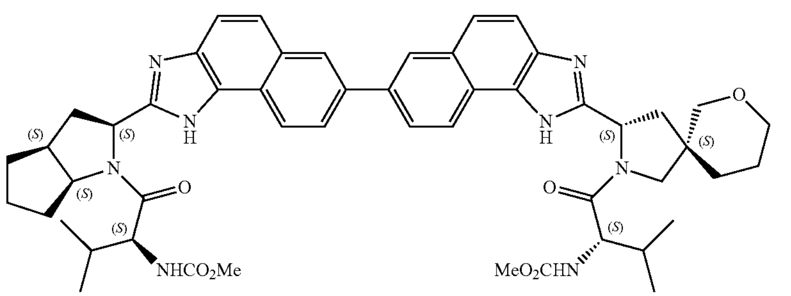 |
| 10 | 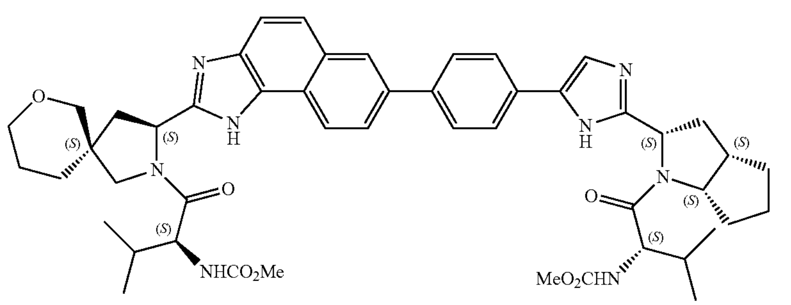 |

| Compound | Structure |
|---|---|
| 11 | 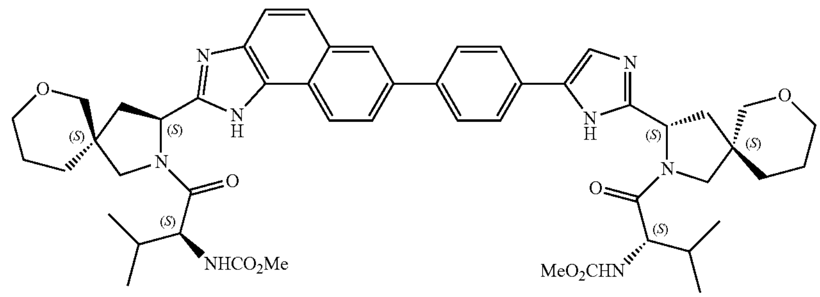 |
| 13 | 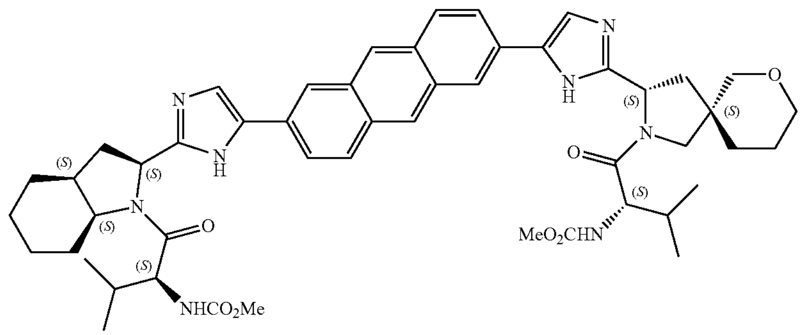 |
| 14 | 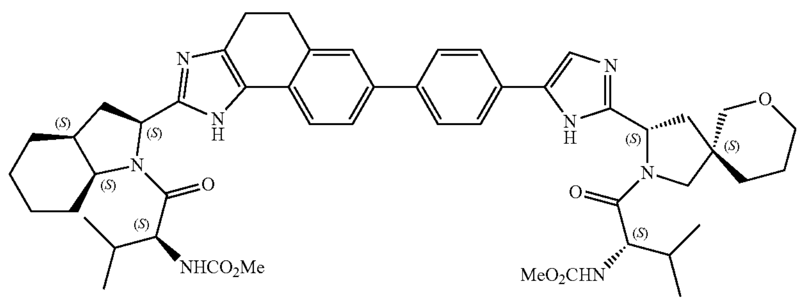 |
| 15 | 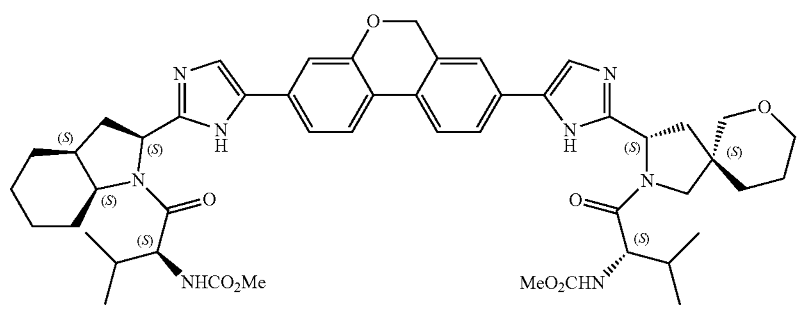 |
| 16 | 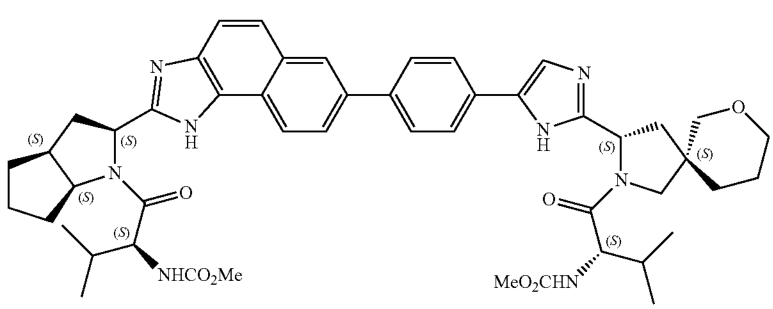 |

-continued

| Compound | Structure |
|---|---|
| 17 | 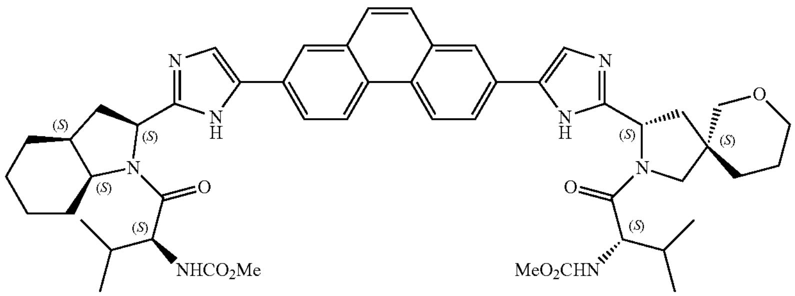 |
| 18 | 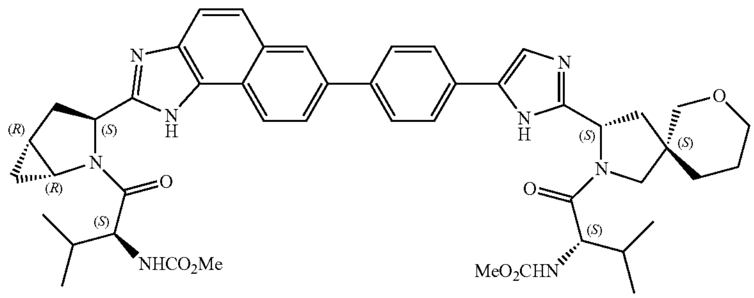 |
| 19 | 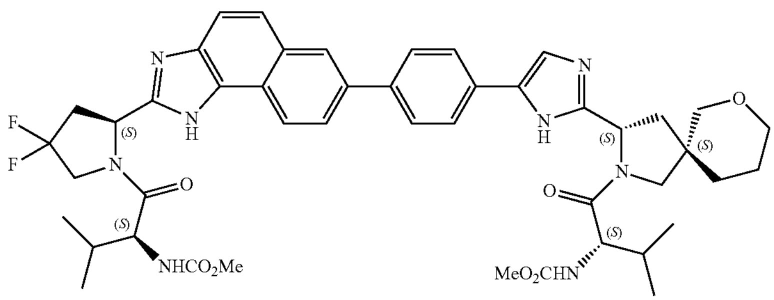 |
| 20 | 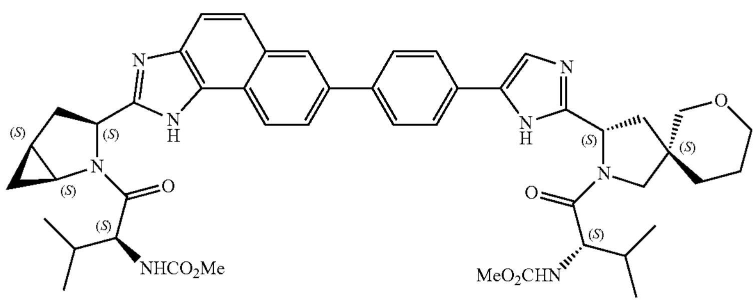 |
| 21 | 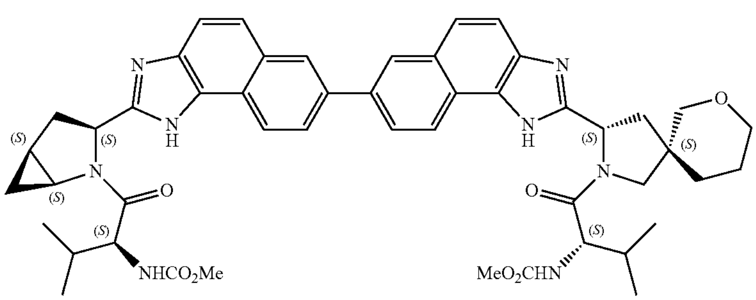 |

-continued

| Compound | Structure |
|---|---|
| 22 | 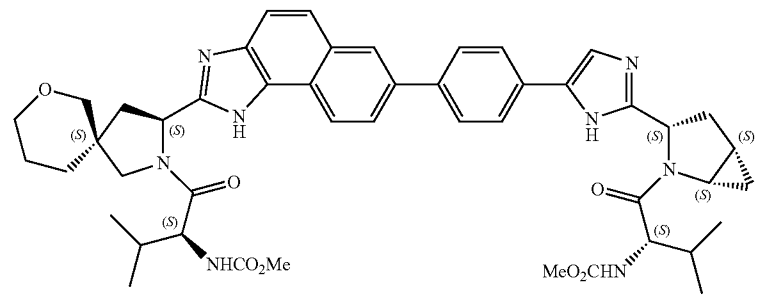 |
| 23 | 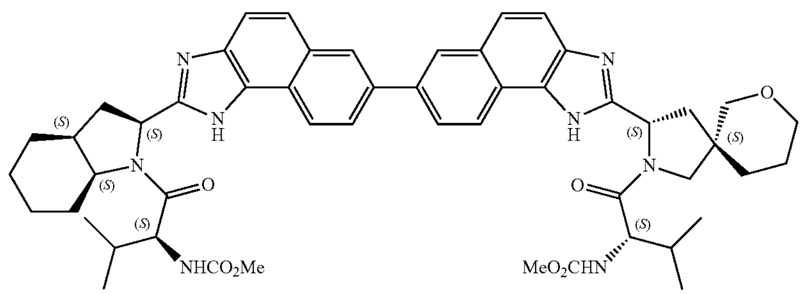 |
| 24 | 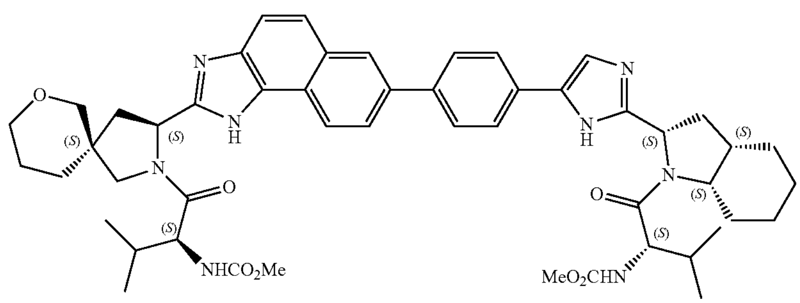 |
| 25 | 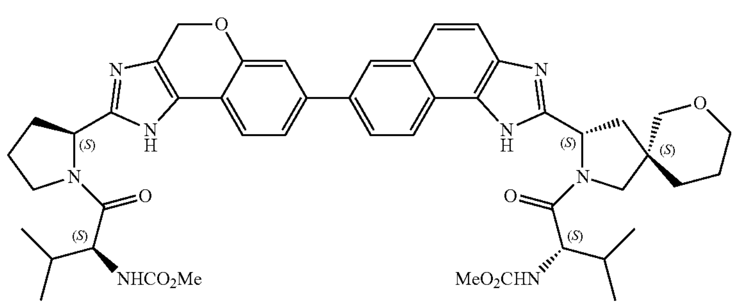 |
| 26 | 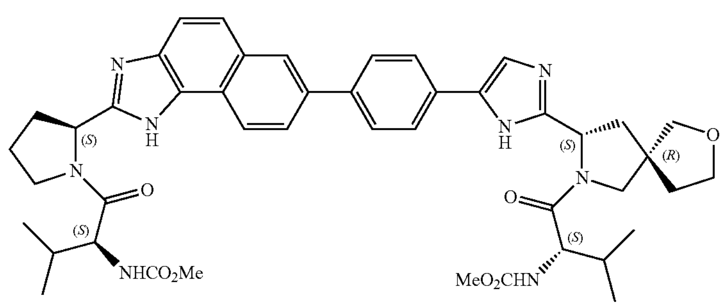 |

-continued

| Compound | Structure |
|---|---|
| 27 | 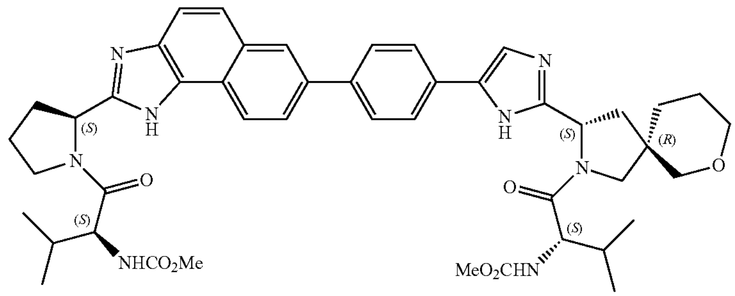 |
| 28 | 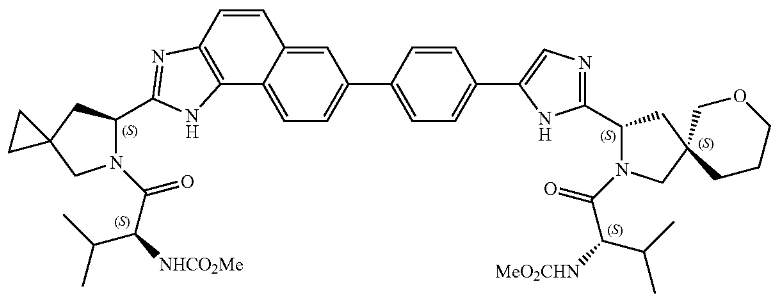 |
| 29 | 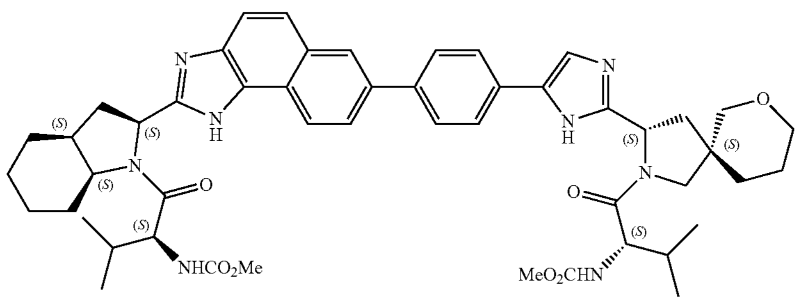 |
| 30 | 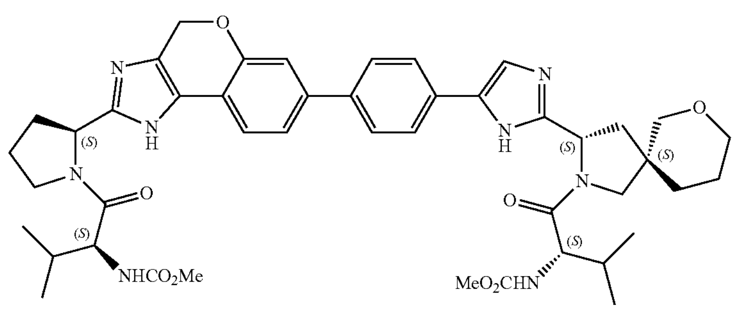 |
| 31 | 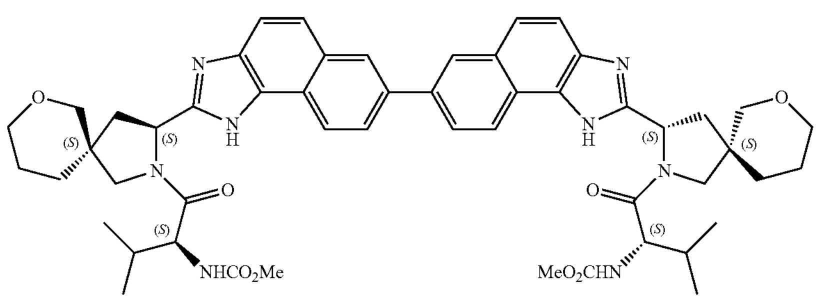 |

| Compound | Structure |
|---|---|
| 32 | 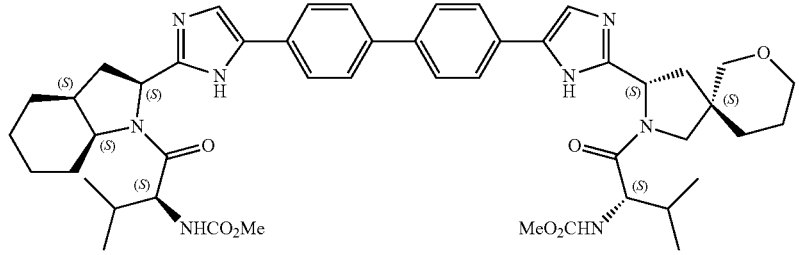 |
| 33 | 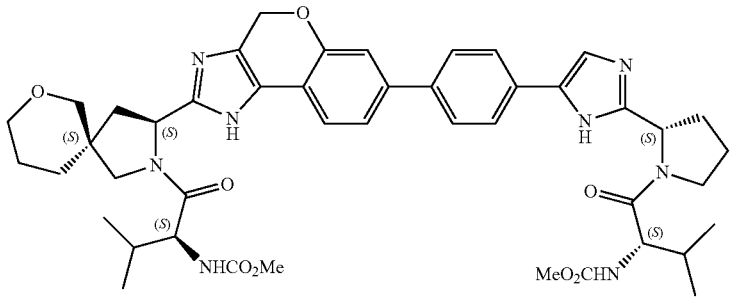 |
| 34 | 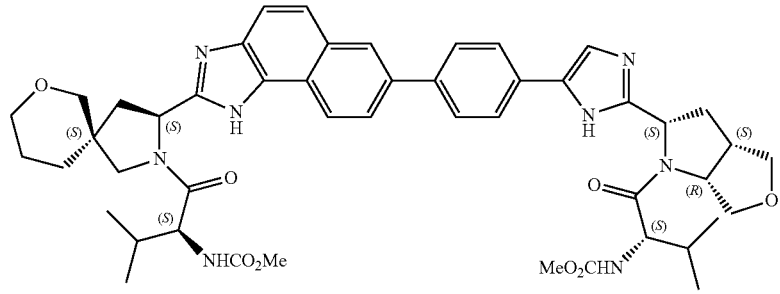 |
| 35 | 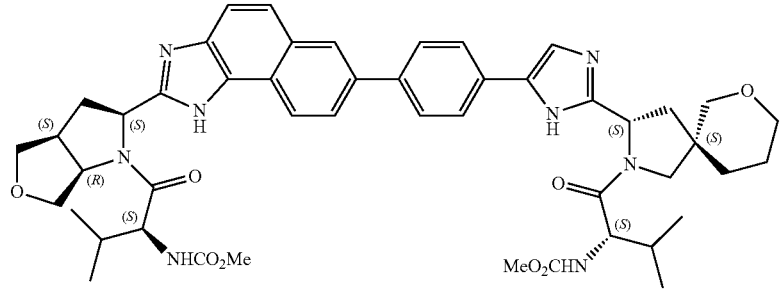 |
| 36 | 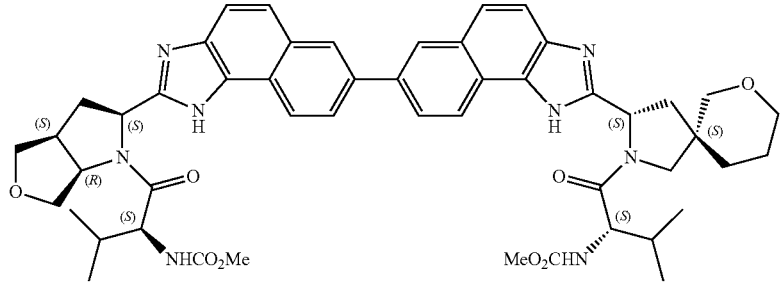 |

-continued

| Compound | Structure |
|---|---|
| 37 | 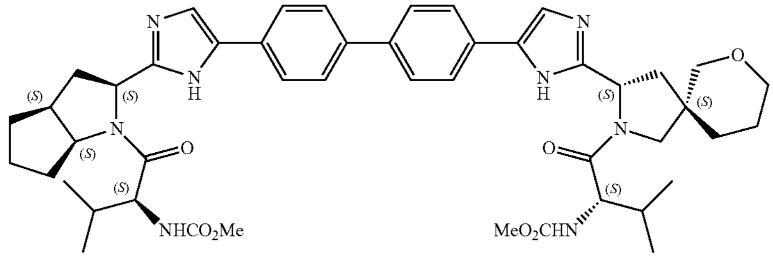 |
| 38 | 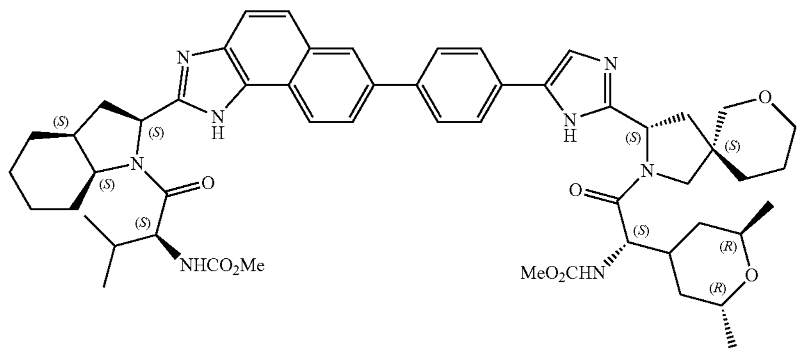 |
| 39 | 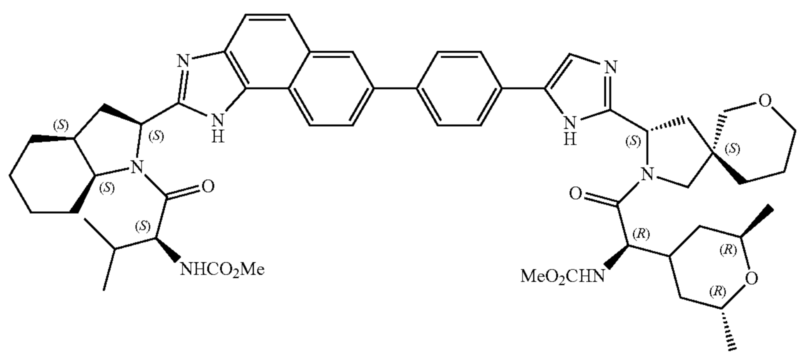 |
| 40 | 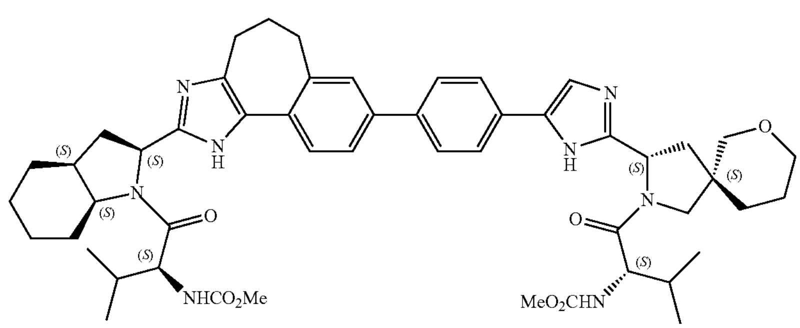 |
| 41 | 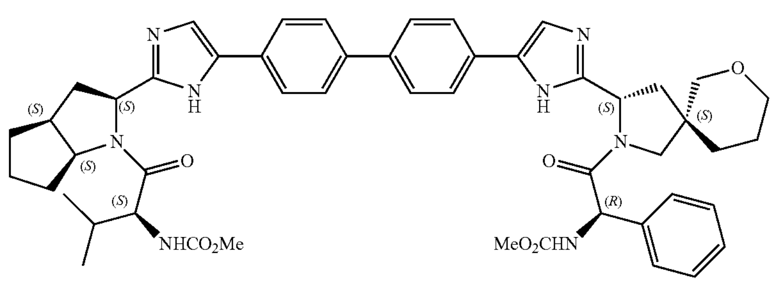 |

| Compound | Structure |
|---|---|
| 42 | 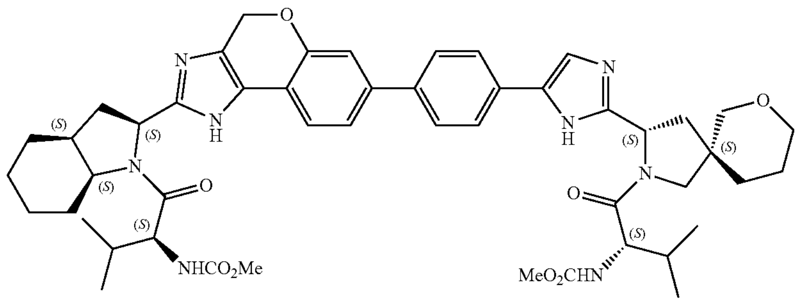 |
| 43 | 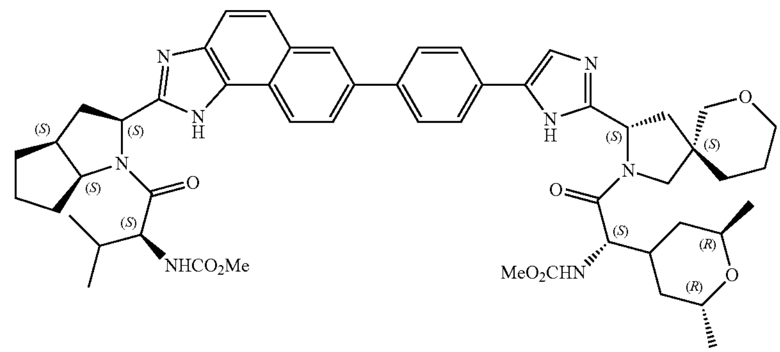 |
| 44 | 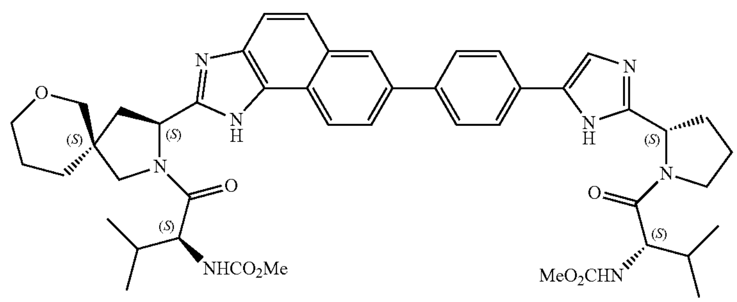 |
| 45 | 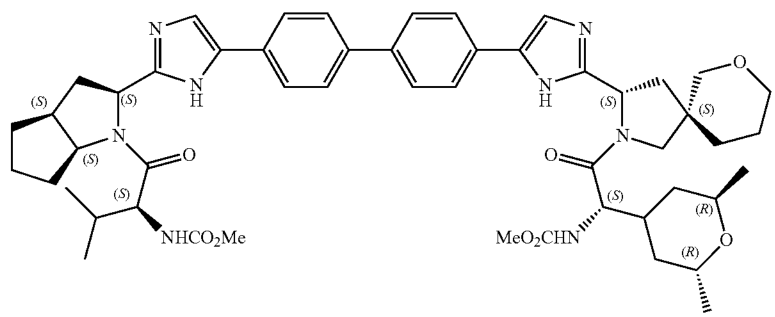 |
| 46 | 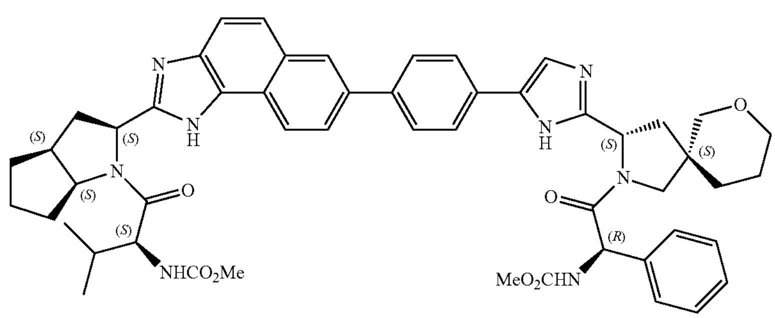 |

-continued

| Compound | Structure |
|---|---|
| 47 | 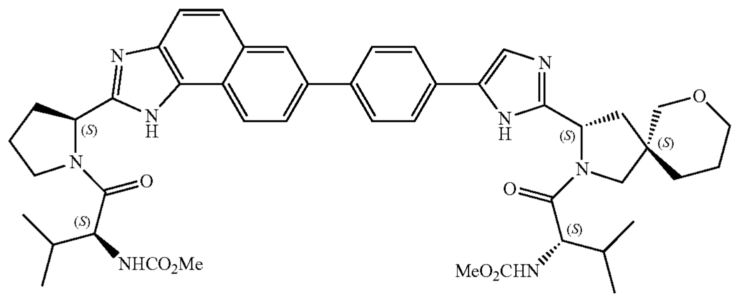 |
| 48 | 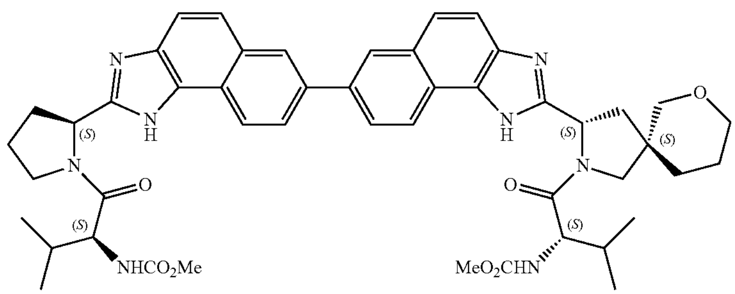 |
| 49 | 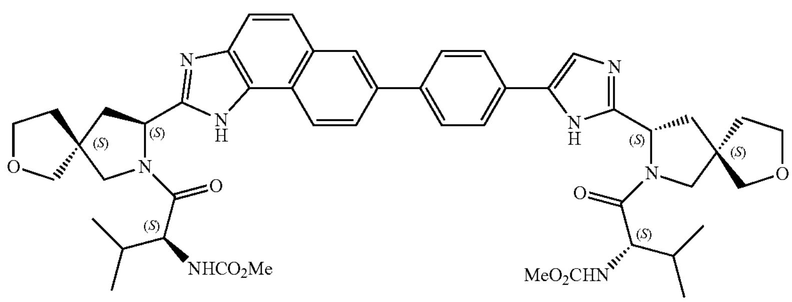 |
| 50 | 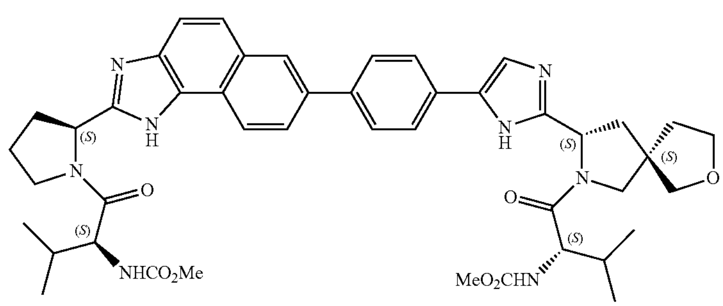 |
| 51 | 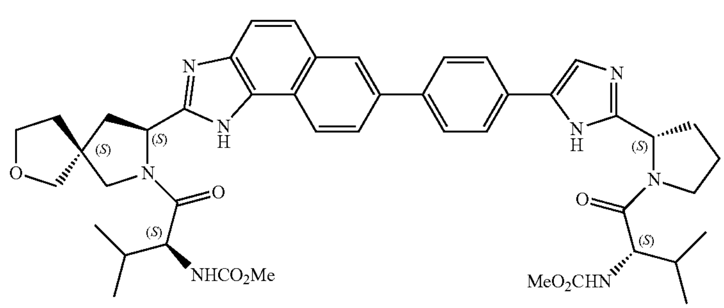 |

It will be appreciated that the description of the present invention herein should be construed in congruity with the laws and principles of chemical bonding. In some instances it may be necessary to remove a hydrogen atom in order to accommodate a substituent at any given location.

It is intended that the definition of any substituent or variable (e.g., $R^1$, $R^3$, X, Y, etc.) at a particular location in a molecule be independent of its definitions elsewhere in that molecule. For example, when X is $C(R^{11})_2$, each of the two $R^{11}$ groups may be the same or different.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It should be understood that the compounds encompassed by the present invention are those that are suitably stable for use as pharmaceutical agent.

It will be further appreciated that reference herein to therapy and/or treatment includes, but is not limited to, prevention, retardation, prophylaxis, therapy and/or cure of the disease. It will further be appreciated that references herein to treatment or prophylaxis of HCV infection includes treatment or prophylaxis of HCV-associated disease such as liver fibrosis, cirrhosis and hepatocellular carcinoma.

A further embodiment of the present invention includes pharmaceutical compositions comprising any single compound or a combination of two or more compounds delineated herein, or a pharmaceutically acceptable salt thereof, with a pharmaceutically acceptable carrier or excipient.

Yet a further embodiment of the present invention is a pharmaceutical composition comprising any single compound or a combination of two or more compounds delineated herein, or a pharmaceutically acceptable salt thereof, in combination with one or more agents known in the art, with a pharmaceutically acceptable carrier or excipient.

It will be further appreciated that compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the present invention include therapies for disease caused by HCV infection that suppresses HCV viral replication by direct or indirect mechanisms. These agents include, but are not limited to, host immune modulators (for example, interferon-alpha, pegylated interferon-alpha, consensus interferon, interferon-beta, interferon-gamma, CpG oligonucleotides and the like); antiviral compounds that inhibit host cellular functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; anti-sense RNA; vaccines comprising HCV antigens or antigen adjuvant combinations directed against HCV; agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7, or host cellular signal pathway, for example, PI3K inhibitors, and the like; and any agent or combination of agents that inhibit the replication of HCV by targeting other proteins of the viral genome involved in the viral replication and/or interfere with the function of other viral targets, such as inhibitors of NS3/NS4A protease, NS3 helicase, NS5B polymerase, NS4A protein and NS5A protein.

According to yet another embodiment, the pharmaceutical compositions of the present invention may further comprise other inhibitor(s) of targets in the HCV life cycle, including, but not limited to, helicase, polymerase, metalloprotease, NS4A protein, NS5A protein, and internal ribosome entry site (IRES).

Accordingly, one embodiment of the present invention is directed to a method for treating or preventing an infection caused by an RNA-containing virus comprising co-administering to a patient in need of such treatment one or more agents selected from the group consisting of a host immune modulator and a second or more antiviral agents, or a combination thereof, with a therapeutically effective amount of a compound or combination of compounds of the present invention, or a pharmaceutically acceptable salt thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome. A non-limiting example of the RNA-containing virus is hepatitis C virus (HCV). In certain embodiments, the hepatitis C virus is an HCV genotype 1a resistant variant, such as M28T, Q30R, L31V, Y93C, or Y93H.

A further embodiment of the present invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the present invention, or a pharmaceutically acceptable salt thereof. A non-limiting example of the RNA-containing virus is hepatitis C virus (HCV).

Yet another embodiment of the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the present invention, or a pharmaceutically acceptable salt thereof. An agent that treats patients for disease caused by hepatitis B (HBV) infection may be for example, but not limited thereto, L-deoxythymidine, adefovir, lamivudine or tenfovir, or any combination thereof. A non-limiting example of the RNA-containing virus is hepatitis C virus (HCV).

A further embodiment of the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the present invention, or a pharmaceutically acceptable salt thereof. The agent that treats patients for disease caused by human immunodeficiency virus (HIV) infection may include, but is not limited thereto, ritonavir, lopinavir, indinavir, nelfmavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. A non-limiting example of the RNA-containing virus is hepatitis C virus (HCV).

It can occur that a patient may be co-infected with hepatitis C virus and one or more other viruses, including but not limited to human immunodeficiency virus (HIV), hepatitis A virus (HAV) and hepatitis B virus (HBV). Thus also contemplated herein is combination therapy to treat such co-infections by co-administering a compound according to the present invention with at least one of an HIV inhibitor, an HAV inhibitor and an HBV inhibitor.

In addition, the present invention provides the use of a compound or a combination of compounds of the invention, or a therapeutically acceptable salt thereof, and one or more agents selected from the group consisting of a host immune modulator and one or more additional antiviral agents, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant. Preferably said additional antiviral agent inhibits replication of HCV either by inhibiting host cellular functions associated with viral replication or by targeting proteins of the viral genome.

When used in the above or other treatments, combination of compound or compounds of the present invention, together with one or more agents as defined herein above, can be employed in pure form or, where such forms exist, or as a pharmaceutically acceptable salt thereof. Alternatively, such combination of therapeutic agents can be administered as a pharmaceutical composition containing a therapeutically effective amount of the compound or combination of compounds of interest, or their pharmaceutically acceptable salt thereof, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, a still further embodiment of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt thereof, and one or more agents as defined herein above, with a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including, but not limited to, agents that interfere with either host or viral mechanisms necessary for the formation and/or replication of a virus in a mammal.

Such agents can be selected from another anti-HCV agent; an HIV inhibitor; an HAV inhibitor; and an HBV inhibitor.

Other agents that can be administered in combination with a compound of the present invention include a cytochrome P450 monooxygenase inhibitor (also referred to herein as a CYP inhibitor), which is expected to inhibit metabolism of the compounds of the invention. Therefore, the cytochrome P450 monooxygenase inhibitor would be in an amount effective to inhibit metabolism of the compounds of this invention. Accordingly, the CYP inhibitor is administered in an amount sufficient to improve one or more pharmacokinetic (PK) features including, but not limited to, plasma concentration, bioavailability, area under the plasma concentration time curve (AUC), elimination half-life, and systemic clearance, of a compound of the invention when one or more of its PK features of said compound is improved in comparison to that in the absence of the CYP inhibitor.

In one embodiment, the invention provides methods for improving the pharmacokinetics of compounds of the invention. The advantages of improving the pharmacokinetics of drugs are recognized in the art (see, for example, US Pat. Publication No's. US 2004/0091527; US 2004/0152625; and US 2004/0091527). Accordingly, one embodiment of this invention provides a method comprising administering an inhibitor of CYP3A4 and a compound of the invention. Another embodiment of this invention provides a method comprising administering a compound of the invention and an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1"). In a preferred embodiment, the CYP inhibitor preferably inhibits CYP3A4. Any CYP inhibitor that improves the pharmacokinetics of the relevant compound of the invention may be used in a method of this invention. These CYP inhibitors include, but are not limited to, ritonavir (see, for example, WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, ditiazem, erythromycin, VX-944, and VX-497. Preferred CYP inhibitors include ritonavir, ketoconazole, troleandomycin, 4-methyl pyrazole, cyclosporin, and clomethiazole.

It will be understood that the administration of the combination of the invention by means of a single patient pack, or patient packs of each formulation, containing within a package insert instructing the patient to the correct use of the invention is a desirable additional feature of this invention.

According to a further aspect of the invention is a pack comprising at least a compound of the invention and a CYP inhibitor and an information insert containing directions on the use of the combination of the invention. In an alternative embodiment of this invention, the pack further comprises one or more of additional agent as described herein. The additional agent or agents may be provided in the same pack or in separate packs.

Another aspect of this involves a packaged kit for a patient to use in the treatment of HCV infection or in the prevention of HCV infection, comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a compound of the invention and a CYP inhibitor (and optionally an additional agent) or derivatives thereof are prepared in a conventional manner. Typically, such a kit will comprise, e.g., a composition of a compound of the invention and optionally the additional agent (s) in a pharmaceutically acceptable carrier (and in one or in a plurality of pharmaceutical formulations) and written instructions for the simultaneous or sequential administration.

In another embodiment, a packaged kit is provided that contains one or more dosage forms for self-administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and idenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The terms "$C_1$-$C_4$ alkyl," "$C_1$-$C_6$ alkyl," "$C_1$-$C_8$ alkyl," "$C_2$-$C_4$ alkyl," or "$C_3$-$C_6$ alkyl," as used herein, refer to saturated, straight- or branched-chain hydrocarbon radicals containing between one and four, one and six, one and eight carbon atoms, or the like, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The terms "$C_2$-$C_8$ alkenyl," "$C_2$-$C_4$ alkenyl," "$C_3$-$C_4$ alkenyl," or "$C_3$-$C_6$ alkenyl," as used herein, refer to straight- or branched-chain hydrocarbon radicals containing from two to eight, or two to four carbon atoms, or the like, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_8$ alkynyl," "$C_2$-$C_4$ alkynyl," "$C_3$-$C_4$ alkynyl," or "$C_3$-$C_6$ alkynyl," as used herein, refer to straight- or branched-chain hydrocarbon radicals containing from two to eight, or two to four carbon atoms, or the like, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$ cycloalkyl", or "$C_4$-$C_7$ cycloalkyl," as used herein, refers to a monocyclic or polycyclic saturated carbocyclic ring compound, and the carbon atoms may be optionally oxo-substituted. Examples of $C_3$-$C_8$ cycloalkyl include, but not limited to, cyclopropyl, cyclobutyl, cyclopentyl, cyclohexyl, cyclopentyl and cyclooctyl; and examples of $C_4$-$C_7$ cycloalkyl include, but not limited to, cyclopentyl, cyclohexyl, bicyclo[2.2.1]heptyl, and the like.

The term "$C_3$-$C_8$ cycloalkenyl" or "$C_5$-$C_7$ cycloalkenyl," as used herein, refers to monocyclic or polycyclic carbocyclic ring compound having at least one carbon-carbon double bond and the carbon atoms may be optionally oxo-substituted. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_5$-$C_7$ cycloalkenyl include, but not limited to, cyclopentenyl, cyclohexenyl, cycloheptenyl, and the like.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as, O, OH, NH, $NH_2$, C(O), $S(O)_2$, C(O)O, C(O)NH, OC(O)O, OC(O)NH, $OC(O)NH_2$, $S(O)_2$NH, $S(O)_2NH_2$, NHC(O)$NH_2$, NHC(O)C(O)NH, $NHS(O)_2$NH, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s).

The term "substituted" refers to substitution by independent replacement of one, two, or three or more of the hydrogen atoms with substituents including, but not limited to, —F, —Cl, —Br, —I, —OH, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O— heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH— heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH— heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The present invention also relates to solvates of the compounds of Formula (I), for example hydrates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional nontoxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantadine). The compositions according to the invention may also be used in combination with gene replacement therapy.

Combination and Alternation Therapy for HCV

It has been recognized that drug-resistant variants of HCV can emerge after prolonged treatment with an antiviral agent. Drug resistance most typically occurs by mutation of a gene that encodes for a protein such as an enzyme used in viral replication, and most typically in the case of HCV, RNA polymerase, protease, or helicase.

Recently, it has been demonstrated that the efficacy of a drug against a viral infection, such as HIV, can be prolonged, augmented, or restored by administering the drug in combination or alternation with a second, and perhaps third, antiviral compound that induces a different mutation from that caused by the principal drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

A compound of the present invention can also be administered in combination or alternation with antiviral agent. Exemplary antiviral agents include ribavirin, interferon, interleukin or a stabilized prodrug of any of them. More broadly described, the compound can be administered in combination or alternation with any of the anti-HCV drugs listed in a table below.

| Table of anti-Hepatitis C Compounds in Current Clinical Development | | |
|---|---|---|
| Drug name | Drug category | Pharmaceutical Company |
| PEGASYS pegylated interferon alfa-2a | Long acting interferon | Roche |
| INFERGEN interferon alfacon-1 | Long acting interferon | InterMune |
| OMNIFERON natural interferon | Long acting interferon | Viragen |

Table of anti-Hepatitis C Compounds in Current Clinical Development

| Drug name | Drug category | Pharmaceutical Company |
|---|---|---|
| ALBUFERON | Long acting interferon | Human Genome Sciences |
| REBIF interferon beta-1a | Interferon | Ares-Serono |
| Interferon lambda | Interferon | BMS |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | InterMune |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monoclonal Antibody | XTL |
| HCV/MF59 | Vaccine | Chiron |
| CIVACIR | Polyclonal Antibody | NABI |
| | Therapeutic vaccine | Innogenetics |
| VIRAMIDINE | Nucleoside Analogue | ICN |
| ZADAXIN (thymosin alfa-1) | Immunomodulator | Sci Clone |
| CEPLENE (histamine) | Immunomodulator | Maxim |
| VX 950/LY 570310 | Protease inhibitor | Vertex/Eli Lilly |
| ISIS 14803 | Antisense | Isis Pharmaceutical/Elan |
| IDN-6556 | Caspase inhibitor | Idun Pharmaceuticals |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wyeth |
| CH-6 | Protease inhibitor | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD2O Monoclonal Antibody | Genetech/IDEC |
| NM283 (Valopicitabine) | Polymerase Inhibitor | Idenix Pharmaceuticals |
| HepX™-C | Monoclonal Antibody | XTL |
| IC41 | Therapeutic Vaccine | Intercell |
| Medusa Interferon | Longer acting interferon | Flamel Technology |
| E-1 | Therapeutic Vaccine | Innogenetics |
| Multiferon | Long Acting Interferon | Viragen |
| BILN 2061 | Protease inhibitor | Boehringer-Ingelheim |
| TMC435350 | Protease inhibitor | Tibotec/Medivir |
| Telaprevir (VX-950) | Protease inhibitor | Vertex |
| Boceprevir (SCH 503034) | Protease inhibitor | Schering-Plough |
| ACH-1625 | Protease inhibitor | Achillion |
| ACH-2684 | Protease inhibitor | Achillion |
| ABT-450 | Protease inhibitor | Abbott/Enanta |
| BI-201335 | Protease inhibitor | Boehringer-Ingelheim |
| PHX-1766 | Protease inhibitor | Phenomix |
| VX-500 | Protease inhibitor | Vertex |
| MK-7009 | protease inhibitor | Merck |
| MK-5172 | protease inhibitor | Merck |
| R7227 (ITMN-191) | protease inhibitor | InterMune |
| Narlaprevir (SCH 900518) | Protease inhibitor | Schering/Merck |
| BI201335 | Protease inhibitor | Boehringer-Ingelheim |
| BMS-650032 | Protease inhibitor | BMS |
| GS-9256 | Protease inhibitor | Gilead |
| GS-9451 | Protease inhibitor | Gilead |
| Alinia (nitazoxanide) | To be determined | Romark |
| ABT-072 | Polymerase Inhibitor | Abbott |
| ABT-333 | Polymerase Inhibitor | Abbott |
| Filibuvir (PF-00868554) | Polymerase Inhibitor | Pfizer |
| VCH-916 | Polymerase Inhibitor | Vertex |
| R7128 (PSI6130) | Polymerase Inhibitor | Roche/Pharmasset |
| IDX184 | Polymerase Inhibitor | Idenix |
| INX-189 | Polymerase Inhibitor | Inhibitex |
| GS-7977 | Polymerase Inhibitor | Gilead |
| PSI-938 | Polymerase Inhibitor | Pharmasset |
| R1626 | Polymerase inhibitor | Roche |
| MK-3281 | Polymerase inhibitor | Merck |
| PSI-7851 | Polymerase inhibitor | Pharmasset |
| ANA598 | Polymerase inhibitor | Anadys Pharmaceuticals |
| BI-207127 | Polymerase inhibitor | Boehringer-Ingelheim |
| GS-9190 | Polymerase inhibitor | Gilead |
| GS-9669 | Polymerase inhibitor | Gilead |
| VCH-759 | Polymerase Inhibitor | Vertex |
| VX-135 | Polymerase Inhibitor | Vertex |
| VX-222 | Polymerase Inhibitor | Vertex |
| TMC647055 | Polymerase Inhibitor | Janssen |
| MBX-700 | Polymerase Inhibitor | Microbiotix/Merck |
| Clemizole | NS4B inhibitor | Eiger Biopharmaceuticals |
| A-832 | NS5A inhibitor | ArrowTherapeutics |
| BMS-790052 | NS5A inhibitor | Bristol-Myers-Squibb |
| BMS-824393 | NS5A inhibitor | Bristol-Myers-Squibb |
| GS-5885 | NS5A inhibitor | Gilead |
| GS-5816 | NS5A inhibitor | Gilead |
| PPI-688 | NS5A inhibitor | Presidio |
| ACH-3102 | NS5A inhibitor | Achillion |
| IDX-719 | NS5A inhibitor | Idenix |
| ITX5061 | Entry inhibitor | iTherx |
| GS-9450 | Caspase inhibitor | Gilead |
| ANA773 | TLR agonist | Anadys |
| CYT107 | immunomodulator | Cytheris |
| SPC3649 (LNA-antimiR™-122) | microRNA | Santaris Pharma |
| Debio 025 | Cyclophilin inhibitor | Novartis/Debiopharm |
| SCY-635 | Cyclophilin inhibitor | Scynexis |

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are: Ac for acetyl; AcOH for acetic acid; AIBN for azobisisobutyro-nitrile; BINAP for 2,2'-bis(diphenylphosphino)-1,1'-binaphthyl; Boc$_2$O for di-tert-butyl-dicarbonate; Boc for t-butoxycarbonyl; Bpoc for 1-methyl-1-(4-biphenylyl)ethyl carbonyl; BtOH for 1-hydroxy-benzotriazole; Bz for benzoyl; Bn for benzyl; BocNHOH for tert-butyl N-hydroxycarbamate; t-BuOK for potassium tert-butoxide; Bu$_3$SnH for tributyltin hydride; BOP for (benzotriazol-1-yloxy)tris(dimethylamino)phosphonium Hexafluoro-phosphate; Brine for sodium chloride solution in water; Cbz for carbobenzyloxy; CDI for carbonyl-diimidazole; CH$_2$Cl$_2$ for dichloromethane; CH$_3$ for methyl; CH$_3$CN for acetonitrile; Cs$_2$CO$_3$ for cesium carbonate; CuCl for copper (I) chloride; CuI for copper (I) iodide; dba for dibenzylidene acetone; dppb for diphenylphosphino butane; DBU for 1,8-diazabicyclo-[5.4.0]undec-7-ene; DCC for N,N'-dicyclohexylcarbodiimide; DEAD for diethylazodi-carboxylate; DIAD for diisopropyl azodicarboxylate; DIBAL-H for diiso-butylaluminium hydride; DIPEA or (i-Pr)$_2$EtN for N,N-diisopropylethyl amine; Dess- Martin periodinane for 1,1,1-tris(acetyloxy)-1,1-dihydro-1,2-benziodoxol-3-(1H)-one; DMAP for 4-dimethylaminopyridine; DME for 1,2-dimethoxy-ethane; DMF for N,N-dimethylformamide; DMSO for dimethyl sulfoxide; DMT for di(p-methoxyphenyl)-phenylmethyl or dimethoxytrityl; DPPA for diphenylphosphoryl azide; EDC for N-(3-dimethylaminopropyl)-N'-ethylcarbodiimide; EDC HCl for N-(3-dimethylamino-propyl)-N'-ethylcarbodiimide hydrochloride; EtOAc for ethyl acetate; EtOH for ethanol; Et$_2$O for diethyl ether; Fmoc for 9-fluorenylmethoxy-carbonyl; Grubbs-1 catalyst for benzylidene bis(tricyclohexyl-phosphine)dichloro-ruthenium; HATU for O-(7-azabenzotriazol-1-yl)-N,N,N',N'-tetramethyluronium hexafluorophosphate; HCl for hydrogen chloride; HOBT for 1-hydroxybenzotriazole; K$_2$CO$_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethylpiperidinate; MeOH for methanol; Mg for magnesium; MOM for methoxymethyl; Ms for mesyl or —SO$_2$—CH$_3$; Ms$_2$O for methanesulfonic anhydride or mesyl-anhydride; NaBH$_4$ for sodium borohydride; NaBH$_3$CN for sodium cyanoborohydride; NaN(TMS)$_2$ for sodium bis(trimethylsilyl)-amide; NaCl for sodium chloride; NaH for sodium hydride; NaHCO$_3$ for sodium bicarbonate or sodium hydrogen carbonate; Na$_2$CO$_3$ sodium carbonate; NaOH for sodium hydroxide; Na$_2$SO$_4$ for sodium sulfate; NaHSO$_3$ for sodium bisulfite or sodium hydrogen sulfite; Na$_2$S$_2$O$_3$ for sodium thiosulfate; NH$_2$NH$_2$ for hydrazine; NH$_4$HCO$_3$ for ammonium bicarbonate; NH$_4$Cl for ammonium chloride; NMMO for N-methylmorpholine N-oxide; NaIO$_4$ for sodium periodate; Ni for nickel; OH for hydroxyl; OsO$_4$ for osmium tetroxide; Pd for palladium; Ph for phenyl; PMB for p-methoxybenzyl; POPd for dihydrogen dichlorobis(di-tert-butylphosphinito-κP)-palladate(II); Pd$_2$(dba)$_3$ for tris(dibenzylidene-acetone) dipalladium (0); Pd(PPh$_3$)$_4$ for tetrakis(triphenylphosphine)palladium (0); PdCl$_2$(PPh$_3$)$_2$ for trans-dichlorobis(triphenyl-phosphine)palladium (II); Pt for platinum; Rh for rhodium; rt for room temperature; Ru for ruthenium; SEM for (trimethylsilyl)ethoxy-methyl; TBAF for tetrabutylammonium fluoride; TBS for tert-butyl dimethylsilyl; TEA or Et$_3$N for triethylamine; Teoc for 2-trimethylsilyl-ethoxy-carbonyl; TFA for trifluoroacetic acid; THF for tetrahydrofuran; TMEDA for N,N,N',N'-tetramethylethylenediamine; TPP or PPh$_3$ for triphenyl-phosphine; Troc for 2,2,2-trichloroethyl carbonyl; Ts for tosyl or —SO$_2$—C$_6$H$_4$CH$_3$; Ts$_2$O for tolylsulfonic anhydride or tosyl-anhydride; TsOH for p-tolyl-sulfonic acid; TMS for trimethylsilyl; TMSCl for trimethylsilyl chloride; or Zhan-1b catalyst for 1,3-bis(2,4,6-trimethylphenyl)-4,5-dihydroimidazol-2-ylidene[2-(iso-propoxy)-5-(N,N-dimethyl-aminosulfonyl)phenyl]-methylene ruthenium(II) dichloride.

Synthetic Methods

The compounds and processes of the present invention will be better understood in connection with the following synthetic schemes that illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

The compounds of the present invention may be prepared via several different synthetic routes from a variety of imidazole, tricyclic or pentacyclic heteroaryl by fusing an imidazole with a bicyclic or tetracyclic aryl or heteroaryl, and related intermediates. An exemplary method is shown in Schemes 1, 2, 3, and 4. A retro-synthesis of those title compounds include direct formation of a suitable heterocycle optionally with a suitable aryl or heteroaryl linkage, followed by attachment of a suitable capping group (such as —C(O)R$^6$), plus some functional group manipulations in between and/or after. Various imidazole or polycyclic heteroaryl with a fusing imidazole intermediates are known to those skilled in the art, for example see the encyclopedic volumes edited by A. R. Katrizky, et al, "Comprehensive Heterocyclic Chemistry" 1984; "Comprehensive Heterocyclic Chemistry II" 1996; "Comprehensive Heterocyclic Chemistry III" 2008.

A general synthesis and further elaboration of some tricyclic heteroaryl related intermediates by fusing a bicyclic ring with imidazole are summarized in Scheme 1. Similar procedure may be used to synthesis of pentacyclic heteroaryl related intermediates by fusing an imidazole with a tricyclic aryl or heteroaryl.

The synthesis starts from the construction of an optionally substituted naphthimidazole 1-2, which may be obtained by condensation of an amino acid or its derivatives 1-1.1 or 1-1.2 with 6-bromonaphthalene-1,2-diamine 1-1 under the conditions to those skilled in the art. The imidazole ring closure may be realized either in one pot by heat, optionally in the presence of an acid and/or with a dehydration reagent such as polyphosphoric acid; or in two steps: 1) amide formation between diamine 1-1 and amino acid 1-1.1 or 1-1.2 in the presence of a condensation reagent such as EDC.HCl, DCC or the like; or through mixed anhydride approach by reacting acid 1-1.1 or 1-1.2 with a chloroformate such as methyl chloroformate, isobutyl chloroformate, or the like, in the presence of a base such as TEA, DIPEA, DMAP, N-methylmorpholine, or the like, followed by treating the mixed anhydride with diamine 1-1; and 2) the heterocyclic ring closure in the presence of an acid such as acetic acid, sulfuric acid or the like or a dehydration reagent such as HATU or the like, optionally with heat.

Scheme 1

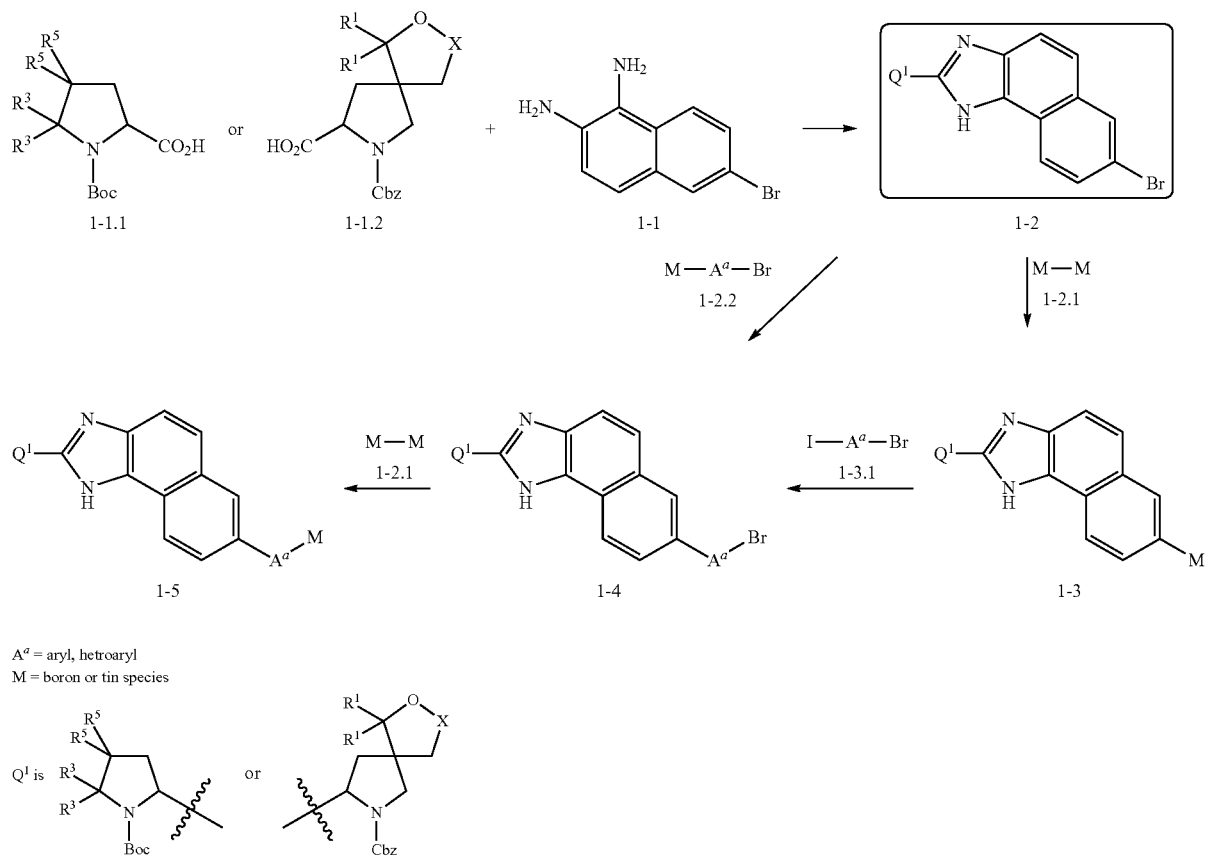

$A^a$ = aryl, hetroaryl
M = boron or tin species

The naphthimidazole bromide 1-2 may be subjected to Suzuki, Stille or related coupling conditions known to those skilled in the art (see reviews: A. Suzuki, *Pure Applied Chem.*, 1991, 63, 419; A. Suzuki, *Handbook of Organopalladium Chemistry for Organic Synthesis*, 2002, 1, 249; A. Anastasia, et al, *Handbook of Organopalladium Chemistry for Organic Synthesis*, 2002, 1, 311; F. Bellina, et al, *Synthesis*, 2004, 2419; M. G. Organ, et al, *Synthesis* 2008, 2776; A. T. Lindhardt, et al, *Chem.—A European I*, 2008, 14, 8756; E. A. B. Kantchev, et al, *Angew. Chem. Int. Ed.*, 2007, 46, 2768; V. Farina, et al, *Advances in Metal-Organic Chem.*, 1996, 5:1) with different coupling partners to provide a variety of key imtermediates. For example, bromide 1-2 may be converted to key intermediate 1-4 by selective reacting with metallic reagent 1-2.2 under the Suzuki or Stille conditions which are known to those skilled in the art. Alternatively, intermediate 1-4 may be prepared by treating bromide 1-2 with dimetallic agent 1-2.1 to afford organometallic 1-3, followed by coupling with bromoiodoaryl compound 1-3.1, both may be under Suzuki or Stille reaction conditions. The bromide 1-4 may be further converted to organometallic 1-5 with dimetallic agent 1-2.1 using the conditions described above to prepare 1-3.

It should be noted that optionally the NH group of the naphthimidazole related intermediates listed above may be protected with an amino protecting group, such as SEM (i.e. SEM-Cl, NaH), Boc, Cbz, Teoc, Troc, or the like.

Scheme 2

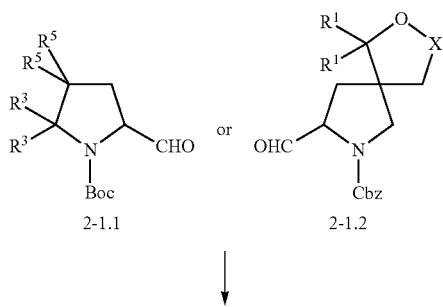

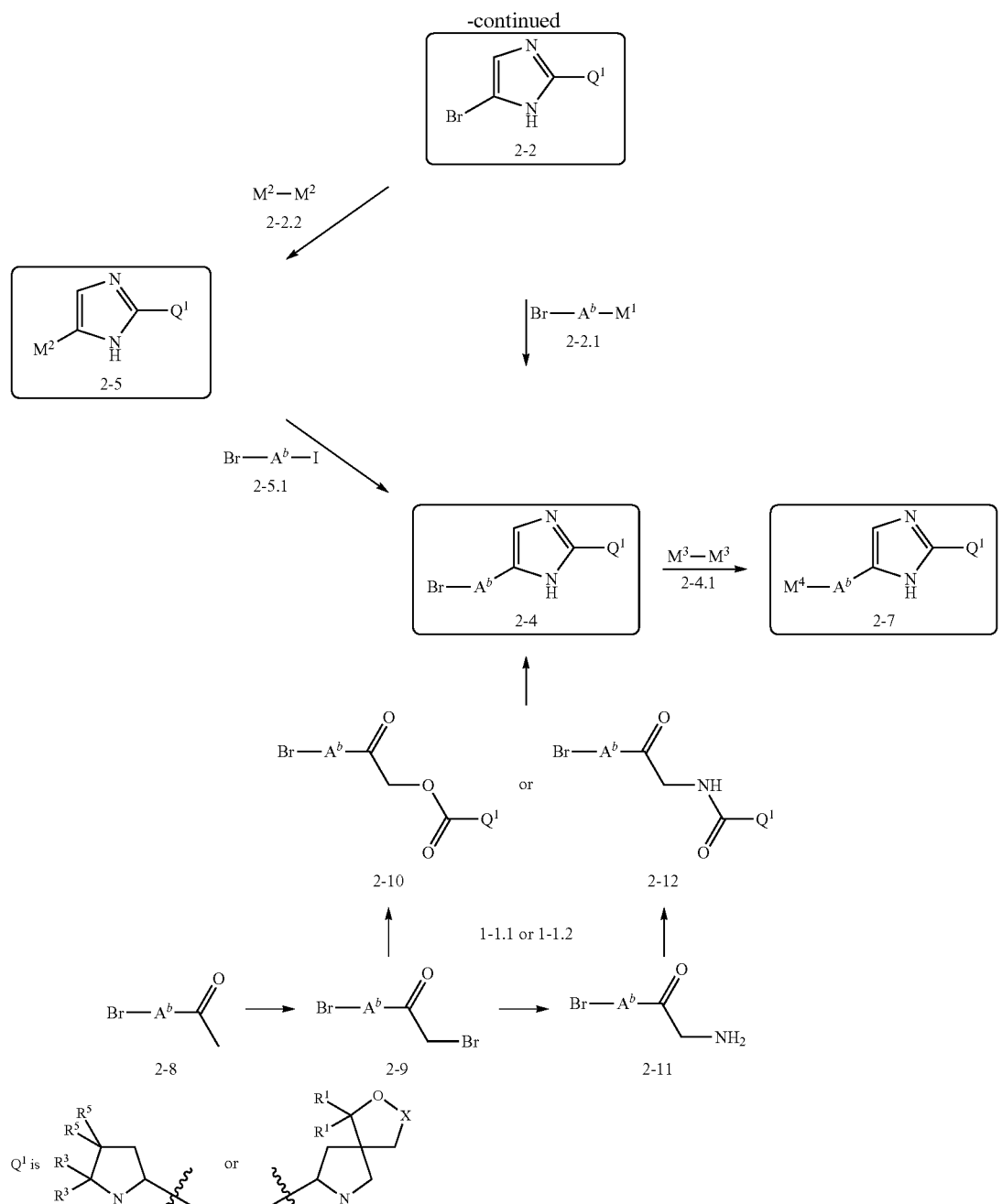

$A^b$ = aryl, heteroaryl
$M^1$, $M^2$, $M^4$ = tin or boron species

A typical synthesis of imidazole related intermediates are analogous to that of the naphthimidazole intermediates. As shown in Scheme 2, bromo-imidazole 2-2 can be synthesized by condensation of amino acid derived aldehyde 2-1.1 or 2-1.2 and glyoxal in the presence of methanolic ammonia; followed by bromination of the imidazole ring under the conditions which are known to those skilled in the art. The bromination of the imidazole ring may be realized either in one pot by NBS, bromine, 2,4,4,6-tetrabromo-2,5-cyclohexadienone, or the like; or in two steps: 1) dibromide formation in the presence of excess bromination reagent such as NBS, bromine, 2,4,4,6-tetrabromo-2,5-cyclohexadienone, or the like, optionally with heat; and 2) reduction of the dibromide to monobromide in the presence of a reducing reagent such as $NaHSO_3$, $Na_2S_2O_3$, $Na_2SO_3$, or the like. Bromide 2-2 then may be served as a common intermediate for many other imidazole derivatives using the chemistry discussed in Scheme 1. For example, bromide 2-2 may be converted to key intermediate 2-4 by selectively reacting with metallic reagent 2-2.1 under the Suzuki or Stille conditions to provide key intermediate 2-4. Alternatively, intermediate 2-4 may be prepared by treating bromide 2-2 with dimetallic agent 2-2.2 to afford organometallic 2-5, followed by coupling with bromoiodoaryl compound 2-5.1, both may be under the previously described Suzuki or Stille reaction conditions. The bromide 2-4 may be further converted to organometallic 2-7 with dimetallic agent 2-4.1 using the conditions described above for the preparation of intermediate 2-5.

Yet alternatively, aryl or heteroaryl bromide 2-4 may also be derived from bromoketone 2-9, which can be prepared from the corresponding ketone 2-8 in the presence of a bromination reagent such as NBS, bromine, or the like, optionally in the presence of an acid and/or with heating. Bromoketone 2-9 may be either converted to the corresponding amine 2-11 through azide substitution followed by reduction, or coupled with protected amino acid 1-1.1 or 1-1.2 in the presence of a base such as $Et_3N$ or DIPEA to afford keto-ester 2-10. Similarly, amine 2-11 may be converted to the corresponding keto-amide 2-12 via condensation with appropriate amino acid under standard amide formation conditions. Both 2-12 and 2-13 may be transformed to key intermediate 2-4 via heating with $NH_4OAc$ under thermal or microwave conditions.

Scheme 2a

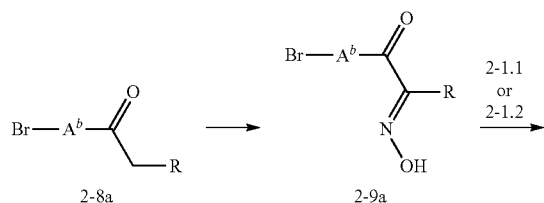

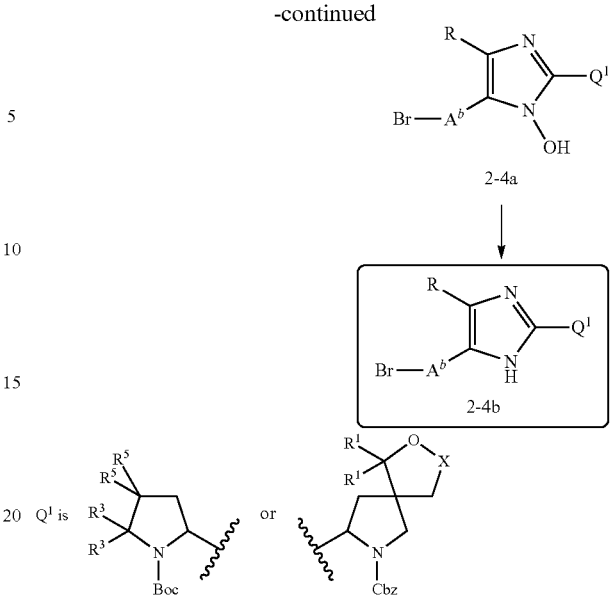

The synthesis of 4,5-disubstituted imidazole related intermediates are analogous to that described in Scheme 2. Alternatively, these imidazole intermediates can be synthesized from ketone 2-8a (Scheme 2a) through nitrosation (sodium nitrite, HCl) to ketooxime 2-9a, which can be cyclized with aldehyde 2-1.1 or 2-1.2 to 1-hydroxyimidazole 2-4a in the presence of ammonia or ammonium hydroxide. Reduction of 2-4a with a suitable reducing reagent such as triethyl phosphite can lead to the requisite imidazole 2-4b.

Scheme 3

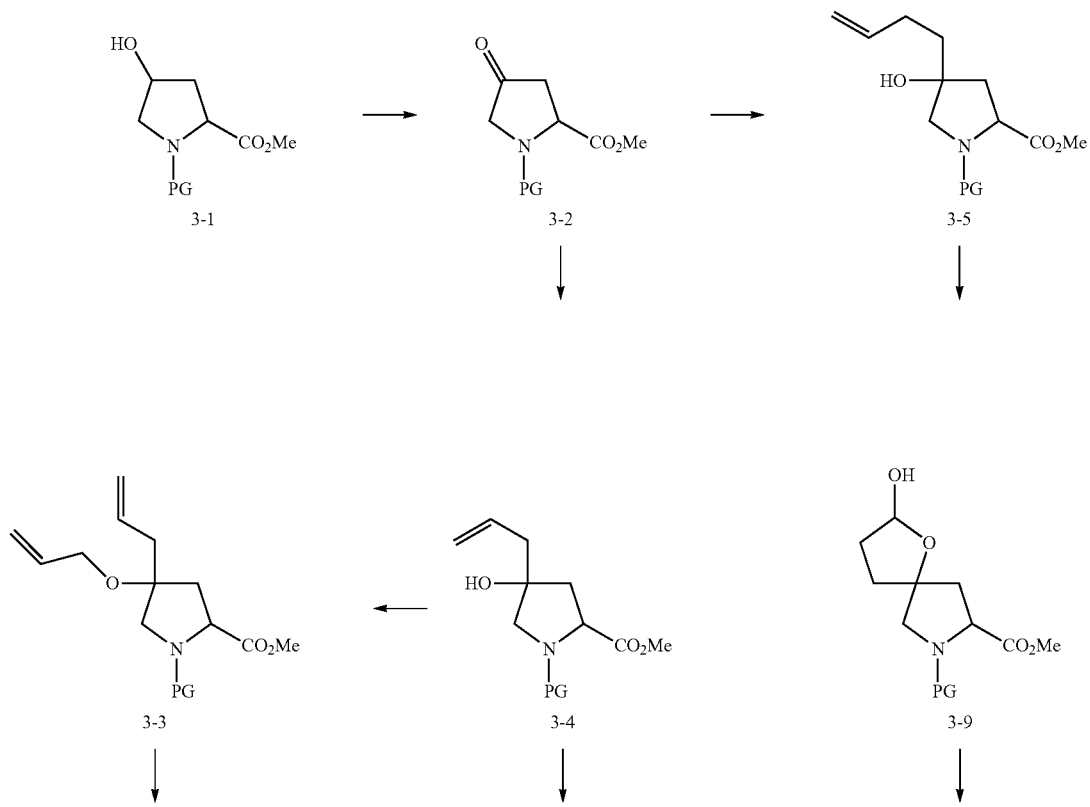

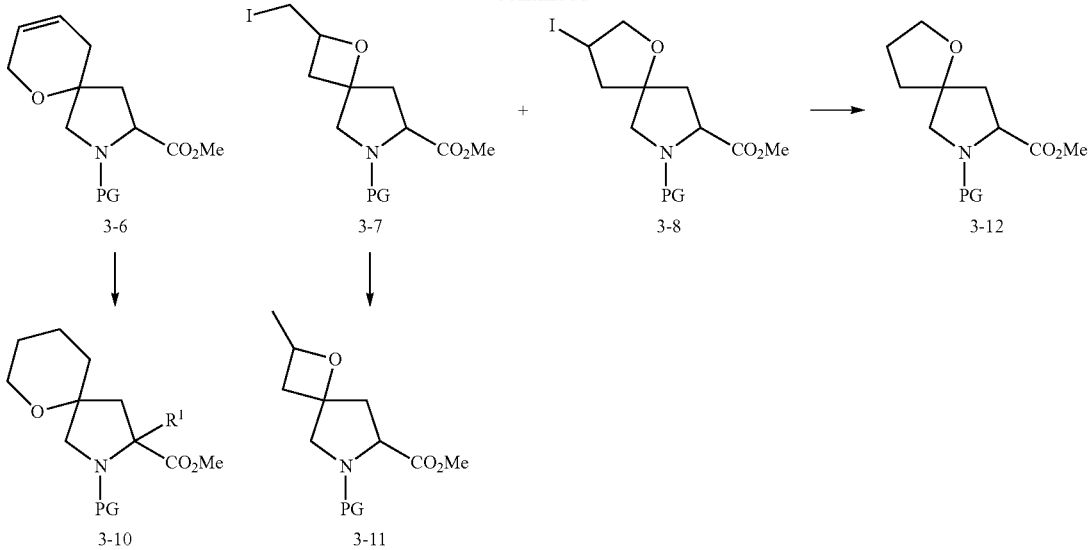

PG = Boc or Cbz

The synthesis of the compounds of the present invention containing certain spiro tetrahydrofuranyl (THF) or tetrahydropyranyl (THP) proline intermediates which may be prepared from a commercially available 4-hydroxyproline derivatives, such as 3-1 (Scheme 3). Compound 3-1 containing a hydroxy group substituted at the C4-position of the pyrrolidine ring may be converted into various bicyclic amino acid methyl esters 3-6 to 3-12. Oxidation of 3-1 by a variety of oxidation agents such as ruthenium(III) chloride/ NaIO$_4$ in wet CH$_3$CN may afford ketone 3-2. More reagents and conditions for the oxidation of an alcohol to a ketone can be found in *Comprehensive Organic Transformations*, R. C. Larock Ed., Wiley-RCH, 1999, page 1236-1249. 3-2 may then serve as a universal intermediate for further derivatization to bicyclic intermediates 3-10, 3-11 and 3-12 with different ring sizes. The allylation or homoallylation of 3-2 may be realized either by various types of nucleophilic addition, such as Grignard addition and Barbier reaction, or by electrophilic addition mediated by allylsilane or allyltin in the presence of Lewis acid. Alkene 3-4 may be converted into bicyclic 3-7 and 3-8 through iodo-etherification conditions such as I2 and NaHCO$_3$ in aprotic solvent. These iodides may be further reduced to 3-11 and 3-12 under radical conditions (i.e. TMS$_3$SiH and AIBN) in aprotic solvent with heat. Alternatively, the homoallylation product 3-5 may be oxidatively cleaved either by ozonolysis or OsO$_4$/NaIO$_4$ to generate hemiacetal 3-9 through an aldehyde intermediate. 3-9 may be selectively reduced by a variety of reducing agents such as BH$_3$ or Et$_3$SiH optionally in the presence of Lewis acid to provide bicyclic 3-12. The double allylation product 3-3 may be converted into dihydropyrane ring 3-6 by ring closing metathesis, which may be further transformed into tetrahydropyrane ring 3-10 under various hydrogenation conditions.

With a variety of suitably substituted imidazoles such as those listed in Schemes 1 and 2 in hand, the compounds of the present invention may be prepared through various coupling strategy or a combination of strategies to connect two fragments. The said strategy may include, but not limited to, Stille coupling, Suzuki coupling, Sonogashira coupling, Heck coupling, Buchwald amidation, Buchwald amination, amide coupling, ester bond formation, William etherification, Buchwald etherification, alkylation, pericyclic reaction with different variations, or the like.

Scheme 4

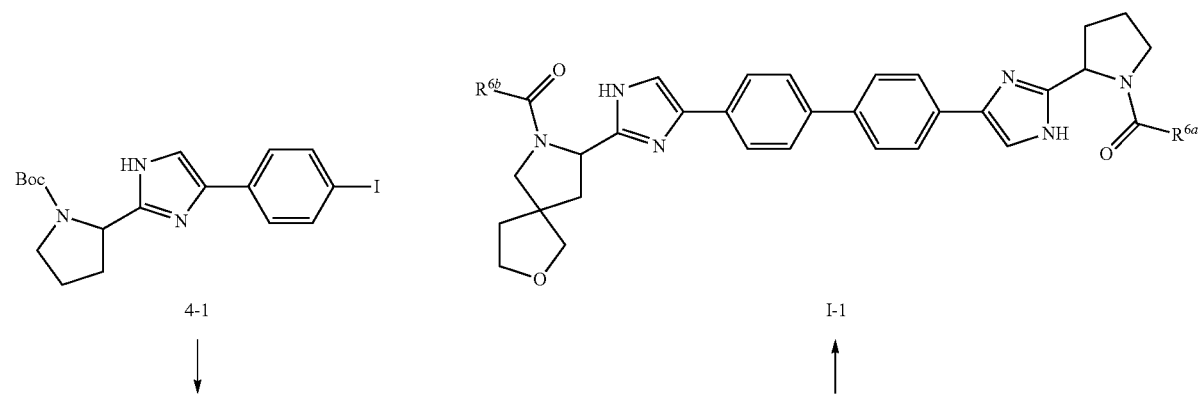

-continued

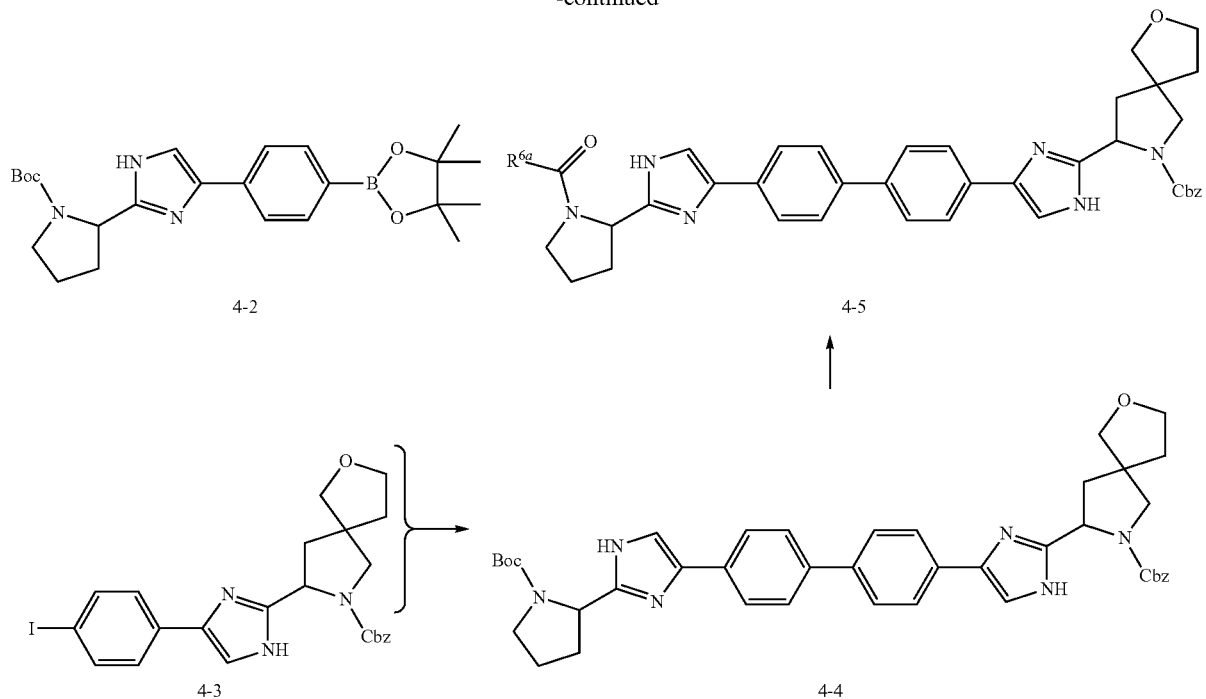

R⁶ᵃ and R⁶ᵇ are independent R⁶ as previously defined

An example of the strategies that may be used to connect the two imidazole fragments is shown in Scheme 4. Iodides 4-1, 4-3 and boronate derivative 4-2 may be prepared using procedures similar to that described previously. Iodide 4-3 may be coupled with boronate 4-2 under Suzuki condition in the presence of a Pd-catalyst to generate a core structure 4-4, which may be converted to the compounds of the present invention I-1 after selective deprotection of Boc or Cbz and installation of capping groups. Thus 4-5 may be obtained in two steps: 1) deprotection of the Boc by an acid such as HCl or TFA; and 2) the released amine functionality may be acylated with a carboxylic acid (R⁶ᵃCOOH) under standard acylation conditions, for example a coupling reagent such as HATU or HOBt and EDC in the presence of an organic base such as DIPEA. Various carboxylic acids including amino acids in racemic or optical form are commercially available, and/or can be synthesized in racemic or optical form, see references cited in reviews by D. Seebach, et al, *Synthesis*, 2009, 1; C. Cativiela and M. D. Diaz-de-Villegas, *Tetrahedron: Asymmetry*, 2007, 18, 569; 2000, 11, 645; and 1998, 9, 3517; and experimental examples compiled in patent application WO 08/021927A2 by C. Bachand, et al, from BMS, which is incorporated herein by reference. Compound 4-5 then may be served as a common intermediate for further derivatizations to the title compounds I-1 after a Pd-catalyzed hydrogenative deprotection and acylation with carboxylic acid R⁶ᵇCOOH using similar procedures described above.

Scheme 5

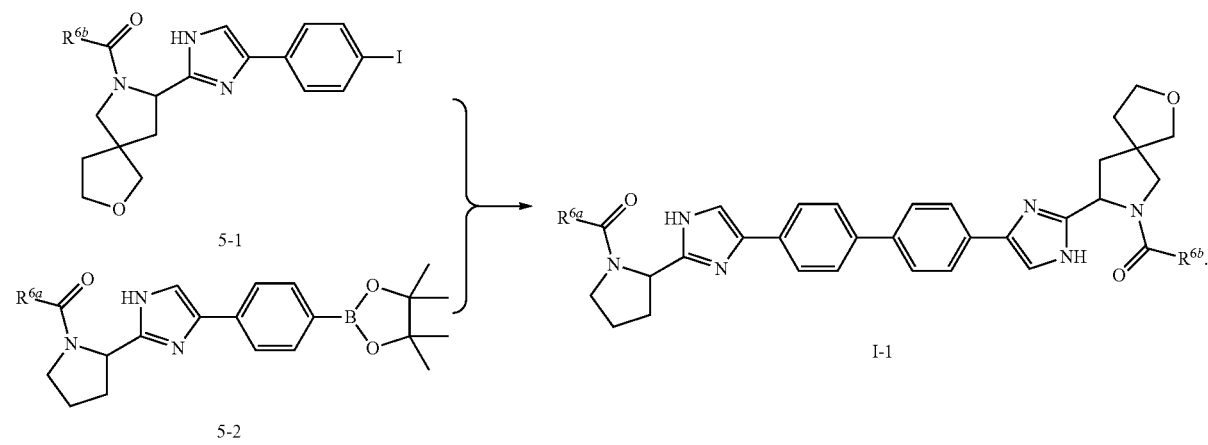

R⁶ᵃ and R⁶ᵇ are independent R⁶ as previously defined

Alternatively, as shown in Scheme 5, the compounds of the present invention (for example I-1) may also be derived from key intermediates 5-1 and 5-2 using the Suzuki coupling procedures described previously. Both intermediates 5-1 and 5-2 have the desired acyl group already installed from 4-2 and 4-3 using similar sequences shown in Scheme 4.

alkylation, palladium catalyzed allylation, carboxylation or Michael addition. The two electrophiles may be the same or different. Suitable electrophiles include, but not limited to, alkyl halide, allyl halide, propargyl halide, ethyl carbonate, chloroformate, acrylate, allyl acetate, and allyl t-butyl carbonate. After certain step(s) of functional group manipulation, 6-2 can be converted to 6-3 with a free hydroxyl and

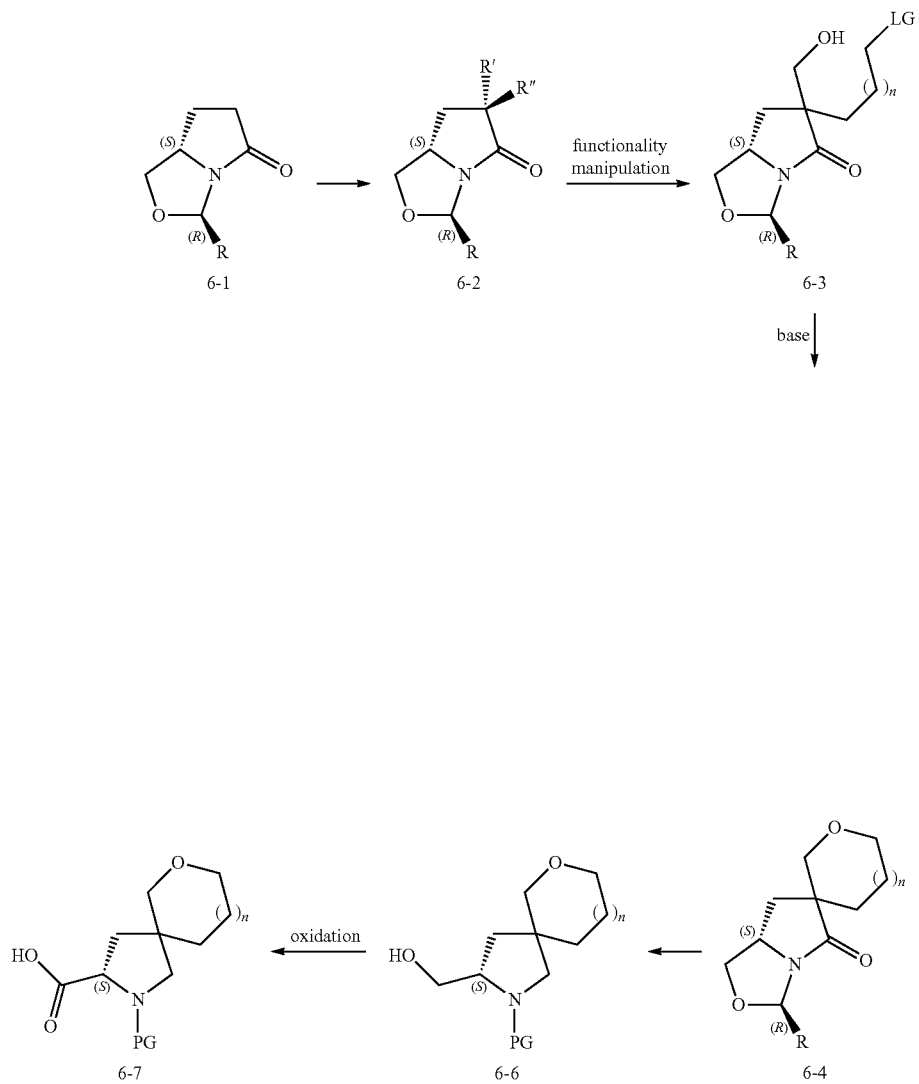

R is alkyl or aryl
R', R" are alkyl, allyl, propargyl, CO$_2$R
LG is a leaving group
n = 0 or 1

Alternatively, the synthesis of the compounds of the present invention containing certain spiro tetrahydrofuranyl (THF) or tetrahydropyranyl (THP) proline intermediates which may be prepared from a commercially available protected (S)-pyroglutaminol, such as 6-1 (Scheme 6). When treated with a strong base, such as t-BuOK, LiHMDS, NaHMDS, NaH, Et$_3$N, DBU, K$_2$CO$_3$, Cs$_2$CO$_3$, or the like, in an aprotic solvent or a mixture of aprotic solvents, 6-1 can react with up to two suitable eletrophiles to install germinal substituents (R' and R") as in compound 6-2 through reactions to those skilled in the art, such as but not limited to a leaving group (LG). In the presence of a suitable base, such as t-BuOK, LiHMDS, NaHMDS, NaH, Et$_3$N, DBU, pyridine, K$_2$CO$_3$, Cs$_2$CO$_3$, or the like, 6-3 can undergo an intramolecular cyclization to form the desired spiro ether linkage as in compound 6-4. From 6-4, deprotection of the cyclic aminal and reduction of the lactam followed by protection of the released secondary amine afford 6-6. Oxidation of the primary alcohol provides the desired spiro-THF or THP proline derivatives 6-7.

Scheme 7

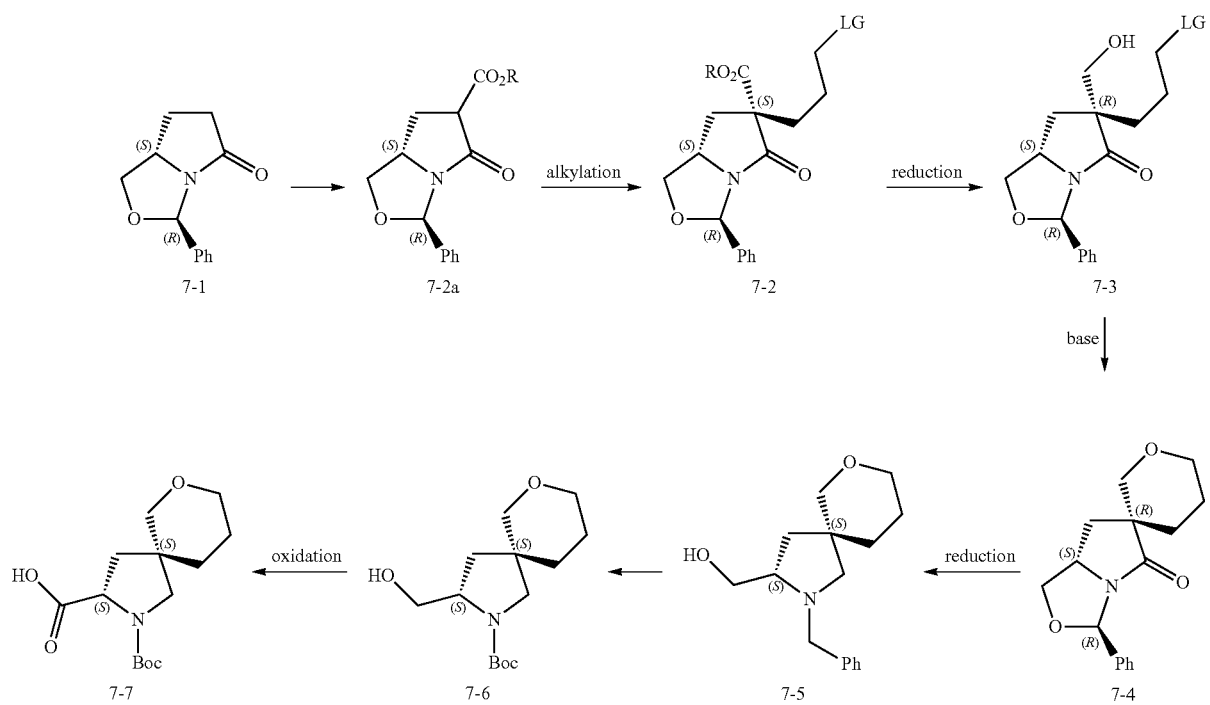

R is an alkyl; LG is a leaving group

Scheme 7 exemplifies a synthesis of the compounds of the present invention containing a spiro-THP proline intermediates 7-7 from a benzaldehyde-protected pyroglutaminol 7-1. In the presence of a base, 7-1 can be activated via 1,3-dicarbonyl 7-2a after installing a carboxylate by reacting with a alkyl carbonate or chloroformate. 7-2a can be further alkylated with an alkylating reagent with a leaving group, such as 1,3-dibromopropane, 1-bromo-3-chloropropane or the like, in the presence of a base, to afford 7-2. The above stepwise conversion from 7-1 to 7-2 may be combined into an one-pot reaction fashion using similar conditions described above. The carboxylate in 7-2 can be selectively reduced to alcohol 7-3 with a suitable reducing reagent, such as $NaBH_4$, $NaBH(OAc)_3$, $NaBH_3CN$, $LiBHEt_3$, DIBAL, $LiBH_4$, $Ca(BH_4)_2$, $CaCl_2$—$NaBH_4$, $LiAlH(OBu-t)_3$, or the like. Intramolecular cyclization of ether formation to 7-4 can be performed under basic conditions, optionally in the presence of a silver salt, such as silver oxide or silver carbonate. 7-4 may be reduced with $LiAlH_4$ to a benzylated amine 7-5, which can be protected as a Boc-derivative 7-6 with $Boc_2O$, optionally in the presence of a base, such as $Et_3N$, $iPr_2NEt$, pyridine, DMAP, $K_2CO_3$, $NaHCO_3$, or the like. Oxidation of 7-6 with a high valent metal reagent, such as ruthenium oxide, chromium oxide, or the like, optionally in the presence of sodium periodate, can furnish the requisite 7-7.

The compounds of the present invention containing two "capping groups", defined as $R^6C(O)$—, may be prepared using procedures similar to that described in published literature, such as WO2008021927, WO2012109080 and WO2012154777, which are incorporated by reference.

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Intermediate A1

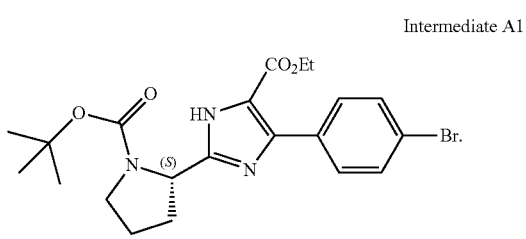

Step A1a. Into a solution of ethyl 3-(4-bromophenyl)-3-oxopropanoate (25 g, 92.2 mmol) in 1,4-dioxane (20 mL) was added bromine (4.73 mL, 92.2 mmol) at 0° C. The mixture was stirred at 0° C. for 1.5 hours before all volatiles were evaporated off to the crude desired product as a yellow oil (32.8 g, quantitative), which was used for the next step without further purification. $^1$H NMR (CDCl$_3$) 7.88 (d, 2H), 7.66 (d, 2H), 5.59 (s, 1H), 3.31 (q, 2H), 2.27 (t, 3H).

Step A1b. Into a solution of the compound from step A1a (32.8 g, 92.2 mmol) in acetonitrile (200 mL) was added (S)-1-(tert-butoxycarbonyl)pyrrolidine-2-carboxylic acid (21.0 g, 96.8 mmol) and DIPEA (17.7 mL, 101.3 mmol). The mixture was stirred at rt for 14 hours before all volatile were evaporated. The residue was partitioned between water (100 mL) and EtOAc (300 mL) and the organic phase was separated, dried (Na$_2$SO$_4$) and concentrated to afford a brown slurry, which was filtered through a silica plug (20 g) and eluted with EtOAc. The fractions with desired compound was collected and concentrated to afford a light yellow oil (42 g, 94%), which was resuspended in toluene (200 mL) followed by addition of ammonium acetate (67 g, 870 mmol). The mixture was stirred at 95° C. for 16 hours before being partitioned between aqueous NaHCO$_3$ and EtOAc. The organic phase was separated, dried (Na$_2$SO$_4$) and concentrated to afford a brown slurry, which was purified by chromatography (silica, EtOAc-hexanes) to afford a light yellow oil. It was recrystallized with EtOAc and hexanes to provide the desired compound as light yellow powder (16 g, 39% over 2 steps). ESIMS m/z=464.30, 466.30 [M+H]$^+$.

Intermediate A2

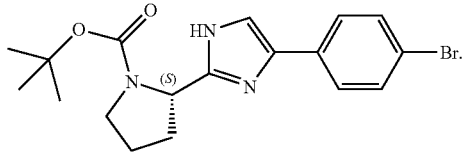

Step A2a. To a mixture of 2,4'-dibromoacetophenone (5.00 g, 18.0 mmol) and N-Boc-L-proline (3.87 g, 18.0 mmol) in CH$_3$CN (60 mL) was added triethylamine (5.40 mL, 37.8 mmol) slowly. The mixture was stirred at rt until the disappearance of the starting material. The volatiles were evaporated and the residue was partitioned (EtOAc—water). The organics were washed with brine, dried (Na$_2$SO$_4$), filtered and evaporated. The residue was purified by chromatography (silica, hexanes-ethyl acetate) to give the desired compound as a light yellow foam (6.73 g, 91%). $^1$H NMR (CDCl$_3$) 7.76 (t, J=8.0 Hz, 2H), 7.63 (dd, J=5.0, 8.5 Hz, 2H), 5.51, 5.16 (2d, J=16.0 Hz, 1H), 5.32, 5.28 (2d, J=16.5 Hz, 1H), 4.48, 4.40 (dd, J=5.0, 8.5 Hz, 1H), 3.56 (m, 1H), 3.43 (m, 1H), 2.30 (m, 2H), 2.06 (m, 1H), 1.92 (m, 1H), 1.46, 1.43 (2s, 9H).

Step A1b. To a solution of the compound from step A2a (6.73 g, 16.3 mmol) in toluene (100 mL) was added ammonium acetate (25.1 g, 0.327 mol) and the mixture was heated at 100° C. for 14 hours. The volatiles were evaporated and the residue was partitioned (EtOAc—aq. NaHCO$_3$). The organics were washed with brine, dried (Na$_2$SO$_4$), filtered and evaporated. The residue was purified by chromatography (silica, hexanes-ethyl acetate) to give the desired compound as a yellow foam (6.10 g, 95%). ESIMS m/z=392.24, 394.24 [M+H]$^+$. $^1$HNMR (CDCl$_3$) 7.57 (bs, 1H), 7.48 (m, 3H), 7.23 (s, 1H), 4.97 (m, 1H), 3.42 (m, 2H), 2.99 (m, 1H), 2.16 (m, 2H), 1.97 (m, 1H), 1.46 (s, 9H).

Intermediate A3

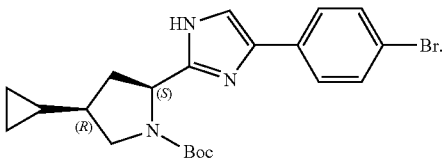

Step A3a. Into a suspension of 3-bromopropyltriphenyl phosphonium bromide (41.03 g, 88 mmol) in 1,2-dimethoxylethane (200 mL) was added NaH (60%, 7.04 g, 176.0 mmol) and 2 drops ethanol. The mixture was stirred at 65° C. for 6.5 hours. (S)-1-(tert-butoxy-carbonyl)-4-oxopyrrolidine-2-carboxylic acid (5.05 g, 22.0 mmol) was added. The mixture was further stirred 2 days at 65° C. before cooled and quench with ice. After being concentrated, the residue was partitioned (H$_2$O—EtOAc). The organic phase was separated and extracted with K$_2$CO$_3$ (1 N, 10 mL). The combined aqueous phase was cooled in an ice/water bath, HCl (Conc.) was added to bring the pH to 1 to 2. This cloudy mixture was extracted with EtOAc (×3). The combined organic phase was dried (Na$_2$SO$_4$) and concentrated to give yellow oil and was used directly in the next step.

Step A3b. The solution of the crude product from step A3a in benzene/MeOH (20 mL/20 mL) was treated with (trimethylsilyl)diazomethane solution (2.0 M in hexanes) in small portions until no more the nitrogen gas was generated. The reaction was concentrated and was purified by chromatography (silica, EtOAc-hexanes) to afford a colorless oil (4.62 g, 78% over two steps, a mixture of olefin regio isomers). ESIMS m/z=168.10 [M-Boc+2H]$^+$.

Step A3c. The solution of the compound from step A3b (4.62 g, 177.2 mmol) in MeOH (40 mL) was treated with ruthenium (5 wt % on carbon, 250 mg) under hydrogen (60 psi) at room temperature for 1 day. The mixture was passed through a short plug of silica gel column and was concentrated to afford a light yellow oil (4.78 g) and was used directly in the next step. ESIMS m/z=170.10 [M-Boc+2H]$^+$.

Step A3d. The solution of the crude compound from step A3c in EtOH (25 mL) and water (20 mL) was added LiOH monohydrate (720 mg, 17.05 mol) at room temperature overnight before was concentrated to give a yellow oil. This crude product was dissolved in water, washed with MTBE, and was brought to pH 2 by adding HCl (4 M). The resulting mixture was extracted with EtOAc and CH$_2$Cl$_2$. The combined organic phase was dried (Na$_2$SO$_4$) and concentrated to give a pale yellow syrup (4.32 g, 90% for two steps), which slowly solidified upon standing at room temperature. ESIMS m/z=156.09 [M-Boc+2H]$^+$.

Step A3e. The desired compound was prepared from the compound from step A3d and 2,4'-dibromoacetophenone following the procedures similar to that described in Intermediate A2. ESIMS m/z=432.01, 434.01 [M+H]$^+$.

Intermediate A4

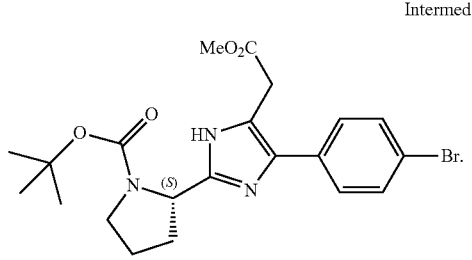

The desired compound was prepared from methyl 4-(4-bromophenyl)-4-oxobutanoate and (S)-1-(tert-butoxycarbonyl)pyrrolidine-2-carboxylic acid according to patent US20090068140. ESIMS m/z=464.18, 466.18 [M+H]$^+$.

Intermediate A5

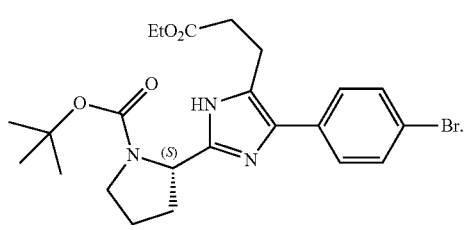

The desired compound was prepared from ethyl 5-(4-bromophenyl)-5-oxopentanoate and (S)-1-(tert-butoxycarbonyl)pyrrolidine-2-carboxylic acid using procedures described similar to that described in steps A1a and A1b. ESIMS m/z=492.16, 494.16 [M+H]$^+$.

Intermediate A6

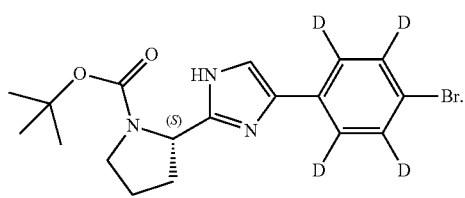

Step A6a. A solution of 4'-bromoacetophenone-d$_7$ (0.500 g, 2.43 mmol) in AcOH (10 mL) was treated with bromine (0.12 mL, 2.43 mmol) for 24 hours before being evaporated to dryness. The residue was partitioned (EtOAc—aqueous saturated NaHCO$_3$) and the organics were washed with brine, dried (Na$_2$SO$_4$), filtered and evaporated to give the desired compound as a white crystal (0.672 g, 98%).
Step A6b. A mixture of the compound from step A6a (0.670 g, 2.38 mmol) and N-Boc-L-proline (0.511 g, 2.38 mmol) in CH$_3$CN (20 mL) was added DIPEA (0.59 mL, 4.75 mmol) slowly. It was stirred at rt until the disappearance of the starting material. The volatiles were evaporated and the residue was partitioned (EtOAc—water). The organics were washed with brine, dried (Na$_2$SO$_4$) and evaporated to give the crude desired compound as a yellow brown oil (1.06 g). ESIMS m/z=416.32, 418.32 [M+H]$^+$.
Step A6c. A solution of the compound from step A6b (at most 2.38 mmol) in toluene (24 mL) was added ammonium acetate (3.66 g, 47.5 mmol) and the resultant mixture was heated up at 100° C. for 14 hours. The volatiles were evaporated and the residue was partitioned (EtOAc—aq. NaHCO$_3$). The organics were washed with brine, dried (Na$_2$SO$_4$), filtered and evaporated. The residue was purified by flash column chromatography (silica, hexanes-ethyl acetate) to give the desired compound as a yellow brown powder (0.749 g, 2 steps, 78%). ESIMS m/z=396.20, 398.20 [M+H]$^+$.

Intermediate A7

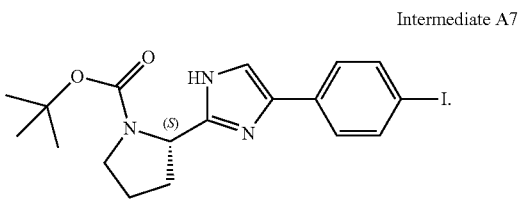

Step A7a. Into a mixture of 2-bromo-1-(4-iodophenyl)ethanone (5 g, 15.4 mmol) and (S)-1-(tert-butoxycarbonyl)pyrrolidine-2-carboxylic acid (3.48 g, 16.1 mmol) in acetonitrile (40 mL) was added diisopropylethylamine (2.4 mL, 17 mmol). The resulting mixture was stirred at rt for 3 hours before being partitioned between EtOAc and aqueous NaHCO$_3$. The organic phase was separated, dried (Na$_2$SO$_4$) and concentrated to afford a brown oil. It was purified by flash column chromatography (silica, hexane-EtOAc) to give the desired product as light yellow oil (6.0 g, 86%). ESIMS m/z=481.94 [M+Na]$^+$.
Step A1b. The mixture of compound from step A7a (6.0 g, 12.5 mmol) and ammonium acetate (15.1 g, 196 mmol) in toluene (80 mL) was stirred at 80° C. for 3 hours before being partitioned between water and aqueous NaHCO$_3$. The organic phase was separated, dried (Na$_2$SO$_4$) and concentrated to afford a deep red oil. It was purified by flash column chromatography (silica, hexane-EtOAc) to give the desired product as light yellow solid (5.34 g, 93%). ESIMS m/z=439.83 [M+H]$^+$.

Intermediate A8

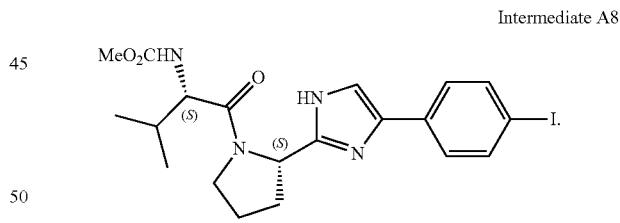

Step A8a. A solution of Intermediate A7 (2.000 g, 4.553 mmol) in 1,4-dioxane (25 mL) was treated with HCl in 1,4-dioxane (4 M, 50 mL) at rt for 1.5 hours. The volatiles were evaporated off to give the crude desired compound as a yellow solid which was used directly in the next step. ESIMS m/z=339.89 [M+H]$^+$.
Step A8b. The mixture of L-valine (50 g, 0.427 mol) in 1,4-dioxane (140 mL) was added water (630 mL), NaOH (54.7 g, 1.4 mol) and methyl chloroformate (65.7 mL, 0.85 mol). The resulting solution was stirred at 60° C. for 22 hours before being added CH$_2$Cl$_2$ (400 mL). The aqueous phase was separated and extracted with CH$_2$Cl$_2$ (400 mL) before acidification with hydrochloric acid (37% in water, 90 mL). The cloudy suspension was extracted with EtOAc (500 mL) twice and the combined organic phases were dried (Na₂SO₄) and concentrated to afford a white solid, which was recrystallized with hexane and EtOAc to afford the desired product as colorless needle like crystals (54 g, 72%). ¹H NMR (d⁶-DMSO) 12.52 (s, 1H), 7.33 (d, 1H), 3.85 (dd, 1H), 3.56 (s, 3H), 2.06 (m, 1H), 0.98 (m, 6H).

Step A8c. A mixture of the crude compounds from step A8a (4.553 mmol at most) and A8b (0.798 g, 4.553 mmol) in DMF (15 mL) was treated with HATU (1.644 g, 4.325 mmol) in the presence of DIPEA (7.93 mL, 45.53 mmol) for 1.5 hours at rt and the volatiles were evaporated off. The residue was partitioned (EtOAc—H₂O). The organics were washed with brine, dried (Na₂SO₄), filtered and evaporated. The residue was purified by chromatography (silica, hexanes-ethyl acetate containing 1% Et₃N) to give the desired compound as a yellow foam (2.026 g, 90% over 2 steps). ESIMS m/z=496.90 [M+H]⁺.

Intermediate A9

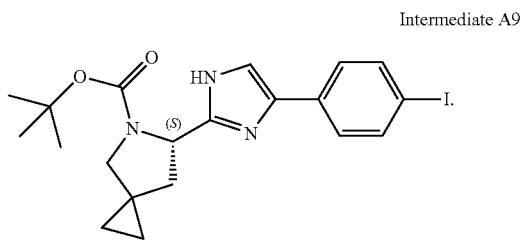

Step A9a. To a solution of (6S)-5-[(tert-butoxy)carbonyl]-5-azaspiro[2.4]heptane-6-carboxylic acid (prepared according to WO 2009/102325, 3.210 g, 13.30 mmol) and 2-bromo-1-(4-iodophenyl)ethanone (5.044 g, 13.97 mmol) in acetonitrile (100 mL) was added DIPEA (5.79 mL, 33.26 mmol) dropwise. The resulting solution was stirred at rt for 3 hours before being concentrated. The residue was purified by chromatography (silica, hexanes-ethyl acetate) to afford the desired compound as a yellow foam (6.191 g, 96%). ESIMS m/z=486.26 [M+H]⁺.

Step A9b. To a solution of the compound from step A9a (6.191 g, 12.76 mmol) in toluene (60 mL) was added ammonium acetate (10.82 g, 0.140 mol). The resulting mixture was heated at 110° C. for 15 hours before being cooled down and concentrated. The residue was partitioned (EtOAc—H₂O). The organic phase was washed with brine, dried (Na₂SO₄), filtered and concentrated. The crude product was purified by chromatography (silica, hexanes-ethyl acetate) to afford the desired compound as a yellow foam (5.730 g, 96%). ESIMS m/z=466.26 [M+H]⁺.

Intermediate A10

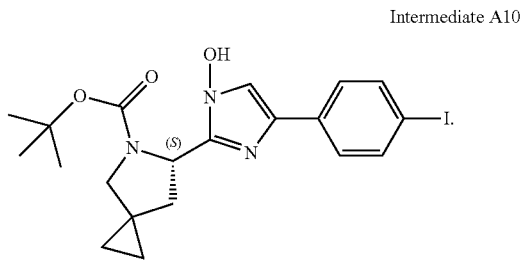

Step A10a. To a solution of 4'-iodoacetophenone (4.000 g, 16.26 mmol) in THF (65 mL) cooled at 0° C. was added isopentyl nitrile (4.55 mL, 32.51 mmol), followed by HCl in 1,4-dioxane (4 M, 5.28 mL, 21.13 mmol). The resulting red solution was stirred at 0° C. for 30 minutes and then at rt for 6 hours before being concentrated. The residue was partitioned (Et₂O—saturated NaHCO₃). The organics were washed with brine, dried (Na₂SO₄), filtered and evaporated. The residue was purified by chromatography (silica, CH₂Cl₂-ethyl acetate) to give the desired compound 2-(4-iodophenyl)-2-oxoacetaldehyde oxime as a yellow solid (1.530 g, 34%).

Step A10b. A mixture of the compound from step A10a (0.183 g, 0.666 mmol), (S)-tert-butyl 6-formyl-5-azaspiro [2.4]heptane-5-carboxylate (prepared according to WO 2011/006960, 0.150 g, 0.666 mmol) and ammonium acetate (0.257 g, 3.329 mmol) in glacial acetic acid (4 mL) was stirred at 120° C. for 1.5 hours before being cooled down and concentrated. The residue was purified by chromatography (silica, hexanes-ethyl acetate) to give the desired compound (S)-tert-butyl 6-(1-hydroxy-4-(4-iodophenyl)-1H-imidazol-2-yl)-5-azaspiro[2.4]heptane-5-carboxylate as a yellow sticky oil (0.106 g, 33%). ESIMS m/z=482.09 [M+H]⁺.

Intermediate A11

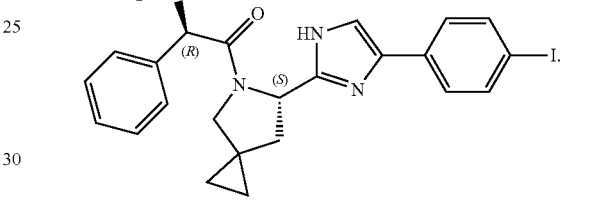

Step A11a. A solution of Intermediate A9 (1.000 g, 2.149 mmol) in CH₂Cl₂ (12 mL) was treated with HCl in 1,4-dioxane (4 M, 20 mL) for 2 hours. The volatiles were evaporated off to give the crude desired compound as a yellow solid, which was used directly in the next step.

Step A11b. To a mixture of the crude compound from step A11a (2.149 mmol at most) and (R)-(methoxycarbonyl) amino phenyl acetic acid (prepared according to WO 2008/021927, 0.450 g, 2.149 mmol) in CH₃CN (20 mL) was added DIPEA (3.74 mL, 21.49 mmol), followed by HATU (0.817 g, 2.149 mmol). The solution was stirred at rt for 1 hour. The volatiles were evaporated off. The residue was purified by chromatography (silica, hexanes-ethyl acetate) to give the desired compound as a yellow foam (0.930 g, 78% over 2 steps). ESIMS m/z=557.18 [M+H]⁺.

Intermediate A12

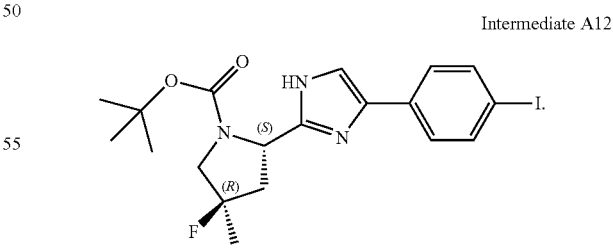

Step A12a. Into a solution of N-carbobenzoxy-4-oxo-L-proline (1.00 g, 4.37 mmol) in THF (60 mL) at −78° C. was added MeMgBr (3M in Et₂O, 3.20 mL, 9.61 mmol). The resultant mixture was kept at −78° C. for 1 hour before being warmed up to rt for 14 hours. The reaction was quenched with 1N aqueous HCl to pH 2, and the volatiles were evaporated off. The residue was partitioned (EtOAc—H₂O)

and the organics were dried (Na₂SO₄), filtered and evaporated to give the crude desired compound as a yellow brown oil (0.842 g) which was directly used in the next step. ESIMS m/z=246.20 [M+H]⁺.

Step A12b. Into a solution of the crude compound from step A12a (4.37 mmol at most) in MeOH (15 mL) and benzene (15 mL) was added TMSCHN₂ (2M in hexane) until the yellow color did not fade. The volatiles were evaporated and the residue was purified by chromatography (silica, hexanes-ethyl acetate) to give the desired compound as a light yellow solid (0.480 g, ~80% purity). ESIMS m/z=260.20 [M+H]⁺.

Step A12c. Into a solution of the compound from step A12b (0.480 g, ~80% purity, 1.57 mmol) in CH₂Cl₂ (30 mL) at 0° C. was added DAST (0.42 mL, 3.15 mmol). The reaction was kept at 0° C. for 1 hour before being quenched with aqueous NaHCO₃. The residue was partitioned (CH₂Cl₂—H₂O) and the organics were dried (Na₂SO₄), filtered and evaporated. The residue was purified by chromatography (silica, hexanes-ethyl acetate) to give the desired compound as a colorless oil (0.259 g, 23% over 3 steps). ESIMS m/z=262.15 [M+H]⁺.

Step A12d. The crude acid compound was prepared from the compound from step A12c using procedures similar to that described in step C1e. ESIMS m/z=248.08 [M+H]⁺.

Step A12e. The desired compound was prepared from the compound from step A15d using procedures similar to that described in Intermediate A7. ESIMS m/z=472.09 [M+H]⁺.

Intermediate A13

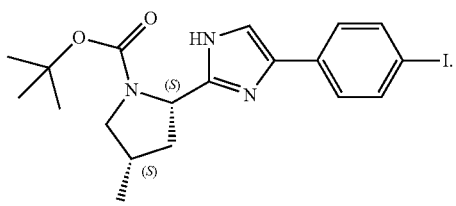

Step A13a. The desired compounds were prepared from the compound from (S)-1-benzyl 2-methyl 4-methylenepyrrolidine-1,2-dicarboxylate as a diasteromeric mixture using procedures similar to that described in step A16b. ¹H NMR (CDCl₃): 4.38, 4.25, 4.18 (m, m, m, totally 1H), 3.76, 3.74 (s, s, totally 3H), 3.75, 3.67 (m, m, totally 1H), 2.40 (m, 1H), 2.23, 2.08 (m, m, totally 1H), 1.83, 1.55 (m, m, totally 1H), 1.48, 1.41 (s, s, totally 3H), 1.05 (M, 3H).

Step A13b. The desire compound (2S,4S)-tert-butyl 2-(4-(4-iodophenyl)-1H-imidazol-2-yl)-4-methylpyrrolidine-1-carboxylate (ESIMS m/z=454.11 [M+H]⁺) was prepared as major isomer from the compounds from step A13a using procedures similar to that described in Intermediate A7 after chromatographic separation (silica, hexanes-ethyl acetate).

Intermediate A14

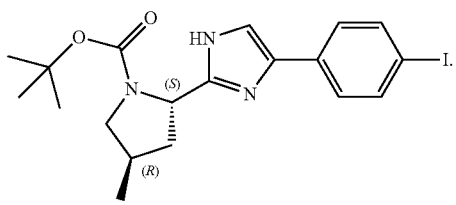

The desired compound (2S,4R)-tert-butyl 2-(4-(4-iodophenyl)-1H-imidazol-2-yl)-4-methylpyrrolidine-1-carboxylate was isolated as minor isomer in step A13b. ESIMS m/z=454.16 [M+H]⁺.

Intermediate A15

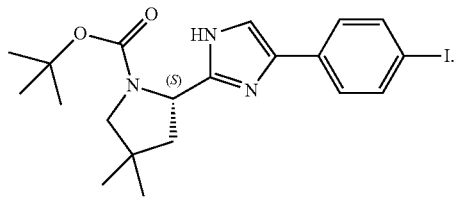

Step A15a. To a solution of (+)-(3R,7aS)-tetrahydro-3-phenyl-3H,5H-pyrrolo[1,2-c]oxazol-5-one (1.51 g, 7.49 mmol) in THF (15 mL) was added a solution of LiHMDS (1.0 M in THF, 34 mL, 34 mmol) at −78° C. under N₂. The mixture was stirred at −78° C. for 30 minutes before MeI (2.78 mL, 44.4 mmol) was added at −78° C. The mixture was slowly warmed up to ~−10° C. before being quenched with saturated NH₄Cl solution and evaporated. The residue was partitioned (EtOAc—H₂O). The organics were washed with brine, dried (Na₂SO₄), filtered and evaporated. The residue was purified by chromatography (silica, EtOAc-hexanes) to give the desired compound as a light yellow solid (1.29 g, 75.4%). ESIMS m/z=232.06 [M+H]⁺.

Step A15b. The desired compound was prepared from the compound from step A15a using procedures similar to that described in Intermediate A9 and C6. ESIMS m/z=468.19 [M+H]⁺.

Intermediate A16

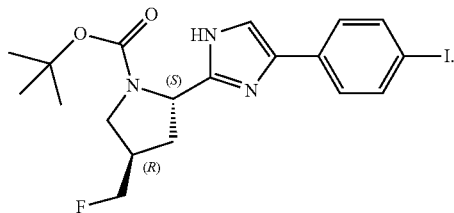

Step A16a. A solution of (S)-1-benzyl 2-methyl 4-methylenepyrrolidine-1,2-dicarboxylate (666 mg, 2.42 mmol) in THF (8 mL) was treated with 9-borabicyclo-[3,3,1]nonane (9-BBN, 0.5 M in THF, 7 mL, 0.42 mmoL) at rt for 4 hours before NaOH (2.5 N, 2 mL) was added followed by hydrogen peroxide (H₂O₂, 30% in water, 1 mL) slowly. The mixture was stirred at rt overnight before being concentrated. The residue was dissolved in water, acidified to pH ~2 by HCl (4 M) and extracted with EtOAc. The organics were dried (Na₂SO₄), filtered and evaporated. The residue was dissolved in MeOH (14 mL) and benzene (14 mL) and treated with TMSCHN₂ (2 M in hexanes) dropwise until the yellow color persisted. The solution was concentrated. The residue was purified by chromatography (silica, hexanes-ethyl acetate) to give the desired compounds as a colorless oil and isomeric mixture (401 mg, 51%). ESIMS m/z=294.2 [M+H]⁺.

Step A16b. A solution of compound from A16a (248 mg, 0.845 mmol) in CH₂Cl₂ (3 mL) was treated at rt with Deoxo-Fluor (376 mg, 1.7 mmol) for two hours before a second portion of Deoxo-Fluor (376 mg, 1.7 mmol) was added. The mixture was stirred at rt overnight before being quenched dropwise with aqueous NaHCO$_3$ at 0° C. and partitioned (CH$_2$Cl$_2$—H$_2$O). The organics were washed with brine, dried (Na$_2$SO$_4$), filtered and evaporated. The residue was purified by chromatography (silica, hexanes-ethyl acetate) to give the desired compounds as a colorless oil and isomeric mixture (130 mg, 85%). ESIMS m/z=296.11 [M+H]$^+$.

Step A16c. A solution of the crude compound from step A16b (130 mg, 0.44 mmol) in EtOH (2 mL) and water (2 mL) was treated with LiOH.H$_2$O (18.5 mg, 0.44 mmol) at rt for 4 hours before being concentrated. The residue was dissolved in H$_2$O (5 mL) and acidified to pH ~2 by HCl (4 N). The mixture was extracted with EtOAc and CH$_2$Cl$_2$. The organics were dried (Na$_2$SO$_4$), filtered and evaporated to give the crude desired compounds as a colorless oil and isomeric mixture (140 mg, 113%). ESIMS m/z=282.10 [M+H]$^+$.

Step A16d. A solution of compound from step A16c (0.44 mmol at most) and di-tert-butyl dicarbonate (96 mg, 0.44 mmol) in MeOH (10 mL) was treated with Pd/C (10 wt %, 50 mg) under hydrogen (60 psi) overnight at rt before being filtered through Celite. The filtrate was concentrated to give the crude desired compound as a colorless oil and isomeric mixture, which was used directly in the next steps. ESIMS m/z=148.2 [M-Boc+2H]$^+$.

Step A16e. The desired compound (2S,4R)-tert-butyl 4-(fluoromethyl)-2-(5-(4-iodophenyl)-1H-imidazol-2-yl) pyrrolidine-1-carboxylate (ESIMS m/z=472.17 [M+H]$^+$) was prepared as major isomer from the compound from step A16d using procedures similar to that described in Intermediate A9 after chromatographic separation (silica, hexanes-ethyl acetate).

Intermediate A17

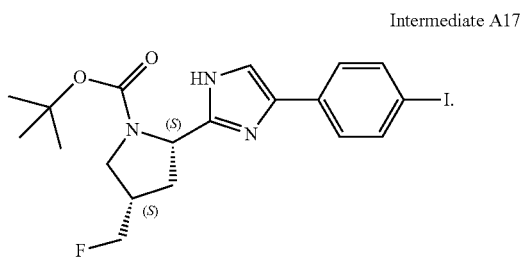

The desired compound (2S,4S)-tert-butyl 4-(fluoromethyl)-2-(5-(4-iodophenyl)-1H-imidazol-2-yl)pyrrolidine-1-carboxylate was isolated from the step A16e as a minor isomer. ESIMS m/z=472.21 [M+H]$^+$.

Intermediate A18

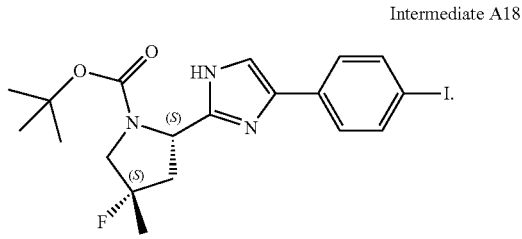

Step A18a. To a suspension of AD-mix a (2.9 g) in t-BuOH/H$_2$O (10 mL/10 mL) cooled with ice/water was added a solution of tert-butyl 2-methyl 4-methylenepyrroli-dine-1,2-dicarboxylate (505 mg, 2.1 mmol) in t-BuOH (1 mL). The mixture was gradually warmed up to rt and stirred overnight before Na$_2$SO$_3$ (3 g) was added. After another hour, the mixture was partitioned (CH$_2$Cl$_2$-water). The aqueous was extracted with CH$_2$Cl$_2$. The combined organics were washed with brine, dried (Na$_2$SO$_4$), filtered and evaporated. The residue was purified by chromatography (silica, hexanes-ethyl acetate) to give the desired compound as a colorless oil (mixture of diastereomers, 515 mg, 85%). ESIMS m/z=176.17 [M-Boc+2H]$^+$.

Step A18b. A solution of the compound from step A18a (512 mg, 1.86 mmol) in CH$_2$Cl$_2$ (5 mL) was treated with DIPEA (0.45 mL, 2.58 mmol) and MsCl (0.16 mL, 2.07 mmol) for 2 hours at 0° C. before being partitioned (CH$_2$Cl$_2$-water). The organics were washed with brine, dried (Na$_2$SO$_4$), filtered and evaporated to give the crude desired compound as a colorless oil (725 mg), which was used directly in the next step. ESIMS m/z=254.20 [M-Boc+2H]$^+$.

Step A18c. A solution of the compound from step A18b (1.82 mmol at most) in DMF (5 mL) was treated with 15-crown-5 (80 mg, 0.36 mmol) and NaI (1.36 g, 9.1 mmol) in the presence of K$_2$CO$_3$ (1.12 g, 8.12 mmol) at 90° C. overnight before being cooled down and partitioned (EtOAc-water). The organics were washed with water, brine, dried (Na$_2$SO$_4$), filtered and evaporated. The residue was purified by chromatography (silica, hexanes-ethyl acetate) to give the desired compound as a colorless oil (396 mg, 56%) containing an isomeric impurity. ESIMS m/z=386.10 [M+H]$^+$.

Step A18d. A solution of the compound from step A18c (516 mg, 1.34 mmol) in toluene (10 mL) was treated with totally 4 portions of Bu$_4$SnH (0.36 mL, 1.34 mmol) and AIBN (22 mg, 0.134 mmol) for 12 hours at 110° C. before being cooled down and evaporated. The residue was purified by chromatography (silica, hexanes-ethyl acetate) to give the desired compound as a colorless oil (177 mg, 51%) as a single isomer. ESIMS m/z=260.10 [M+H]$^+$.

Step A18e. A solution of the compound from step A18d (170 mg, 0.655 mmol) in CH$_2$Cl$_2$ (3 mL) was treated with DAST (0.18 mL, 1.32 mmol) at 0° C. for 1 hours before being quenched with aqueous NaHCO$_3$ dropwisely and partitioned (CH$_2$Cl$_2$-water). The organics were washed with brine, dried (Na$_2$SO$_4$), filtered and evaporated. The residue was purified by chromatography (silica, hexanes-ethyl acetate) to give the desired compound as a colorless oil (177 mg, 51%). ESIMS m/z=260.10 [M+H]$^+$.

Step A18f. The desired compound was prepared from the compound from step A18e using procedures similar to that described in Intermediate A7. ESIMS m/z=472.11 [M+H]$^+$.

Intermediate A19

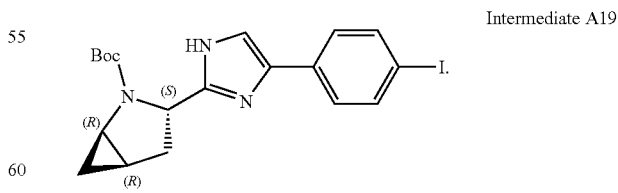

The desired compound was prepared from (1R,3S,5R)-2-(tert-butoxycarbonyl)-2-azabicyclo[3.1.0]hexane-3-carboxylic acid (prepared according to WO 2009/102325) using procedures similar to that described in Intermediate A9. ESIMS m/z=452.04 [M+H]$^+$.

Intermediate A20

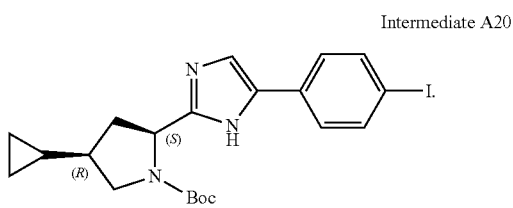

Step A20a. A solution of (S')-1-tert-butyl 2-methyl 4-methylenepyrrolidine-1,2-dicarboxylate (1.98 g, 7.2 mmol) in THF (20 mL) was treated with 9-BBN (0.5 M in THF, 21.6 mL, 10.80 mmol) at rt for 6 hours before H₂O (20 mL) was added at 0° C. followed by sodium perborate tetrahydrate (NaBO₃.4H₂O, 3.38 g, 22 mmol). The mixture was stirred at rt overnight before being filtered through Celite. The filtrate was extracted with EtOAc. The organics were dried (Na₂SO₄), filtered and evaporated. The residue was purified by chromatography (silica, hexanes-ethyl acetate) to give the desired compounds as a colorless oil and isomeric mixture (1.15 g, 61%). ESIMS m/z=260.16 [M+H]⁺.

Step A20b. A solution of DMSO (1.11 mL, 15.6 mmol) in CH₂Cl₂ (20 mL) was treated with oxalyl chloride (1.02 mL, 11.7 mmol) at −78° C. for 0.5 hour before a solution of the compounds from step A20a (1.15 g, 3.9 mmol) in CH₂Cl₂ (5 mL) was added. After 1 hour at −78° C., the mixture was warmed up to −30° C. before TEA (3 mL) was added. After 1 hour, H₂O (20 mL) was added at 0° C. The mixture was partitioned (CH₂Cl₂—H₂O). The organics were washed with brine, dried (Na₂SO₄), filtered and evaporated. The residue was purified by chromatography (silica, hexanes-ethyl acetate) to give the desired compounds as a colorless oil and isomeric mixture (0.98 g, 85%).

Step A20c. A solution of the compounds from A20b (840 mg, 3.26 mmol) in THF (5 mL) was added into a suspension of methyltriphenylphosphonium bromide (Ph₃PCH₃Br, 2.33 g, 6.53 mmol) and potassium t-butoxide (t-BuOK, 660 mg, 5.88 mmol) in THF (10 mL) (pre-mixed for 1 hour) at 0° C. The mixture was stirred at 0° C. for 3 hours before being quenched with H₂O (20 mL) and partitioned (EtOAc—H₂O). The organics were washed with brine, dried (Na₂SO₄), filtered and evaporated. The residue was purified by chromatography (silica, hexanes-ethyl acetate) to give the desired compounds as a colorless oil and isomeric mixture (0.55 g, 70%).

Step A20d. A solution of compounds from A20c (342 mg, 1.34 mmol) in CH₂Cl₂ (5 mL) was treated with TFA (0.31 mL, 4.02 mmol) at rt for 3 hours before being concentrated. The residue was dissolved in CH₂Cl₂ (5 mL) and treated with benzyl chloroformate (0.39 mL, 2.7 mol) in the presence of the DIPEA (1 mL) overnight before being partitioned (EtOAc—H₂O).

The organics were washed with brine, dried (Na₂SO₄), filtered and evaporated. The residue was purified by chromatography (silica, hexanes-ethyl acetate) to give the desired compounds as a colorless oil and isomeric mixture (410 mg, 105%, contaminated with a small amount of benzyl alcohol). ESIMS m/z=290.12 [M+H]⁺.

Step A20e. To a solution of diethylzinc (ZnEt₂, 2.75 mL) in CH₂Cl₂ (30 mL) was added TFA (2.06 mL, 26.8 mmol) very slowly at 0° C. over 30 minutes under N₂. After 30 minutes, a solution of diiodomethane (CH₂I₂, 2.16 mL, 26.8 mmol) in CH₂Cl₂ (10 mL) was added slowly. The mixture was stirred at 0° C. for 30 minutes before a solution of the compounds from step A20d (1.34 mmol at most) in CH₂Cl₂ (10 mL) was added. The resulting mixture was stirred for 3 days at rt before being quenched with aqueous NH₄Cl and partitioned (CH₂Cl₂—H₂O). The organics were washed with brine, dried (Na₂SO₄), filtered and evaporated. The residue was purified by chromatography (silica, hexanes-ethyl acetate) to give the desired compounds as a colorless oil and isomeric mixture (289 mg, 70%). ESIMS m/z=304.16 [M+H]⁺.

Step A20f. A solution of the compounds from step A20e (286 mg, 0.94 mmol) and di-tert-butyl dicarbonate (281 mg, 1.3 mmol) in MeOH (10 mL) was treated with palladium hydroxide (Pd(OH)₂ on carbon, 20 wt %, 25 mg) under hydrogen (60 psi) at rt for 4.5 hours before being filtered through Celite. The filtrate was evaporated to give the desired compounds as a colorless oil and isomeric mixture (350 mg) which was used directly in the next step. ESIMS m/z=270.16 [M+H]⁺.

Step A20g. The desired compound was prepared as a minor product from the compound from step A20f using procedures similar to that described in steps A3d, A9a and A9b. ESIMS m/z=480.40 [M+H]⁺.

Intermediate A21

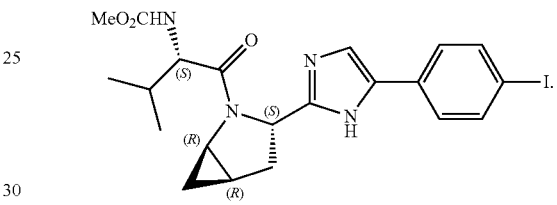

The desired compound was prepared from Intermediate A19 and the compound from step A8b using procedure similar to that described in Intermediate A8. ESIMS m/z=509.15 [M+H]⁺.

Intermediate A22

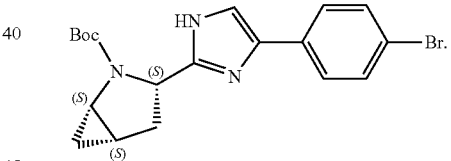

Step A22a. A solution of tert-butyl (S)-5-oxopyrrolidine-2-carboxylate (5.0 g, 27.0 mmol) in acetonitrile (100 mL) was treated with (Boc)₂O (8.83 g, 40.5 mmol) in the presence of DMAP (660 mg, 5.4 mmol) at rt for 42 hours. After concentration, the residue was purified by chromatography (silica, hexanes-EtOAc) to give the desired compound as a light yellow oil (7.92 g, 103%), which was used directly in the next step.

Step A22b. In to a solution of the compound from step A22a (7.92 g, 27 mmol at most) in THF (50 mL) was added DIBAL-H (1 M in hexanes, 40.5 mL) slowly over 30 minutes at −70° C. (inner). After stirring 2 hour at −70° C., trifluroacetic acid (1.0 mL, 13.5 mmol) was added slowly. TEA (22.6 mL, 162 mmol) and trifluoroacetic anhydride (4.88 mL, 35.1 mmol) were added slowly in sequence at <−65° C. (inner). The inner temperature was raised to −35° C. in 1 hour, DMAP (220 mg, 1.8 mmol) was added. The cooling bath was removed. The mixture was stirred for one more hour before citric acid (10% in H₂O, 10 mL) was added. It was filtered and partitioned (EtOAc-H₂O). The organic phase was washed with brine, dried and concentrated. The residue was purified by chromatography (silica, hexanes-EtOAc) to give the desired compound as a light yellow oil (4.43 g, 60% two steps). $^1$HNMR (acetone-d6) 6.55 (d, 1H), 4.91 (d, 1H), 4.46 (m, 1H), 3.08 (m, 1H), 2.57 (m, 1H), 1.48 (d, 9H), 1.43 (d, 9H).

Step A22c. In to a solution of the compound from step A22b (4.43 g, 17.32 mmol) in toluene (10 mL) and (trifluoromethyl)benzene (PhCF$_3$, 12 mL) at −30° C. (inner), chloroiodomethane (ClCH$_2$I, 4.8 mL, 65.8 mmol) was added; followed by diethyl zinc (Et$_2$Zn, 1.1 M in toluene, 30 mL, 33.0 mmol) over 30 minutes. After stirred 20 hours at such −30° C., additional ClCH$_2$I (4.8 mL, 65.8 mmol) and Et$_2$Zn (1.1 M in toluene 30 mL, 33.0 mmol) were charged and the mixture was kept at −20 for another 24 hours. Citric acid (10% in H$_2$O, 50 mL) was added slowly to quench the reaction. The mixture was partitioned (EtOAc-H$_2$O). The organic phase was washed with brine, dried and concentrated. The residue was purified by chromatography (silica, hexanes-EtOAc) to give the desired compound as a colorless oil (2.07 g, 44%). $^1$H NMR (CDCl$_3$) 4.40, 4.32 (dd, dd, total 1H), 3.46, 3.37 (m, m, total 1H), 2.55, 2.45 (m, m, total 1H), 2.0, 1.95 (d, d, total 1H), 1.48-1.35 (m, 19H), 0.82 (m, 1H), 0.62, 0.58 (m, m, total 1H).

Step A22d. A solution of the compound from step A22c (1.0 g, 3.53 mmol) in CH$_2$Cl$_2$ (4 mL) was treated with HCl (4 M, in dioxane, 8 mL) at rt for 44 hours. It was concentrated to give the desired compound as a brown syrup, which was used directly in next step.

Step A22e. A solution of the crude compound from step A22d (3.53 mmol at most) in aqueous NaOH (1M, 7 mL) and dioxane (10 mL) was treated with Boc$_2$O (1.15 g, 5.3 mmol) at rt for 14 hours. The volatile was evaporated off, the residue was partitioned (MTBE-H$_2$O). The aqueous phase was acidified with aqueous HCl (4 M) to PH 2 and was extracted with EtOAc. The organic phase was concentrated and dried to give the desired compound as a white solid (663 mg, 83% 2 steps). $^1$H NMR (CDCl$_3$) 4.60 (brd m, 1H), 3.55 (brd s, 1H), 2.65, 2.42, 2.15 (brd s, brd s, brd s, total 2H), 1.55, 1.45 (brd s, brd, s total 10H), 0.88, 0.75, 0.68 (brd s, brd s, brd s, total 2H).

Step A22f. The desired compound was prepared from the compound of step A22e and 2,4'-dibromoacetophenone using procedures similar to that described in intermediates A2. ESIMS m/z=404.24, 406.24 [M+H]$^+$.

Intermediate A23

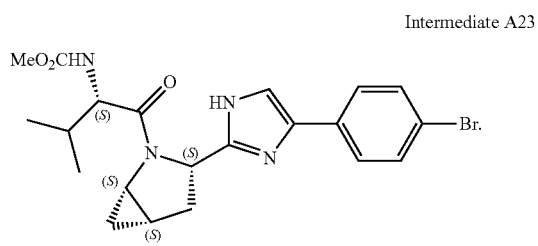

The desired compound was prepared from Intermediate A22 using procedures similar to that described in intermediates A8. ESIMS m/z=461.25, 463.25 [M+H]$^+$.

Intermediate A24

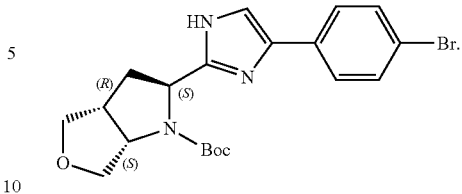

The desired compound was prepared from (2S,3aR,6aS)-1-(tert-butoxycarbonyl)hexa-hydro-1H-furo[3,4-b]pyrrole-2-carboxylic acid (prepared from (S)-5-phenylmorpholin-2-one and 2-(allyloxy)acetaldehyde by procedures similar to that described in JP 2009298713) using procedures similar to that described in Intermediate A2. ESIMS m/z=434.22, 436.22 [M+H]$^+$.

Intermediate B1

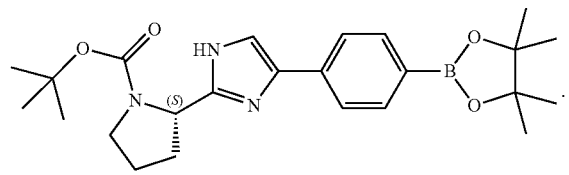

To a mixture of the compound from step A2b (1.00 g, 2.55 mmol), bis(pinacolato)diboron (1.35 g, 5.33 mmol) and potassium acetate (0.640 g, 6.53 mmol) in 1,4-dioxane (20 mL) was added Pd(PPh$_3$)$_4$ (0.147 g, 0.128 mmol). The mixture was degassed and heated at 80° C. under N$_2$ for 14 hours. The volatiles were evaporated and the residue was partitioned (EtOAc—water). The organics were washed with brine, dried (Na$_2$SO$_4$), filtered and evaporated. The residue was purified by chromatography (silica, hexanes-ethyl acetate) to give the desired compound as a light yellow solid (0.978 g, 87%). ESIMS m/z=440.39 [M+H]$^+$. $^1$HNMR (CDCl$_3$) 11.03, 10.55 (2s, 1H), 7.79 (m, 3H), 7.45 (m, 1H), 7.26 (m, 1H), 4.97 (m, 1H), 3.41 (m, 2H), 3.06, 2.91 (2 m, 1H), 2.17 (m, 2H), 1.97 (m, 1H), 1.49 (s, 9H), 1.35 (s, 12H).

Intermediate B2

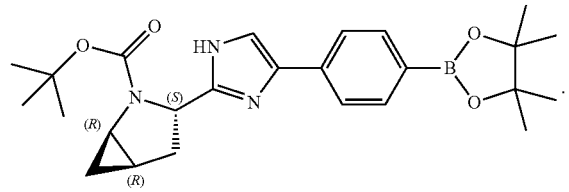

The desired compound was prepared from (1R,3S,5R)-2-(tert-butoxycarbonyl)-2-azabicyclo[3.1.0]hexane-3-carboxylic acid (prepared according to WO 2009/102325) following the procedures similar to that described in intermediates A2 and B1. ESIMS m/z=451.17 [M+H]$^+$.

Intermediate B3

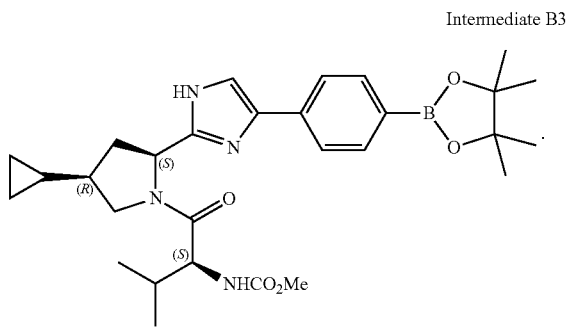

The desired compound was prepared from Intermediate A3 and the compound from step A8b following the procedures similar to that described in Intermediates A8 and B1. ESIMS m/z=537.31 [M+H]+.

Intermediate B4

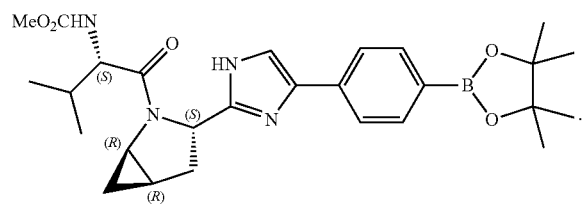

The desired compound was prepared from (1R,3S,5R)-2-(tert-butoxy-carbonyl)-2-azabicyclo[3.1.0]hexane-3-carboxylic acid (prepared according to WO 2009/102325), 2,4'-dibromoacetophenone and the compound from step A18b following procedures similar to that described in Intermediates A2, A8, and B1. ESIMS m/z=509.25 [M+H]+.

Intermediate B5

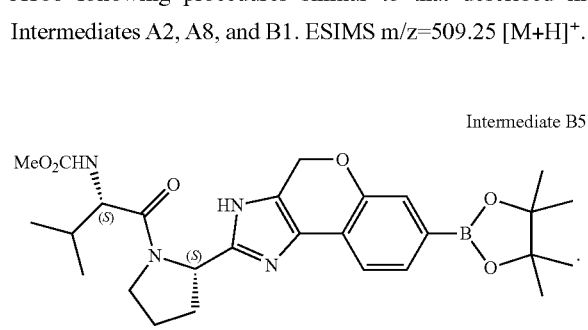

Into a solution of Intermediate F4 (214 mg, 0.44 mmol) in dioxane (5 mL) was added bis(pinacolato)diboron (149 mg, 0.587 mmol), Pd(dppf)Cl$_2$ (22 mg, 0.03 mmol), and potassium acetate (74 mg, 0.75 mmol). The mixture was degassed and heated at 100° C. for 2.5 hours before cooling. It was concentrated to afford a brown oil, which was purified by flash column chromatography (silica, EtOAc-hexanes) to afford the desired compound as a brownish foam (122 mg, 78%). ESIMS m/z=525.47 [M+H]+.

Intermediate B6

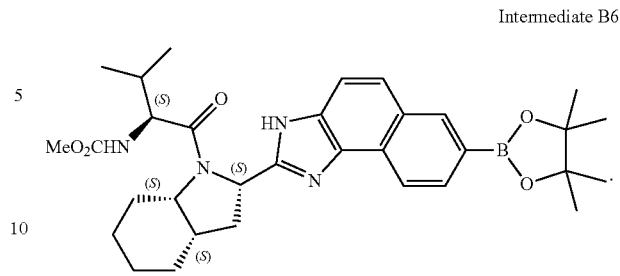

Into a solution of Intermediate F8 (4.12 g, 7.81 mmol) and the bis(pinacolato)diboron (3.96 g, 15.62 mmol) in 1,4-dioxane (80 mL) was added potassium acetate (1.92 g, 19.53 mmol) and Pd(dppf)Cl$_2$ (570 mg, 0.78 mmol). After degassing, the solution was stirred at 100° C. for 1.5 hours before being allowed to cool down. It was concentrated to a dark solid, which was purified by chromatography (silica, EtOAc-hexanes, twice) to afford the desired compound as a yellow foam (3.98 g, 89%). ESIMS m/z=575.26 [M+H]+.

Intermediate B7

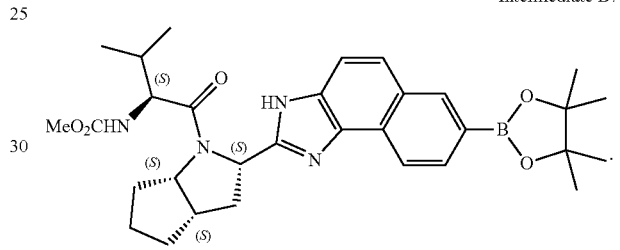

The desired compound was prepared from Intermediate F10 using the procedures similar to that described in Intermediate B6. ESIMS m/z=561.34 [M+H]+.

Intermediate B8

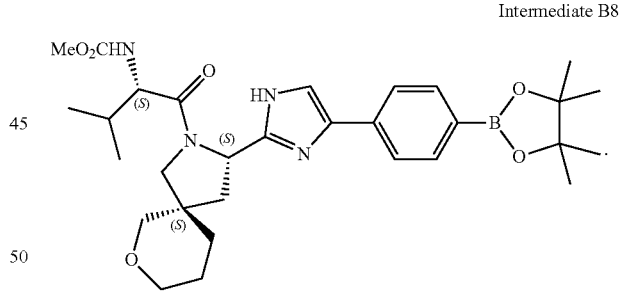

The desired compound was prepared from Intermediate C3 using the procedures similar to that described in Intermediate B6. ESIMS m/z=567.52 [M+H]+.

Intermediate B9

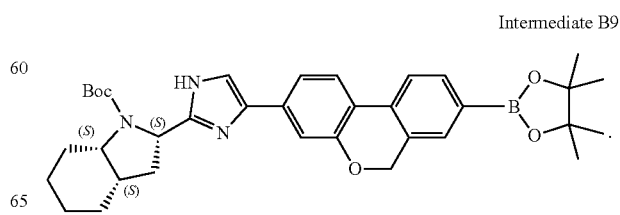

A mixture of Intermediate J1 (118 mg, 0.233 mmol), bis(pinacolato)diboron (72 mg, 0.28 mmol), potassium acetate (68 mg, 0.70 mmol), 2-Dicyclohexylphosphino-2',4',6'-triiso-propylbiphenyl (Xphos, 22 mg, 0.047 mmol), and Pd$_2$(dba)$_3$ (21 mg, 0.047 mmol) in 1,4-dioxane (3 mL) was degassed and heated at 100° C. under N$_2$ for 1.5 hours. The volatiles were evaporated and the residue was purified by chromatography (silica, hexanes-ethyl acetate) to give the desired compound as a light yellow solid (114 mg, 81%). ESIMS m/z=598.63 [M+H]$^+$.

Intermediate B10

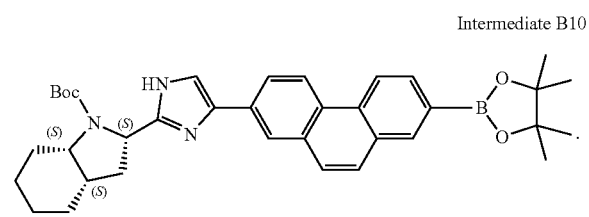

A mixture of Intermediate J2 (0.38 g, 0.69 mmol), bis(pinacolato)diboron (0.353 g, 1.39 mmol), potassium acetate (0.204 g, 2.08 mmol) and Pd(dppf)Cl$_2$ (51 mg, 0.069 mmol) in 1,4-dioxane (6 mL) was degassed and heated at 95° C. under N$_2$ for 1 hour. The volatiles were evaporated and the residue was purified by chromatography (silica, hexanes-ethyl acetate) to give the desired compound as a light yellow solid (0.34 g, 82%). ESIMS m/z=594.34 [M+H]$^+$.

Intermediate B11

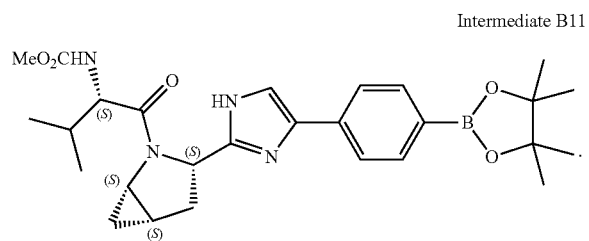

The desired compound was prepared from Intermediate A23 using procedures similar to that described in intermediates B1. ESIMS m/z=509.29 [M+H]$^+$.

Intermediate B12

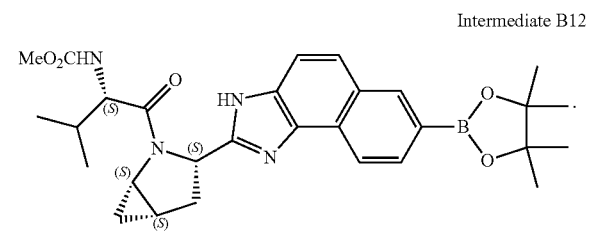

The desired compound was prepared from Intermediate F17 using procedures similar to that described in Intermediate B1. ESIMS m/z=533.36 [M+H]$^+$.

Intermediate B13

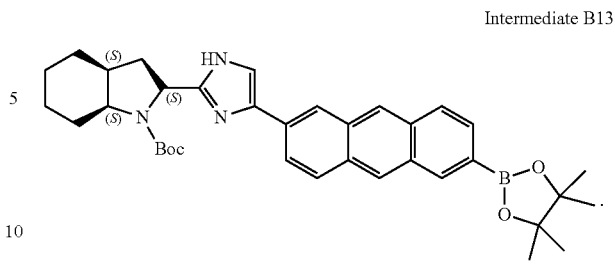

A mixture of Intermediate J3 (40.7 mg, 0.0745 mmol), bis(pinacolato)diboron (37.8 mg, 0.149 mmol), KOAc (18.3 mg, 0.186 mmol) and Pd(dppf)Cl$_2$ (5.4 mg, 7.45 µmol) in 1,4-dioxane (2 mL) was degassed and then heated at 100° C. for 1.5 hours under N$_2$ before cooling and concentration. The residue was taken up in dichloromethane and filtered. The filtrate was directly purified by flash column chromatography (silica, hexanes-ethyl acetate) to give the desired compound as a yellow oil (25.1 mg, 57%). ESIMS m/z=594.63 [M+H]$^+$.

Intermediate C1

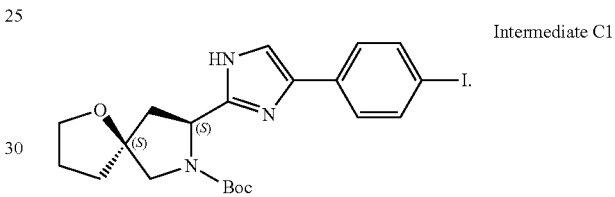

Step C1a. To a suspension of activated zinc powder (6.37 g, 97.5 mmol) in dry THF (100 mL) was added allyl bromide (8.5 mL, 97.4 mmol) dropwise. The resulting light yellow solution was cooled with ice-water before the 1-benzyl-2-methyl 4-oxopyrrolidine-1,2-dicarboxylate (18.0 g, 65 mmol) was added dropwise. The reaction mixture was stirred at 0° C. and warmed up to rt and kept at rt overnight before being quenched with HCl (1 N). The mixture was partitioned (EtOAc—H$_2$O). The organics were washed with brine, dried (Na$_2$SO$_4$) and evaporated. The residue was purified by chromatography (silica, EtOAc-hexanes) to afford the desired compounds as a mixture of diastereomers (~6:1) and as a light yellow oil (13.66 g, 66%). ESIMS m/z=320.15 [M+H]$^+$.

Step C1b. To a solution of the compounds from step C1a (0.200 g, 0.627 mmol) in CH$_3$CN (4 mL) were added NaHCO$_3$ (0.211 g, 2.51 mmol) and iodine (0.477 g, 1.88 mmol). The resultant mixture were heated up to 50° C. for 4 hours before charging additional NaHCO$_3$ (0.211 g, 2.51 mmol) and iodine (0.477 g, 1.88 mmol). The reaction was kept at 50° C. for another 3 hours before being cooled down and quenched by aqueous Na$_2$S$_2$O$_3$. The volatiles were evaporated off and the residue was partitioned (EtOAc—H$_2$O). The organics were washed with brine, dried (Na$_2$SO$_4$), filtered and evaporated. The residue was purified by flash column chromatography (silica, EtOAc-hexanes) to give the desired compound as a colorless oil (79.8 mg, 29%). ESIMS m/z=468.23 [M+Na]$^+$.

Step C1c. Into a solution of the compound from step C1b (1.18 g, 2.66 mmol) in toluene (50 mL) were added tris(trimethylsilyl)silane (2.05 mL, 6.66 mmol) and 2,2'-azo-bis-isobutyronitrile (26.2 mg, 0.160 mmol). The resultant mixture were degassed and heated up to 90° C. under N$_2$ for 3 hours before being allowed to cool down and evaporated to dryness. The residue was purified by flash column chromatography (silica, EtOAc-hexanes) to give the desired compound as a colorless oil (0.333 g, 39%). ESIMS m/z=320.16 [M+H]+.

Step C1d. Into a solution of the compound from step C1c (0.170 g, 0.533 mmol) in MeOH (6 mL) were added palladium hydroxide (20 wt % on carbon, 50.0 mg) and Boc$_2$O (0.174 g, 0.799 mmol). The resulting mixture was hydrogenated under 60 psi hydrogen gas at rt for 1 day before being filtered through a plug of Celite. The filtrate was concentrated and purified by flash column chromatography (silica, EtOAc-hexanes) to give the desired compound as a colorless oil (0.127 g, 84%). ESIMS m/z=308.14 [M+Na]+.

Step C1e. Into a solution of the compound from step C1d (0.127 g, 0.447 mmol) in EtOH (4 mL) at 0° C. was added lithium hydroxide monohydrate (22.5 mg, 0.536 mmol) in H$_2$O (2 mL). The resulting mixture was gradually warmed up to rt for 1 day before being evaporated to dryness. The residue was partitioned (Et$_2$O—H$_2$O) and the aqueous phase was acidified to pH~2 at 0° C. The mixture was then partitioned (CH$_2$Cl$_2$—H$_2$O) and the organics were washed with brine, dried (Na$_2$SO$_4$), filtered and evaporated to give the crude desired compound as a colorless oil (0.122 g, 100%). ESIMS m/z=319.14 [M+Li+CH$_3$CN]+.

Step C1f. Into a solution of the crude compound from step C1e (0.224 mmol at most) in CH$_3$CN (4 mL) were added 2-bromo-1-(4-iodophenyl)ethanone (76.2 mg, 0.235 mmol) and DIPEA (56.0 μL, 0.447 mmol). The resultant mixture was stirred at room temperature for 1 hour before being evaporated to dryness. The residue was partitioned (EtOAc—H$_2$O) and the organics were washed with brine, dried (Na$_2$SO$_4$), filtered and evaporated. The residue was purified by flash column chromatography (silica, EtOAc-hexanes) to give the desired compound as a colorless oil (98.8 mg, 2 steps 86%). ESIMS m/z=515.92 [M+H]+.

Step C1g. Into a solution of the crude compound from step C1f (98.8 mg, 0.192 mmol) in toluene (8 mL) was added NH$_4$OAc (0.296 g, 3.84 mmol). It was heated at 100° C. for 12 hours before being cooled down and evaporated to dryness. The residue was partitioned (EtOAc—H$_2$O) and the organics were washed with brine, dried (Na$_2$SO$_4$), filtered and evaporated. The residue was purified by flash column chromatography (silica, EtOAc-hexanes) to give the desired compound as a light yellow oil (70.8 mg, 75%). ESIMS m/z=495.93 [M+H]+.

Intermediate C2

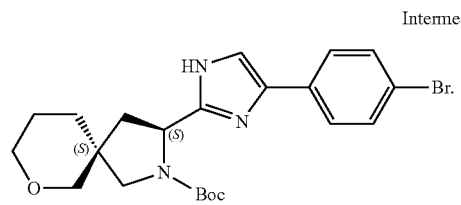

Step C2a. To a solution of the compound of step F5c or F5j (1.40 mmol at most) in acetonitrile (10 mL) at rt was added 2,4'-dibromoacetophenone (389 mg, 1.40 mmol), followed by DIPEA (0.7 mL, 4.0 mmol). The mixture was stirred at rt for 5 hours. The volatiles were evaporated. The residue was directly purified by flash column chromatography (silica, ethyl hexanes-acetate) to afford the desired compound as a yellow solid (453 mg, 70% two steps). ESIMS m/z=504.17, 506.17 [M+Na]+.

Step C2b. A mixture of compound from step C2a (453 mg, 0.94 mmol) and ammonium acetate (794 mg, 10.32 mol) in xylenes (10 mL) was stirred at 140° C. in a sealed tube for 4 hours before being cooled and partitioned (EtOAc—aqueous NaHCO$_3$). The organic layer was washed with brine, dried (Na$_2$SO$_4$) and evaporated. The residue was purified by flash column chromatography (silica, hexanes-acetate) to afford the desired compound as a yellow foam (390 mg, 90%). ESIMS m/z=462.24, 464.24 [M+H]+.

Intermediate C3

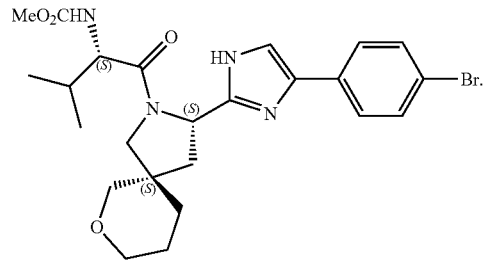

The desired compound was prepared from Intermediate C4 and the compound from step A8b using the procedures similar to that described in Intermediate F8. ESIMS m/z=519.18, 521.18 [M+H]+.

Intermediate C4

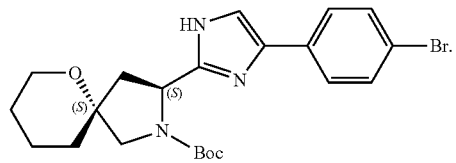

Step C4a. A mixture of the compounds from step C1a (596 mg, 2 mmol, ~8:1 diastereomeric mixture), allyl tert-butyl carbonate (1.26 g, 8 mmol), Pd$_2$(dba)$_3$ (46 mg, 0.05 mmol) and 1,4-bis(diphenylphosphino)butane (dppb, 43 mg, 0.1 mmol) in THF (10 mL) was degassed and then heated at 75° C. under N$_2$ for 1.5 hours. After being cooled down, it was concentrated. The residue was purified by chromatography (silica, hexanes-ethyl acetate) to give the desired compound as a yellow oil containing an isomeric impurity (605 mg, 93%). ESIMS m/z=326.26 [M+H]+.

Step C4b. A mixture of the compound from step C4a (677 mg, 2.08 mmol) and 1,3-bis(2,4,6-trimethylphenyl)-4,5-dihydroimidazol-2-ylidene[2-(iso-propoxy)-5-(N,N-dimethylaminosulfonyl)phenyl]methylene ruthenium(II) dichloride (Zhan-1B catalyst, 76.4 mg, 0.104 mmol) in toluene (650 mL) was degassed and then heated at 75° C. under N$_2$ for 15 hours. After being cooled down, it was concentrated. The residue was purified by chromatography (silica, hexanes-ethyl acetate) to give the desired compound as a light yellow oil containing an isomeric impurity (585 mg, 94%). ESIMS m/z=298.19 [M+H]+.

Step C4c. A mixture of palladium (10 wt % on carbon, 0.115 g) and the compound from step C4b (1.150 g, 3.876 mmol) in methanol (20 mL) at rt was purged with hydrogen and stirred at rt under H$_2$ (60 psi) for 2 days. It was filtered through a short pad of Celite and concentrated to afford the desired compound as a colorless oil containing an isomeric impurity (1.120 g, 97%). ESIMS m/z=322.25 [M+Na]+.

Step C4d. A mixture of the compounds from step C4c (1.120 g, 3.741 mmol) and LiOH.H$_2$O (0.188 g, 4.490 mmol) in EtOH/H$_2$O (1/1, 18 mL) was stirred at rt for 20 hours. EtOH was evaporated off. The aqueous residue was acidified with 3 M HCl solution to pH ~2 and extracted with EtOAc and dichloromethane. The organics were washed with brine, dried (Na$_2$SO$_4$), filtered and evaporated to afford the desired compounds as a white foam (1.100 g, 100%). ESIMS m/z=308.24 [M+Na]$^+$.

Step C4e. To a solution of the compounds from step C4d (0.270 g, 0.946 mmol) and 2,4'-dibromoacetophenone (0.289 g, 1.041 mmol) in acetonitrile (5 mL) was added DIPEA (0.33 mL, 1.892 mmol) dropwise at rt. It was stirred at room temperature for 2 hours before being concentrated. The residue was purified by flash column chromatography (silica, EtOAc-hexanes) to afford the desired compounds as a yellow oil (0.410 g, 90%). ESIMS m/z=504.30, 506.30 [M+Na]$^+$.

Step C4f. To a solution of the compounds from step C4d (0.410 g, 0.850 mmol) in xylenes (8 mL) was added ammonium acetate (0.786 g, 10.20 mmol). It was heated at 140° C. in a sealed tube for 4 hours before being allowed to cool down and partitioned (aqueous NaHCO$_3$—EtOAc). The organic phase was washed with brine, dried (Na$_2$SO$_4$), filtered and concentrated. The residue was purified by flash column chromatography (silica, EtOAc-hexanes) to afford the desired compound as a yellow foam (0.280 g, 71%). ESIMS m/z=462.32, 464.32 [M+H]$^+$.

Intermediate C5

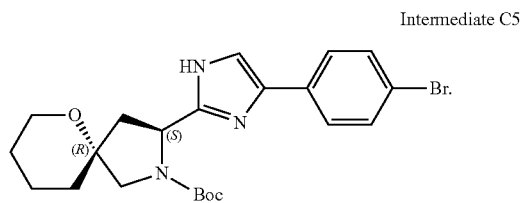

The desired compound was isolated from step C4f as a minor product. ESIMS m/z=462.23, 464.22 [M+H]$^+$.

Intermediate C6

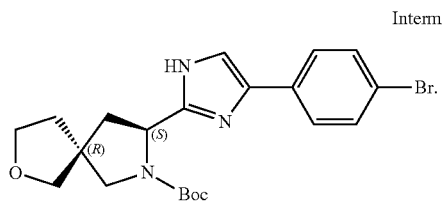

Step C6a. To a solution of LiHMDS (1.0 M in THF, 5.17 mL, 5.17 mmol) in THF (20 mL) at −78° C. was added a solution of (+)-(3R,7aS)-tetrahydro-3-phenyl-3H,5H-pyrrolo[1,2-c]oxazol-5-one (0.500 g, 2.460 mmol) in THF (10 mL) under N$_2$. The mixture was stirred at −78° C. for 30 min before ClCO$_2$Me (0.19 mL, 2.460 mmol) was added at −78° C. After 30 minutes at −78° C., the reaction was quenched with saturated NH$_4$Cl solution. The mixture was allowed to warm up to rt and the volatiles were evaporated. The residue was partitioned (EtOAc—H$_2$O). The organics were washed with brine, dried (Na$_2$SO$_4$), filtered and evaporated. The residue was purified by chromatography (silica, hexanes-ethyl acetate) to give the desired compound as a colorless oil (0.598 g, 93%). ESIMS m/z=262.13 [M+H]$^+$.

Step C6b. To a solution of the compound from step C6a (0.350 g, 1.340 mmol) in THF (13 mL) at 0° C. was added Na (60% in mineral oil, 64.3 mg, 1.607 mmol). After addition, the cooling bath was removed. The mixture was stirred at rt for 15 minutes before allyl bromide (0.13 mL, 1.474 mmol) was added. After 1 hour at rt, the reaction was quenched with saturated NH$_4$Cl solution. The mixture was partitioned (EtOAc—H$_2$O). The organics were washed with brine, dried (Na$_2$SO$_4$), filtered and evaporated. The residue was purified by chromatography (silica, hexanes-ethyl acetate) to give the desired compounds as two separated diastereomers: minor diastereomer (less polar, 56.0 mg, 14%), (3R,6R,7aS)-methyl 6-allyl-5-oxo-3-phenylhexahydropyrrolo[1,2-c]oxazole-6-carboxylate, ESIMS m/z=302.19 [M+H]$^+$; $^1$H NMR (CDCl$_3$) 7.44-7.33 (m, 5H), 6.32 (s, 1H), 5.75-5.66 (m, 1H), 5.19-5.18 (m, 1H), 5.16 (s, 1H), 4.28-4.22 (m, 2H), 3.78 (s, 3H), 3.57-3.52 (m, 1H), 2.90 (dd, J=6.7, 13.4 Hz, 1H), 2.85 (dd, J=7.9, 14.1 Hz, 1H), 2.58 (dd, J=6.7, 14.1 Hz, 1H), 1.89 (dd, J=6.6, 13.2 Hz, 1H); major diastereomer (more polar, 0.222 g, 55%), (3R,6S,7aS)-methyl 6-allyl-5-oxo-3-phenylhexahydropyrrolo[1,2-c]oxazole-6-carboxylate, ESIMS m/z=302.19 [M+H]$^+$; $^1$H NMR (CDCl$_3$) 7.46-7.33 (m, 5H), 6.33 (s, 1H), 5.82-5.73 (m, 1H), 5.23-5.18 (m, 2H), 4.28 (dd, J=6.2, 6.5 Hz, 1H), 4.08-4.02 (m, 1H), 3.82 (s, 3H), 3.67 (t, J=8.3 Hz, 1H), 2.80 (dd, J=7.5, 14.0 Hz, 1H), 2.71 (dd, J=7.1, 14.0 Hz, 1H), 2.54 (dd, J=4.9, 12.8 Hz, 1H), 2.38 (dd, J=7.9, 13.8 Hz, 1H).

Step C$_6$c. To a solution of the major diastereomer from step C$_6$b (0.160 g, 0.585 mmol) in THF/H$_2$O (1/1, 6 mL) at rt was added OsO$_4$ (4 wt % in H$_2$O, 7.5 µL, 0.012 mmol), followed by NaIO$_4$ (0.263 g, 1.229 mmol). The resulting mixture was stirred at rt for 2 hours before being quenched with saturated Na$_2$S$_2$O$_3$ solution. The mixture was partitioned (EtOAc—H$_2$O). The organics were washed with brine, dried (Na$_2$SO$_4$), filtered and evaporated to afford the desired compound as a colorless oil (0.133 g), which was used directly for next step.

Step C$_6$d. To a solution of the compound from step C$_6$c (0.133 g, 0.438 mmol at most) in EtOH (5 mL) at 0° C. was added NaBH$_4$ (33.2 mg, 0.877 mmol). After 20 minutes at 0° C., the resulting mixture was stirred at rt for 2.5 hours. More NaBH$_4$ (16.6 mg, 0.438 mmol) was added. After 2 hours at rt, the reaction was quenched with saturated NH$_4$Cl solution. The volatiles were evaporated. The residue was taken up in EtOAc (with 5% MeOH) and filtered. The filtrate was evaporated to dryness. The residue was purified by chromatography (silica, EtOAc-MeOH) to give the desired compound as a white foam (67.6 mg, 46% over 2 steps). ESIMS m/z=278.17 [M+H]$^+$.

Step C6e. To a solution of the compound from step C6d (0.793 g, 2.860 mmol) in pyridine (28 mL) at rt was added tosyl chloride (TsCl, 0.600 g, 3.145 mmol). The resulting solution was stirred at rt for 40 hours. More TsCl (0.600 g, 3.145 mmol) was added. After 24 hours at rt, the reaction was quenched with saturated NaHCO$_3$ solution. The mixture was evaporated to dryness. The residue was taken up in CH$_2$Cl$_2$ and filtered. The filtrate was directly purified by chromatography (silica, hexanes-ethyl acetate) to give the desired compound as a colorless oil (0.511 g, 69%). ESIMS m/z=260.16 [M+H]$^+$.

Step C6f. To a solution of the compound from step C6e (0.540 g, 2.082 mmol) in THF (20 mL) at rt was added LiAlH$_4$ (1.0 M in Et$_2$O, 4.16 mL, 4.16 mmol). The resulting mixture was heated at 60° C. for 2 hours before being cooled down. The reaction was quenched by carefully adding H$_2$O (0.16 mL), followed by 15% NaOH solution (0.16 mL) and then H$_2$O (0.32 mL). The suspension was filtered through a short pad of Celite. The filtrate was evaporated to give the desired compound as a white semi-solid (0.572 g), which was used directly for the next step. ESIMS m/z=248.20 [M+H]⁺.

Step C6g. To a solution of the compound from step C6f (2.082 mmol at most) in MeOH (15 mL) at rt was added HOAc (0.16 mL, 2.71 mmol), followed by Pd/C (10 wt %, 0.100 g). The resulting mixture was stirred at rt under H₂ (60 psi) for 2 hours before being filtered through a short pad of Celite. The filtrate was evaporated to give the desired compound as a colorless oil, which was used directly for the next step. ESIMS m/z=158.11 [M+H]⁺.

Step C6h. To a solution of the compound from step C6g (2.082 mmol at most) in 1,4-dioxane/H₂O (1/2, 21 mL) at rt was added NaHCO₃ (1.399 g, 16.66 mmol), followed by (Boc)₂O (0.545 g, 2.498 mmol). The resulting mixture was stirred at rt for 15 hours. The volatiles were evaporated. The residue was partitioned (EtOAc—H₂O). The organics were washed with brine, dried (Na₂SO₄), filtered and evaporated. The residue was purified by chromatography (silica, hexanes-ethyl acetate) to give the desired compound as a colorless oil (0.252 g, 45% over 3 steps). ESIMS m/z=258.18 [M+H]⁺.

Step C6i. To a biphasic mixture of the compound from step C6h (0.252 g, 0.979 mmol) in CCl₄—CH₃CN—H₂O (3/4/5, 12 mL) at rt was added RuCl₃·xH₂O (4.1 mg, 0.020 mmol), followed by NaIO₄ (0.419 g, 1.959 mmol). The resulting mixture was stirred at rt for 2 hours. The volatiles were evaporated. The residue was taken up in EtOAc and filtered. The filtrate was washed with brine, dried (Na₂SO₄) and filtered. The solid from the filtration was dissolved in diluted brine, acidified to pH ~2 and extracted with EtOAc. The combined organics were washed with brine, dried (Na₂SO₄), filtered and evaporated. The residue was purified by chromatography (silica, EtOAc-MeOH) to give the desired compound as a colorless oil (0.260 g, 98%). ESIMS m/z=272.24 [M+H]⁺.

Step C6j. The desired compound was prepared from the compounds of step C6i and 2,4'-dibromoacetophenone using the procedures similar to that described in Intermediate C2. ESIMS m/z=448.48, 450.48 [M+H]⁺.

Intermediate C7

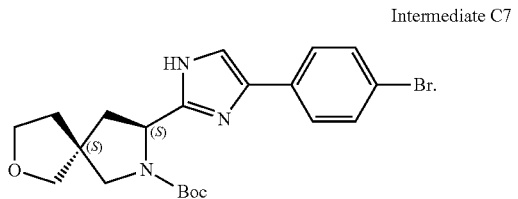

The desired compound was prepared from the minor diastereomer of step C6b using the procedures similar to that described in Intermediate C6. ESIMS m/z=470.31, 472.31 [M+Na]⁺.

Intermediate C8

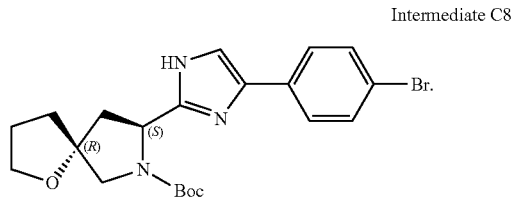

The desired compound was prepared from the minor diastereomer of step C1a using the procedures similar to that described in Intermediate C1. ESIMS m/z=470.30, 472.30 [M+Na]⁺.

Intermediate C9

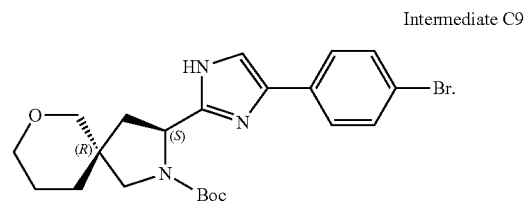

Step C9a. To a solution of the minor diastereomer from step A18b (1.380 g, 4.580 mmol) in THF (25 mL) at rt was added 9-BBN (0.5 M in THF, 22.90 mL, 11.45 mmol). The resulting mixture was stirred at rt for 5 hours before another batch of 9-BBN (0.5 M in THF, 36.64 mL, 18.32 mmol) was added. The solution was stirred at rt for 15 hours. H₂O (~40 mL) was added, followed by NaBO₃·4H₂O (9.642 g, 59.53 mmol). The mixture was stirred at rt for 2 hours before being partitioned (EtOAc—H₂O). The aqueous layer was back-extracted with EtOAc. The combined organics were washed with brine, dried (Na₂SO₄), filtered and evaporated. The residue was purified by flash column chromatography (silica, hexanes-EtOAc) to give (3R,6S,7aS)-6-(hydroxymethyl)-6-(3-hydroxypropyl)-3-phenyltetrahydropyrrolo[1,2-c]oxazol-5(1H)-one as a colorless oil (1.140 g, 85%). ESIMS m/z=292.15 [M+H]⁺.

Step C9b. Into a solution of the compound from step C9a (957 mg, 3.28 mmol), Ag₂O (1.14 g, 4.92 mmol) and NaI (110 mg, 0.63 mol) in DCM (10 mL) was added a solution of TsCl (688 mg 3.61 mmol) in DCM (5 mL) dropwise. The resulting mixture was stirred for 16 hours at room temperature before being passed through a pad of Celite. The filtrate was concentrated. The residue was purified by flash column chromatography (silica, EtOAc-hexanes) to afford the desired compound as a yellow solid (745 mg, 51%). ESIMS m/z=446.23 [M+H]⁺.

Step C9c. Into a solution of the compound from step C9b (745 mg, 1.67 mmol) in THF (35 mL) was added NaH (180 mg, 4.5 mmol). The resulting mixture was heated at 30° C. for 16 hours before being allowed to cool down and quenched with ice/water. The mixture was partitioned (EtOAc—H₂O). The organic phase was separated, dried (Na₂SO₄) and concentrated to afford an oil, which was purified by flash column chromatography (silica, EtOAc-hexanes) to afford the desired compound as a white solid (402 mg, 88%). ESIMS m/z=274.16 [M+H]⁺.

Step C9d. Into a solution of the compound from step C9c (405 mg, 1.47 mmol) in THF (5 mL) was added LiAlH₄ (1 M in THF, 3 mL, 3 mmol). The resulting mixture was heated at 60° C. for 2 hours before being allowed to cool down. H₂O (0.1 mL), NaOH (10%, 0.15 mL) and H₂O (0.5 mL) were added in sequence. The resulting suspension was passed through a pad of Celite. The filtrate was partitioned (H₂O—EtOAc). The organic phase was separated, dried (Na₂SO₄) and concentrated. The residue was purified by flash column chromatography (silica, EtOAc-hexanes) to afford the desired compound as a colorless oil (337 mg, 88%). ESIMS m/z=262.16[M+H]⁺.

Step C9e. Into a solution of the compound from step C9d (337 mg, 1.29 mmol) in MeOH (6 mL) was added Pd/C (10%, 30 mg). The resulting mixture was stirred under H₂ (60 psi) for 6 hours before being filtered through a pad of Celite. The filtrate was concentrated to give a colorless oil and was used directly for next step. ESIMS m/z=172.13[M+H]$^+$.

Step C9f. Into a solution of the compound from step C9e (1.29 mmol at most) and NaHCO$_3$ (650 mg, 8 mmol) in H$_2$O (4 mL) and dioxane (2 mL) was added Boc$_2$O (340 mg, 1.55 mmol). The resulting solution was stirred at room temperature overnight before the volatiles were evaporated. The crude product was partitioned (EtOAc—H$_2$O). The organic phase was separated, dried (Na$_2$SO$_4$) and concentrated. The residue was purified by flash column chromatography (silica, EtOAc-hexanes) to afford the desired compound as a white solid (305 mg, 87% over two steps). ESIMS m/z=272.18 [M+H]$^+$.

Step C9g. Into a solution of the compound from step C9f (305 mg, 1.22 mmol) and RuCl$_3$.xH$_2$O (4.6 mg, 0.0225 mmol) in CCl$_4$ (3 mL)/ACN (4 mL)/H$_2$O (5 mL) was added NaIO$_4$ (477 mg, 2.24 mmol). The resulting mixture was stirred at room temperature for 2 hours before being filtered through a pad of Celite. The filtrate was partitioned (EtOAc—H$_2$O). The organic phase was separated, dried (Na$_2$SO$_4$) and concentrated to afford an oil (330 mg), which was used directly in the next step. ESIMS m/z=230.11 [M+H-56]$^+$ Step C9h. The desired compound was prepared from the compound of step C9g using the procedures similar to that described in Intermediate C1. ESIMS m/z=462.37, 464.37 [M+H]$^+$.

Intermediate C10

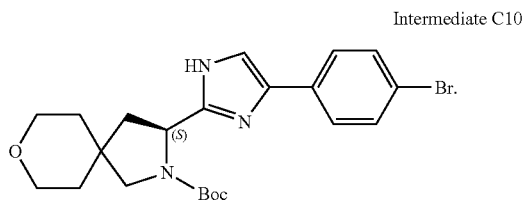

Step C10a. To a solution of (+)-(3R,7aS)-tetrahydro-3-phenyl-3H,5H-pyrrolo[1,2-c]oxazol-5-one (2.10 g, 9.85 mmol) in THF (60 mL) at −78° C. was added LiHMDS (1 M in THF, 39.4 mL, 39.4 mmol). The resultant mixture was kept at −78° C. for 30 minutes before slow addition of allyl bromide (5.0 mL, 59.1 mmol). The reaction was allowed to gradually warm up to 0° C. and quenched by aqueous NH$_4$Cl solution. The volatiles were evaporated and the residue was partitioned (EtOAc—H$_2$O). The organics were dried (Na$_2$SO$_4$), filtered and evaporated. The residue was purified by chromatography (silica, hexanes-ethyl acetate) to give the desired diallylation compound as a very light yellow oil (2.30 g, 78%). ESIMS m/z=284.16 [M+H]$^+$.

Step C10b. A stream of ozone, generated from an ozone generator, was bubbled through a solution of the compound from step C10a (2.30 g, 8.11 mmol) in MeOH (85 mL) at −78° C. until the appearance of blue color. The extra Ozone was removed by the oxygen flow before the addition of NaBH$_4$ (2.46 g, 64.9 mmol) at −78° C. The mixture was gradually warmed up to rt for and kept at rt for 16 hours before being quenched by 2M aqueous HCl to pH 5. The volatiles were evaporated off and the residue was partitioned (EtOAc—H$_2$O). The organics were dried (Na$_2$SO$_4$), filtered and evaporated. The residue was purified by chromatography (silica, hexanes-ethyl acetate) to give the desired compound as a colorless oil (1.61 g, 68%). ESIMS m/z=292.15 [M+H]$^+$.

Step C10c. Into a mixture of the compound from step C10b (1.52 g, 5.21 mmol), Ag$_2$O (1.81 g, 7.80 mmol) and KI (0.173 g, 1.04 mmol) in CH$_2$Cl$_2$ (40 mL) was added TsCl (1.09 g, 5.73 mmol) in CH$_2$Cl$_2$ (20 mL) slowly. The resultant mixture was stirred at rt for 24 hours before being filtered through Celite. The filtrates were evaporated and the residue was purified by chromatography (silica, hexanes-ethyl acetate) to give the desired compound as a colorless oil (1.38 g, 60%) with the recovery of the compound from step 568b (0.473 g, 31%). ESIMS m/z=446.07 [M+H]$^+$.

Step C10d. Into a solution of the compound from step C10c (1.38 g, 3.11 mmol) in THF (62 mL) was added NaH (60% in mineral oil, 0.187 g, 4.67 mmol). The resultant mixture was stirred at rt for 24 hours before being quenched by aqueous NH$_4$Cl. The volatiles were evaporated and the residue was partitioned (EtOAc—H$_2$O). The organics were dried (Na$_2$SO$_4$), filtered and evaporated. The residue was purified by chromatography (silica, hexanes-ethyl acetate) to give the desired compound as a colorless oil (0.726 g, 86%). ESIMS m/z=274.10 [M+H]$^+$.

Step C10e. Into a solution of the compound from step C10d (0.726 g, 2.66 mmol) in THF (50 mL) was added LiAlH$_4$ (1M in THF, 5.3 mL, 5.32 mmol). The resultant mixture was heated to 60° C. for 3 hours before being quenched by sequential addition of H$_2$O (0.20 mL), 15% aqueous NaOH (0.20 mL) and H$_2$O (0.60 mL) at 0° C. The mixture was passed through Celite and the filtrates were evaporated. The residue was partitioned (EtOAc—H$_2$O) and the organics were dried (Na$_2$SO$_4$), filtered and evaporated. The residue was purified by chromatography (silica, hexanes-ethyl acetate) to give the desired compound as a colorless oil (0.718 g). ESIMS m/z=262.21 [M+H]$^+$.

Step C10f. Into a mixture of compound from step C10e (2.66 mmol at most) and AcOH (0.30 mL, 5.32 mmol) in MeOH (16 mL) was added palladium (10 wt % on carbon, 54.8 mg). The resulting mixture was hydrogenated under 60 psi H$_2$ at rt for 4 hours before being filtered through Celite. The filtrate was concentrated to give the crude desired compound as a colorless oil (0.782 g). ESIMS m/z=172.17 [M+H]$^+$.

Step C10g. Into a mixture of the crude compound from step C10f (2.66 mmol at most) and NaHCO$_3$ (1.79 g, 21.3 mmol) in 1,4-dioxane (10 mL) and H$_2$O (20 mL) was added Boc$_2$O (0.696 g, 3.19 mmol). The resultant mixture was stirred at rt for 1 day before being evaporated to dryness. The residue was partitioned (EtOAc—H$_2$O) and the organics were dried (Na$_2$SO$_4$), filtered and evaporated. The residue was purified by chromatography (silica, hexanes-ethyl acetate) to give the desired compound as a colorless oil (0.610 g, 3 step 85%). ESIMS m/z=272.26 [M+H]$^+$.

Step C10h. Into a solution of the compound from step C10g (0.610 g, 2.25 mmol) in carbon tetrachloride (9 mL), CH$_3$CN (12 mL) and H$_2$O (15 mL) were added RuCl$_3$.XH$_2$O (9.3 mg, 45.0 μmol) and NaIO$_4$ (0.963 g, 4.50 mmol). The resultant mixture was stirred at rt for 4 hours before being partitioned (CH$_2$Cl$_2$—H$_2$O). The aqueous phase was acidified to pH 3 and was extracted by CH$_2$Cl$_2$. The combined organics were dried (Na$_2$SO$_4$), filtered and evaporated to give the crude desired compound as a light brown foam (0.640 g). ESIMS m/z=286.24 [M+H]$^+$.

Step C10i. The desired compound was prepared from the compound of step C10h using the procedures similar to that described in Intermediate C1. ESIMS m/z=462.26, 464.26 [M+H]$^+$.

Intermediate F1

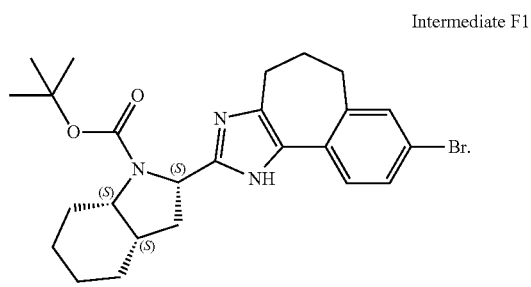

Step F1a. A solution of 2-bromo-6,7,8,9-tetrahydro-5H-benzo[7]annulen-5-one (480 mg, 2 mmol) in acetic acid (10 mL) was treated with bromine (102 µL, 2 mmol) for 2 hour at rt before partition (EtOAc—water). The organics were washed with NaHCO$_3$, brine, dried (Na$_2$SO$_4$), filtered and evaporated to give the desired compound as a yellow solid (750 mg), which was used directly in the next step.

Step F1b. A solution of the crude compound from step F1a (732 mg) and (2S,3aS,7aS)-1-(tert-butoxycarbonyl)octahydro-1H-indole-2-carboxylic acid (620 mg, 2.3 mmol) in acetonitrile (10 mL) was treated with DIPEA (1.2 mL) for 7 hours at 60° C. before being cooled and concentrated. The residue was purified by chromatography (silica, hexanes-EtOAc) to give the desired compound as yellow foam (266 mg, 22%). ESIMS m/z=506.07, 508.07 [M+H]$^+$.

Step F1c. A solution of the compound from step F1b (266 mg, 0.525 mmol) in toluene (10 mL) was treated with NH$_4$OAc (445 mg 5.77 mmol) for 12 hour at 125° C. before cooling and partition (EtOAc-H$_2$O), the organic phase was washed with H$_2$O, aqueous NaHCO$_3$, brine, dried and concentrated. The residue was purified by chromatography (silica, hexanes-EtOAc) to give the desired compound as a light yellow foam (39 mg, 15%). ESIMS m/z=486.13, 488.13 [M+H]$^+$.

Intermediate F2

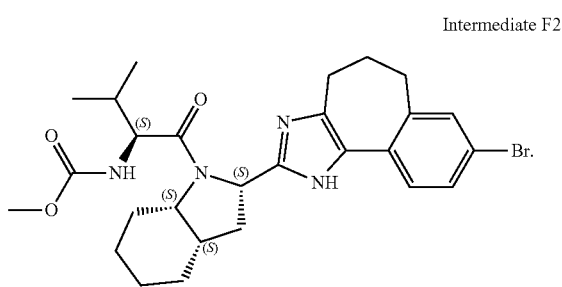

Step F1a. A solution of Intermediate F1 (39 mg, 0.08 mmol) in CH$_2$Cl$_2$ (2 mL) was treated with HCl in 1,4-dioxane (4 M, 0.5 mL) for 1 hour. The volatiles were evaporated off to give the crude desired compound as a yellow solid which was directly used in the next step. ESIMS m/z=385.99, 387.99 [M+H]$^+$.

Step F2b. A mixture of the crude compound from step F2a (0.08 mmol at most) and the compound from step A9b, 15.4 mg, 0.088 mmol) in DCM (3 mL) was treated with HATU (32 mg, 0.084 mmol) in the presence of DIPEA (0.5 mL) for 2 hours at rt. The volatiles were evaporated off to provide brownish syrup, which was purified by flash column chromatography (silica, EtOAc-Hexanes) to give the desired compound as a light yellow oil (37 mg, 85% 2 steps). ESIMS m/z=543.16, 545.16 [M+H]$^+$.

Intermediate F3

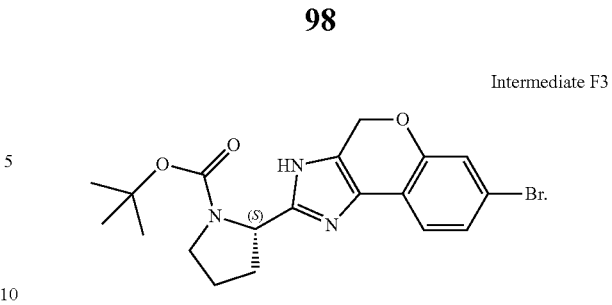

Step F3a. A mixture of 7-bromochroman-4-one (2.50 g, 11.01 mmol) and NaOAc (2.71 g, 33.04 mmol) in EtOH (20 mL) and H$_2$O (20 mL) was treated with hydroxylamine hydrochloride (1.15 g, 16.52 mmol) under reflux for 25 minutes before H$_2$O (50 ml) was added. After being cooled at 0° C. for 2 hours, the yellow solid precipitate was collected by filtration to give the crude desired compound (2.2 g, 83%), which was used directly in next step.

Step F3b. A solution of the crude compound from step F3a (9.10 mmol at most) in CH$_2$Cl$_2$ (80 mL) was treated with p-toluenesulfonyl anhydride (3.24 g, 10 mmol) in the presence of TEA (1.71 mL, 10.9 mmol) for 2 hour at rt before partition (CH$_2$Cl$_2$—water). The organics were washed with brine, dried (Na$_2$SO$_4$), filtered and evaporated to give the desired compound as a yellow solid (3.38 g, 94%), which was used directly in next step.

Step F3c. Potassium ethoxide (24% w/w in EtOH, 3.41 mL, 8.96 mmol) and H$_2$O (0.6 mL) were added into a solution of the crude compound from step F3b (3.38 g, 8.53 mmol) in EtOH (18 mL) and toluene (36 mL). It was stirred for 19 hours at rt before HCl (4N in dioxane, 8 mL) was added at 0° C. Stirring was continued for 0.5 hour. It was concentrated. The resulting solid was stirred in diethyl ether (50 mL) for 2 h before filtration to give the crude desired compound as a yellow solid (3.11 g), which was used directly in the next step. ESIMS m/z=242.05, 244.05 [M+H]$^+$.

Step F3d. A solution of the crude compound from step F3c (557 mg, 2 mmol) and N-methyl morpholine (0.48 mL, 4.4 mmol) in DMF (4 mL) was treated with a pre-made solution of N-Boc-proline (430 mg, 2 mmol), HATU (760 mg, 2 mmol) and N-methyl morpholine (0.48 mL, 4.4 mmol) in DMF (4 mL) for 2 hour at rt before partition (EtOAc-H$_2$O). The organic phase was washed with H$_2$O, aqueous NaHCO$_3$, aqueous NH$_4$Cl, brine, dried and concentrated. The residue was purified by chromatography (silica, hexanes-EtOAc) to give the desired compound as a light yellow solid (525 mg, 60%). ESIMS m/z=461.21, 463.21 [M+Na]$^+$.

Step F1e. A solution of the compound from step F3d (730 mg, 1.66 mmol) in xylene (10 mL) was treated NH$_4$OAc (1.28 g, 16.6 mmol) for 4 hour at 130° C. before cooling and partition (EtOAc-H$_2$O). The organic phase was washed with H$_2$O, aqueous NaHCO$_3$, brine, dried and concentrated. The residue was purified by chromatography (silica, hexanes-EtOAc) to give the desired compound as a light yellow foam (324 mg, 46%). ESIMS m/z=442.21, 444.21 [M+Na]$^+$.

Intermediate F4

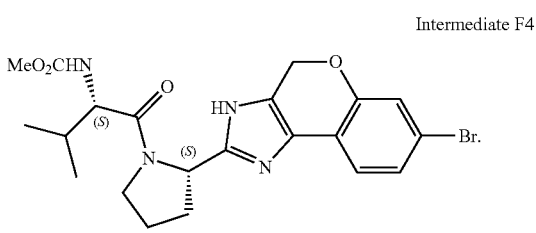

Step F4a. A solution of Intermediate F3 (121 mg, 0.29 mmol) in CH$_2$Cl$_2$ (2 mL) was treated with HCl in 1,4-dioxane (4 M, 1 mL) for 1 hour. The volatiles were evaporated off to give the crude desired compound as a yellow solid which was directly used in the next step. ESIMS m/z=319.96, 321.96 [M+H]$^+$.

Step F4b. A mixture of the crude compound from step F4a (0.29 mmol at most) and the compound from step A8b (55 mg, 0.32 mmol) in CH$_2$Cl$_2$ (3 mL) was treated with HATU (121 mg, 0.32 mmol) in the presence of DIPEA (0.5 mL) for 2 hours at rt. The volatiles were evaporated off to provide a brown syrup, which was purified by flash column chromatography (silica, EtOAc-Hexanes) to give the desired compound as a light yellow solid (140 mg, 100% 2 steps). ESIMS m/z=477.22, 479.22 [M+H]$^+$.

Intermediate F5

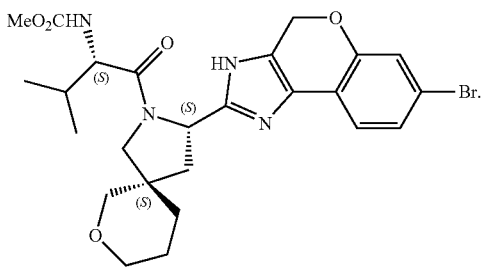

Step F5a. To a solution of LiHMDS (1.0 M in THF, 5.17 mL, 5.17 mmol) in THF (20 mL) at −78° C. was added a solution of (+)-(3R,7aS)-tetrahydro-3-phenyl-3H,5H-pyrrolo[1,2-c]oxazol-5-one (0.500 g, 2.460 mmol) in THF (10 mL) under N$_2$. The mixture was stirred at −78° C. for 30 min before ClCO$_2$Me (0.19 mL, 2.460 mmol) was added at −78° C. After 30 minutes at −78° C., the reaction was quenched with saturated NH$_4$Cl solution. The mixture was allowed to warm up to rt and the volatiles were evaporated. The residue was partitioned (EtOAc—H$_2$O). The organics were washed with brine, dried (Na$_2$SO$_4$), filtered and evaporated. The residue was purified by chromatography (silica, hexanes-ethyl acetate) to give the desired compound as a colorless oil (0.598 g, 93%). ESIMS m/z=262.13 [M+H]$^+$.

Step F5b. To a solution of the compound from step F5a (0.350 g, 1.340 mmol) in THF (13 mL) at 0° C. was added Na (60% in mineral oil, 64.3 mg, 1.607 mmol). After addition, the cooling bath was removed. The mixture was stirred at rt for 15 minutes before allyl bromide (0.13 mL, 1.474 mmol) was added. After 1 hour at rt, the reaction was quenched with saturated NH$_4$Cl solution. The mixture was partitioned (EtOAc—H$_2$O). The organics were washed with brine, dried (Na$_2$SO$_4$), filtered and evaporated. The residue was purified by chromatography (silica, hexanes-ethyl acetate) to give the desired compounds as two separated diastereomers: minor diastereomer (less polar, 56.0 mg, 14%), (3R,6R,7aS)-methyl 6-allyl-5-oxo-3-phenylhexahydropyrrolo[1,2-c]oxazole-6-carboxylate, ESIMS m/z=302.19 [M+H]$^+$; $^1$H NMR (CDCl$_3$) 7.44-7.33 (m, 5H), 6.32 (s, 1H), 5.75-5.66 (m, 1H), 5.19-5.18 (m, 1H), 5.16 (s, 1H), 4.28-4.22 (m, 2H), 3.78 (s, 3H), 3.57-3.52 (m, 1H), 2.90 (dd, J=6.7, 13.4 Hz, 1H), 2.85 (dd, J=7.9, 14.1 Hz, 1H), 2.58 (dd, J=6.7, 14.1 Hz, 1H), 1.89 (dd, J=6.6, 13.2 Hz, 1H); major diastereomer (more polar, 0.222 g, 55%), (3R,6S,7aS)-methyl 6-allyl-5-oxo-3-phenylhexahydropyrrolo[1,2-c]oxazole-6-carboxylate, ESIMS m/z=302.19 [M+H]$^+$; $^1$H NMR (CDCl$_3$) 7.46-7.33 (m, 5H), 6.33 (s, 1H), 5.82-5.73 (m, 1H), 5.23-5.18 (m, 2H), 4.28 (dd, J=6.2, 6.5 Hz, 1H), 4.08-4.02 (m, 1H), 3.82 (s, 3H), 3.67 (t, J=8.3 Hz, 1H), 2.80 (dd, J=7.5, 14.0 Hz, 1H), 2.71 (dd, J=7.1, 14.0 Hz, 1H), 2.54 (dd, J=4.9, 12.8 Hz, 1H), 2.38 (dd, J=7.9, 13.8 Hz, 1H).

Step F5c. The desired proline analog, (3S,5S)-2-(tert-butoxycarbonyl)-7-oxa-2-azaspiro[4.5]decane-3-carboxylic acid, was prepared from the major diastereomer in step F5b using procedures similar to that described in steps C9a to C9g. ESIMS m/z=308.40 [M+Na]$^+$ (weak).

Alternatively, the desired compound of step F5c was prepared by steps F5d to F5j.

Step F5d. Into a 12 L flask fitted with a mechanical stirrer and a thermometer was charged THF (1.2 L). It was cooled to −20° C. NaHMDS (1.0 M in THF, 3.00 L, 3.00 mol) was added over 10 minutes. The solution was cooled down to −20° C. A solution of (+)-(3R,7aS)-tetrahydro-3-phenyl-3H, 5H-pyrrolo[1,2-c]oxazol-5-one (290.0 g, 1.427 mol) in THF (400 mL) was added through an addition funnel over 15 minutes. The resulting orange solution was stirred at −20° C. for 20 minutes under N$_2$. ClCO$_2$Me (110.3 mL, 1.427 mol) was added dropwise over 45 minutes while keeping the internal temperature below −20° C. The resulting solution was stirred at −20° C. for 20 minutes. 3-Bromo-1-chloropropane (564.4 mL, 5.708 mol) was added over 5 minutes. The mixture was allowed to warm up and heated to 65° C. The mixture was stirred at 65° C. for 4 hours before being allowed to cool down and stand at rt overnight. The suspension was cooled with an ice-water bath. A few crystals of bromocresol purple were added. Acetic acid was added slowly until the blue tone of the mixture disappeared (~0.8 mL added). Saturated NaHCO$_3$ solution (300 mL) was added. The mixture was allowed to warm up to rt. The clear top layer was decanted, washed with brine (*2), dried (Na$_2$SO$_4$), filtered and evaporated. The bottom layer in the flask was combined with the brine washes, diluted with water and extracted with EtOAc (×1). The organic layer was washed with brine (×1), dried (Na$_2$SO$_4$), filtered and evaporated. All the residues were combined and split into 4 portions, which were purified by flash column chromatography (1.5 KG silica gel column, 0-60% ethyl acetate in hexanes) to afford the desired compound as a yellow waxy solid (320.0 g, 66%). ESIMS m/z=338.20 [M+H]$^+$.

Step F5e. Into a 5 L flask fitted with a mechanical stirrer and a thermometer was charged MeOH (1.8 L). It was cooled down to −10° C. CaCl$_2$ (118.3 g, 1.066 mol) was added over 2 minutes. The solution was cooled back to −10° C. The powder of the compound from step F5d (120.0 g, 0.552 mol) was added over 3 minutes. The mixture was stirred at −10° C. for 20 minutes. The compound powder was not completely dissolved. NaBH$_4$ (24.190 g, 0.6394 mol) was added in 4 equal portions every 15 minutes while maintaining the internal temperature below −5° C. After addition, the milky suspension was stirred at −10° C. for 40 minutes. Saturated NH$_4$Cl solution (200 mL) was added carefully while maintaining the internal temperature below 0° C. The mixture was diluted with EtOAc (2 L). More saturated NH$_4$Cl solution (~6 L) and water (1 L) were added to get a clear mixture. The layers were separated. The aqueous layer was extracted with EtOAc (4 L×2). The organic layers were combined, washed with brine (×1), dried ($Na_2SO_4$), filtered and evaporated. The residue was purified by filtering through a short pad of silica gel (800 g) to afford the desired compound as a clear yellow-green oil (94.0 g, 85%). ESIMS m/z=310.24 $[M+H]^+$.

Step F5f. Into a solution of NaHMDS (1.0 M in THF, 1.13 L, 1.13 mol) in THF (3.5 L) at 5° C. was added a solution of the compound from step F5e (290 g, 0.936 mol) in THF (1 L) over 2 hours. The resulting mixture was allowed to warm up to rt and stirred at rt for 1 hour. It was cooled back to 5° C. with an ice-water bath and aqueous saturated $NH_4Cl$ solution was added to adjust the pH of the solution to ~7. The mixture was diluted with EtOAc (8 L) and washed with water, brine (×2). The combined aqueous layers were extracted with EtOAc (4 L) and washed with brine. The combined organics were dried ($Na_2SO_4$), filtered and evaporated. The residue was recrystallized from EtOAc-Hexanes to afford the desired compound as a white solid (207.7 g). The mother liquid was concentrated and purified by flash column chromatography (750 g silica gel, 0~100% ethyl acetate in hexanes) to afford another crop (18.0 g) of the desired product as a white solid. ESIMS m/z=274.26 $[M+H]^+$.

Step F5g. Into a 12 L flask fitted with a mechanical stirrer and a thermometer was charged the compound from step F5f (325.0 g, 1.189 mol) and THF (3.25 L) at rt. $LiAlH_4$ (1.0 M in THF, 1.427 L, 1.427 mol) was added through an addition funnel over 40 minutes. After addition, the resulting mixture was heated to 60° C. and stirred at 60° C. for 2 hours before being allowed to cool down with an ice-water bath. The reaction was quenched carefully by $H_2O$ (54.15 mL), followed by 15% NaOH solution (54.15 mL) and then $H_2O$ (162.45 mL). The resulting suspension was filtered through a short pad of Celite, washing with THF (2 L). The filtrate was evaporated. The residue was further purified by filtering through a short pad of silica gel (700 g) with EtOAc/MeOH (95/5) to give the desired compound as a yellow solid (277.7 g, 89%). ESIMS m/z=262.26 $[M+H]^+$.

Step F5h. Into a solution of the compound from step F5g (286.0 g, 1.094 mol) in MeOH (1.4 L) at rt was added 10% $Pd(OH)_2/C$ (10 wt %, 28.6 g), followed by $(Boc)_2O$ (286.6 g, 1.313 mol). The resulting mixture was purged with hydrogen 3 times and stirred at rt under hydrogen (60 psi) for 4 hours before being filtered through a short pad of Celite. The filtrate was evaporated. The residue was purified by flash column chromatography (2×750 g silica gel column, 10~100% ethyl acetate in hexanes) to afford the desired compound as a colorless oil (285.0 g, 96%). ESIMS m/z=272.23 $[M+H]^+$.

Step F5i. Preparation of Jones reagent (2.54 M chromium trioxide in 4.1M sulfuric acid): To a flask containing $H_2O$ (3.2 L) was charged portionwise solid $CrO_3$ (2.14 kg, 21.4 mol, highly toxic!) with stirring. Under cooling (ice-water bath), it was slowly charged 95~98% $H_2SO_4$ (1.84 L) via a dropping funnel during which period the temperature increased up to 35° C. Upon cooling to about 15° C., it was further charged more $H_2O$ (2.96 L) to give about 8.4 L of the Jones reagent at the concentration of about 2.54 M.

Step F5j. A solution of the compound from step F5h (285.0 g, 1.050 mol) in acetone (2.5 L) was cooled to below 5° C. Jones reagent from step F5i (2.54M chromium trioxide in 4.1M sulfuric acid, 500 mL, about 1.2 equiv.) was added over 60 minutes while the internal temperature gradually rising up to 30° C. 15 minutes after finishing the addition, more Jones reagent (41 mL, about 0.1 equiv.) was added. The ice-water bath was then removed. The suspension was stirred at rt for 30 minutes. The reaction was quenched by adding isopropanol (300 mL) over 15 minutes. The mixture was stirred at rt for 15 minutes to give an upper clear solution and a lower layer of solid. The upper clear solution was decanted and concentrated to leave an oil-like residue which contained most of the product. The solid was dissolved in water (2.5 L) and combined with the above concentrated residue oil. The mixture was extracted with toluene (2 L), and then toluene/EtOAc (1/1, 0.8 L). The combined organic layers were washed with brine (0.7 L) to give the crude product solution in toluene. The toluene solution containing the product was extracted three times with 1 M NaOH (1 L*1, 0.5 L*2). The combined aqueous extracts were cooled with an ice-water bath. 6 M HCl was added while maintaining the internal temperature below 20° C. until pH ~2 (about 380 mL added). The mixture was extracted with EtOAc (1.5 L*1, 2 L*1). The combined organic layers were washed with brine, dried over $Na_2SO_4$, filtered and concentrated. The residue was azeotropically evaporated with toluene (*3) and xylenes (*2), dried under vacuum to afford the desired compound as an off-white solid (218.7 g, 73%). ESIMS m/z=308.25 $[M+Na]^+$ (weak).

Step F5k. The desired compound was prepared from the compounds of steps F5a and F3c using procedures similar to that described in Intermediates F3 and F4. ESIMS m/z=547.22, 549.22 $[M+H]^+$.

Intermediate F6

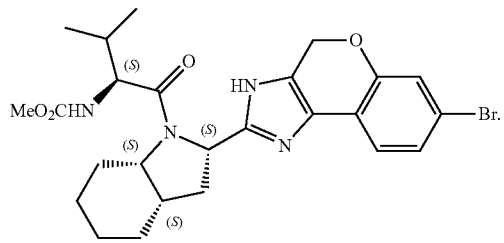

The desired compound was prepared from the compounds of step F3c and (2S,3aS,7aS)-1-(tert-butoxycarbonyl)octahydro-1H-indole-2-carboxylic acid using procedures similar to that described in Intermediates F3 and F4. ESIMS m/z=531.42, 533.42 $[M+H]^+$.

Intermediate F7

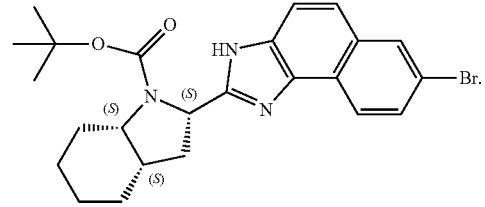

Step F7a. To a solution of (2S,3aS,7aS)-1-(tert-butoxycarbonyl)octahydro-1H-indole-2-carboxylic acid (3.18 g, 11.8 mmol) and commercially available 6-bromonaphthalene-1,2-diamine (3.08 g, 13.0 mmol) in acetonitrile (100 mL) was added EDC.HCl (2.96 g, 15.5 mmol), followed by DMAP (144 mg, 1.18 mmol). The mixture was stirred at rt overnight and concentrated to afford a dark syrup, which was purified by chromatography (silica, EtOAc-hexanes) to afford the desired compounds (a mixture of regio-isomers) as a dark brown oil (5.42 g, 94%). ESIMS m/z=488.14, 490.14 [M+H]⁺.

Step F7b. A solution of the compounds from step F7a in acetic acid (50 mL) was heated at 60° C. for 1 hour before cooling. It was concentrated before being partitioned between H₂O and EtOAc. The organic phase was washed with aqueous NaHCO₃, brine, dried (Na₂SO₄), and concentrated. The residue was purified by chromatography (silica, EtOAc-hexanes) to afford the desired compound as a yellow solid (5.42 g, 95%). ESIMS m/z=470.18, 472.18 [M+H]⁺.

Intermediate F8

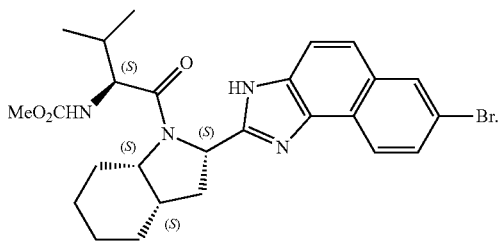

Step F8a. A solution of Intermediate F7 (3.94 g, 8.37 mmol) in CH₂Cl₂ (30 mL) was treated with HCl in 1,4-dioxane (4 M, 10 mL) at rt for 1 hour. The volatiles were evaporated off to give the crude desired compound as a yellow solid, which was used directly in the next step. ESIMS m/z=370.08, 372.08 [M+H]⁺.

Step F8b. A mixture of the crude compounds from step F8a and A8b (1.61 g, 9.20 mmol) in CH₂Cl₂ (30 mL) was treated with HATU (3.25 g, 8.54 mmol) in the presence of DIPEA (8 mL) at rt for 3 hours and the volatiles were evaporated off. The crude product was purified by chromatography (silica, EtOAc-hexanes) to give the desired compound as a yellow solid (4.62 g, 100%). ESIMS m/z=527.16, 529.16 [M+H]⁺.

Intermediate F9

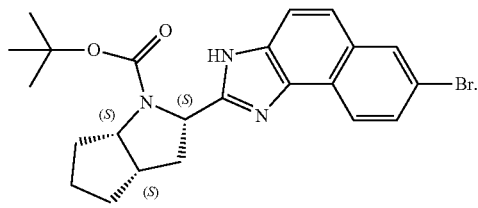

Step F9a. To a solution of benzyl (S,S,S)-2-azabicyclo [3.3.0]octane-3-carboxylate hydrochloride (5.000 g, 17.74 mmol) in dichloromethane (90 mL) at rt was added (Boc)₂O (4.066 g, 18.63 mmol) and DIPEA (6.80 mL, 39.04 mmol). The mixture was stirred at rt for 2 hours before being concentrated. The residue was purified by flash column chromatography (330 g silica gel column, 0-40% ethyl acetate in hexanes) to give the desired compound as a colorless oil (6.190 g, 100%).

Step F9b. To a solution of the compound from step F9a (6.190 g, 17.90 mmol) in MeOH (90 mL) at rt was added 20% Pd(OH)₂/C (25.1 mg, 0.2 mol %). The mixture was purged with hydrogen and stirred at rt under hydrogen (balloon) overnight before being filtered through a short pad of Celite. The filtrate was evaporated to give the desired compound as a colorless oil (7.820 g, 105%), which was used directly for the next step.

Step F9c. To a solution of the compound from step F9b (2.50 g, 9.79 mmol) and 6-bromonaphthalene-1,2-diamine (2.44 g, 10.3 mmol) in acetonitrile (100 mL) was added EDC.HCl (2.44 g, 12.7 mmol) and DMAP (119 mg, 0.979 mmol). The solution was stirred at rt overnight and concentrated to afford a dark syrup, which was purified by chromatography (silica, EtOAc-hexanes) to afford the desired compounds (a mixture of regio-isomers) as a dark brown oil (4.18 g, 90%). ESIMS m/z=474.12, 476.12 [M+H]⁺.

Step F9d. A solution of compounds (mixture of regio-isomers) from step F9c in acetic acid (50 mL) was heated at 60° C. for 1 h before being allowed to cool down. The mixture was concentrated before being partitioned between H₂O and EtOAc. The organic phase was separated, and washed with aqueous NaHCO₃ (*3), brine, dried (Na₂SO₄), and concentrated to afford a brown slurry, which was purified by chromatography (silica, EtOAc-hexanes) to afford the desired compound as a yellow foam (3.98 g, 98%). ESIMS m/z=478.16, 480.16 [M+Na]⁺.

Intermediate F10

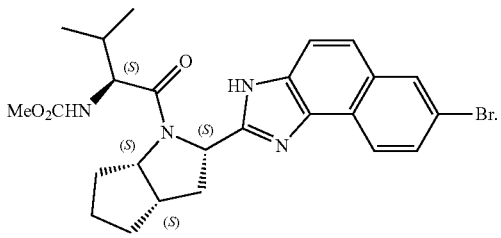

The desired compound was prepared from Intermediate F9 and the compound from step A8b using the procedures similar to that described in Intermediate F8. ESIMS m/z=356.11, 358.11 [M+H]⁺.

Intermediate F11

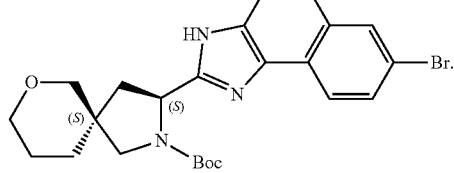

The desired compound was prepared from the compound of step F5c or F5j and 6-bromo-naphthalene-1,2-diamine using the procedures similar to that described in Intermediates F7 and F9. ESIMS m/z=486.51, 488.51 [M+H]⁺.

Intermediate F12

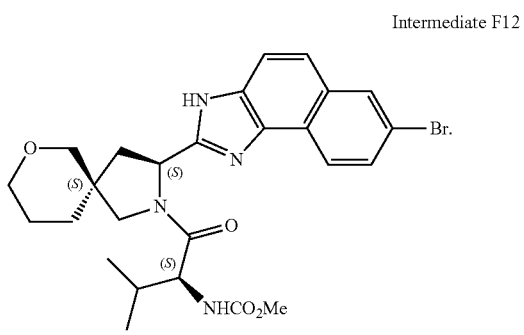

The desired compound was prepared from Intermediate F11 and the compound from step A8b using the procedures similar to that described in Intermediate F8. ESIMS m/z=543.25, 545.26 [M+H]+.

Intermediate F13

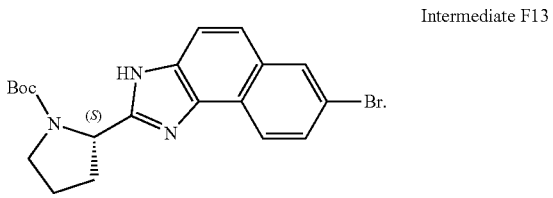

Step F13a. Into a solution of N-Boc-L-Proline (0.386 g, 1.79 mmol) and 6-bromo-naphthalene-1,2-diamine (0.425 g, 1.79 mmol) in acetonitrile (18 mL) was added EDC.HCl (0.447 g, 2.33 mmol) and DMAP (21.9 mg, 0.179 mmol). It was stirred at rt for 3 hours and concentrated to afford a dark syrup, which was purified by chromatography (silica, EtOAc-hexanes) to afford the desired compounds (a mixture of regio-isomers) as a dark brown oil (0.74 g, 95%). ESIMS m/z=434.07.14, 436.07 [M+H]+.

Step F13b. A solution of the compounds (a mixture of regio-isomers) from step F13a in acetic acid (8 mL) was heated at 60° C. for 2 hours before being cooled. It was concentrated before partition between H2O, EtOAc and DCM. The organic phase was washed with aqueous NaHCO3 (*2), brine, dried (Na2SO4), and concentrated. The residue was purified by chromatography (silica, EtOAc-hexanes) to afford the desired compound as a yellow solid (0.71 g, 100%). ESIMS m/z=438.14, 440.14 [M+Na]+.

Intermediate F14

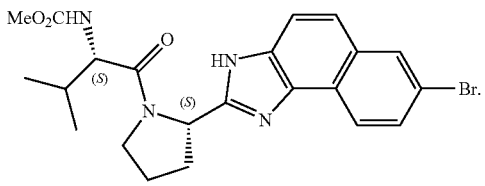

Step F14a. A solution of Intermediate F13 (0.71 g, 1.70 mmol) in CH2Cl2-MeOH (3:1, 6 mL) was treated with HCl in 1,4-dioxane (4 M, 12 mL) at rt for 2 hours. The volatiles were evaporated off to give the crude desired compound as a yellow solid, which was used directly in next step.
Step F14a. A mixture of the crude compounds from step F14a (1.70 mmol at most) and A8b (0.30 g, 1.70 mmol) in MeCN (17 mL) was treated with HATU (0.648 g, 1.70 mmol) in the presence of DIPEA (2.97 mL, 17.0 mmol) at rt for 1 hour. The volatiles were evaporated off. The crude was purified by chromatography (silica, EtOAc-hexanes) to give the desired compound as a yellow foam contaminated with tetramethylurea (0.92 g, 100%). ESIMS m/z=473.21, 475.21 [M+H]+.

Intermediate F15

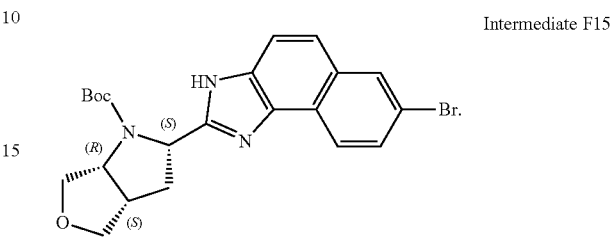

Step F15a. Into a solution of (2R,3aS,6aR)-1-(tert-butoxycarbonyl)hexahydro-1H-furo[3,4-b]pyrrole-2-carboxylic acid (prepared from (R)-5-phenylmorpholin-2-one and 2-(allyloxy)acetaldehyde by procedures similar to that described in JP 2009298713, 1.13 g, 4.4 mmol), benzyl alcohol (0.95 g, 8.8 mmol), DIPEA (2.27 g, 17.6 mmol) and DMAP (54 mg, 0.44 mmol) in CH2Cl2 (25 mL) was HATU (4.18 g, 11 mmol) at rt. The resulting solution was stirred at rt overnight. It was concentrated and the residue was purified by chromatography (silica, EtOAc-hexanes) to afford the desired product contaminated with benzyl alcohol (1.40 g, 78%). ESIMS m/z=370.25 [M+Na]+.

Step F15b. Into a solution of the compounds from step F15a (1.3 g) in CH2Cl2 (4 mL) was added 4N HCl solution in dioxane (6 mL, 24 mmol). The resultant mixture were stirred at rt for 1.5 hours before concentration. It was triturated with MBTE. The insoluble was dissolved in water (20 mL), basified with 10% Na2CO3 aqueous solution to PH 10. The mixture was then extracted with EtOAc. The organics were washed with brine, dried (Na2SO4), filtered and evaporated. The residue was purified by flash column chromatography (silica, EtOAc-hexanes) to give the desired compound as a colorless oil (0.77 g, 83%). ESIMS m/z=248.21 [M+H]+.

Step F15c. Into a mixture of the compound from step F15b (0.77 g, 3.11 mmol) and K2CO3 (94.6 mg, 0.684 mmol) in DMF (3 mL) in ice-water bath was added NCS (0.482 g, 3.61 mmol) in three portions. It was stirred at 0° C. for 1 hour before addition of DBU (0.79 g, 5.2 mmol). The mixture was slowly warmed up to rt and stirred overnight. The residue was partitioned (ether—H2O) and the organics were washed with water, brine, dried (Na2SO4), filtered and evaporated to give the desired compound as a colorless oil (0.75 g, 97%). ESIMS m/z=246.2 [M+H]+.

Step F15d. Into a solution of the compound from step F15c (0.170 g, 0.533 mmol) in EtOH (5 mL) were added Pd/C (5 wt % on carbon, 400 mg). The mixture was hydrogenated under 60 psi hydrogen gas at room temperature for 1 day before being filtered through a plug of Celite. The filter cake was washed with 40 mL MeOH. The filtrate was concentrated to give crude product as yellow oil (0.47 g, 95%). ESIMS m/z=158.13 [M+H]+.

Step F15e. Into a solution of the compound from step F15d (0.47 g, 3.0 mmol) in dioxane-H2O (6 mL-4 mL) at rt were added NaOH (156 mg, 3.9 mmol) and (Boc)2O (1.31 g, 6.0 mmol). The mixture was stirred at 35° C. overnight before partition (Et2O—H2O). The aqueous phase was acidified to pH ~2 at 0° C. and extracted with EtOAc. The organics were washed with brine, dried (Na₂SO₄), filtered and evaporated to give the crude desired compound as a colorless oil (0.24 g, 31%). ESIMS m/z=280.13 [M+Na]⁺.

Step F15f. The desired compound was prepared from the compound of step F15e and 6-bromo-naphthalene-1,2-diamine using procedures similar to that described in Intermediate F13. ESIMS m/z=458.15, 460.15 [M+H]⁺.

Intermediate F16

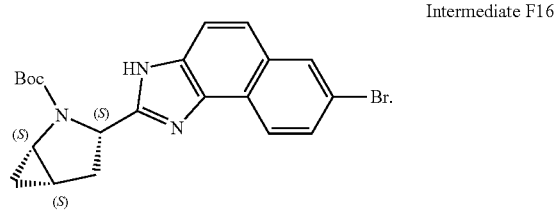

The desired compound was prepared from the compound of step A22e and 6-bromo-naphthalene-1,2-diamine using procedures similar to that described in Intermediate F7. ESIMS m/z=428.23, 430.23 [M+H]⁺.

Intermediate F17

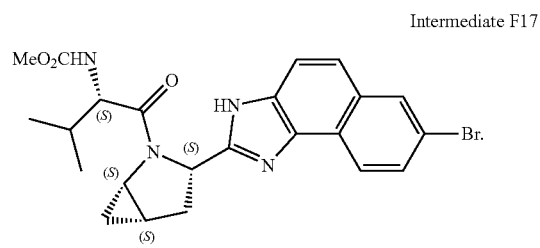

The desired compound was prepared from Intermediate F16 using procedures similar to that described in Intermediate F14. ESIMS m/z=485.23, 487.23 [M+H]⁺.

Intermediate F18

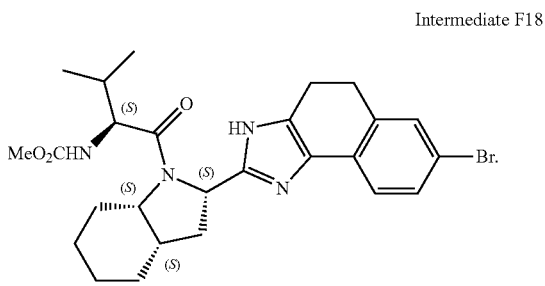

The desired compound was prepared from Boc-L-octahydroindole-2-carboxylic acid and 6-bromo-1-tetralone following the procedures similar to that described in Intermediate F2. ESIMS m/z=529.20, 531.20 [M+H]⁺.

Intermediate F19

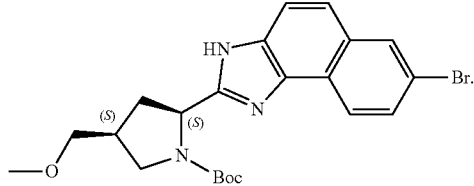

Step F19a. A solution of (S)-1-tert-butyl 2-methyl 4-methylenepyrrolidine-1,2-dicarboxylate (5.7 g, 23.6 mmol) in THF (50 mL) was treated with 9-BBN (0.5 M in THF, 71 mL, 35.5 mmoL) at rt for 5 hours before H₂O (50 mL) was added at 0° C. Sodium perborate (NaBO₃.H₂O, 12.3 g, 80 mmol) was added and the mixture was stirred overnight at rt. It was filtered through Celite and the filtrate was partitioned (EtOAc-H₂O). The organics were dried (Na₂SO₄), filtered and evaporated. The crude was purified by chromatography (silica, hexanes-ethyl acetate) to give the desired compounds as an diastereomeric mixture and as a colorless oil (4.20 g, 68%).

Step F19b. A solution of the compounds from step F19a (1.45 g, 5.6 mmol) in THF (15 mL) and H₂O (15 mL) was treated with LiOH (161 mg, 6.7 mmol) at rt for 4 hours before concentration. The residue was dissolved in water and acidified to pH 2 by HCl (4 M). It was extracted with EtOAc. The organics were dried (Na₂SO₄), filtered and evaporated to give the desired compounds as a white solid (1.30 g, 95%), which was used directly in the next step.

Step F19c. A solution of the compounds from step F19b (1.30 g, 5.3 mmol) in DMF (10 mL) was treated with NaH (60% w/w, 466 mg, 11.7 mmol) at 0° C. for 30 minutes before MeI (0.36 mL, 5.83 mmol) was added. It was stirred 1.5 hours at rt before being quenched with ice-water and extraction with MTBE. The aqueous was acidified to pH 2 by HCl (4 M) and extracted with EtOAc. The extracts were dried (Na₂SO₄), filtered and evaporated to give the desired compounds as an orange syrup (0.94 g, 68%), which is a mixture of inseparable diastereomers.

Step F19d. The desired compound was prepared and separated as a major product (more polar) from the compounds of step F19c and 6-bromo-naphthalene-1,2-diamine following the procedures similar to that described in Intermediate F7. ESIMS m/z=460.17, 462.17 [M+H]⁺.

Intermediate F20

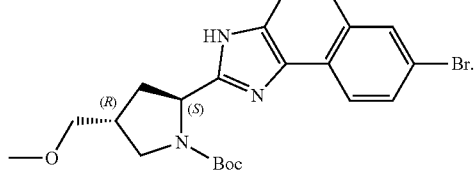

The desired compound was prepared and separated as a minor product (less polar) in step F19c. ESIMS m/z=460.13, 462.13 [M+H]⁺.

Intermediate F21

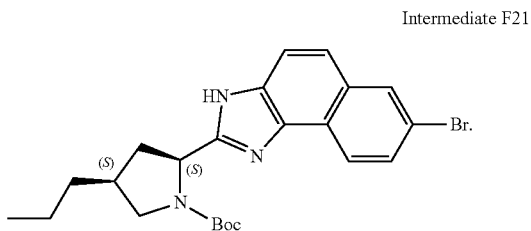

Step F21a. A suspension of (1-propyl)triphenylphosphonium bromide (6.16 g, 16 mmol) in THF (5 mL) was treated with potassium tert-butoxide (1M solution in THF, 16 mL, 16 mmol) at rt for 1.5 hours before (S)-1-(tert-butoxycarbonyl)-4-oxopyrrolidine-2-carboxylic acid (0.916 g, 4.0 mmol) in THF (5 mL) was added. It was stirred at rt for 16 hours. It was quenched with water (100 mL) and extracted with diethyl ether (2×100 mL). The aqueous layer was separated and acidified with aqueous potassium hydrogen sulfate at rt to pH 3, and extracted twice with ethyl acetate (100 mL). The organics was washed with brine and evaporated to give the crude desired compounds as a mixture of Z/E isomers. A solution of this crude in MeOH (20 mL) was treated with diazotrimethylsilylmethane (TMSCHN$_2$, 4.5 mL, 2.0 M in hexanes, 9.0 mmol) at rt for 0.5 hour. The volatiles were evaporated off and the residue was purified by chromatography (silica, EtOAc-hexanes) to give the desired compound as a mixture of Z/E isomers (0.88 g, 81%). ESIMS m/z=292.26 [M+Na]$^+$.

Step F21b. A mixture of the compound from step F21a (0.54 g, 2.0 mmol) and palladium (10% on carbon, 54 mg) was stirred at rt for 2 days under hydrogen (60 psi). It was filtered through Celite, the filtrate was concentrated to give the desired compound as a mixture of diastereomers (0.53 g, 97%).

Step F21c. A solution of the crude compound from step F21b (0.52 g, 1.91 mmol) in THF-H$_2$O (6 mL/2 mL) was treated with LiOH (0.16 g, 3.82 mmol) at room temperature for 72 hours. The volatile was evaporated off and the residue was diluted with water (10 mL) and extracted with ether (10 mL). The aqueous was acidified to a pH 3 with aqueous potassium hydrogen sulfate in ice-water bath. It was extracted with EtOAc. The extracts was dried with Na$_2$SO$_4$ and concentrated to afford the desired compounds as a white solid (0.46 g, 93%, cis/trans 3/1). ESIMS m/z=280.23 [M+Na]$^+$.

Step F21d. A solution of the compound from step F21c (0.20 g, 0.78 mmol) and 6-bromonaphthalene-1,2-diamine (0.19 g, 0.81 mmol) in acetonitrile (8 mL) was treated with EDC.HCl (0.19 g, 1.0 mmol) and DMAP (9.4 mg, 0.08 mmol) at rt overnight. It was concentrated to afford a dark syrup, which was purified by chromatography (silica, EtOAc-hexanes) to afford the desired compounds (mixture of regio-isomers and diastereomers) as a dark brown oil (0.30 g, 81%). ESIMS m/z=498.34, 500.34 [M+Na]$^+$.

Step F21e. A solution of the compounds from step F21d (0.29 g, 0.61 mmol) in acetic acid (4 mL) was heated at 60° C. for 1 hour. It was concentrated and the residue was partitioned between H$_2$O and EtOAc. The organic phase was separated, washed with aqueous NaHCO$_3$ and brine, and dried (Na$_2$SO$_4$). It was concentrated to afford a brown slurry, which was purified by chromatography (silica, EtOAc-hexanes) to afford the desired compound as a major isomer (yellow solid, 0.20 g, 71%). ESIMS m/z=458.38, 460.38 [M+H]$^+$.

Intermediate H1

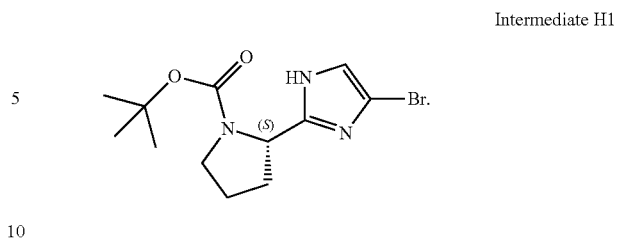

The desired compound was prepared according to a procedure described in WO 2008/021927.

Intermediate H2

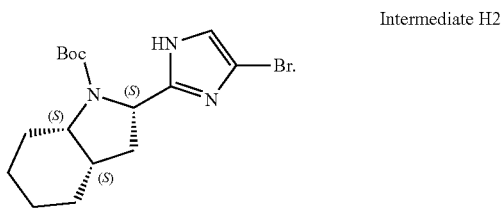

Step H2a. A mixture of the (2S,3aS,7aS)-1-(tert-butoxycarbonyl)octahydro-1H-indole-2-carboxylic acid (0.808 g, 3.0 mmol), O,N-dimethylhydroxyamine hydrochloride (0.32 g, 3.3 mmol), HATU (1.37 g, 3.6 mmol) and DIPEA (0.93 g mg, 7.2 mmol) in DMF (15 mL) was stirred at rt overnight before partition (EtOAc—H$_2$O). The organics were washed with saturated sodium bicarbonate, water, brine, dried (Na$_2$SO$_4$), filtered and evaporated. The residue was dissolved in diethyl ether (30 mL) and washed with water, dried (Na$_2$SO$_4$), filtered and concentrated to give the desired compound as a pale yellow oil (849 mg, 90%). ESIMS m/z=235.1 [M+Na-Boc]$^+$.

Step H2b. A solution of the compound from step H2a (849 mg, 2.7 mmol) in THF (18 mL) was treated with LiAlH$_4$ (1M in THF, 3 mL, 3.0 mmol) at −78° C. for 1 hour and 0° C. for 2 hours. It was quenched with 7.7 mL potassium bisulfate solution (3.0 g KHSO$_4$ in 50 mL water). After stirring at rt for 15 minutes, it was partitioned (EtOAc—H$_2$O). The organics were washed with brine, dried (Na$_2$SO$_4$), filtered and evaporated to give the crude desired aldehyde (0.71 g, 100%). ESIMS m/z=276.16 [M+Na]$^+$.

Step H2c. Into a solution of the crude compound from step H2b (0.71 g, 2.9 mmol at most) MeOH-water (6 mL/2 mL) were added ammonium hydroxide (28%, 2 mL) and glyoxal (40% in water, 2 mL, 13.8 mmol). It was stirred at rt overnight. Saturated sodium bicarbonate was added and the mixture was extracted with CH$_2$Cl$_2$. The organics were washed with water, brine, dried (Na$_2$SO$_4$), filtered and evaporated to give the crude product which was purified by flash column chromatography (silica, hexanes-EtOAc (1% Et$_3$N)) to give the desired compound as a light yellow solid (398 mg, 49%). ESIMS m/z=292.24 [M+H]$^+$.

Step H2d. Into a solution of the compound from step H2c (0.39 g, 1.37 mmol) in THF (6 mL) was added NBS (0.51 g, 2.87 mmol) at 0° C. It was slowly warmed up to rt and stirred at rt for 16 hours before evaporation. The residue was purified by flash column chromatography to give the desired compound as yellow solid (510 mg, 83%). ESIMS m/z=470.19, 472.19, 474.19 [M+Na]$^+$.

Step H2e. A mixture of the compound from step H2d in EtOH—H$_2$O (4 mL-4 mL) and sodium sulfite (Na$_2$SO$_3$, 1.42 g, 11.3 mmol) was reflux for 16 hours. Additional Na$_2$SO$_3$ (1.42 g, 11.3 mmol) was charged and reflux was continued for another 24 hours. After cooling, it was partitioned (EtOAc—H₂O). The organics were washed with brine, dried (Na₂SO₄), filtered, concentrated, and purified by silica gel chromatography to give the desired compound (0.31 g, ESIMS m/z=392.28, 394.28 [M+Na]⁺) and the compound of step H3d (88 mg).

Intermediate H3

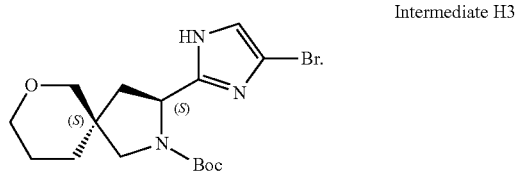

The desired compound was prepared from the compound of step F5c or F5j following the procedures similar to that described in Intermediate H2. ESIMS m/z=408.29, 410.29 [M+Na]⁺.

Intermediate J1

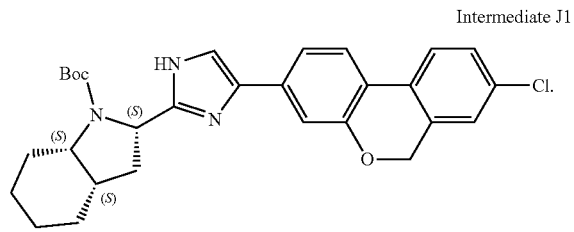

A mixture of 2-(8-chloro-6H-benzo[c]chromen-3-yl)-4,4,5,5-tetramethyl-1,3,2-dioxa-borolane (prepared according to WO 2012/068234, 200 mg, 0.58 mmol), Intermediate H3 (136 mg, 0.367 mmol), NaHCO₃ (123 mg, 1.47 mmol) and Pd(PPh₃)₄ (42.4 mg, 0.037 mmol) in DME-H₂O (6 mL-2 mL) was stirred at 90° C. for 16 hour under N₂ before cooling to rt and partition (EtOAc—H₂O). The organics were washed with brine, dried (Na₂SO₄), filtered, concentrated, and purified by silica gel chromatography to give the desired compound (0.12 g, 65%) ESIMS m/z=506.39, 508.34 [M+H]⁺.

Intermediate J2

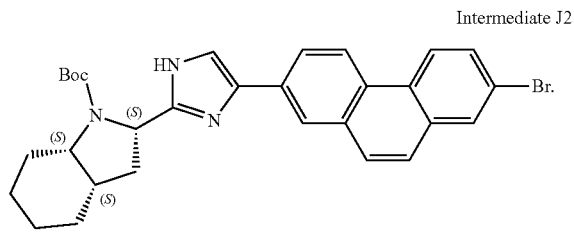

Step J2a. A mixture of 2,7-dibromophenanthrene (1.00 g, 3.0 mmol), tributyl-(1-ethoxyvinyl)tin (1.08 g, 3.0 mmol), Pd(PPh₃)₄ (139 mg, 0.12 mmol) and Pd(PPh₃)₂C₁₂ (84.2 mg, 0.12 mmol) in dioxane (28 mL) was stirred at 85° C. overnight before being cooled to rt. Water (8.0 mL) and NBS (561 mg, 3.15 mmol) were added sequentially. After 1 hour, it was partitioned (EtOAc—water). The organics were washed with brine, dried (Na₂SO₄) and evaporated to give the crude desired compound.

Step J2b. A mixture of the crude compound from step J2a (3.0 mmol at most) and (2S,3aS,7aS)-1-(tert-butoxycarbonyl)octahydro-1H-indole-2-carboxylic acid (1.61 g, 6.0 mmol) and DIPEA (1.04 mL, 6.0 mol) in acetonitrile (30 mL) was stirred at rt for 16 hours. The volatiles were evaporated off. The residue was purified by flash column chromatography to give the desired compound as an oil (0.72 g, 42% over 2 steps). ESIMS m/z=588.41, 590.41 [M+Na]⁺.

Step J2c. A mixture of the compound from step J2b (0.72 g, 1.38 mmol) and ammonium acetate (1.27 g, 16.5 mmol) in xylene (10 mL) was heated at 140° C. in a sealed tube for 4 hours. The volatiles were evaporated and the residue was partitioned (EtOAc—aqueous NaHCO₃). The organics were washed with brine, dried (Na₂SO₄), filtered and evaporated. The residue was purified by chromatography (silica, hexanes-ethyl acetate) to give the desired compound as a brown foam (0.38 g, 50%). ESIMS m/z=546.17, 548.17 [M+H]⁺.

Intermediate J3

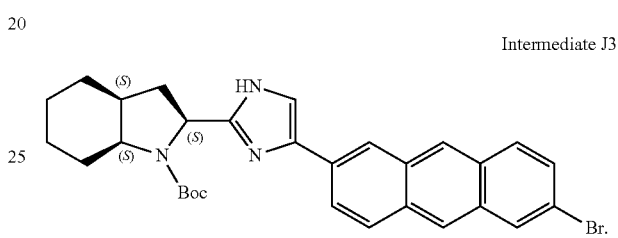

Step J3a. A mixture of 2,6-dibromoanthracene (0.300 g, 0.893 mmol), tributyl (1-ethoxy-vinyl)tin (0.31 mL, 0.893 mmol) and Pd(PPh₃)₄ (0.103 g, 89.3 μmol) in 1,4-dioxane (9 mL) was degassed and heated at 85° C. under N₂ for 16 hours before cooling. Water (3 mL) and NBS (0.167 g, 0.937 mmol) were added. The suspension was stirred at rt for 1 hour before partition (EtOAc-H₂O). The organics were washed with brine, dried (Na₂SO₄), filtered and evaporated to afford a yellow solid, which was used directly for next step.

Step J3b. To a solution of the crude compound from step J3a (0.893 mmol at most) and Boc-L-octahydroindole-2-carboxylic acid (0.481 g, 1.786 mmol) in acetonitrile (9 mL) was added DIPEA (0.30 mL, 1.696 mmol) dropwise at rt. The solution was stirred at room temperature for 3 days before partition (EtOAc—aq. NaHCO₃). The organics were washed with brine, dried (Na₂SO₄), filtered and evaporated. The residue was purified by flash column chromatography (silica, EtOAc-hexanes) to afford the desired compound as a yellow solid (0.145 g, 29% over 3 steps). ESIMS m/z=588.09, 590.09 [M+Na]⁺.

Step J3c. To a solution of the compound from step J3b (0.145 g, 0.256 mmol) in xylenes (2.5 mL) was added ammonium acetate (0.237 g, 3.072 mmol). The resulting mixture was heated at 140° C. in a sealed tube for 4 h before being allowed to cool down and partitioned (aq. NaHCO₃—EtOAc). The organic phase was washed with brine, dried (Na₂SO₄), filtered and concentrated. The residue was purified by flash column chromatography (silica, EtOAc-hexanes) to afford the desired compound as a yellow oil (40.7 mg, 29%). ESIMS m/z=546.41, 548.41 [M+H]⁺.

The following desired intermediates were prepared using procedures similar to that described above.

| Intermediate | Structure | ESIMS m/z [M + H]+ or [M + Na]+ |
|---|---|---|
| A25 | 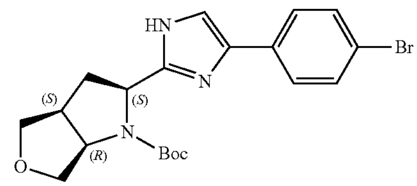 | 434.18, 436.18 |
| A26 | 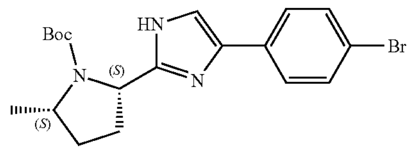 | 406.27, 408.27 |
| B14 | 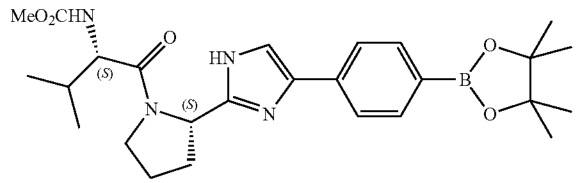 | 497.30 |
| B15 | 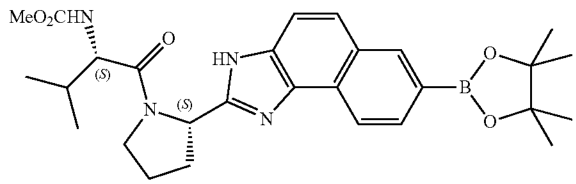 | 521.67 |
| B16 | 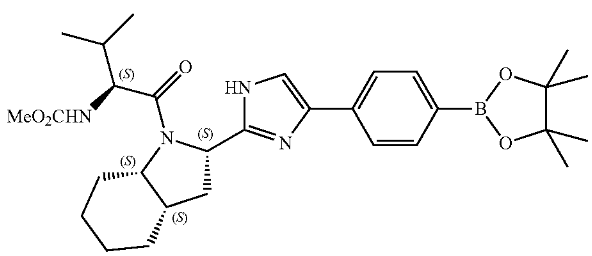 | 551.16 |
| B17 | 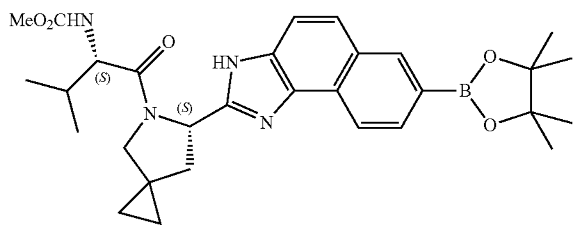 | 547.62 |
| B18 | 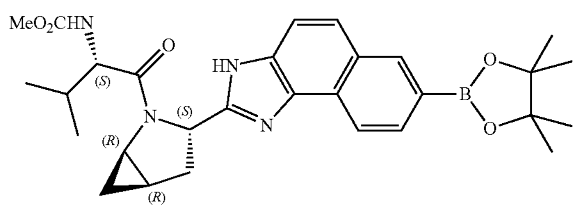 | 533.23 |

| Intermediate | Structure | ESIMS m/z [M + H]+ or [M + Na]+ |
|---|---|---|
| B19 | 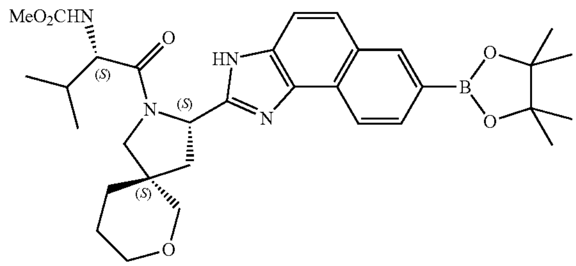 | 591.54 |
| B20 | 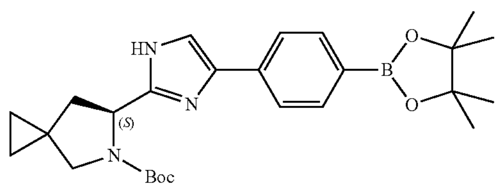 | 466.29 |
| B21 | 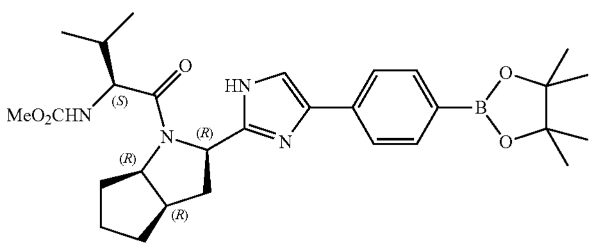 | 561.34 |
| F22 | 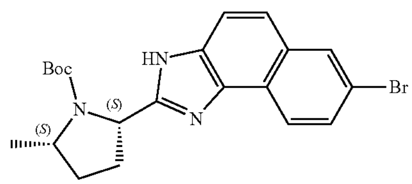 | 452.23, 454.23 |
| F23 | 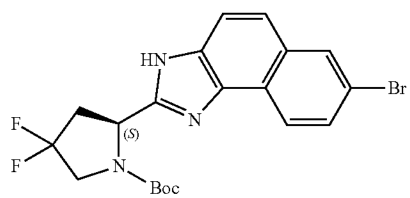 | 474.28, 476.28 |
| F24 | 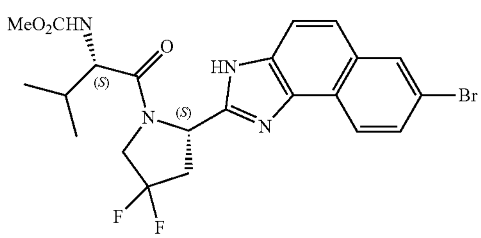 | 509.33, 511.34 |
| F25 | 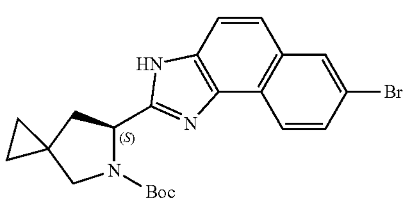 | 442.31, 444.31 |

-continued

| Intermediate | Structure | ESIMS m/z [M + H]+ or [M + Na]+ |
|---|---|---|
| F26 | 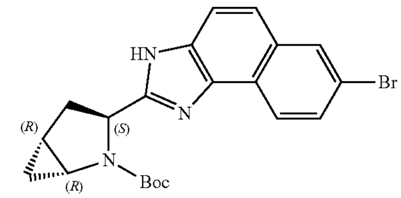 | 428.47, 430.47 |
| F27 | 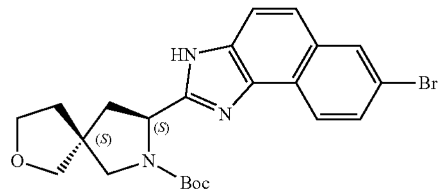 | 472.28, 474.28 |

Example 1

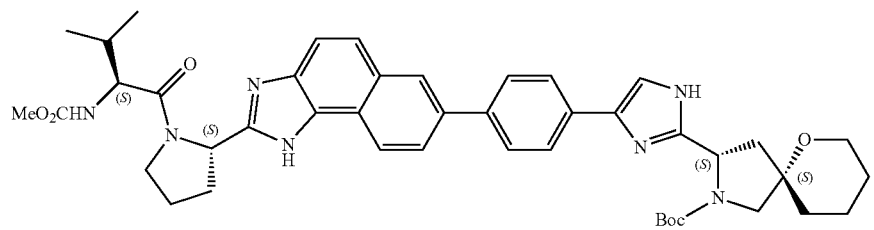

A mixture of Intermediates C4 (35.0 mg, 75.7 μmol) and B15 (47.3 mg, 90.8 μmol), NaHCO3 (25.4 mg, 0.303 mmol) and Pd(PPh3)4 (8.7 mg, 7.6 μmol) in DME (3 mL) and H2O (1 mL) was degassed and heated at 98° C. under N2 for 3 hours. The volatiles were evaporated off. The residue was purified by flash column chromatography (silica, hexanes-EtOAc-MeOH) to give the title compound as a yellow solid (41.7 mg, 71%). ESIMS m/z=776.74 [M+H]+.

Example 2

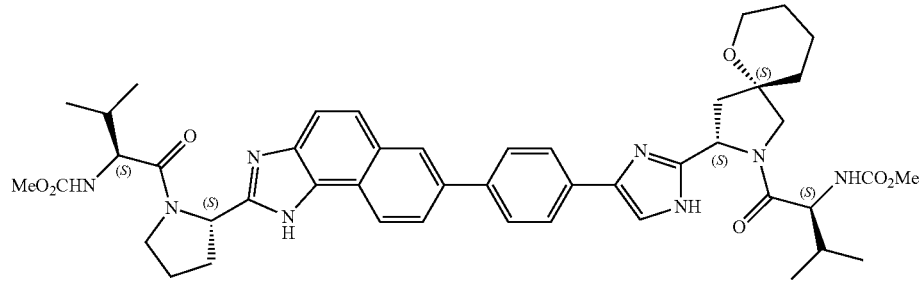

Step 2a. A solution of the compound from Example 1 (41.7 mg, 53.7 μmol) in CH2Cl2-MeOH (3:1, 2 mL) was treated with HCl in 1,4-dioxane (4 M, 2 mL) at room temperature for 2 hours. The volatiles were evaporated off to give the crude desired compound as a yellow solid which was used directly for the next step.

Step 2b. A mixture of the crude compounds from step 2a (53.7 μmol at most) and A8b (9.4 mg, 53.7 μmol) in DMF (3 mL) was treated with HATU (20.4 mg, 53.7 μmol) in the presence of DIPEA (0.14 mL, 0.806 mmol) for 1 hour at room temperature. The volatiles were evaporated off. The residue was purified by flash column chromatography (silica, silica, hexanes-EtOAc-MeOH-Et3N), and then by reverse phase HPLC (CH3CN—H2O) to give the title compound as a light yellow solid (32 mg, 71% over 2 steps). ESIMS m/z=833.69 [M+H]+.

Example 3

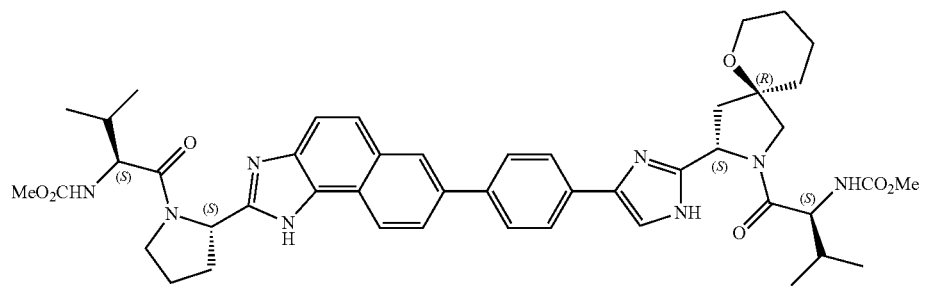

The title compound was prepared from Intermediates C5 and B15 and the compound of step A9b following a procedure similar to that described in Examples 1 and 2. ESIMS m/z=833.73 [M+H]+.

Example 4

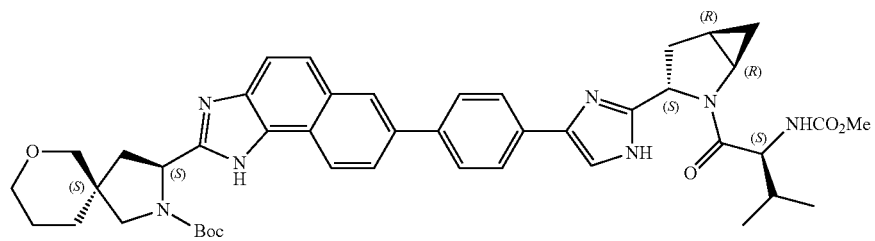

The title compound was prepared from Intermediates B4 and F11 following procedures similar to that described in Example 1. ESIMS m/z=788.68 [M+H]+.

Example 5

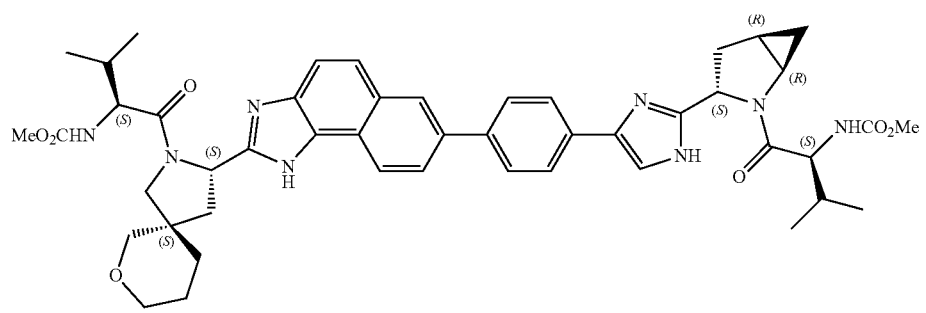

The title compound was prepared from the compound of Example 4 following the procedures similar to that described in Example 2. ESIMS m/z=845.57 [M+H]+.

Example 6

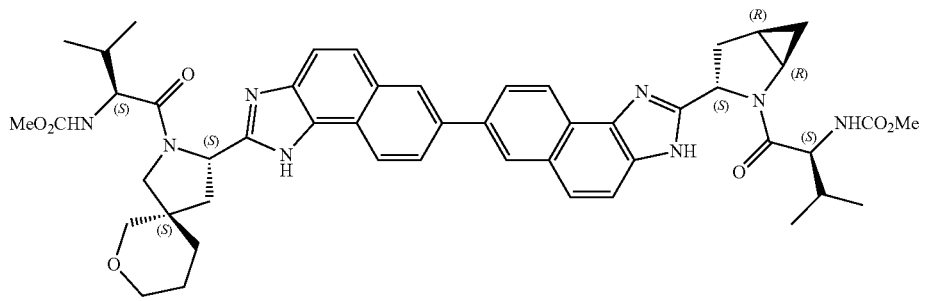

The title compound was prepared from Intermediates F11 and B18 and the compound of step A8b following procedures similar to that described in Examples 1 and 2. ESIMS m/z=869.51 [M+H]$^+$.

Example 7

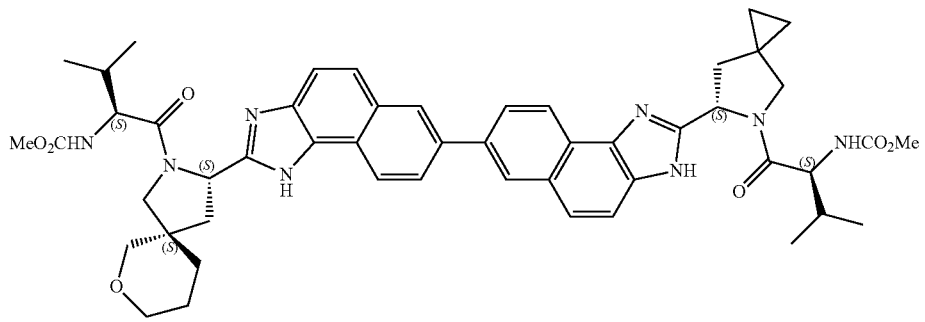

The title compound was prepared from Intermediates F11 and B17 and the compound of step A8b following procedures similar to that described in Examples 1 and 2. ESIMS m/z=883.76 [M+H]$^+$.

Example 8

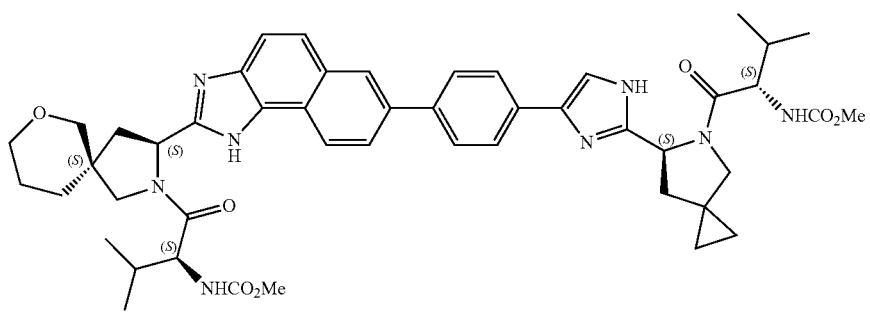

The title compound was prepared from Intermediates B20 and F11 and the compound of step A8b following procedures similar to that described in Examples 1 and 2. ESIMS m/z=859.70 [M+H]$^+$.

Example 9

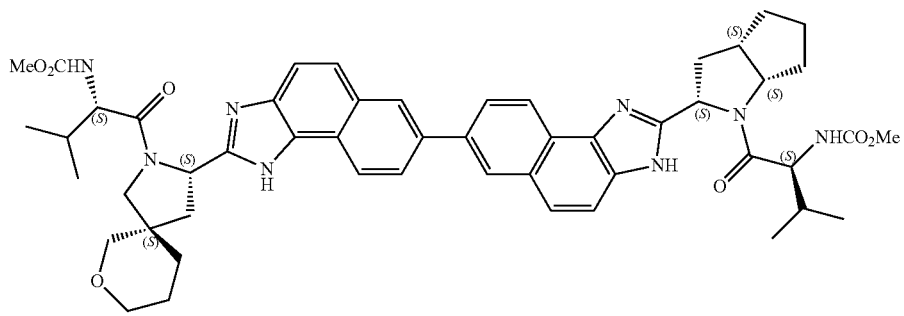

The title compound was prepared from Intermediates F11 and B7 and the compound of step A8b following procedures similar to that described in Examples 1 and 2. ESIMS m/z=897.77 [M+H]+.

Example 10

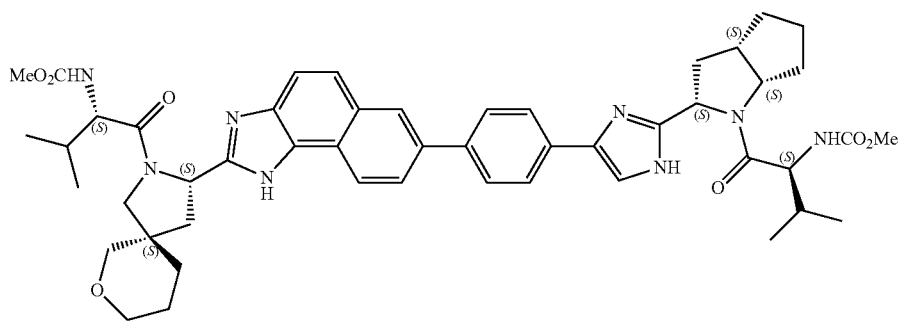

The title compound was prepared from Intermediates F12 and B21 following procedures similar to that described in Example 1. ESIMS m/z=873.65 [M+H]+.

Example 11

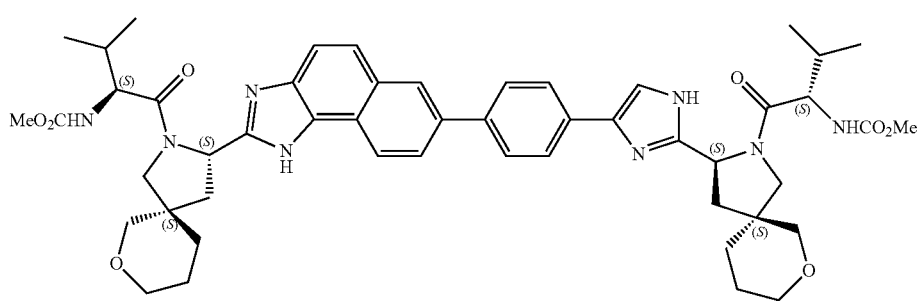

The title compound was prepared from Intermediates F12 and B8 following procedures similar to that described in Example 1. ESIMS m/z=903.79 [M+H]+.

Example 12

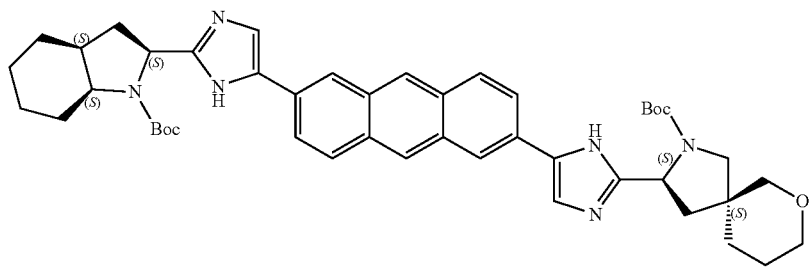

A mixture of Intermediates H3 (16.3 mg, 0.0423 mmol) and B13 (25.1 mg, 0.0423 mmol), NaHCO$_3$ (14.2 mg, 0.169 mmol) and Pd(PPh$_3$)$_4$ (4.9 mg, 4.23 μmol) in DME (3 mL) and H$_2$O (1 mL) was degassed and then heated at 98° C. under N$_2$ for 4 hours before cooling. The volatiles were evaporated. The residue was taken up in dichloromethane and filtered. The filtrate was directly purified by flash column chromatography (silica, hexanes-ethyl acetate, with 1% MeOH and 1% Et$_3$N in ethyl acetate) to give the desired compound as a yellow oil (12.5 mg, 38%). ESIMS m/z=773.48 [M+H]$^+$.

Example 13

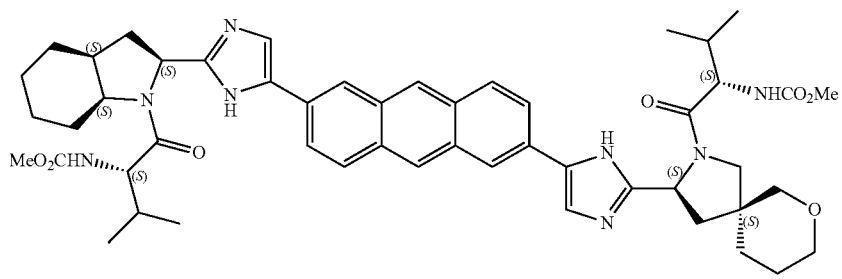

The title compound was prepared from the compound from Example 12 following the procedures similar to that described in Example 8. ESIMS m/z=887.73 [M+H]$^+$.

Example 14

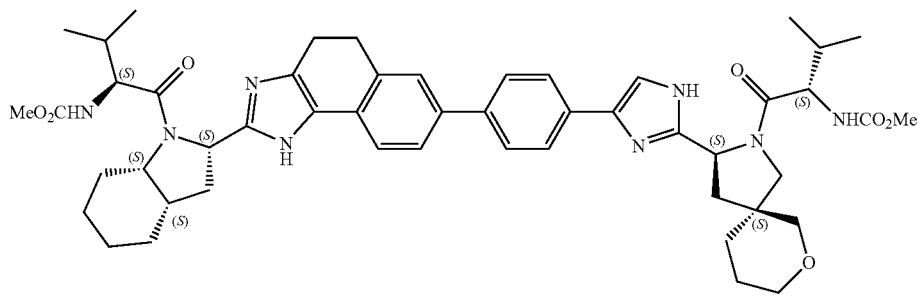

The title compound was prepared from Intermediates F18 and B8 following procedures similar to that described in Example 1. ESIMS m/z=889.56 [M+H]$^+$.

Example 15

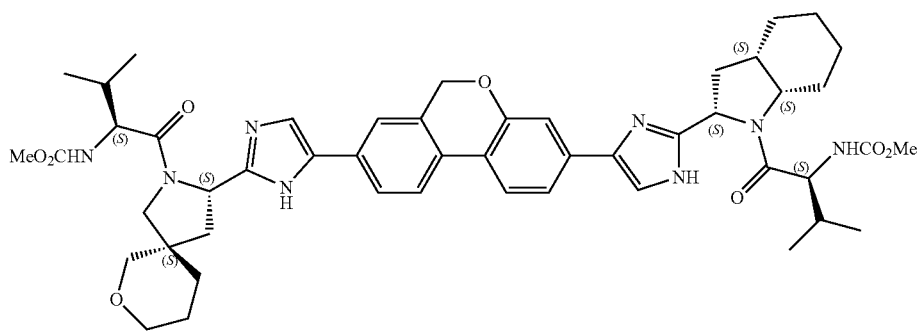

Step 15a. Into a solution of the Intermediates B9 (114 mg, 0.19 mmol) and H3 (41 mg, 0.106 mmol) and NaHCO$_3$ (35.6 mg, 0.424 mmol) in 1,2-dimethoxyethane (4.5 mL) and H$_2$O (1.5 mL) was added Pd(PPh$_3$)$_4$ (24.5 mg, 0.021 mmol). The mixture is degassed and heated to 100° C. under N$_2$ for 16 hours. The volatiles were evaporated and the residue was partitioned (EtOAc—H$_2$O). The organic phase was washed with brine, dried (Na$_2$SO$_4$), filtered and evaporated. The residue was chromatographed (silica, CH$_2$Cl$_2$-MeOH) to give the title compound as a light yellow solid (39 mg, 50%). ESIMS m/z=777.81 [M+H]$^+$.

Step 15b. A solution of the compound from step 15a (39 mg, 0.05 mmol) in CH$_2$Cl$_2$—MeOH (2 mL-0.6 mL) was treated with HCl in 1,4-dioxane (4 M, 3 mL) for 2 hours. The volatiles were evaporated off to give the crude desired compound as a yellow solid which was directly used in the next step.

Step 15c. A mixture of the crude compounds from step 15b (0.05 mmol at most) and A9b (17.5 mg, 0.10 mmol) in DMF (3.0 mL) was treated with HATU (38 mg, 0.10 mmol) in the presence of DIPEA (0.09 mL, 0.50 mmol) for 30 min. at rt. The volatiles were evaporated off to provide a brown syrup, which was purified by chromatography (silica, CH$_2$Cl$_2$-MeOH) and Prep-HPLC (MeCN—H$_2$O) to give the title compound as a white solid (22 mg, 49% over 2 steps). ESIMS m/z=891.65 [M+H]$^+$.

Example 16

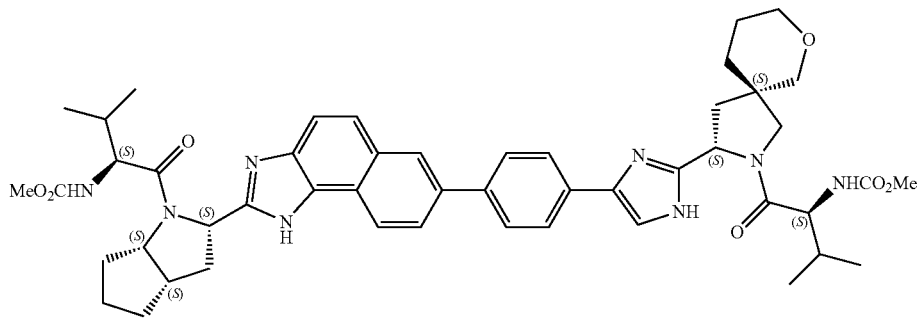

Into a mixture of the Intermediates B7 (165 mg, 0.30 mmol) and C3 (130 mg, 0.25 mmol) in DME (10 mL) and water (3 mL) was charged NaHCO$_3$ (84 mg, 1.0 mmol) and Pd(PPh$_3$)$_4$ (29 mg, 0.025 mmol). It was degassed and stirred at 98° C. for 3 hours before cooling. The mixture was concentrated and the residue was purified by chromatography (silica, EtOAc/hexanes and EtOAc/MeOH/TEA) to afford the title compound as a yellow solid (186 mg, 85%). ESIMS m/z=873.54 [M+H]$^+$.

Example 17
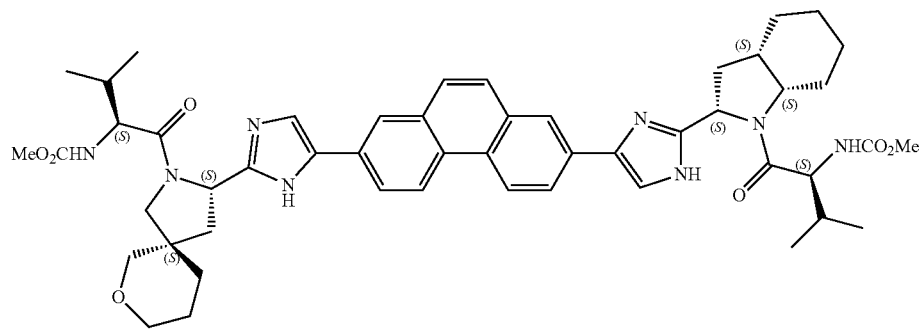
The title compound was prepared from Intermediates B10 and H3 using procedures similar to that described in example 15. ESIMS m/z=887.8 [M+H]+.
The following title compounds were prepared using procedures similar to that described above.
| Example | Structure | ESIMS m/z [M + H]+ |
|---|---|---|
| 18 | 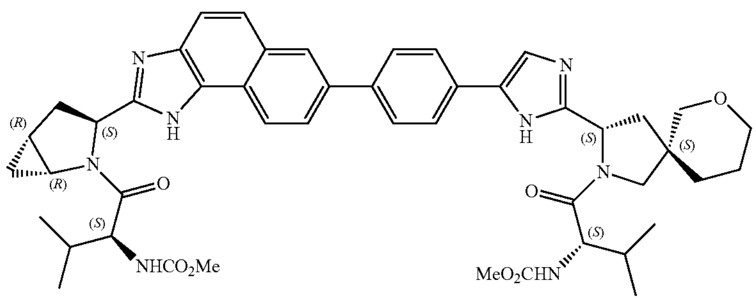 | 846.09 |
| 19 | 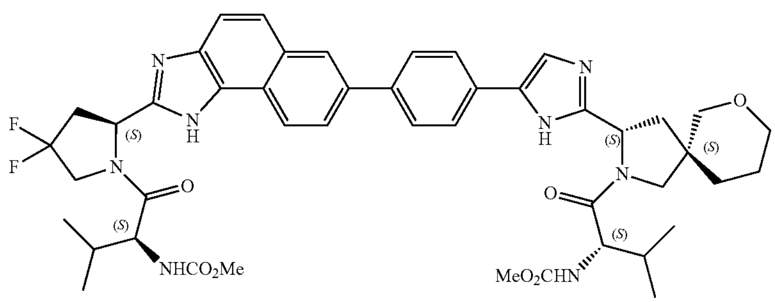 | 867.79 |
| 20 | 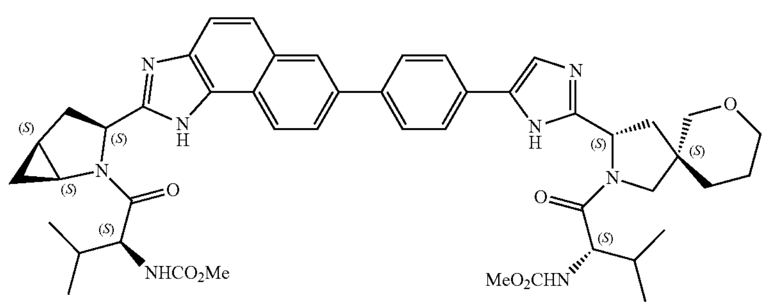 | 845.58 |

-continued

| Example | Structure | ESIMS m/z [M + H]+ |
|---|---|---|
| 21 | 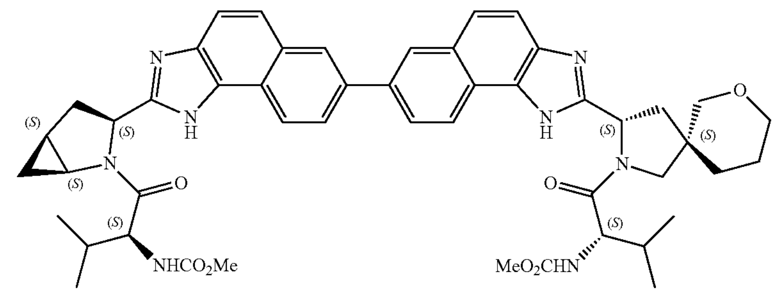 | 869.75 |
| 22 | 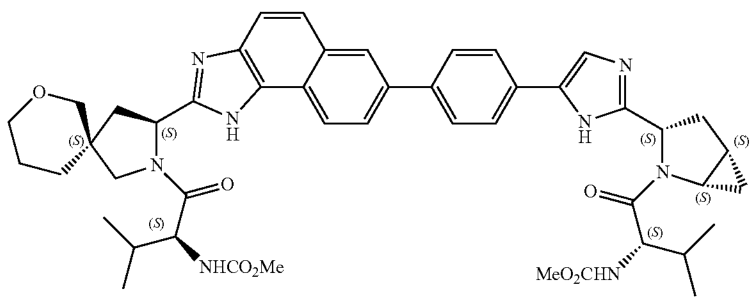 | 845.69 |
| 23 | 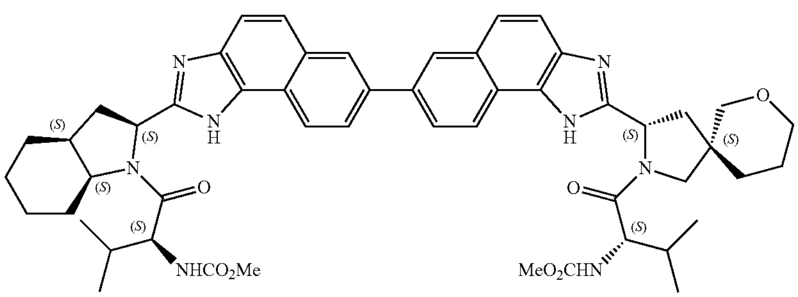 | 911.50 |
| 24 | 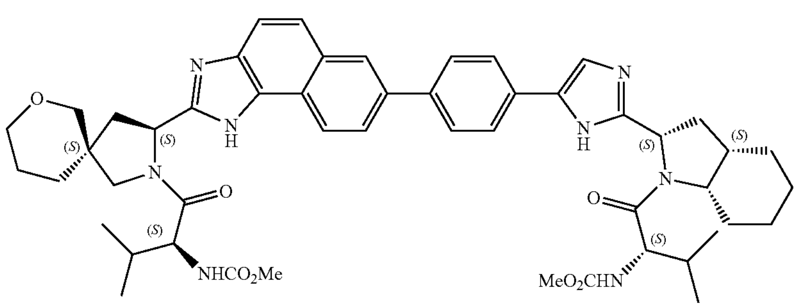 | 887.48 |
| 25 | 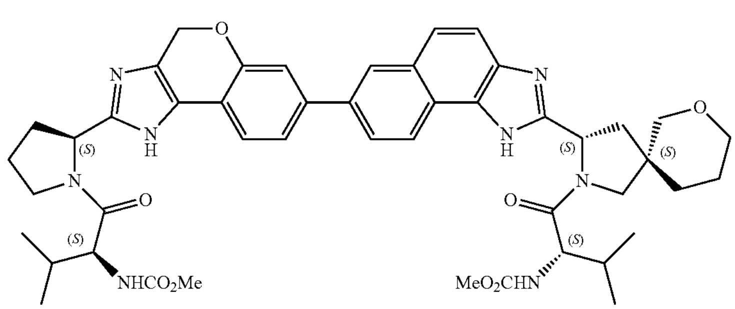 | 861.86 |

| Example | Structure | ESIMS m/z [M + H]+ |
|---|---|---|
| 26 | 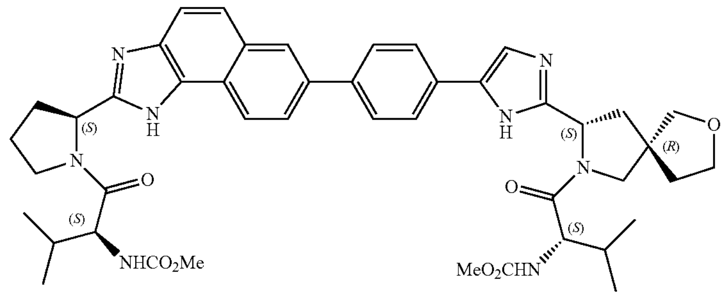 | 819.74 |
| 27 | 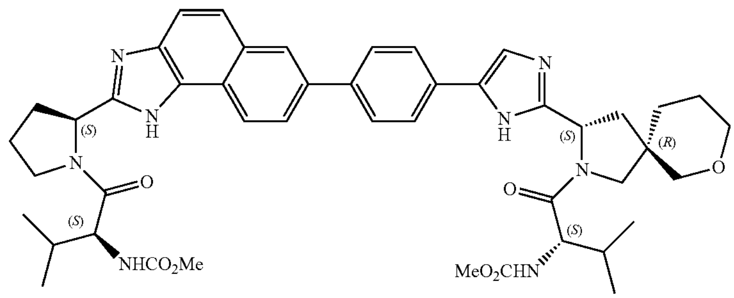 | 833.69 |
| 28 | 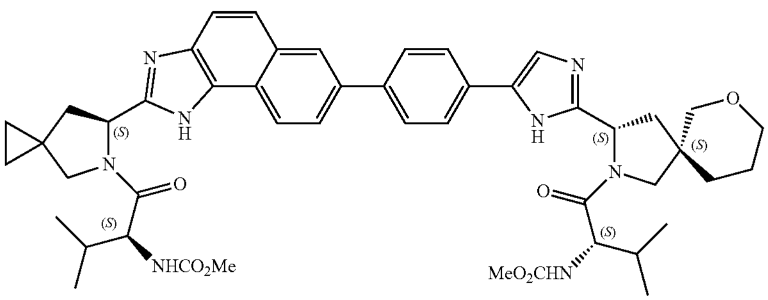 | 859.68 |
| 29 | 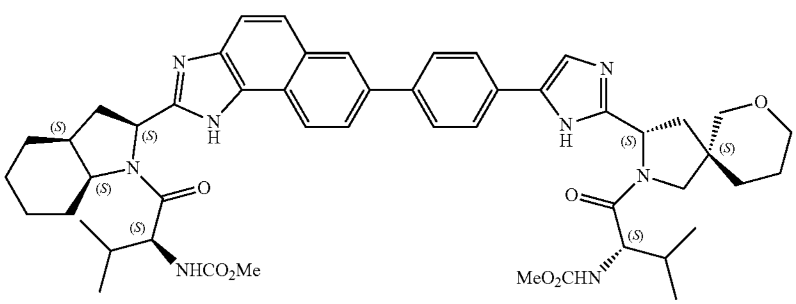 | 887.53 |
| 30 | 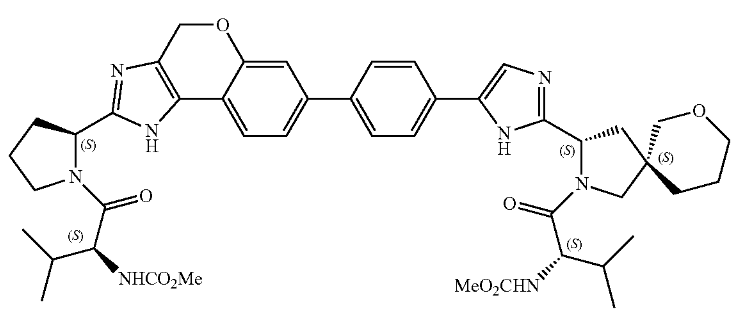 | 837.52 |

-continued

| Example | Structure | ESIMS m/z [M + H]+ |
|---|---|---|
| 31 | 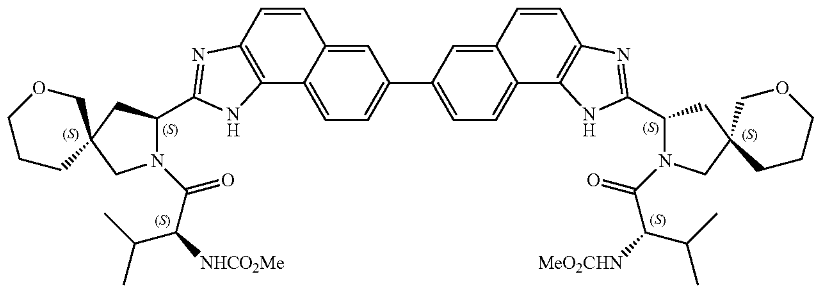 | 927.71 |
| 32 | 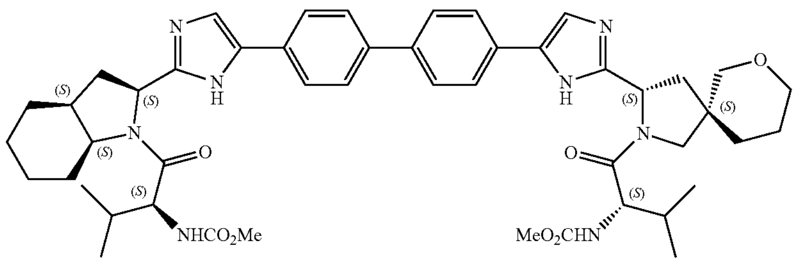 | 863.89 |
| 33 | 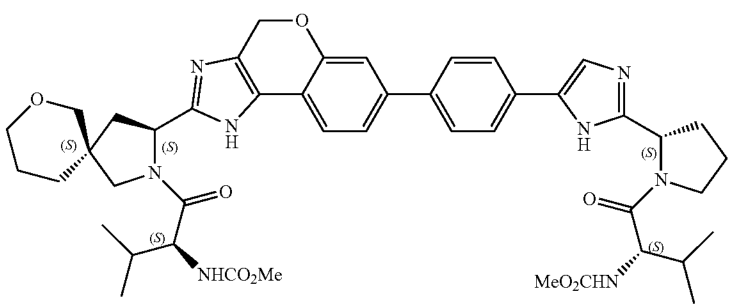 | 837.52 |
| 34 | 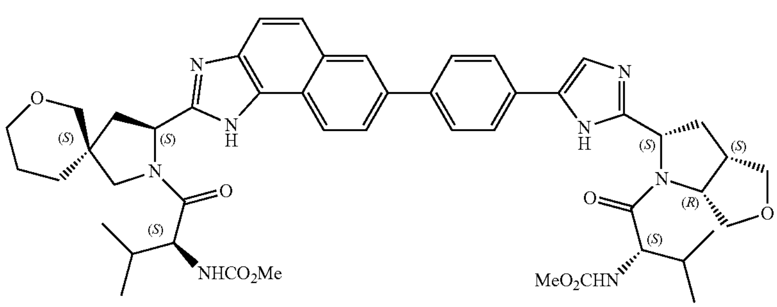 | 875.50 |
| 35 | 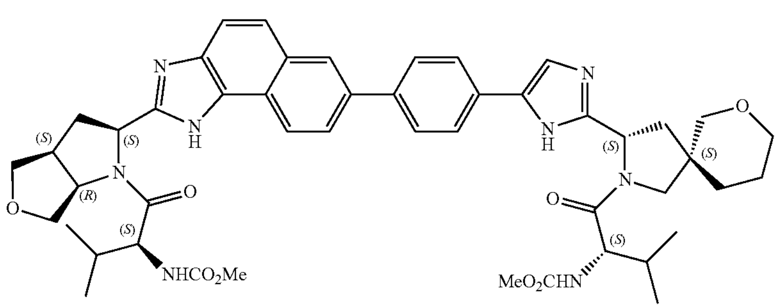 | 875.49 |

| Example | Structure | ESIMS m/z [M + H]+ |
|---|---|---|
| 36 | 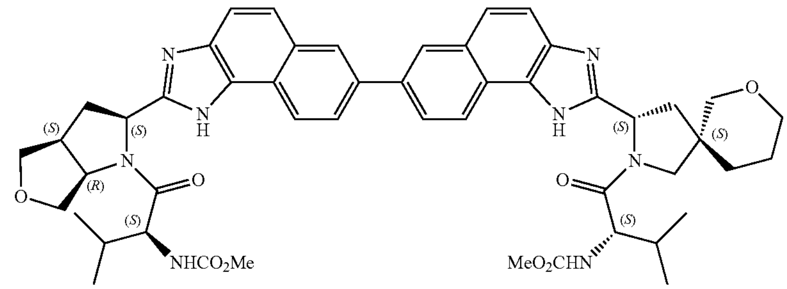 | 899.78 |
| 37 | 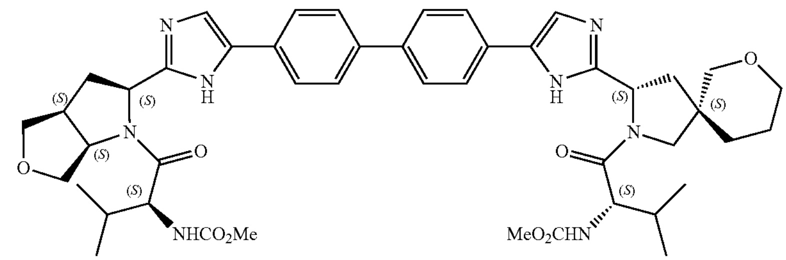 | 849.78 |
| 38 | 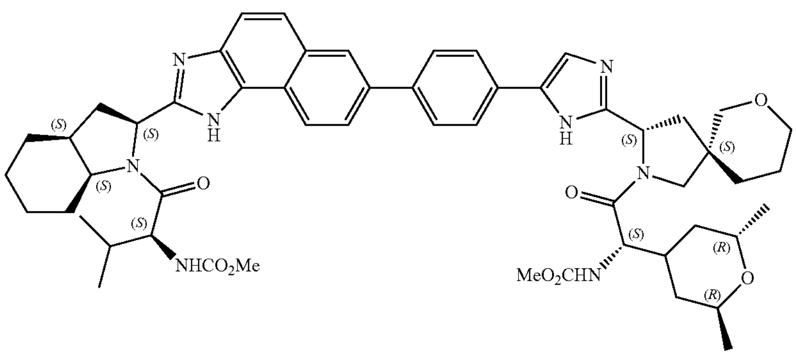 | 957.87 |
| 39 | 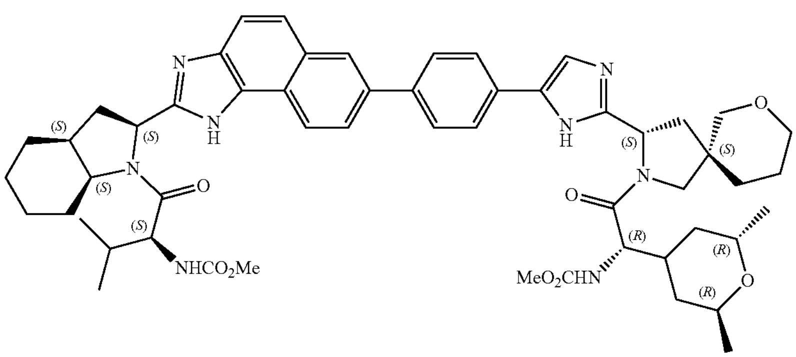 | 957.92 |
| 40 | 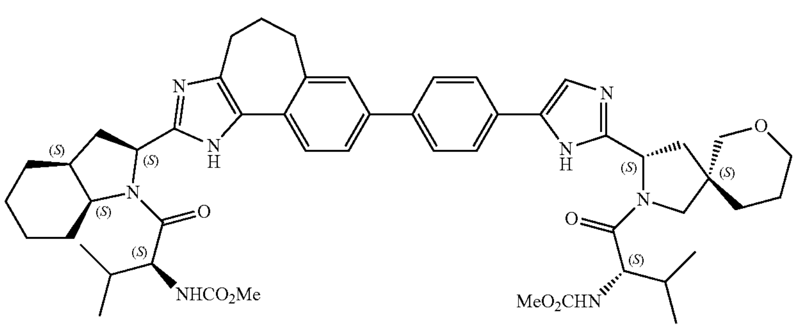 | 903.90 |

| Example | Structure | ESIMS m/z [M + H]+ |
|---|---|---|
| 41 | 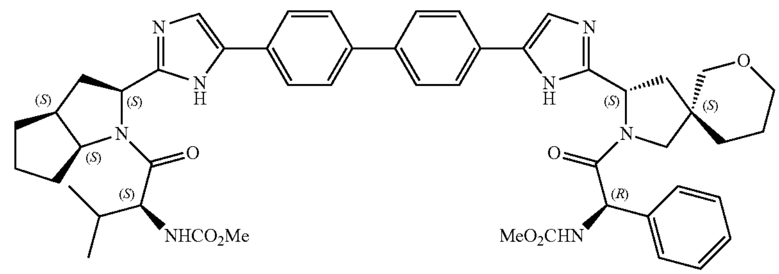 | 883.91 |
| 42 | 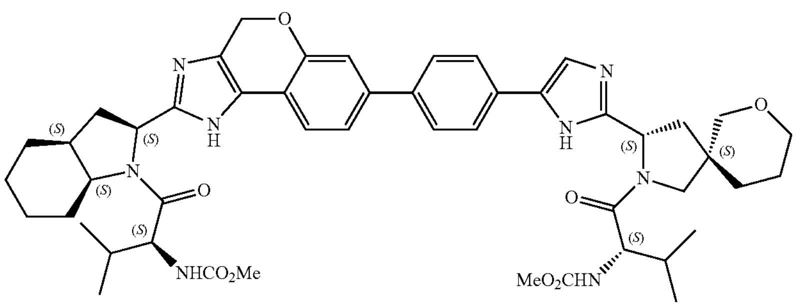 | 891.58 |
| 43 | 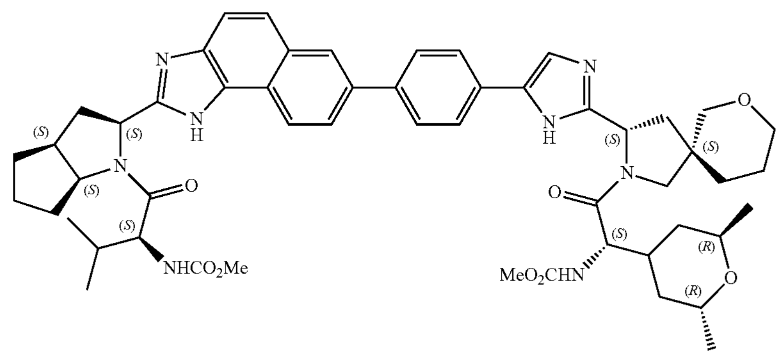 | 943.73 |
| 44 | 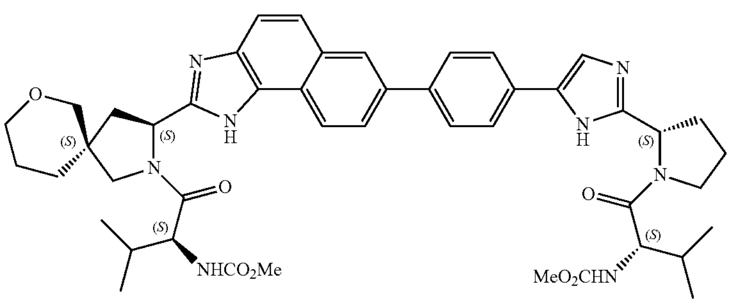 | 833.78 |
| 45 | 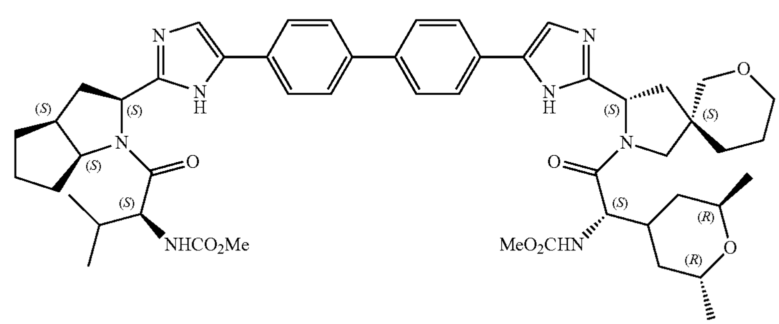 | 919.86 |

| Example | Structure | ESIMS m/z [M + H]+ |
|---|---|---|
| 46 | 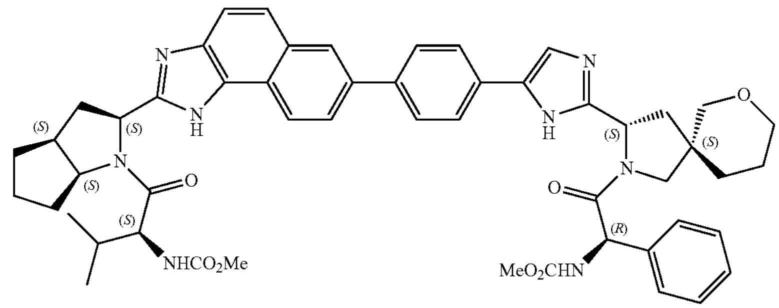 | 907.95 |
| 47 | 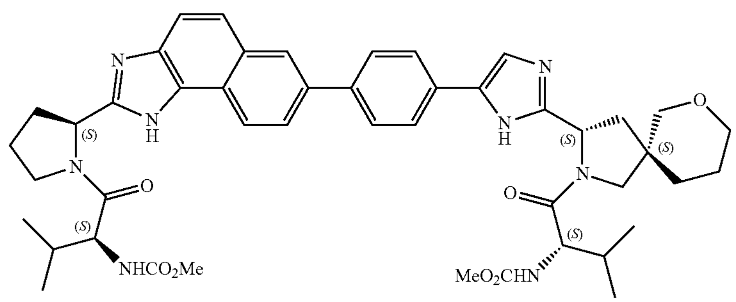 | 833.71 |
| 48 | 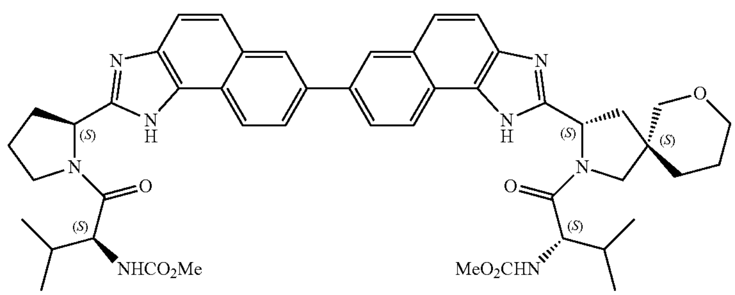 | 857.52 |
| 49 | 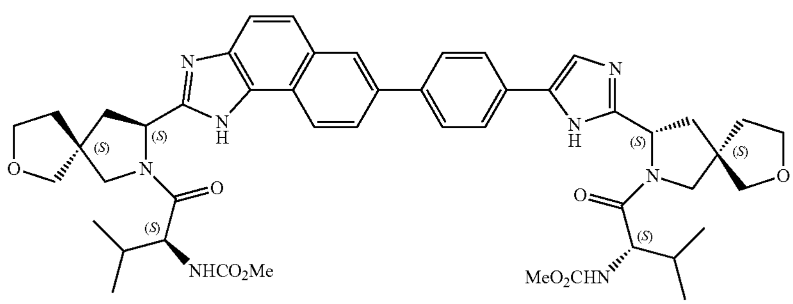 | 875.78 |
| 50 | 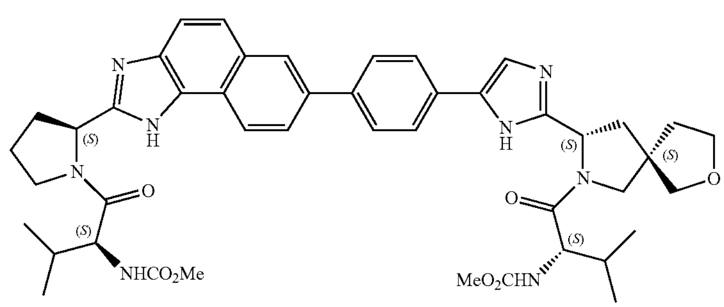 | 819.82 |

| Example | Structure | ESIMS m/z [M + H]+ |
|---|---|---|
| 51 | 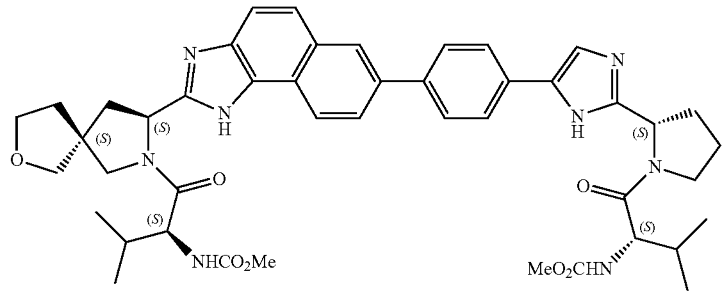 | 819.83 |
| 81 | 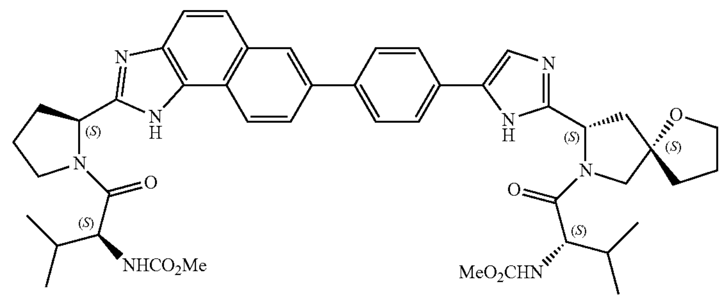 | 819.76 |
| 82 | 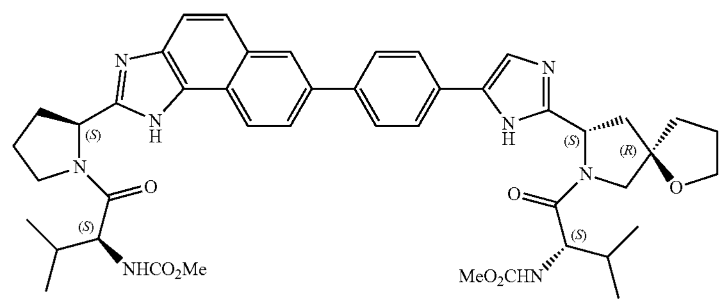 | 819.67 |
| 83 | 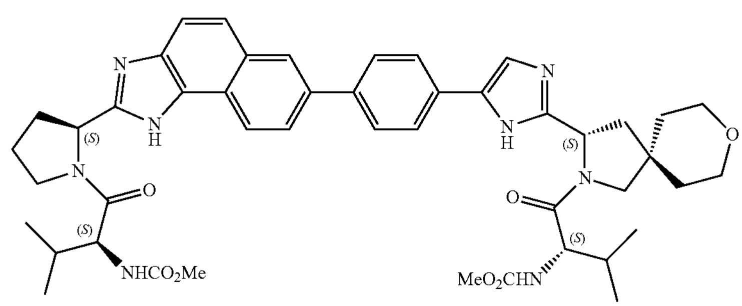 | 833.72 |
| 101 | 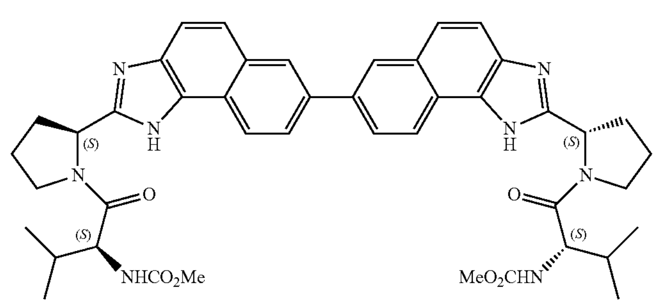 | 787.47 |

| Example | Structure | ESIMS m/z [M + H]+ |
|---|---|---|
| 102 | 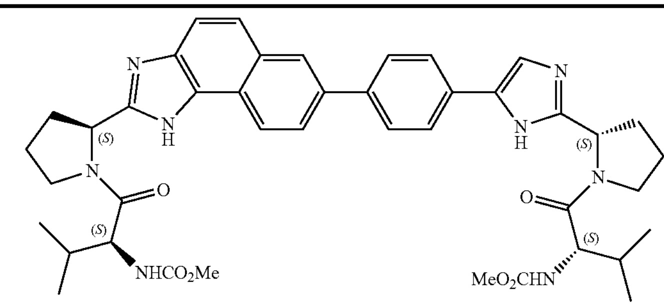 | 763.93 |
| 103 | 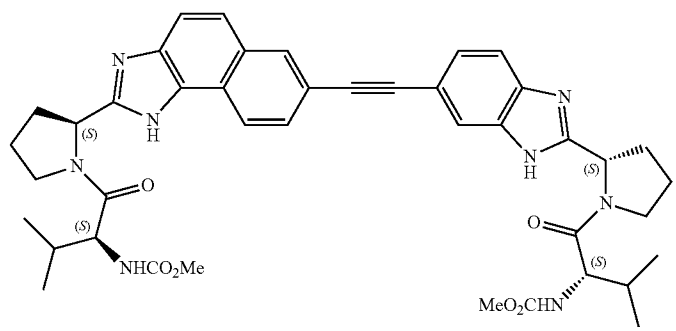 | 761.79 |

IV and PO Single Dose Pharmacokinetic Studies in SD Rats

The pharmacokinetics of selected compounds was characterized in male Sprague-Dawley (SD) rats (250-300 g). In this study, two groups of naïve SD rats (N=1 per group) received the selected compound either as an intravenous (IV) bolus dosing (N=2, 2 mg/kg or less if limited by solubility) via the tail vein or by oral gavage (N=3, 20 mg/kg). The intravenous (IV) dosing vehicle was 5% ethanol and 95% of 20% 2-hydroxypropyl β-cyclodextrin in water. The oral dosing vehicle was 33% of Microemulsion Preconcentrate #5 (a lipid based self-emulsifying drug delivery system, SEDDS) and 67% of 50 mM citrate buffer (final pH 3.6).

Serial blood samples (approximately 0.3 mL each) were collected from jugular vein or other suitable vein at specified time points. For the IV dosing group, the blood samples were collected predose and at 0.08, 0.25, 0.50, 1, 3, 6, 8, and 24 hours after the start of dosing. For the oral group, the blood samples were collected predose and at 0.08, 0.25, 0.50, 1, 3, 6, 8, and 24 hours after dosing. The blood samples were collected into VACUTAINER™ tubes containing EDTA-K3 as the anti-coagulant and were centrifuged at approximately 4° C. to obtain plasma. The plasma samples were stored at −20° C. until analysis by LC/MS/MS.

A bioanalytical method utilizing high performance liquid chromatography coupled to tandem mass spectrometry (LC/MS/MS) was developed for analysis of the selected compound in rat plasma. Detection was performed using multiple reaction monitoring (MRM); Ions representing the precursor (M+H)+ species was selected in quadrupole 1 (Q1) and collided with nitrogen gas in the collision cell (Q2) to generate specific product ion, which was subsequently monitored by quadrupole 3 (Q3). Standard curve and quality control samples were prepared in male rat plasma and processed in the same way as the test samples to generate quantitative data.

Pharmacokinetic parameters were generated using non-compartmental pharmacokinetic analysis (Phoenix Win-Nonlin, version 6.3). Values below the lower limit of quantification (LLOQ) were assigned a value of zero if predose and treated as missing thereafter. Area under the curve (AUC) was calculated using the linear trapezoidal rule. The oral bioavailability (% F) was determined by comparison of the area under the curve (AUC) of the compound in plasma following oral administration to that generated following intravenous administration.

Biological Activity

1. HCV Replicon Cell Lines

HCV replicon cell lines (kindly provided by R. Bartenschlager) isolated from colonies as described by Lohman et al. (Lohman et al. (1999) Science 285: 110-113, expressly incorporated by reference in its entirety) and used for all experiments. The HCV replicon has the nucleic acid sequence set forth in EMBL Accession No.: AJ242651, the coding sequence of which is from nucleotides 1801 to 8406.

The coding sequence of the published HCV replicon was synthesized and subsequently assembled in a modified plasmid pBR322 (Promega, Madison, Wis.) using standard molecular biology techniques. One replicon cell line ("SGR 11-7") stably expresses HCV replicon RNA which consists of (i) the HCV 5'UTR fused to the first 12 amino acids of the capsid protein, (ii) the neomycin phosphotransferase gene (neo), (iii) the IRES from encephalomyocarditis virus (EMCV) and (iv) HCV NS2 to NS5B genes and the HCV 3'UTR. Another replicon cell line ("Huh-luc/neo-ET") described by Vrolijk et. al. (Vrolijk et. al. (2003) Journal of Virological Methods 110:201-209, expressly incorporated by reference in its entirety) stably expresses HCV replicon RNA which consists of (i) the HCV 5'UTR fused to the first 12 amino acids of the capsid protein, (ii) the firefly luciferase reporter gene, (iii) the ubiquitin gene, (iv) the neomycin phosphotransferase gene (neo), (v) the IRES from encephalomyocarditis virus (EMCV) and (vi) HCV NS3 to NS5B genes that harbor cell culture adaptive mutations (E1202G, T1280I, K1846T) and the HCV 3'UTR.

These cell lines are maintained at 37° C., 5% $CO_2$, 100% relative humidity in DMEM (Cat#11965-084, Invitrogen), with 10% fetal calf serum ("FCS", Invitrogen), 1% non-essential amino acids (Invitrogen), 1% of Glutamax (Invitrogen), 1% of 100× penicillin/streptomycin (Cat#15140-122, Invitrogen) and Geneticin (Cat#10131-027, Invitrogen) at 0.75 mg/ml or 0.5 mg/ml for 11-7 and Huh-luc/neo-ET cells, respectively.

2. HCV Replicon Assay—qRT-PCR $EC_{50}$ values of single agent compounds were determined by HCV RNA detection using quantitative RT-PCR, according to the manufacturer's instructions, with a TAQMAN® One-Step RT-PCR Master Mix Reagents Kit (Cat# AB 4309169, Applied Biosystems) on an ABI Model 7500 thermocycler. $EC_{50}$ values of combinations are similarly determined by HCV RNA detection using quantitative RT-PCR. The TAQMAN primers to use for detecting and quantifying HCV RNA obtained from Integrated DNA Technologies. HCV RNA is normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat# AM1812). Chemical agent cytotoxicity is evaluated using an MTS assay according to the manufacturer's directions (Promega).

3. HCV Replicon Assay—Luciferase

Since clinical drug resistance often develops in viral infections following single agent therapies, there is a need to assess the additive, antagonistic, or synergistic properties of combination therapies. We use the HCV replicon system to assess the potential use of the compound of the present invention or in combination therapies with Interferon alpha, cyclosporine analogs and inhibitors targeting other HCV proteins. The acute effects of a single or combinations of drugs are studied in the "Huh-luc/neo-ET" replicon with each chemical agent titrated in an X or Y direction in a 6 point two-fold dilution curve centered around the $EC_{50}$ of each drug. Briefly, replicon cells are seeded at 7,000 cells per well in 90 ul DMEM (without phenol red, Invitrogen Cat.#31053-036) per well with 10% FCS, 1% non-essential amino acids, 1% of Glutamax and 1% of 100× penicillin/streptomycin and incubated overnight at 37° C., 5% $CO_2$, 100% relative humidity. 16-20 h after seeding cells, test compounds previously solubilized and titrated in dimethyl sulfoxide ("DMSO") from each X plate and Y plate are diluted 1:100 in DMEM (without phenol red, Invitrogen Cat.#31053-036) with 10% FCS, 1% non-essential amino acids, 1% of Glutamax and 1% of 100× penicillin/streptomycin and added directly to the 96-well plate containing cells and growth medium at a 1:10 dilution for a final dilution of compound and DMSO of 1:1000 (0.2% DMSO final concentration). Drug treated cells are incubated at 37° C., 5% $CO_2$, 100% relative humidity for 72 hours before performing a luciferase assay using 100 ul per well BriteLite Plus (Perkin Elmer) according to the manufacturer's instructions. Data analysis utilizes the method published by Prichard and Shipman (Antiviral Research, 1990, 14:181-205). Using this method, the combination data is analyzed for antagonistic, additive, or synergistic combination effects across the entire combination surface created by the diluted compounds in combination.

4. Measuring Inhibitory Effects in an HCV Replicon System

The activity of compounds was determined against HCV replicons representing genotypes (GT) 1a, 1b, 2a, and 3a. To generate stable Huh-7.5-based cell lines, HCV replicons were engineered to express the Renilla luciferase reporter (hRluc) fused to the neomycin phosphotransferase (Neo) gene. GT2a and GT3a HCV replicons were based on the JFH-1 subgenomic replicon (Kato et al. 2003 Gastroenterology, 125:1808-1817), in which the NS5A gene was replaced with that of strains J6 and S52 (GT2a and G3a, respectively). The activity of compounds against GT1a replicons encoding NS5A mutations (M28T, Q30R, L31M, Y93C, and Y93H) was also determined in a transient replication assay. The parental GT1a and GT2a replicons (pH/SG-Neo(L+I) and pSG-Neo-JFH1, respectively) were licensed from Apath LLC (Saint Louis, Mo.). The parental GT 1b replicon (pFKi389lucubineo_3_3'_ET) was licensed from ReBLikon GmbH (Germany). HCV replicons were constructed by standard molecular biology techniques described below. All replicon constructs were verified by restriction enzyme digestion and DNA sequencing.

Generation of GT 1a Subgenomic Replicon:

pH/SG-Neo(L+I) was modified to add the firefly luciferase reporter gene and additional adaptive mutations by replacing the pH/SG-Neo(L+I) NS3-NS5A coding region with the corresponding sequence of pH77-S, creating pH/SG-lucubineo-H77S as described (Borawski J et al. 2009, J Virol 83: 10058-10074). Subsequently, the firefly luciferase-Neo cassette was replaced with the hRluc-Neo cassette. To create a unique cloning site, the NotI restriction site in NS5B was removed using QuickChange II XL Site-Directed Mutagenesis Kit (Agilent) and the following primers: NotI KO Fwd 5'-CTC AAA CTC ACT CCA ATA GC<u>T</u> GCC GCT GGC CGG CTG GAC-3'(G→T mutation removing NotI site underlined) (SEQ. ID No. 1) and NotI KO Rev 5'-GTC CAG CGG CCA GCG GC<u>A</u> GCT ATT GGA GTG AGT TTG AG-3'(C→A mutation removing NotI site underlined) (SEQ. ID No. 2). The resulting vector, pH/SG-lucubineo-H77S-NotIKO, was sequenced to confirm the NS5B gene. The hRluc-Neo cassette was PCR amplified from pF9 cytomegalovirus (CMV) hRluc-Neo Flexi(R) (Promega) using Accuprime Super Mix II (Invitrogen) and the following primers, which introduce restriction sites:

```
AscI hRluc-Neo Fwd,
                                      (SEQ ID No. 3)
5'-GGG CGC GCC ATG GCT TCC AAG GTG TAC G-3'
(AscI site underlined),
and NotI hRluc Rev,
                                      (SEQ ID No. 4)
5'-CGC GGC CGC TCA GAA GAA CTC GTC AAG-3'
(NotI site underlined).
```

The amplification product was subcloned into pCR2.1-TOPO (Invitrogen). The resulting plasmid was digested with AscI and NotI, and the excised hRluc-Neo fragment was ligated using the Promega Rapid Ligation Kit (Promega) into pH/SG-lucubineo-H77S-NotIKO digested with the same enzymes.

Generation of GT 1b Subgenomic Replicon:

The hRluc-Neo cassette was PCR amplified from pF9 cytomegalovirus (CMV) hRluc-Neo Flexi(R) (Promega) using Accuprime Super Mix II (Invitrogen) and the following primers, which introduce restriction sites:

AscI hRluc-Neo Fwd,
(SEQ. ID No. 3)
5'-GGG CGC GCC ATG GCT TCC AAG GTG TAC G-3'
(AscI site underlined),
and NotI hRluc Rev,
(SEQ ID No. 4)
5'-CGC GGC CGC TCA GAA GAA CTC GTC AAG-3'
(NotI site underlined).

The amplification product was subcloned into pCR2.1-TOPO (Invitrogen). The resulting plasmid was digested with AscI and NotI, and the excised hRluc-Neo fragment was ligated using the Roche Quick Ligation Kit (Roche) into pFKi389lucubineo_3_3'_ET digested with the same enzymes.

Generation of GT2a Chimeric Replicons Expressing NS5A from GT2a (Strain J6) and GT3a (Strain S52):

The plasmid pSG-hRlucNeo-JFH1 was generated from pSG-Neo-JFH1 (Kato et al. 2003, Gastroentrology 125: 1808-1817). A fragment containing the JFH-1 5' NTR—hRluc-Neo gene and two unique restriction sites (AgeI and PmeI) was synthesized (Integrated DNA Technologies, Coralville, Iowa). The resulting synthetic plasmid was digested with AgeI and PmeI and the excised fragment (5'NTR-hRluc-Neo) was ligated into pSG-Neo-JFH1 digested with the same enzymes to generate pSG-hRlucNeo-JFH1. To allow expression of heterologous NS5A sequences, an NS5A shuttle vector was generated from pSG-Neo-JFH1, in which the entire coding sequence of NS5A plus the first eight codons of NS5B were replaced with an AfeI restriction site. This was done by Infusion cloning (Clontech, Mountain View, Calif.) from two PCR products that were generated using pSG-Neo-JFH1 as a template and the following primer pairs:

NsiI-Fwd
(SEQ. ID No. 5)
5'-AAG TAC ATC GCC ACA TGC ATG CAA GCT GAC CTT GAG GTC ATG ACC-3'
and AfeI-Rev
(SEQ. ID No. 6)
5'-AGC GCT GCA TGG GAT GGG GCA GTC CTC AG-3';

AfeI-Fwd
(SEQ. ID No. 7)
5'-CCC ATC CCA TGC AGC GCT CTA ATA ACT CCC TGT AGC CCC GAA G-3'
and SnaBI-Rev
(SEQ. ID No. 8)
5'-CAT GGG CCC TCC TAC GTA AAG TCT CTC AGT CAG CGA GTG TAT GG-3'.

Underlined sequences denote regions of overlap necessary for Infusion cloning. Purified PCR products were cloned directly into an NsiI/SnaBI digested pSG-Neo-JFH1 following the manufacturer's instructions to generate pSG-Neo-JFH1-5Ashuttle. The 2023 base pair AgeI/PmeI fragment from pSG-hRlucNeo-JFH1 was then ligated into pSG-Neo-JFH1-5Ashuttle to generate pSG-hRlucNeo-JFH1-5Ashuttle. To generate the 2a-2a-(J6) and 2a-3a-(S52) NS5A chimeric replicons, the full length NS5A sequences from GT2a strain J6 (accession AF177036) and GT3a strain S52 (accession GU814263), with the addition of the first eight codons of JFH-1 NS5B (5'-TCC ATG TCA TAC TCC TGG ACC GGG-3'), were synthesized by GeneArt (Life Technologies, Carlsbad Calif.). J6 and S52 NS5A sequences were then PCR amplified from the synthetic clones using the appropriate forward primer:

J6NS5A-F
(SEQ. ID No. 9)
5'-CCC ATC CCA TGC AGC GGC TCG TGG CTC CGC GAT GTG TGG-3'
or

S52NS5A-F
(SEQ. ID No. 10)
5'-CCC ATC CCA TGC AGC GGC GAT TGG CTG CGT GAC ATC TGG-3'
and the reverse primer JFH-5B-R
(SEQ. ID No. 11)
5'-GGG AGT TAT TAG AGC CCC GGT CCA GGA GTA TGA CAT GGA-3'.

Underlined sequences denote regions of overlap with pSG-hRlucNeo-JFH1-5Ashuttle necessary for Infusion cloning. Purified PCR products were directly cloned into AfeI-digested shuttle vector by Infusion cloning following the manufacturer's instructions.

Generation of NS5A Mutations in GT1a Replicon:

pH/SG-PI-hRluc-H77S is a cell culture adapted, bicistronic GT1a subgenomic replicon expressing hRluc under the control of a chimeric HCV-poliovirus IRES. Expression of the HCV nonstructural protein NS3 through NS5 is driven by the encephalomyocarditis virus (EMCV) IRES. Five adaptive mutations (Q41R and V629I in NS3; K34R in NS4A; K68R and 52321 in NS5A) allow efficient replication in cell culture (Yi and Lemon. 2004, J. Virol. 78(15): 7904-7915). NS5A mutations M28T, Q30R, L31V, Y93C, and Y93H (GT1a NS5A numbering) were introduced into the pH/SG-PI-hRluc-H77S plasmid using the QuickChange II XL Site-Directed Mutagenesis Kit (Agilent Technologies, Santa Clara, Calif.) and the following primer pairs:

1a-M28T-f
(SEQ. ID No. 12)
5'-GCT GAA AGC CAA GCT CAC GCC ACA ACT GCC TGG-3',

1a-M28T-r
(SEQ. ID No. 13)
5'-CCA GGC AGT TGT GGC GTG AGC TTG GCT TTC AGC-3';

1a-Q30R-f
(SEQ. ID No. 14)
5'-GCC AAG CTC ATG CCA CGC CTG CCT GGG ATT CC-3',

1a-Q30R-r
(SEQ. ID No. 15)
5'-GGA ATC CCA GGC AGG CGT GGC ATG AGC TTG GC-3';

1a-L31V-f
(SEQ. ID No. 16)
5'-GCT CAT GCC ACA AGT GCC TGG GAT TCC TTG-3',

1a-L31V-r
(SEQ. ID No. 17)
5'-CAA GGA ATC CCA GGC ACT TGT GGC ATG AGC-3';

-continued

1a-Y93C-f
(SEQ. ID No. 18)
5'-CGT TCC CCA TTA ACG CC<u>T GCA</u> CCA CGG GCC CCT G-3',

1a-Y93C-r
(SEQ. ID No. 19)
5'-CAG GGG CCC GTG GTG CAG GCG TTA ATG GGG AAC G-3';

1a-Y93H-f
(SEQ. ID No. 20)
5'-CGT TCC CCA TTA ACG CC<u>C ACA</u> CCA CGG GCC CCT G-3',

1a-Y93H-r
(SEQ. ID No. 21)
5'-CAG GGG CCC GTG GTG TGG GCG TTA ATG GGG AAC G-3'.

Underlined sequences in forward primers (-f) indicate position of mutation.

Cell Maintenance and Replicon Assays:

Stable HCV replicon cell lines were grown in complete media (Dulbecco's modified Eagle medium [DMEM], 2 mM L-glutamine, 0.1 mM essential amino acids, 1 mM sodium pyruvate, 10% heat inactivated fetal bovine serum) with the addition 500 µg/ml gentamycin (G418). Huh7-lunet cells were maintained in the same medium without the addition of G418. Cells were routinely passaged at a dilution of 1:4 two times a week. The assay medium for both luciferase reporter HCV replicon and cytotoxicity assays used phenol red-free DMEM and lacked G418. For each stable replicon assay, a sixteen point half-log dilution series of compound was stamped (0.5 ul compound per well) into three replica 384-well plates, to which cells were added directly (4000 cells/well). For the transient replication assay, Huh7-lunet cells in ice-cold phosphate buffered saline (PBS) were electroporated (BioRad electroporator; 950 uF, 270V) with 10 ug purified in vitro transcribed HCV replicon RNA, followed by resuspension in complete media and plating (8000 cells/well) into compound stamped 384-well plates. Luciferase activity of compound-treated cells was measured relative to DMSO-treated cells after 72 h incubation using RENILLA-GLO™ Luciferase Assay (Promega). Cytotoxicity ($CC_{50}$) in the GT1b replicon cell line was analyzed using CELL TITER-GLO™ (Promega).

The compounds of the present invention may inhibit HCV by mechanisms in addition to or other than NS5A inhibition. In one embodiment the compounds of the present invention inhibit HCV replicon and in another embodiment the compounds of the present invention inhibit NS5A.

The compounds of the present invention can be effective against the HCV 1b genotype. It should also be understood that the compounds of the present invention can inhibit multiple genotypes of HCV. In one embodiment compound of the present invention are active against the 1a, 1b, 2a, 2b, 3a, 4a, and 5a genotypes. In another embodiment compound of the present invention are active against the HCV resistant mutants. The table set forth below shows the $EC_{50}$ values of representative compounds of the present invention against the HCV 1a, 1b, 2a-J6, 3a genotype and 1a NS5A resistant variants from the above described qRT-PCR or luciferase assay. $EC_{50}$s are in pM against HCV GT 1a and GT 1b; and nM against GT 2a-J6, GT 3a and GT1a resistant variants (M28T, Q30R, L31V, Y93C and Y93H).

| Compound | 1a | 1b | 2a J6 | 3a | 1a M28T | 1a Q30R | 1a L31V | 1a Y93C | 1a Y93H | F % |
|---|---|---|---|---|---|---|---|---|---|---|
| 2 | 12 | 7 | 27 | 1 | 0.1 | 0.03 | 0.3 | 0.2 | 9 | |
| 3 | 146 | 40 | 267 | 156 | 6 | 5 | 44 | 0.7 | 6 | |
| 5 | 8 | 11 | 3 | 0.5 | 0.03 | 0.05 | 0.1 | 0.06 | 2 | 12.2 |
| 6 | 7 | 12 | 0.07 | 0.08 | 0.06 | 0.04 | 0.2 | 0.02 | 0.8 | 3.5 |
| 7 | 9 | 12 | 0.3 | 0.05 | 0.02 | 0.03 | 0.1 | 0.02 | 1 | 2.5 |
| 8 | 10 | 10 | 8 | 0.9 | 0.06 | 0.1 | 0.2 | 0.1 | 4 | 4.1 |
| 9 | 7 | 6 | 0.04 | 0.06 | 0.03 | 0.01 | 0.07 | 0.03 | 2 | 2.6 |
| 10 | 5 | 5 | 0.2 | 0.2 | 0.04 | 0.02 | 0.05 | 0.2 | 4 | 5.7 |
| 11 | 23 | 52 | 2 | 0.4 | 0.02 | 0.05 | 0.08 | 0.07 | 2 | 7.1 |
| 13 | 36 | 21 | 17 | 0.9 | 0.02 | 0.01 | 0.8 | 0.3 | 9 | |
| 15 | 8 | 12 | 1 | 0.2 | 0.01 | 0.003 | 0.1 | 0.2 | 5 | |
| 16 | 9 | 10 | 0.8 | 0.8 | 0.08 | 0.02 | 0.3 | 0.3 | 8 | 23.7 |
| 17 | 12 | 13 | 22 | 6 | 0.008 | 0.01 | 0.3 | 0.3 | 5 | |
| 18 | 7 | 11 | 2 | 1 | 0.2 | 0.05 | 0.3 | 0.2 | 6 | 3.3 |
| 19 | 8 | 6 | 28 | 40 | 0.1 | 0.06 | 0.4 | 0.2 | 5 | |
| 20 | 14 | 11 | 23 | 1 | 0.9 | 0.2 | 7 | 1 | 18 | |
| 21 | 20 | 30 | 2 | 0.09 | 0.2 | 0.1 | 1 | 0.09 | 4 | 3.4 |
| 22 | 9 | 8 | 6 | 0.6 | 0.1 | 0.1 | 0.9 | 0.3 | 6 | 9.4 |
| 23 | 12 | 7 | 0.05 | 0.06 | 0.02 | 0.01 | 0.07 | 0.02 | 1 | 5.5 |
| 24 | 7 | 6 | 0.3 | 0.1 | 0.02 | 0.02 | 0.07 | 0.09 | 3 | 7.9 |
| 25 | 27 | 68 | 0.8 | 0.6 | 0.5 | 0.2 | 0.6 | 0.09 | 7 | |
| 26 | 25 | 22 | 22 | 2 | 3 | 0.8 | 11 | 0.8 | 42 | |
| 27 | 13 | 22 | 50 | 297 | 0.03 | 0.06 | 0.1 | 0.02 | 1 | |
| 28 | 11 | 11 | 13 | 0.5 | 0.09 | 0.06 | 0.3 | 0.1 | 16 | 7.2 |
| 29 | 6 | 4 | 2 | 0.3 | 0.02 | 0.01 | 0.1 | 0.1 | 7 | 17.1 |
| 30 | 50 | 45 | 1 | 2 | 0.6 | 0.1 | 1 | 0.5 | 13 | |
| 31 | 30 | 58 | 0.3 | 0.1 | 0.007 | 0.02 | 0.03 | 0.007 | 0.2 | 3.8 |
| 32 | 7 | 6 | 2 | 2 | 0.05 | 0.04 | 0.4 | 0.5 | 7 | 24.1 |
| 33 | 27 | 38 | 1 | 0.2 | 0.3 | 0.2 | 0.3 | 0.1 | 4 | |
| 34 | 24 | 41 | 0.7 | 1.5 | 0.03 | 0.02 | 0.08 | 0.09 | 4 | 2.1 |
| 35 | 28 | 49 | 2 | 2 | 0.2 | 0.07 | 0.5 | 0.4 | 26 | 1.1 |
| 36 | 29 | 51 | 0.3 | 1 | 0.08 | 0.04 | 0.2 | 0.06 | 8 | |
| 37 | 8 | 9 | 0.7 | 3 | 0.03 | 0.02 | 0.5 | 1 | 15 | 114 |
| 38 | 8 | 15 | 0.09 | 0.07 | 0.002 | 0.002 | 0.002 | 0.004 | 0.2 | 12.4 |
| 39 | 214 | 29 | 41 | 48 | 0.4 | 0.05 | 4 | 4 | 213 | |

-continued
| Compound | 1a | 1b | 2a J6 | 3a | 1a M28T | 1a Q30R | 1a L31V | 1a Y93C | 1a Y93H | F % |
|---|---|---|---|---|---|---|---|---|---|---|
| 40 | 11 | 8 | 55 | 44 | 0.6 | 0.05 | 1 | 0.7 | 8 | |
| 42 | 6 | 6 | 2 | 1 | 0.2 | 0.05 | 0.2 | 0.6 | 16 | |
| 43 | 15 | 23 | | | 0.04 | 0.03 | 0.06 | 0.04 | 2 | |
| 44 | 10 | 16 | 1 | 0.06 | 0.06 | 0.1 | 0.6 | 0.2 | 6 | 14.8 |
| 45 | 23 | 28 | | | 0.04 | 0.03 | 0.06 | 0.3 | 8 | |
| 47 | 15 | 16 | 0.6 | 0.08 | 0.2 | 0.1 | 1 | 0.3 | 8 | 7.0 |
| 48 | 6 | 9 | 0.03 | 0.07 | 0.05 | 0.05 | 0.5 | 0.02 | 2 | 1.7 |
| 49 | 10 | 9 | 23 | 5 | 1 | 0.2 | 5 | 0.4 | 12 | |
| 50 | 14 | 16 | 13 | 10 | 0.5 | 0.4 | 1 | 0.4 | 7 | |
| 51 | 11 | 16 | 4 | 2 | 0.1 | 0.2 | 0.4 | 0.07 | 4 | 8.6 |
| 81 | 15 | 13 | 45 | 3 | 0.3 | 0.05 | 0.4 | 0.2 | 15 | |
| 82 | 59 | 8 | 40 | 5 | 14 | 3 | 46 | 0.2 | 5 | |
| 83 | 29 | 42 | 32 | 0.7 | 0.9 | 1 | 6 | 1 | 26 | |
| 101 | 11 | 21 | 0.1 | 0.05 | 1 | 0.2 | 6 | 0.5 | 25 | |
| 102 | 15 | 14 | 1 | 0.06 | 1 | 1 | 8 | 0.6 | 22 | |
| 103 | 12 | 4 | 16 | 0.3 | 6 | 3 | 29 | 2 | 112 | |
The tables below present comparative data for certain compounds of Formula (I) and the corresponding reference compounds.
| | 1a EC$_{50}$ (nM) | | | | | | |
|---|---|---|---|---|---|---|---|
| | 1a (H77S) | M28T | Q30R | L31V | Y93C | Y91H | F % |
| 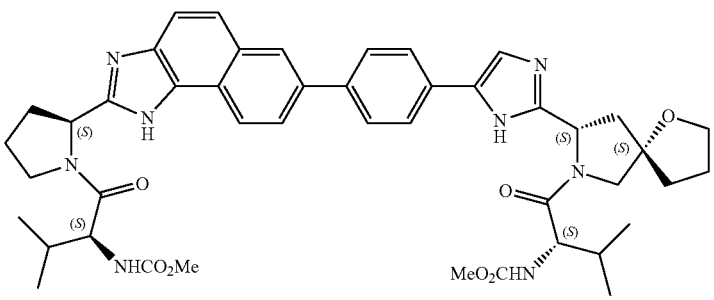 | 0.02 | 0.3 | 0.05 | 0.4 | 0.2 | 15 | |
| 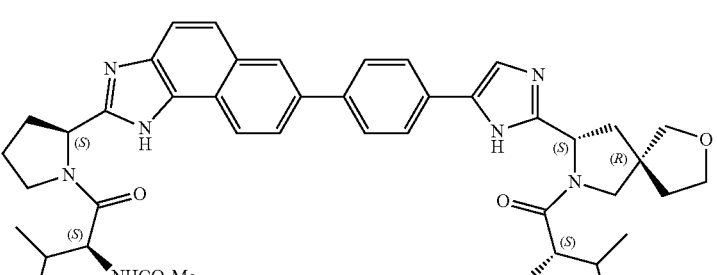 | 0.02 | 3 | 0.8 | 11 | 0.8 | 42 | |
| 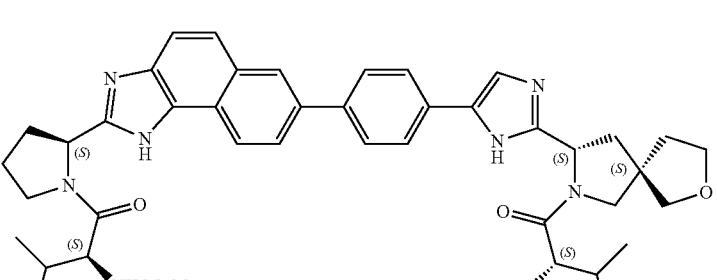 | 0.01 | 0.5 | 0.4 | 1 | 0.4 | 7 | |

|  | 1a EC$_{50}$ (nM) | | | | | |
|---|---|---|---|---|---|---|
|  | 1a (H77S) | M28T | Q30R | L31V | Y93C Y91H | F % |
|  | 0.06 | 14 | 3 | 46 | 0.2 | 5 |

|  | EC$_{50}$ (nM) | | | | | | | |
|---|---|---|---|---|---|---|---|---|
|  |  | 2a-J6 | 3a | 1a M28T | Q30R | L31V | Y93C | Y91H F % |
|  | 1a |  |  |  |  |  |  |  |
|  | 0.01 | 27 | 1 | 0.01 | 0.03 | 0.3 | 0.2 | 9 |
|  | 0.01 | 0.6 | 0.08 | 0.2 | 0.1 | 1 | 0.3 | 8   7.0 |
|  | 0.03 | 32 | 0.7 | 0.9 | 1 | 6 | 1 | 26 |
|  | 0.01 | 50 | 297 | 0.03 | 0.06 | 0.1 | 0.02 | 1 |

| | EC$_{50}$ (nM) | | | | | | | |
|---|---|---|---|---|---|---|---|---|
| | 2a- | | | 1a | | | | |
| | 1a | J6 | 3a | M28T | Q30R | L31V | Y93C | Y91H | F % |
| | 0.15 | 267 | 156 | 6 | 5 | 44 | 0.7 | 6 | |

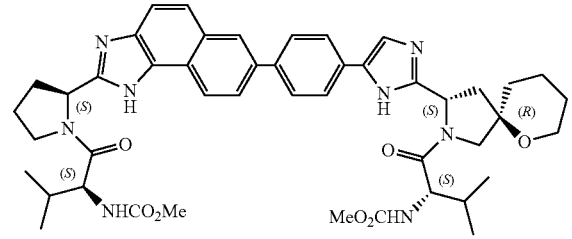

Comparison to Daclatasvir

Generation of GT3a-S52 and GT4a-ED43 Replicons:

The GT3a-S52 replicon plasmid pSGRlucneo-GT3a-S52-HDVR-(ISH) was synthesized by Genscript. This plasmid encodes a GT3a (strain S52, accession GU814264) bicistronic subgenomic replicon encoding the hRluc-Neo reporter gene in the first cistron and NS3-NS5B, driven by an encephalomyocarditis virus (EMCV) internal ribosome entry site (IRES), in the second cistron. The hepatitis delta ribozyme (HDVR) was included after the HCV 3' NTR followed by a unique SpeI restriction site for linearization. This replicon encodes three cell culture adaptive mutations, P1226S (NS3), D1437H (NS3), and S2210I (NS5A), as described previously (Saeed et al 2012 Antimicrob. Agents Chemother. 54: 1878-1887). The GT4a-ED43 replicon plasmid pSGRlucneo-GT4a-ED43-HDVR-(KG) was synthesized by Genscript. This plasmid encodes a GT4a (strain ED43, accession GU814266) bicistronic subgenomic replicon expressing the hRluc-Neo reporter gene in the first cistron and NS3-NS5B, driven by an EMCV IRES, in the second cistron. The HDVR was included after the HCV 3' NTR followed by a unique XbaI restriction site for linearization. This replicon encodes two cell culture adaptive mutations, T1369K (NS3) and R2882G (NS5B), as described previously (Saeed et al 2012 Antimicrob. Agents Chemother. 54: 1878-1887).

To generate stable replicon cell lines, replicon plasmids were linearized by restriction enzyme digestion (GT3a, SpeI; GT4a, XbaI) and purified using a Qiagen MinElute column. RNA was generated from linearized replicon templates using the T7 RiboMax Express Large Scale in vitro transcription system (Promega). Following transcription, reactions were treated with RNase-free DNase and purified using the RNeasy Mini kit (Qiagen). Huh7.5 cells were electroporated (Bio-Rad Gene Pulser: 950 pF, 270V) with 10 µg in vitro transcribed replicon RNA, plated in cell culture dishes, and incubated for 24 h prior to addition of complete medium containing G418 (500 µg/mL). Replicon-containing cells were selected by passaging in the presence of G418 (500 µg/mL) for approximately 4-5 weeks. Selected colonies were pooled, expanded, and cryopreserved prior to compound testing.

Generation of GT2a and Chimeric Replicons Expressing NS5A from Diverse HCV Genotypes:

The plasmid pSG-hRlucNeo-JFH1 was generated from pSG-Neo-JFH1 (Kato et al. 2003, Gastroentrology 125: 1808-1817). A fragment containing the JFH-1 5' NTR-hRluc-Neo gene and two unique restriction sites (AgeI and PmeI) was synthesized (Integrated DNA Technologies, Coralville, Iowa). The resulting plasmid was digested with AgeI and PmeI and the excised fragment (5'NTR-hRluc-Neo) was ligated into pSG-Neo-JFH1 digested with the same enzymes to generate pSG-hRlucNeo-JFH1. To allow expression of heterologous NS5A sequences, an NS5A shuttle vector was generated from pSG-Neo-JFH1, in which the entire coding sequence of NS5A plus the first eight codons of NS5B were replaced with an AfeI restriction site. This was done by Infusion cloning (Clontech, Mountain View, Calif.) from two PCR products that were generated using pSG-Neo-JFH1 as a template and the following primer pairs:

```
NsiI-Fwd
                                        (SEQ. ID No. 5)
5'-AAGTACATCGCCACATGCATGCAAGCTGACCTTGAGGTCATGA
CC-3';

AfeI-Rev
                                        (SEQ. ID No. 6)
5'-AGCGCTGCATGGGATGGGGCAGTCCTCAG-3'

AfeI-Fwd
                                        (SEQ. ID No. 7)
5'-CCCATCCCATGCAGCGCTCTAATAACTCCCTGTAGCCCCGAAG-3';

SnaBI-Rev
                                        (SEQ. ID No. 8)
5'-CATGGGCCCTCCTACGTAAAGTCTCTCAGTCAGCGAGTGTATGG-3'.
```

Purified PCR products were cloned directly into an NsiI/SnaBI digested pSG-Neo-JFH1 following the manufacturer's instructions to generate pSG-Neo-JFH1-5Ashuttle. The 2023 base pair AgeI/PmeI fragment from pSG-hRlucNeo-JFH1 was then ligated into pSG-Neo-JFH1-5Ashuttle to generate pSG-hRlucNeo-JFH1-5Ashuttle.

To express GT6a NS5A chimeric sequences a JFH1-based N-terminal NS5A (NS5A residues 2-107) shuttle vector was constructed by Infusion cloning from two PCR products that were generated using pSG-Neo-JFH1 as a template and the following primers:

```
NsiI-Fwd
                                        (SEQ. ID No. 5)
5'-AAGTACATCGCCACATGCATGCAAGCTGACCTTGAGGTCATG
ACC-3';
```

AfeI-Rev (SEQ. ID No. 6)
5'-AGCGCTGCATGGGATGGGGCAGTCCTCAG-3';

AfeI-Fwd (SEQ. ID No. 10)
5'CCCATCCCATGCAGCGCTATCTGGAGGGTGGCGGCCTCGGAG-3';

SnaBI-Rev (SEQ. ID No. 11).
5'-CATGGGCCCTCCTACGTAAAGTCTCTCAGTCAGCGAGTGTATGG-3'.

Purified PCR products were inserted into an NsiI/SnaBI digested pSG-Neo-JFH1 vector by Infusion cloning following the manufacturer's instructions to generate pSG-Neo-JFH1-Nterm_5Ashuttle. The 2023 base pair AgeI/PmeI fragment from pSG-hRlucNeo-JFH1 was then ligated into pSG-Neo-JFH1-5Ashuttle to generate pSG-hRlucNeo-JFH1-Nterm_5Ashuttle.

To generate NS5A chimeric replicons, a panel of NS5A sequences from diverse HCV genotypes was synthesized (Life Technologies, Carlsbad Calif.) with the addition of the first eight codons of JFH-1 NS5B (5'-TCC ATG TCA TAC TCC TGG ACC GGG-3'). NS5A sequences were then PCR amplified from synthetic constructs using the following forward and reverse primer pairs:

GT2a-2a-J6-f (SEQ. ID No. 22)
CCCATCCCATGCAGCGGCTCGTGGCTCCGCGATGTGTGG;

GT2a-2a-J6-r (SEQ. ID No. 23)
GGGAGTTATTAGAGCCCCGGTCCAGGAGTATGACATGGA;

GT2a-2b-MD2b-f (SEQ. ID No. 24)
CCCATCCCATGCAGCGGGTCTTGGCTCCGGGACGTTTGG;

GT2a-2b-MD2b-r (SEQ. ID No. 23)
GGGAGTTATTAGAGCCCCGGTCCAGGAGTATGACATGGA;

GT2a-2b-J8-f (SEQ. ID No. 25)
CCCATCCCATGCAGCGGGTCTTGGCTCCAG

GT2a-2b-J8-r (SEQ. ID No. 24)
GGGAGTTATTAGAGCCCCGGTCCAGGAGTATGACATGGAGCAGCAGATAACAG;

GT2a-3a-S52-f (SEQ. ID No. 27)
CCCATCCCATGCAGCGGCGATTGGCTGCGTGACATCTGG;

GT2a-3a-S52-r (SEQ. ID No. 23)
GGGAGTTATTAGAGCCCCGGTCCAGGAGTATGACATGGA

GT2a-5a-SA13-f (SEQ. ID No. 28)
CCCATCCCATGCAGCGGCACATGGCTAAGGGCCATTTGG;

GT2a-5a-SA13-r (SEQ. ID No. 23)
GGGAGTTATTAGAGCCCCGGTCCAGGAGTATGACATGGA;

GT2a-6a-EUKH2-f (SEQ. ID No. 29)
CCCATCCCATGCAGCACCTCATGGTTACGCGACGTGTGG;

GT2a-6a-EUKH2-r (SEQ. ID No. 30)
CACCCTCCAGATAGCGAACTTATAGTTCGGCGCAGGAGG;

GT2a-6a-HK6a-f (SEQ. ID No. 31)
CCCATCCCATGCAGCACCTCATGGTTGCGCGACGTGTGG;

GT2a-6a-HK6a-r (SEQ. ID No. 32)
CACCCTCCAGATAGCGAACTTATAGTTCGGCGCAGGAGG;

GT2a-7a-QC69-f (SEQ. ID No. 33)
CCCATCCCATGCAGCGGGAGCTGGCTCCGGGAGGTGTGG;

GT2a-7a-QC69-r (SEQ. ID No. 23)
GGGAGTTATTAGAGCCCCGGTCCAGGAGTATGACATGGA.

Purified PCR products were directly cloned into an AfeI-digested shuttle vectors by Infusion cloning following the manufacturer's instructions.

To generate stable replicon cell lines, replicon plasmids were linearized by restriction enzyme digestion (XbaI) and purified using a Qiagen MinElute column. RNA was generated from linearized replicon templates using the T7 RiboMax Express Large Scale in vitro transcription system (Promega). Following transcription, reactions were treated with RNase-free DNase and purified using the RNeasy Mini kit (Qiagen). Huh7.5 cells were electroporated (Bio-Rad Gene Pulser: 950 µF, 270V) with 10 µg in vitro transcribed replicon RNA, plated in cell culture dishes, and incubated for 24 h prior to addition of complete medium containing G418 (500 µg/mL). Replicon-containing cells were selected by passaging in the presence of G418 (500 µg/mL) for approximately 4-5 weeks. Selected colonies were pooled, expanded, and cryopreserved prior to compound testing.

Generation of NS5A Mutations in GT1a Replicon:

pH/SG-PI-hRluc-H77S is a cell culture adapted, bicistronic GT1a subgenomic replicon expressing hRluc under the control of a chimeric HCV-poliovirus IRES. Expression of the HCV nonstructural proteins NS3 through NS5B is driven by the EMCV IRES. Five adaptive mutations (Q41R and V629I in NS3; K34R in NS4A; K68R and S2321 in NS5A) allow efficient replication in cell culture (Yi and Lemon. 2004, *J. Virol.* 78(15):7904-7915). NS5A mutations were synthesized (Genscript) or introduced into pH/SG-PI-hRluc-H77S using the QuickChange II XL Site-Directed Mutagenesis Kit (Agilent Technologies, Santa Clara, Calif.) and the following primer pairs:

1a-M28T-f (SEQ. ID No. 34)
5'-GCT GAA AGC CAA GCT C<u>AC G</u>CC ACA ACT GCC TGG-3';

1a-M28T-r (SEQ. ID No. 35)
5'-CCA GGC AGT TGT GGC GTG AGC TTG GCT TTC AGC-3';

1a-Q30R-f (SEQ. ID No. 36)
5'-GCC AAG CTC ATG CCA <u>CGC</u> CTG CCT GGG ATT CC-3';

1a-Q30R-r (SEQ. ID No. 37)
5'-GGA ATC CCA GGC AGG CGT GGC ATG AGC TTG GC-3';

1a-L31V-f (SEQ. ID No. 38)
5'-GCT CAT GCC ACA A<u>GT G</u>CC TGG GAT TCC CTT TG-3';

-continued

1a-L31V-r
(SEQ. ID No. 39)
5'-CAA AGG GAA TCC CAG GCA CTT GTG GCA TGA

GC-3';

1a-Y93C-f
(SEQ. ID No. 40)
5'-CGT TCC CCA TTA ACG CCT GCA CCA CGG GCC CCT

G-3';

1a-Y93C-r
(SEQ. ID No. 41)
5'-CAG GGG CCC GTG GTG CAG GCG TTA ATG GGG AAC

G-3';

1a-Y93H-f
(SEQ. ID No. 42)
5'-CGT TCC CCA TTA ACG CCC ACA CCA CGG GCC CCT

G-3';

1a-Y93H-r
(SEQ. ID No. 43)
5'-CAG GGG CCC GTG GTG TGG GCG TTA ATG GGG AAC

G-3'.

Underlined sequences in forward primers (-f) indicate position of mutation.

Cell Maintenance and Replicon Assays:

Stable HCV replicon cell lines were grown in complete media (Dulbecco's modified Eagle medium [DMEM], 2 mM L-glutamine, 0.1 mM essential amino acids, 1 mM sodium pyruvate, 10% fetal bovine serum) with the addition 500 μg/ml gentamycin (G418). Huh7-lunet cells were maintained in the same medium without the addition of G418. Cells were routinely passaged at a dilution of 1:5 two times per week. For stable replicon assays (GT1a-H77, GT1b-Con1, GT2a-JFH, GT2a-J6, GT2a-2b-MD2b, GT2a-2b-J8, GT2a-3a-S52, GT3a-552, GT4a-ED43, GT2a-5a-SA13, GT2a-6a-EUKH2, GT2a-6a-HK6a, and GT2a-7a-QC69), an 8-point 3-fold or half-log dilution series of compound was transferred into three replica 96-well plates containing $1\times10^4$ cells per well in phenol red-free complete media without G418. For the transient replication assay, Huh7-lunet cells in ice-cold phosphate buffered saline (PBS) were electroporated (Bio-Rad Gene pulser: 950 uF, 270V) with 10 μg purified in vitro transcribed HCV replicon RNA, followed by resuspension in phenol red-free complete media without G418 and plating ($1\times10^4$ cells in 200 μL media/well) into three replica 96-well plates prior to compound addition (1 μl compound per well). For stable and transient replicon assays, luciferase activity of compound-treated cells was measured relative to DMSO-treated cells after 72 h incubation using RENILLA-GLO™ Luciferase Assay (Promega).

The table below presents comparative potency data ($EC_{50}$, nM) for compound 16 and a reference compound (daclatasvir, DCV) against HCV replicons representing a diverse panel of NS5A genotypes.

| Replicon | NS5A genotype | Compound 16 $EC_{50}$ (nM) | DCV $EC_{50}$ (nM) |
|---|---|---|---|
| GT1a-H77 | 1a | 0.007 | 0.06 |
| GT1b-Con1 | 1b | 0.008 | 0.02 |
| GT2a-JFH | 2a | 0.004 | 0.008 |
| GT2a-2a-J6 | 2a | 0.49 | 5.8 |
| GT2a-2b-J8 | 2b | 9.9 | 20 |
| GT2a-2b-MD2b | 2b | 21 | 33 |
| GT3a-S52 | 3a | 4.7 | 1.2 |
| GT2a-3a-S52 | 3a | 0.54 | 0.39 |
| GT4a-ED43 | 4a | 0.011 | 0.025 |
| GT2a-5a-SA13 | 5a | 0.005 | 0.009 |
| GT2a-6a-EUKH2 | 6a | 0.014 | 0.143 |
| GT2a-6a-HK6a | 6a | 0.002 | 0.005 |
| GT2a-7a-QC69 | 7a | 0.02 | 0.016 |

The table below presents comparative potency data ($EC_{50}$, nM) for compound 16 and a reference compound (daclatasvir, DCV) against wild type (wt) HCV genotype 1a and mutations (NS5A numbering in the format wt:position:mutation).

| Replicon | Compound 16 $EC_{50}$ (nM) | DCV $EC_{50}$ (nM) |
|---|---|---|
| wt | 0.0014 | 0.0083 |
| K24E | 0.0013 | 0.0022 |
| K24G | 0.0021 | 0.02 |
| K24R | 0.0012 | 0.011 |
| L31M | 0.0106 | 0.67 |
| L31V | 0.15 | 4.5 |
| M28T | 0.049 | 3.4 |
| M28V | 0.0015 | 0.0073 |
| P32L | 0.046 | 1.9 |
| Q30E | 0.74 | 81.5 |
| Q30H | 0.006 | 0.8 |
| Q30K | 0.05 | 7.9 |
| Q30R | 0.012 | 3.4 |
| H58D | 0.01 | 1.2 |
| Y93C | 0.22 | 3.2 |
| Y93H | 10 | 65 |
| Y93N | 19 | 119 |
| K24E Q30R | 1.8 | 3.5 |
| K24E Q30K | 7.9 | 20 |
| K24N Q30R | 1.2 | 8 |
| M28T Q30H | 24 | 733 |
| M28V Y93H | 15 | 17.5 |
| M28V Y93C | 1 | 3.5 |
| M28V Q30R | 0.16 | 1.2 |
| Q30R H58D | 2.8 | 838 |
| Q30R Y93C | 1.4 | 26 |
| Q30R Y93H | 38 | 243 |

Resistance Barrier Analysis in Hepatitis C Virus Genotype 1b Replicon Cells:

Stable HCV genotype 1b replicon Huh7-lunet cells were plated in 100 mm cell culture dishes ($1.5\times10^5$ and $3\times10^5$ cells/dish for DMSO control and compound treated cells, respectively) and incubated for 24 hr (37° C., 5% $CO_2$) prior to compound addition. Compounds (solubilized in DMSO) were prepared in complete media (0.5% DMSO final) and added to cells. Cells were maintained in the presence of compound (or DMSO) and G418 (500 μg/mL) for 3 weeks with media replacement two times per week. Cells were then fixed (4% paraformaldehyde, 30 min at room temperature) and stained (0.5% crystal violet/25% methanol, 20 min room temperature) to allow visualization of surviving cells. Plates were then washed with water to remove excess stain and left to air dry overnight prior to imaging (BioRad Gel Doc XR+Molecular Imager).

The compounds of the invention exhibit a surprisingly high barrier to resistance development. FIG. 1 illustrates comparison of a compound of the invention to daclatasvir in a test that provides a qualitative indication of the occurrence of resistance. The FIG. 1 shows crystal violet staining of surviving HCV genotype 1b replicon cells after 3 weeks in the presence of G418 and either compound 16 or daclatasvir, prepared as described above. The control plate, with DMSO alone (no compound 16 or daclatasvir), is almost completely opaque. At 2× and 10×$EC_{50}$, daclatasvir reduced replicon survival, but many resistant cell colonies survive; only at 100×$EC_{50}$ does daclatasvir largely eliminate replicon cells. Compound 16, by comparison, almost entirely prevented replicon cell survival at just 2×$EC_{50}$. Based on this, compound 16 is expected to be far more effective at eliminating mutant strains of HCV that are resistant to other inhibitors of NS5A (e.g. daclatasvir).

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I):

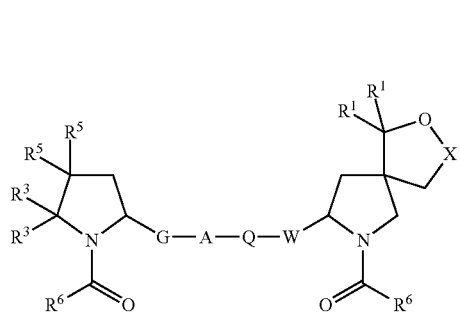

(I)

or a pharmaceutically acceptable salt thereof, wherein:

(i) A and Q are taken together to form an optionally substituted, tricyclic aryl or optionally substituted, tricyclic heteroaryl; and G and W are each independently an optionally substituted imidazolyl; wherein the said imidazolyl groups are C2-attached to the pyrrolidine rings;

(ii) G and A are taken together to form

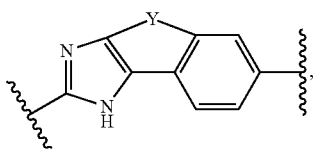

each of which is optionally substituted; W is optionally substituted imidazolyl which is C2-attached to the pyrrolidine ring; and Q is optionally substituted phenyl;

(iii) Q and W are taken together to form

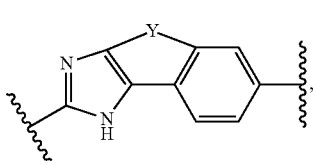

each of which is optionally substituted; G is optionally substituted imidazolyl which is C2-attached to the pyrrolidine ring; and A is optionally substituted phenyl;

(iv) G, A and Q are taken together to form

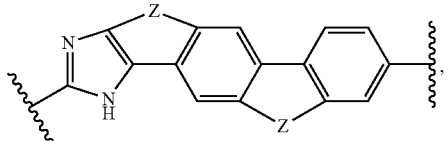

which is optionally substituted; and W is optionally substituted imidazolyl which is C2-attached to the pyrrolidine ring;

(v) W, Q and A are taken together to form

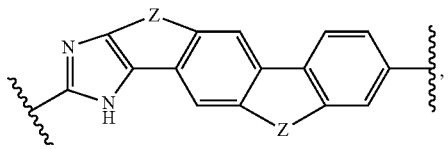

which is optionally substituted; and G is optionally substituted imidazolyl which is C2-attached to the pyrrolidine ring; or (vi) G, A, Q and W are taken together to form

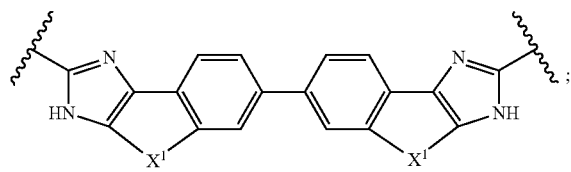

Y is —CH=CH—, —CH$_2$O—, —CH$_2$CH$_2$—, —CH$_2$CH$_2$CH$_2$—, —OCH$_2$CH$_2$—, or —CH$_2$OCH$_2$;

each Z is independently selected from the group consisting of —CH=CH—, —CH$_2$O—, and —CH$_2$CH$_2$;

X is —C(R$^{11}$)$_2$— or —C(R$^{11}$)$_2$C(R$^{11}$)$_2$—;

each X$^1$ is independently selected from the group consisting of absent, —CH=CH—, —CH$_2$O—, —CH$_2$CH$_2$—, —CH$_2$CH$_2$CH$_2$—, —OCH$_2$CH$_2$—, and —CH$_2$OCH$_2$—;

R$^1$, R$^3$, and R$^{11}$ at each occurrence are independently hydrogen or optionally substituted C$_1$-C$_4$ alkyl;

R$^5$ at each occurrence is independently hydrogen, halogen, optionally substituted O(C$_1$-C$_4$ alkyl), optionally substituted C$_3$-C$_8$ cycloalkyl, or optionally substituted C$_1$-C$_4$ alkyl;

alternatively, (i) the two R$^5$ groups are taken together with the carbon atom to which they are attached to form a spiro, optionally substituted C$_3$-C$_8$ cycloalkyl or optionally substituted heterocyclic ring; or (ii) an R$^3$ and an R$^5$ are taken together with the carbon atoms to which they are attached to form a fused and optionally substituted C$_3$-C$_8$ cycloalkyl or a fused and optionally substituted heterocyclic; and R$^6$ at each occurrence is independently C$_1$-C$_8$ alkyl substituted with one or more groups selected from amino, protected amino, N(C$_1$-C$_4$ alkyl)$_2$, hydroxy, O(C$_1$-C$_4$ alkyl), phenyl and tetrahydropyranyl.

2. The compound of claim 1, represented by Formula (II):

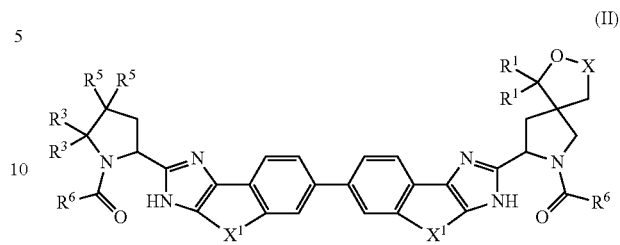

or a pharmaceutically acceptable salt thereof.

3. The compound of claim 1, represented by Formula (III):

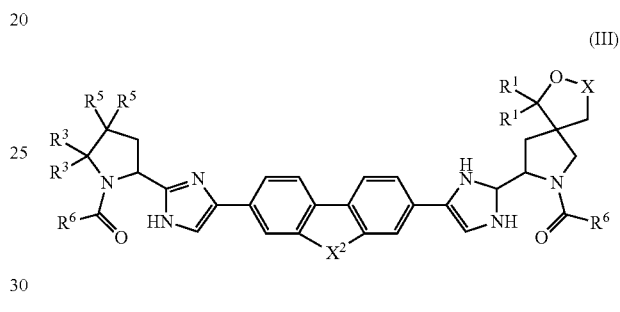

or a pharmaceutically acceptable salt thereof, wherein X$^2$ is selected from the group consisting of absent, —CH$_2$—, O, —CH=CH—, —CH$_2$O, —CH$_2$CH$_2$—, —CH$_2$CH$_2$CH$_2$—, —OCH$_2$CH$_2$—, and —CH$_2$OCH$_2$—.

4. The compound of claim 1, represented by Formula (IVa) or (IVb):

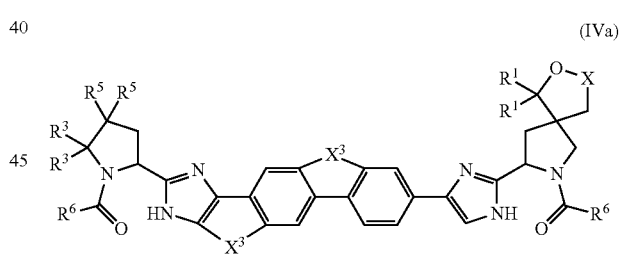

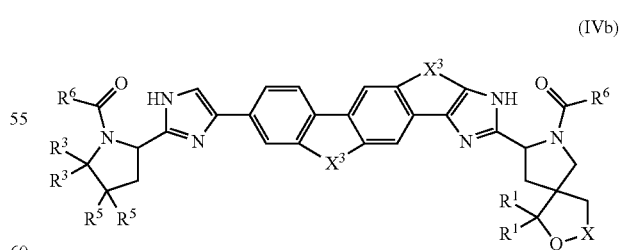

or a pharmaceutically acceptable salt thereof, wherein X$^3$ at each occurrence is independently selected from the group consisting of —CH=CH—, —CH$_2$O—, and —CH$_2$CH$_2$.

5. The compound of claim 1, represented by Formula (Va) or (Vb):

(Va)

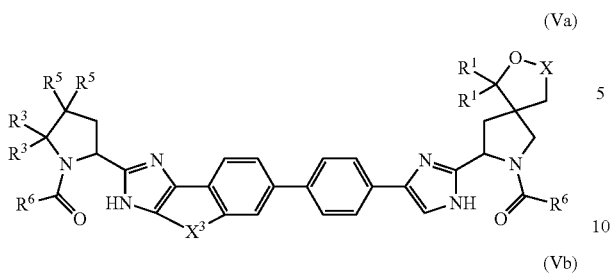

(Vb)

or a pharmaceutically acceptable salt thereof, wherein $X^3$ is selected from the group consisting of —CH=CH—, —CH$_2$O—, and —CH$_2$CH$_2$.

6. The compound of claim 1, represented by Formula (VIa), (VIb) or (VIc):

(VIa)

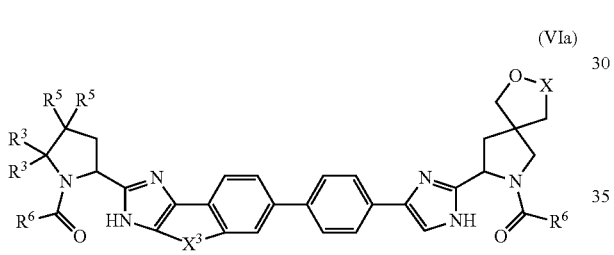

(VIb)

(VIc)

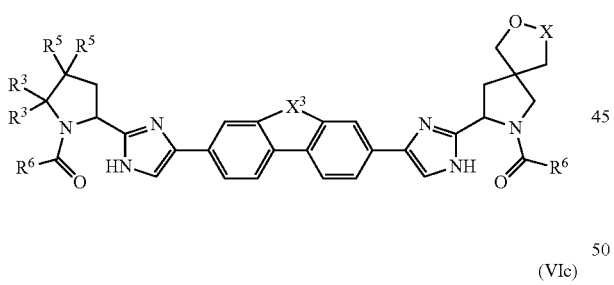

or a pharmaceutically acceptable salt thereof, wherein $X^3$ at each occurrence is each independently selected from the group consisting of —CH=CH—, —CH$_2$O—, and —CH$_2$CH$_2$.

7. A compound represented by Formula (VIIa), (VIIb), (VIIc) or (VIId), (VIIa)

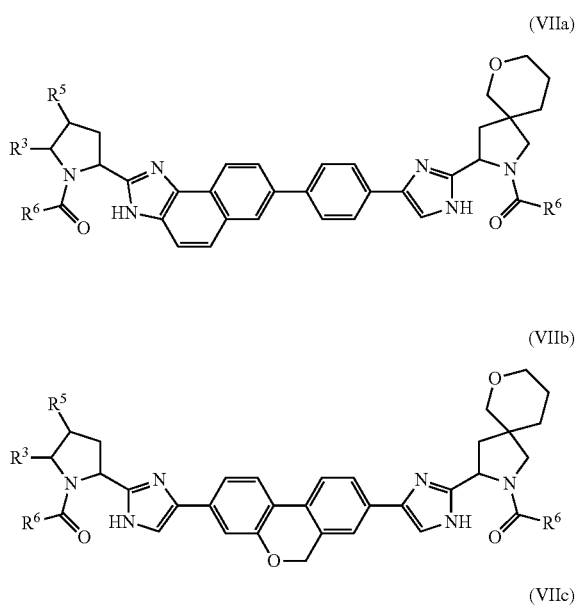

(VIIb)

(VIIc)

(VIId)

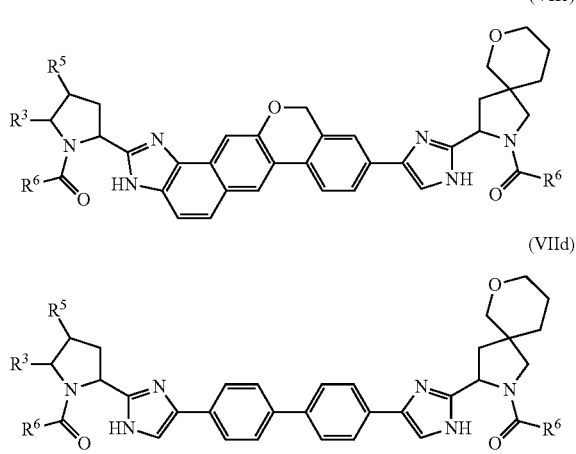

or a pharmaceutically acceptable salt thereof, wherein $R^3$ and $R^5$ are taken together with the carbon atoms to which they are attached to form a fused and optionally substituted $C_3$-$C_8$ cycloalkyl, or fused and optionally substituted heterocyclic; and $R^6$ at each occurrence is independently $C_1$-$C_8$ alkyl substituted with one or more groups selected from amino, protected amino, N($C_1$-$C_4$ alkyl)$_2$, hydroxy, O($C_1$-$C_4$ alkyl), phenyl and tetrahydropyranyl; or $R^6$ is

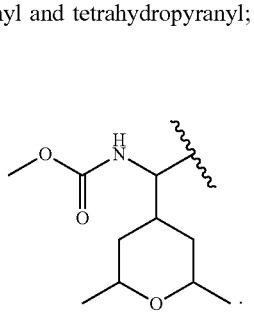

8. The compound of claim 7, represented by Formula (VIIIa), (VIIIb), (VIIIc) or (VIIId), (VIIIa)
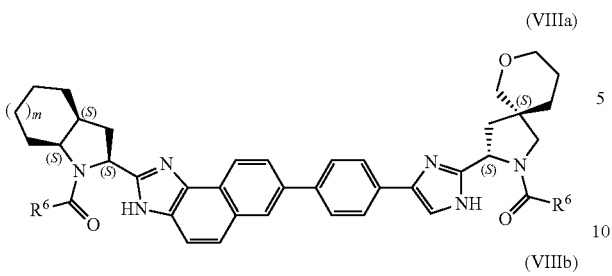
or a pharmaceutically acceptable salt thereof, wherein m=0 or 1 and $R^6C(O)$— is
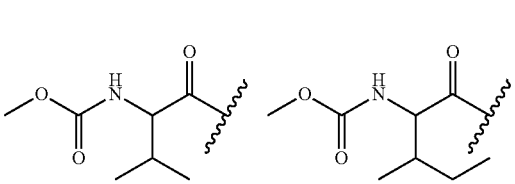
(VIIIb)
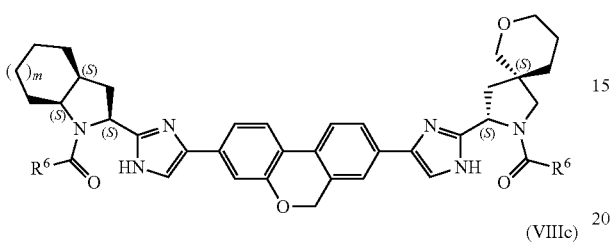
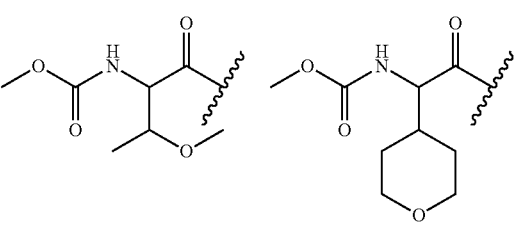
(VIIIc)
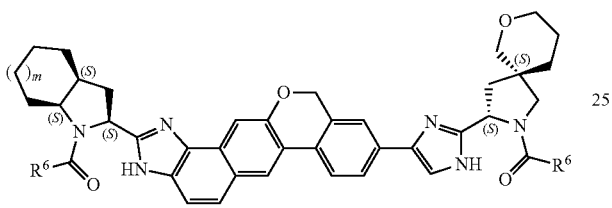
(VIIId)
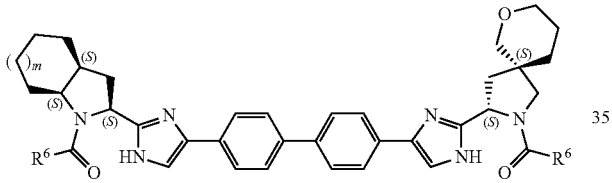
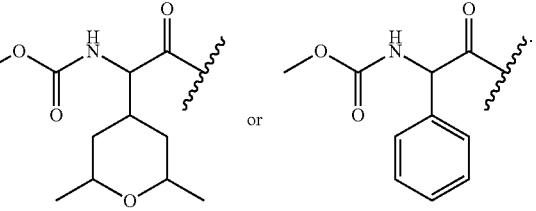
9. A compound selected from compounds 5-11 and 13-51 below:
| Compound | Structure |
|---|---|
| 5 | 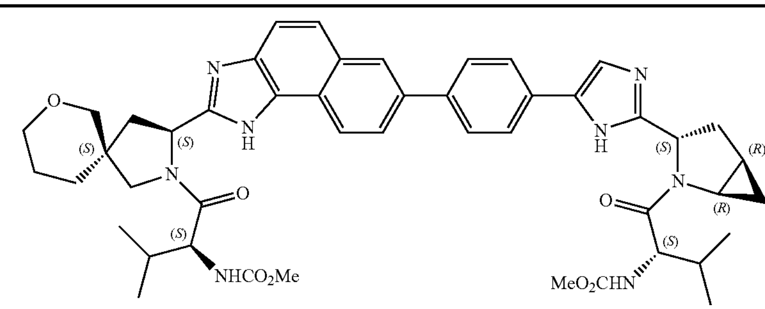 |
| 6 | 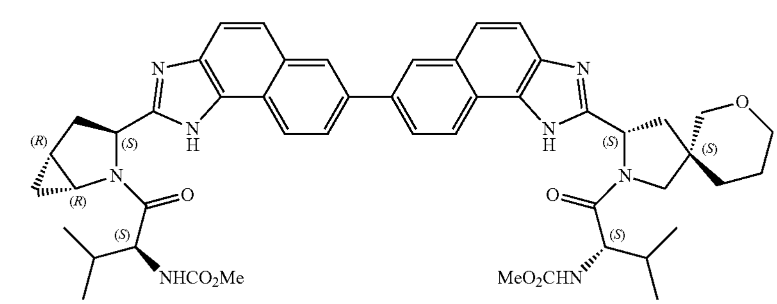 |

-continued

| Compound | Structure |
|---|---|
| 7 | 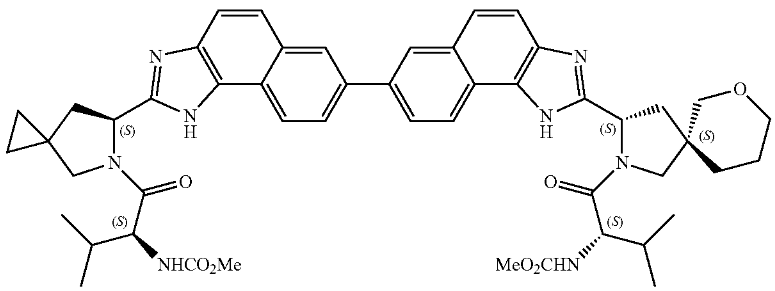 |
| 8 | 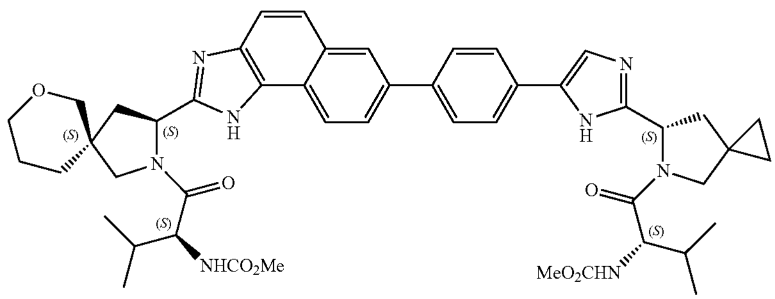 |
| 9 | 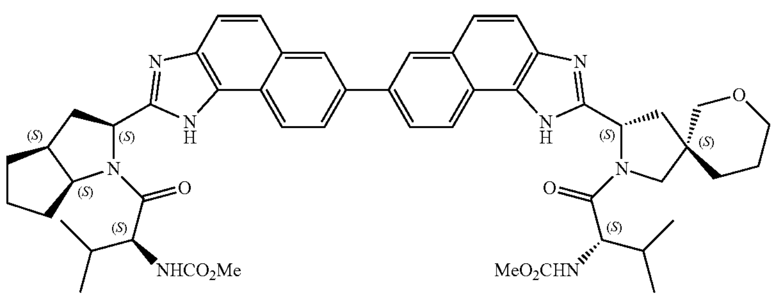 |
| 10 | 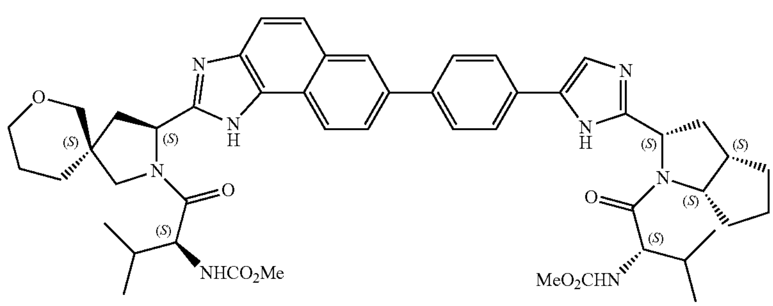 |
| 11 | 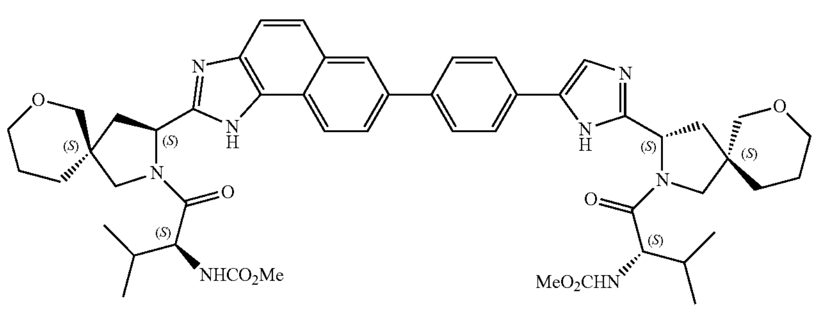 |

| Compound | Structure |
|---|---|
| 13 | 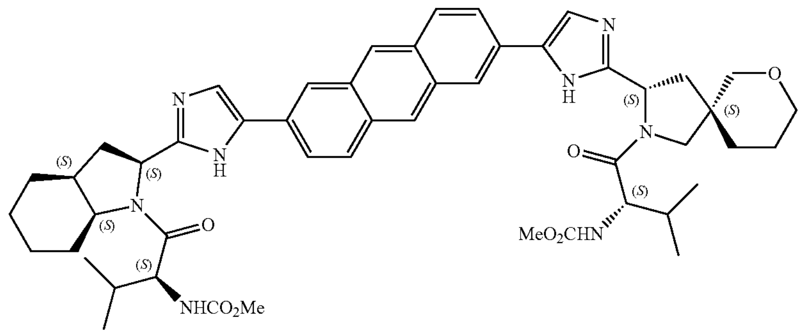 |
| 14 | 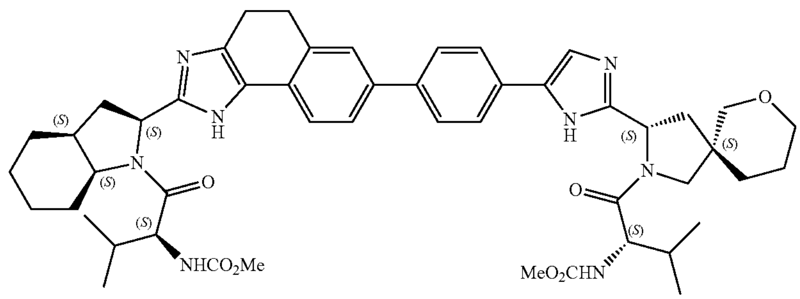 |
| 15 | 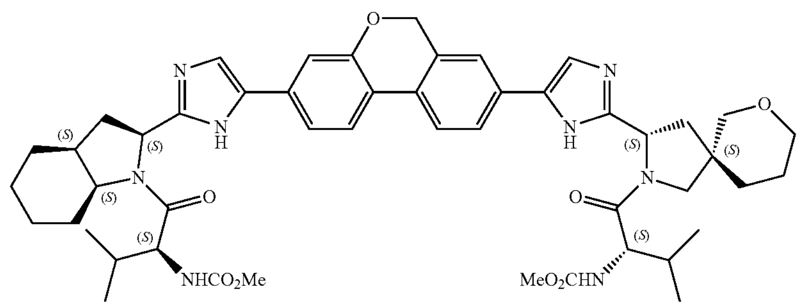 |
| 16 | 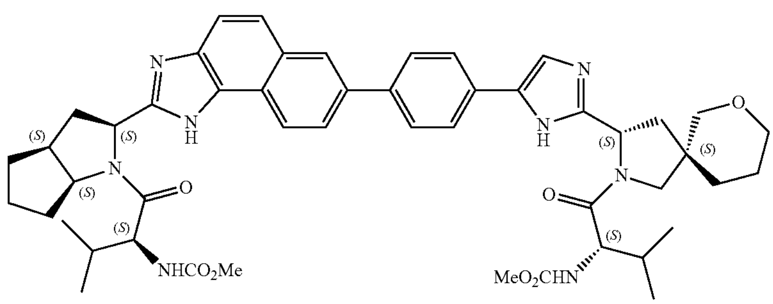 |
| 17 | 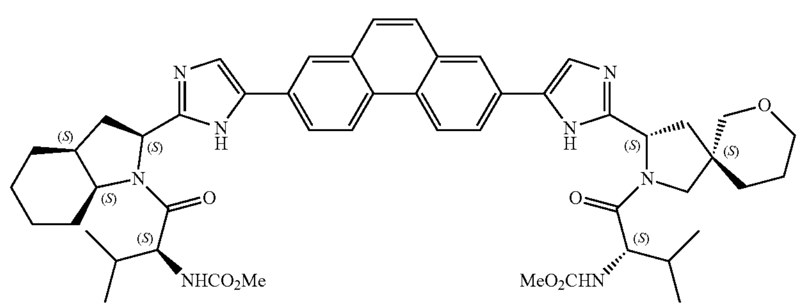 |

-continued

| Compound | Structure |
|---|---|
| 18 | 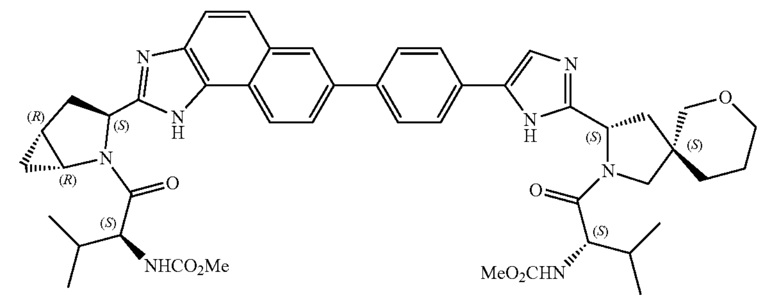 |
| 19 | 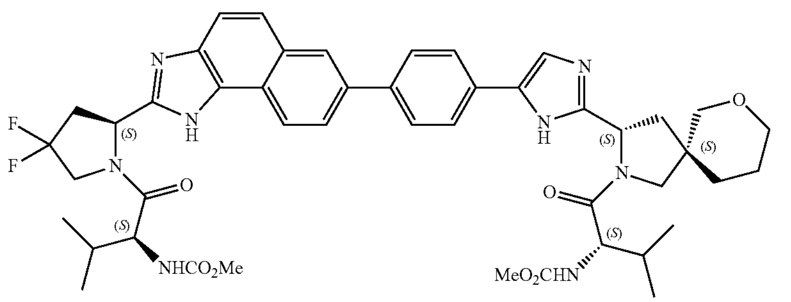 |
| 20 | 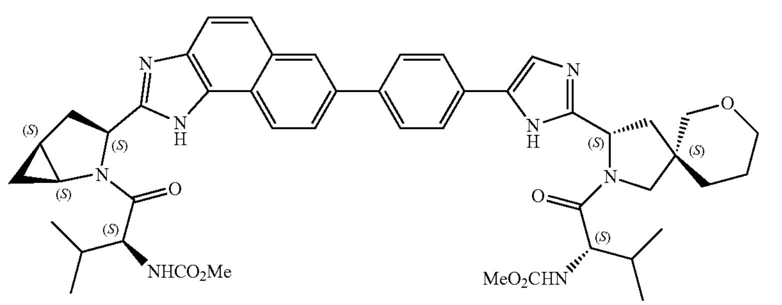 |
| 21 | 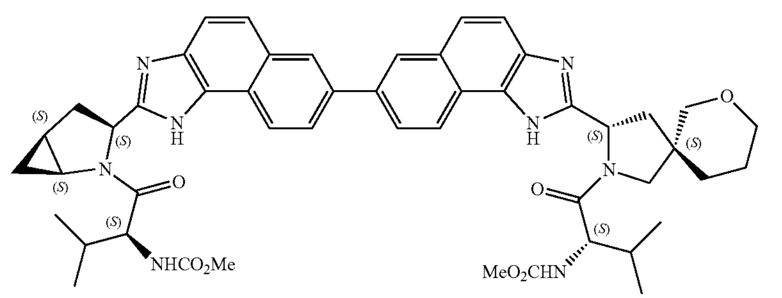 |
| 22 | 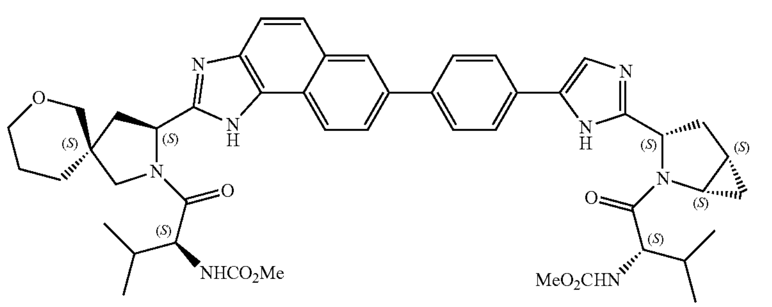 |

| Compound | Structure |
|---|---|
| 23 | 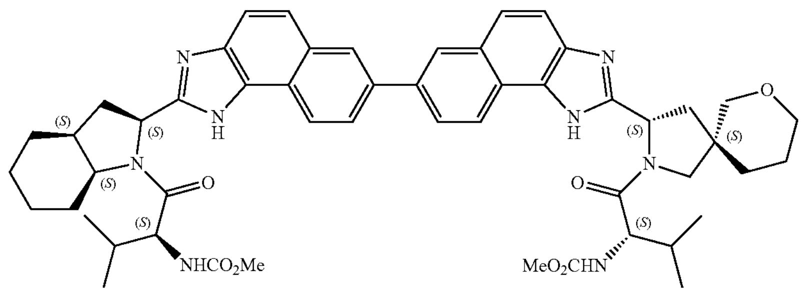 |
| 24 | 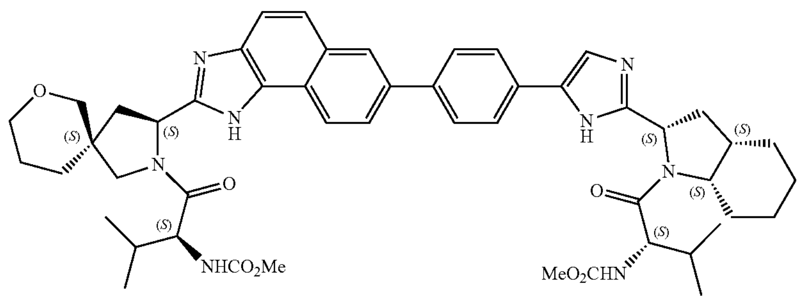 |
| 25 | 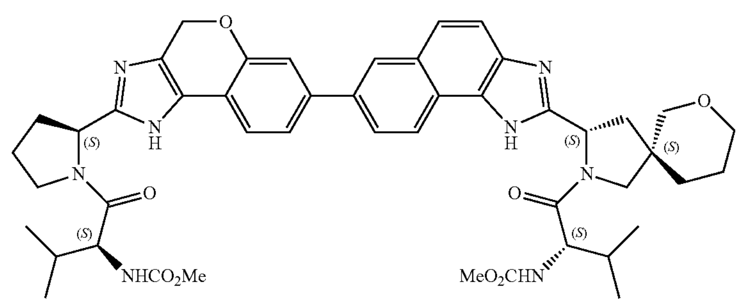 |
| 26 | 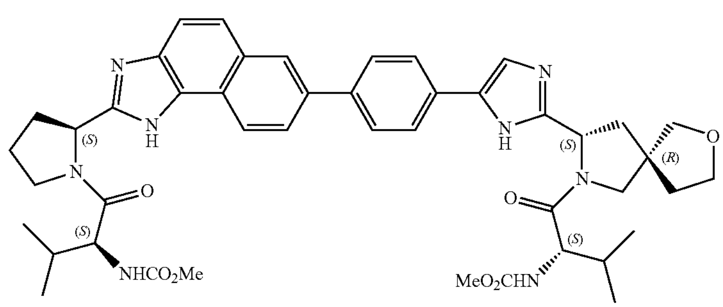 |
| 27 | 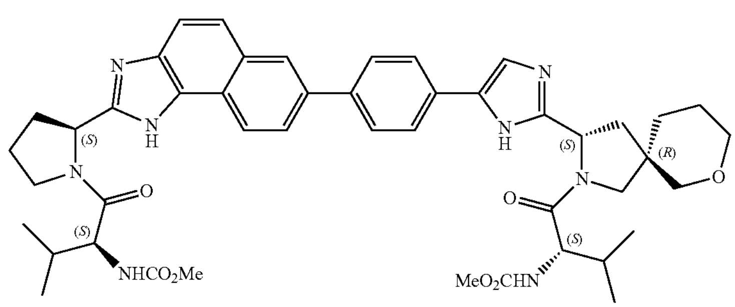 |

| Compound | Structure |
|---|---|
| 28 | 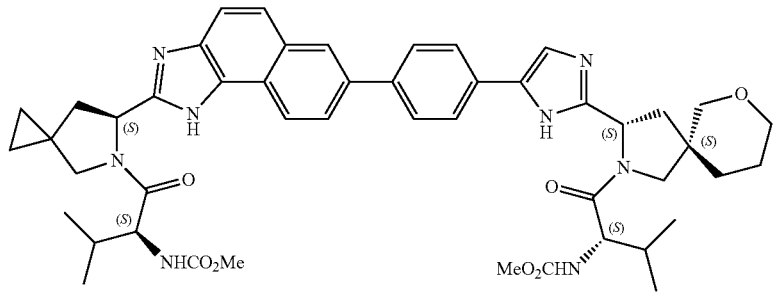 |
| 29 | 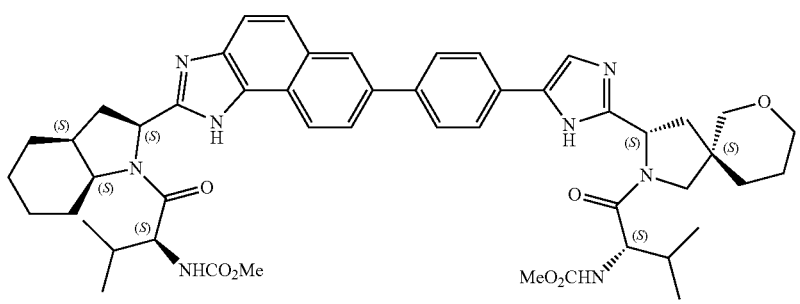 |
| 30 | 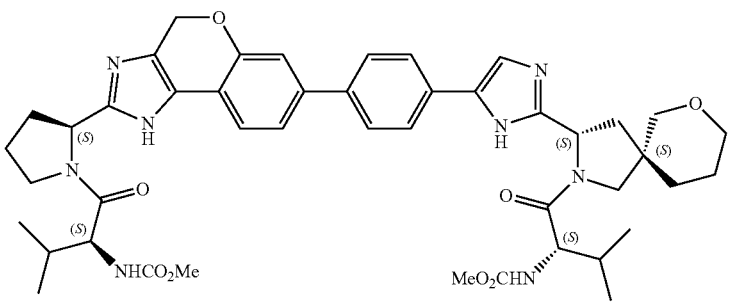 |
| 31 | 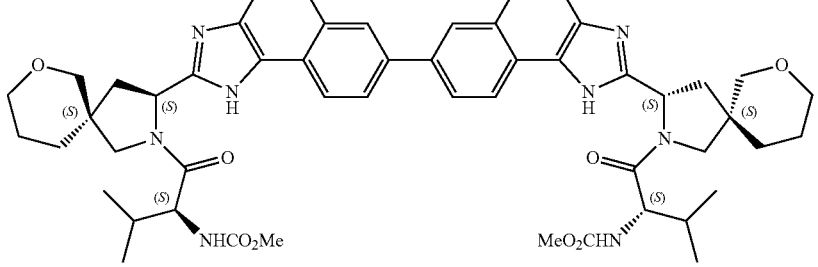 |
| 32 | 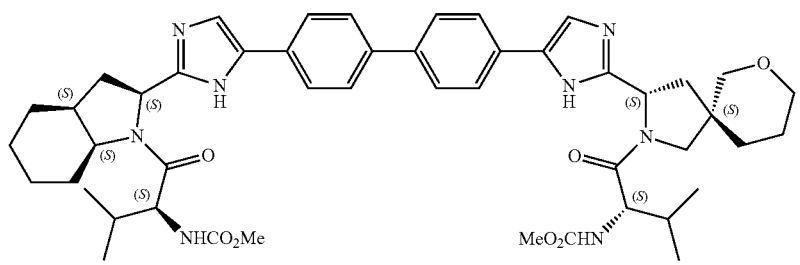 |

-continued
| Compound | Structure |
|---|---|
| 33 | 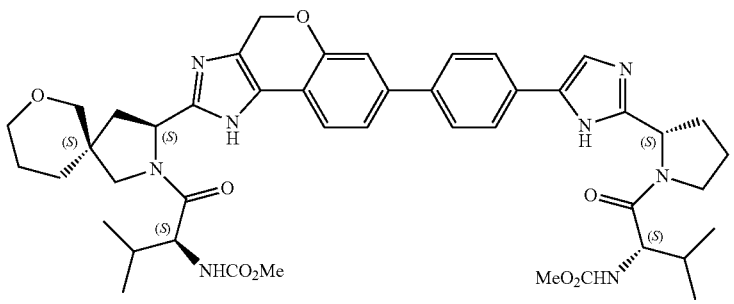 |
| 34 | 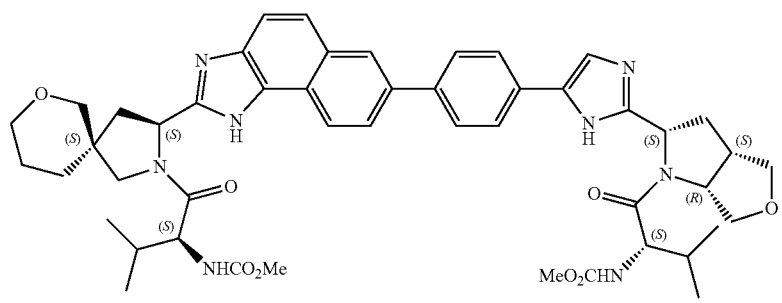 |
| 35 | 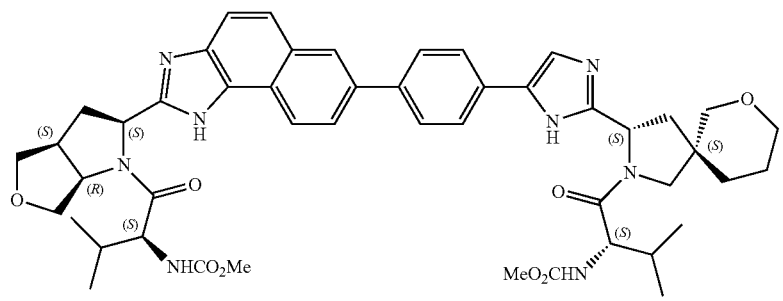 |
| 36 | 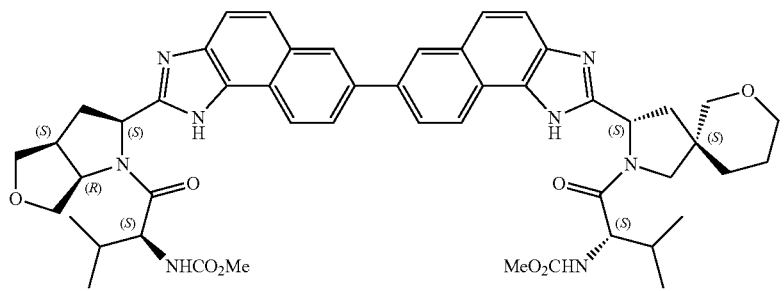 |
| 37 | 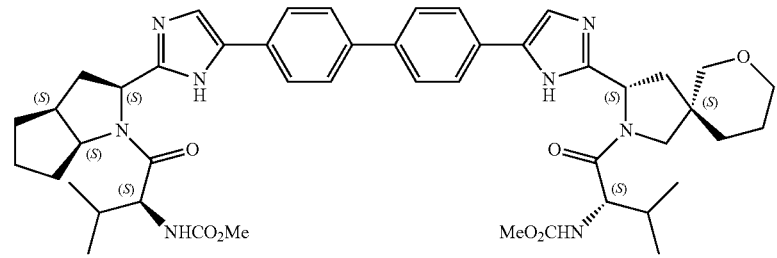 |

| Compound | Structure |
|---|---|
| 38 | 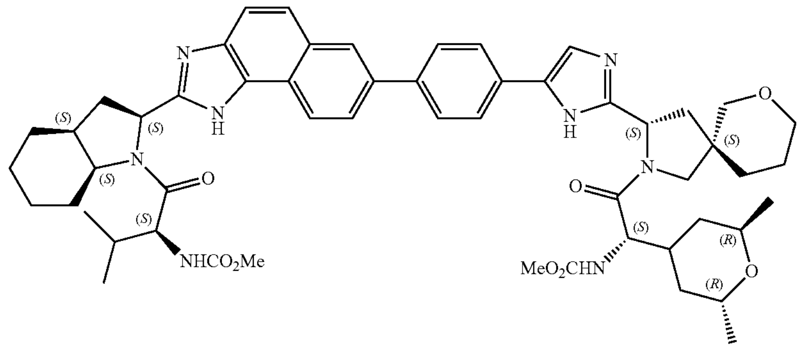 |
| 39 | 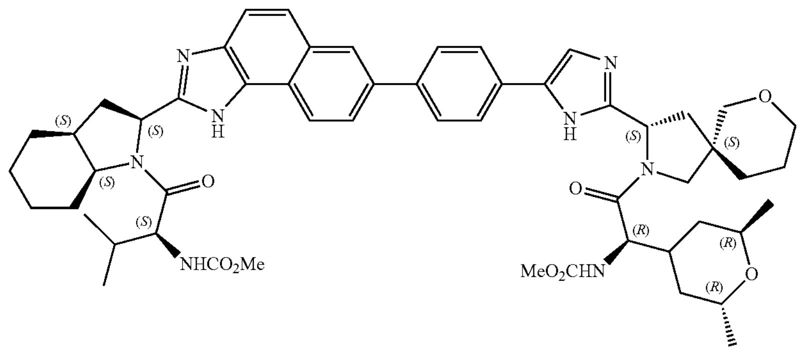 |
| 40 | 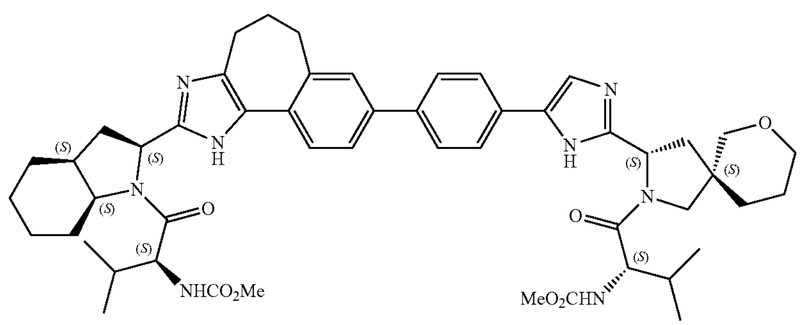 |
| 41 | 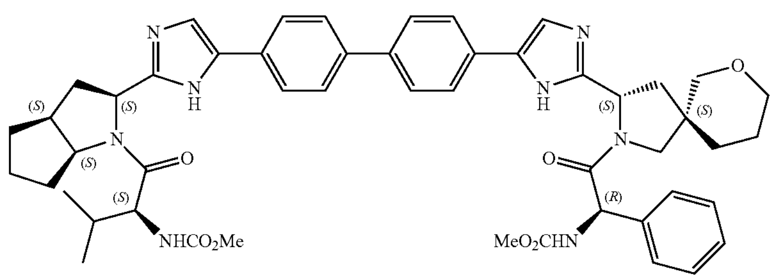 |
| 42 | 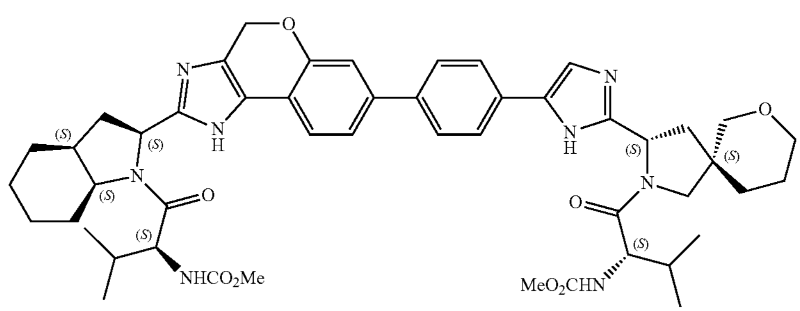 |

| Compound | Structure |
|---|---|
| 43 | 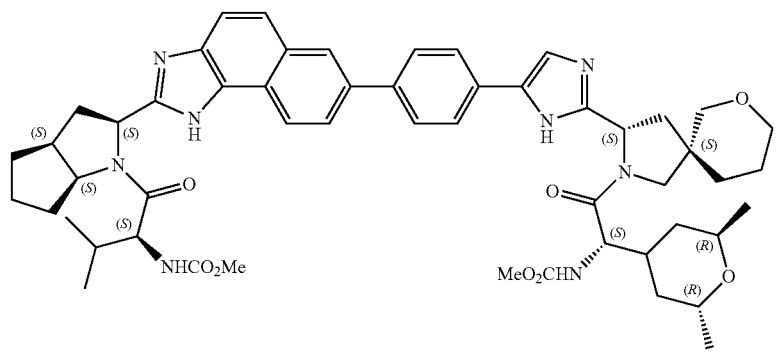 |
| 44 | 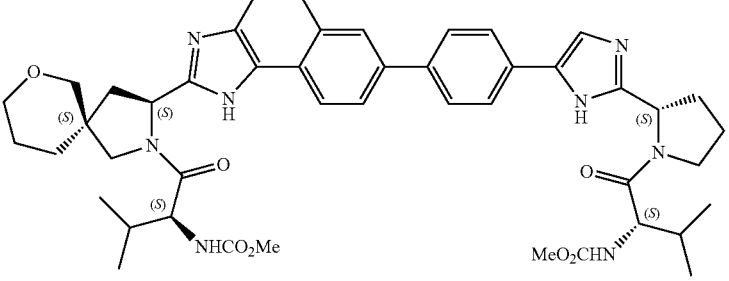 |
| 45 | 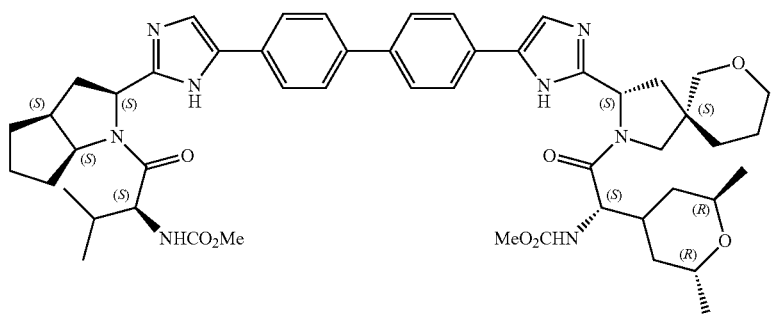 |
| 46 | 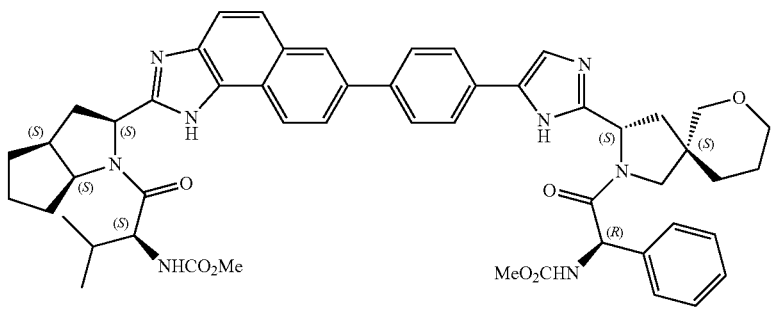 |
| 47 | 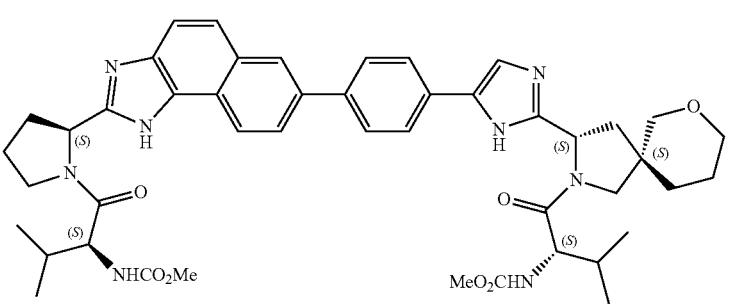 |

| Compound | Structure |
|---|---|
| 48 | 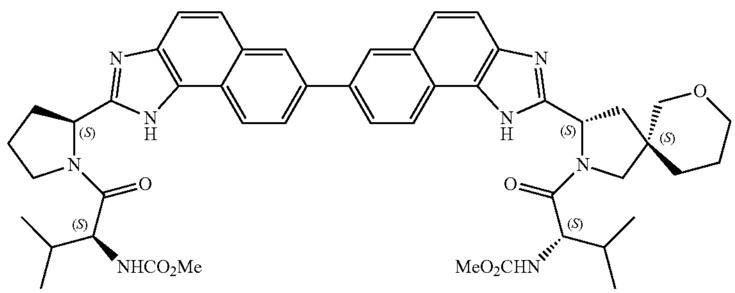 |
| 49 | 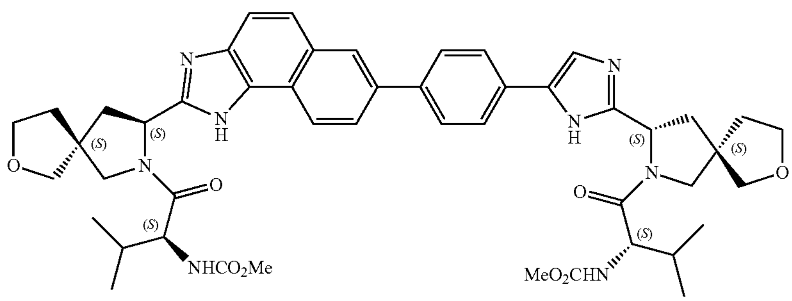 |
| 50 | 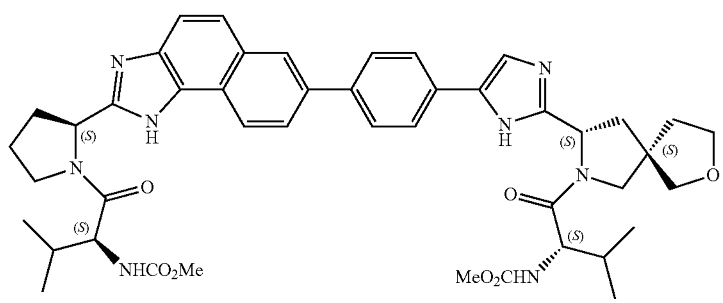 |
| 51 | | or a pharmaceutically acceptable salt thereof.

10. A pharmaceutical composition comprising a compound according to claim 1 or a pharmaceutically acceptable salt thereof and a pharmaceutically acceptable carrier or excipient.

11. A method of inhibiting the replication of hepatitis C virus comprising contacting said virus with an effective amount of a compound or combination of compounds of claim 1, or a pharmaceutically acceptable salt thereof.

12. A method of treating a hepatitis C virus infection in a subject infected with said virus comprising administering to the subject a therapeutically effective amount of a compound or combination of compounds of claim 1, or a pharmaceutically acceptable salt thereof.

13. The method of claim 12, further comprising the step of administering to the subject one or more agents selected from the group consisting of host immune modulators and antiviral agents.

14. The method of claim 13, wherein the host immune modulator is selected from the group consisting of interferon-alpha, pegylated-interferon-alpha, interferon-beta, interferon-gamma, consensus interferon, a cytokine, and a vaccine.

15. The method of claim 13, wherein the antiviral agent inhibits replication of hepatitis C virus by inhibiting a host cellular function associated with viral replication.

16. The method of claim 13, wherein the antiviral agent inhibits the replication of hepatitis C virus by targeting proteins of the viral genome.

17. The method of claim 13, wherein said antiviral agent is an inhibitor of a hepatitis C viral protein, a replication process or a combination thereof, wherein said targeting protein or replication process is selected from the group consisting of helicase, protease, polymerase, metalloprotease, NS4A, NS4B, NS5A, assembly, entry, and IRES.

18. The method of claim 12, further comprising the step of administering to the subject an agent or combination of agents that treat or alleviate symptoms of hepatitis C virus infection selected from cirrhosis and inflammation of the liver.

19. The method of claim 12, wherein the subject is co-infected with hepatitis B virus, further comprising the step of administering to the subject one or more agents that treat hepatitis B virus infection.

20. The method of claim 12, wherein the subject is co-infected with human immunodeficiency virus, further comprising the step of administering to the subject one or more agents that treat human immunodeficiency virus infection.

21. The pharmaceutical composition of claim 10, further comprising an agent selected from interferon, pegylated interferon, ribavirin, amantadine, an HCV protease inhibitor, an HCV polymerase inhibitor, an HCV helicase inhibitor, and an internal ribosome entry site inhibitor.

22. The pharmaceutical composition of claim 10, further comprising a cytochrome P450 monooxygenase inhibitor or a pharmaceutically acceptable salt thereof.

23. The pharmaceutical composition of claim 22, wherein the cytochrome P450 monooxygenase inhibitor is ritonavir.

24. A method of treating hepatitis C virus infection in a subject in need thereof comprising co-administering to said subject a cytochrome P450 monooxygenase inhibitor or a pharmaceutically acceptable salt thereof, and a compound of claim 1 or a pharmaceutically acceptable salt thereof.

* * * * *